(12) United States Patent
Blackwell et al.

(10) Patent No.: US 12,018,059 B2
(45) Date of Patent: Jun. 25, 2024

(54) HUMAN AMYLIN ANALOG POLYPEPTIDES AND METHODS OF USE

(71) Applicant: Intarcia Therapeutics, Inc., Boston, MA (US)

(72) Inventors: William Blackwell, Boston, MA (US); Ved P. Srivastava, Boston, MA (US); James M. Way, Boston, MA (US)

(73) Assignee: I2O THERAPEUTICS, INC., Cambridge, MA (US)

( * ) Notice: Subject to any disclaimer, the term of this patent is extended or adjusted under 35 U.S.C. 154(b) by 848 days.

(21) Appl. No.: 16/598,915

(22) Filed: Oct. 10, 2019

(65) Prior Publication Data
US 2020/0115430 A1 Apr. 16, 2020

Related U.S. Application Data

(60) Provisional application No. 62/744,236, filed on Oct. 11, 2018.

(51) Int. Cl.
| | | |
|---|---|---|
| C07K 14/575 | (2006.01) | |
| A61K 9/00 | (2006.01) | |
| A61K 38/00 | (2006.01) | |
| A61P 3/04 | (2006.01) | |
| A61P 3/10 | (2006.01) | |

(52) U.S. Cl.
CPC .......... *C07K 14/575* (2013.01); *A61K 9/0004* (2013.01); *A61K 9/0019* (2013.01); *A61P 3/04* (2018.01); *A61P 3/10* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 5,321,008 A | | 6/1994 | Beaumont et al. |
| 5,739,106 A | * | 4/1998 | Rink .......... A61P 3/04 |
| | | | 514/12.6 |
| 8,486,890 B2 | * | 7/2013 | Hansen ...... A61P 3/04 |
| | | | 514/6.9 |
| 8,497,347 B2 | | 7/2013 | Mehta et al. |
| 8,895,504 B2 | * | 11/2014 | Schaffer ...... A61P 1/00 |
| | | | 514/6.9 |
| 9,023,789 B2 | | 5/2015 | Dahl et al. |
| 9,593,149 B2 | | 3/2017 | Kruse et al. |
| 10,071,140 B2 | | 9/2018 | Mathiesen et al. |
| 2005/0070472 A1 | | 3/2005 | Gedulin et al. |
| 2009/0099085 A1 | | 4/2009 | Hansen et al. |
| 2010/0311650 A1 | | 12/2010 | Mehta et al. |
| 2012/0046224 A1 | | 2/2012 | Karsdal et al. |
| 2014/0018286 A1 | | 1/2014 | Schaeffer et al. |
| 2016/0272683 A1 | | 9/2016 | Kruse et al. |

FOREIGN PATENT DOCUMENTS

| | | |
|---|---|---|
| WO | WO 2010/046357 A1 | 4/2010 |
| WO | WO 2011/130499 A1 | 10/2011 |
| WO | WO 2012/162547 A2 | 11/2012 |
| WO | WO 2015/155151 A1 | 10/2015 |
| WO | WO 2016/034604 A1 | 3/2016 |
| WO | WO 2016/146739 A1 | 9/2016 |

OTHER PUBLICATIONS

"A Breakthrough Opportunity for SYMLIN: Dual Hormone Pump with Independent Hormone Algorithms", 13 pages (Mar. 2014).
American Diabetes Association. "8. Pharmacologic Approaches to Glycemic Treatment: Standards of Medical Care in Diabetes-2018", *Diabetes Care* 41(Suppl.1):S73-S85, doi.org/10.2337/dc18-S008 (Jan. 2018).
Center for Drug Evaluation and Research Approval Package for Application No. 21-332, Pharmacology Review(s), 179 pages (2005).
Decision Resources, Inc.—Metabolic Disorders Study #1—"Type 1 Diabetes", 153 pages (Aug. 2008).
Decision Resources, Inc.—Decision Base 2009—"Type 1 Diabetes: Opportunities Await Therapies That Offer Alternatives to Subcutaneous Injections of Insulins" 103 pages (2009).
"Blood Glucose Instability is the Achilles Heel of T1D Therapy" 9 pages (May 8, 2014).
Highlights of Prescribing Information—Symlin (Jun. 2014).
IDF Diabetes Atlas, Sixth edition ISBN: 2-930299-85-3 (2013).
The Diabetes Control and Complications Trial Research Group "Lifetime Benefits and Costs of Intensive Therapy as Practiced in the Diabetes Control and Complications Trial", *JAMA* 276(17):1409-1415 (Nov. 1996).
Ozempic—semaglutide injection 0.5mg/1mg—Highlights of Prescribing Information. (2017).
Pharmacology and Toxicology Summary—NDA 21-332 Symlin. 12 pages.
Symlin (pramlintide acetate) injection, prescribing information, 6 pages (2008).

(Continued)

*Primary Examiner* — Sergio Coffa
(74) *Attorney, Agent, or Firm* — Lathrop GPM LLP; Brian C. Trinque

(57) ABSTRACT

This invention relates to isolated polypeptides that are analogs of human amylin. The disclosed amylin analog polypeptides have beneficial physicochemical properties relative to endogenous amylin, such as longer elimination half-lives ($t_{1/2}$) and improved solubility and thermal stability. This invention also relates to methods of using presently disclosed amylin analog polypeptides in a variety of therapeutic indications, as well as methods of producing the same. The disclosed amylin analog polypeptides are particularly useful in methods of treating metabolic diseases or disorders, such as types 1 and 2 diabetes, and providing weight loss.

35 Claims, 4 Drawing Sheets
Specification includes a Sequence Listing.

(56) References Cited

OTHER PUBLICATIONS

Symlin® highlights of prescribing information, 29 pages (Apr. 2016).
Adler et al., "Neuroprotective effects of the amylin analogue pramlintide on Alzheimer's disease pathogenesis and cognition", *Neurobiology of Aging* 35(4):793-801, doi: 10.1016/j.neurobiolaging.2013.10.076 (2014).
Alrefai et al., "Pramlintide: Clinical Strategies for Success", *Diabetes Spectrum* 23(2):124-130, doi.org/10.2337/diaspect.23.2.124 (Mar. 2010).
Amiel et al., "Defective Glucose Counterregulation After Strict Glycemic Control of Insulin-Dependent Diabetes Mellitus", *The New England Journal of Medicine* 316(22):1376-1383, doi: 10.1056/NEJM198705283162205 (May 1987).
Anderson et al., "Optimal management of type 2 diabetes in patients with increased risk of hypoglycemia", *Diabetes, Metabolic Syndrome and Obesity* 7:85-94, doi: 10.2147/DMSO.S48896 (2014).
Andreassen et al., "Prolonged Calcitonin Receptor Signaling by Salmon, but Not Human Calcitonin, Reveals Ligand Bias", *PLOS One* 9(3):e92042, doi.org/10.1371/journal.pone.0092042 (Mar. 2014).
Andreassen et al., "A novel oral dual amylin and calcitonin receptor agonist (KBP-042) exerts antiobesity and antidiabetic effects in rats", *Am J Physiol Endocrinol Metab* 307(1):E24-E33, doi: 10.1152/ajpendo.00121.2014 (2014).
Armour et al., "Pharmacological characterization of receptor-activity-modifying proteins (RAMPs) and the human calcitonin receptor", *Journal of Pharmacological Toxicological Methods* 42(4):217-224, doi: 10.1016/s1056-8719(00)00074-5 (Dec. 1999).
Aronne et al., "Progressive Reduction in Body Weight after Treatment with the Amylin Analog Pramlintide in Obese Subjects: A Phase 2, Randomized, Placebo-Controlled, Dose-Escalation Study", *J Clin Endocrinol Metab* 92:2977-2983 (2007).
Aronne et al., "Enhanced Weight Loss Following Coadministration of pramlintide With sibutramine or phentermine in a Multicenter trial", *Obesity* (Silver Spring) 18(9):1739-1746 (Sep. 2010).
Aviles-Olmos et al., "Exenatide and the treatment of patients with Parkinson's disease", *The Journal of Clinical Investigation* 123(6):2730-2736, doi: 10.1172/JCI68295 (Jun. 2013).
Bailey et al., "Pharmacological characterization of rat amylin receptors: implications for the identification of amylin receptor subtypes", *British Journal of Pharmacology* 166(1):151-167 (May 2012).
Baisley et al., "Antipsychotic-Like Actions of the Satiety Peptide, Amylin, in Ventral Striatal Regions Marked by Overlapping Calcitonin Receptor and RAMP-1 Gene Expression", *The Journal of Neuroscience* 34(12):4318-4325 (Mar. 19, 2014).
Bakhtiani et al., "A review of artificial pancreas technologies with an emphasis on bi-hormonal therapy", *Diabetes, Obesity and Metabolism* 15:1065-1070 (2013).
Bansal et al., "Insulin as a physiological modulator of glucagon secretion", *Am J Physiol Endocrinol Metab* 295:E751-E761, doi: 10.1152/ajpendo.90295.2008 (2008).
Beaumont et al., "Regulation of muscle glycogen metabolism by CGRP and amylin: CGRP receptors not involved", *British Journal of Pharmacology* 115(5):713-715, doi: 10.1111/j.1476-5381.1995.tb14991.x (Jul. 1995).
Bello et al., "Dose combinations of exendin-4 and salmon calcitonin produce additive and synergistic reductions in food intake in non-human primates", *Am J Physiol Regul Integr Comp Physiol* 299:R945-R952 (2010).
Bergenstal et al., "Lack of Glucagon Response to Hypoglycemia in Type I Diabetics After Long-Term Optimal Therapy with a Continuous Subcutaneous insulin infusion pump", *Diabetes* 32(5):398-402, doi.org/10.2337/diab.32.5.398 (May 1983).
Bettge et al., "Occurrence of nausea, vomiting and diarrhoea reported as adverse events in clinical trials studying glucagon-like peptide-1 receptor agonists: A systematic analysis of published clinical trials", *Diabetes Obes Metab* 19(3):336-347 (2017).
Bettge et al., "Occurrence of nausea, vomiting and diarrhoea reported as adverse events in clinical trials studying glucagon-like peptide-1 receptor agonists: A systematic analysis of published clinical trials—Supplemental Materials", *Diabetes Obes Metab* 19(3):336-347 (2017).
Bode et al., "Glycemic Characteristics in Continuously Monitored Patients With Type 1 and Type 2 Diabetes", *Diabetes Care* 28(10):2361-2366, doi: 10.2337/diacare.28.10.2361 (Oct. 2005).
Bolli et al., "Defective Glucose Counterregulation After Subcutaneous Insulin in Noninsulin-dependent Diabetes Mellitus; Paradoxical Suppression of Glucose Utilization and Lack of Compensatory Increase in Glucose Production, Roles of Insulin Resistance, Abnormal Neuroendocrine Responses, and Islet Paracrine Interactions", *J Clin Invest* 73(6):1532-1541, doi: 10.1172/JCI111359 (Jun. 1984).
Bolli et al., "Abnormal Glucose Counterregulation After Subcutaneous Insulin In Insulin-Dependent Diabetes Mellitus", *The New England Journal of Medicine* 310(26):1706-1711 (Jun. 1984).
Bolli et al. "Abnormal Glucose Counterregulation in Insulin-dependent Diabetes Mellitus", *Diabetes* 32:134-141 (1983).
Bolli et al., "A Reliable and Reproducible Test for Adequate Glucose Counterregulation in Type I Diabetes Mellitus", *Diabetes* 33(8):732-737, doi.org/10.2337/diab.33.8.732 (Aug. 1984).
Booe et al., "Structural Basis for Receptor Activity-Modifying Protein-Dependent Selective Peptide Recognition by a G Protein-Coupled Receptor", *Molecular Cell* 58:1040-1052 (Jun. 18, 2015).
Bower et al., "Amylin structure-function relationships and receptor pharmacology: implications for amylin mimetic drug development", *British Journal of Pharmacology* 173(12):1883-1898, doi: 10.1111/bph.13496 (May 18, 2016).
Boyle et al., "Brain Glucose Uptake and Unawareness of Hypoglycemia in Patients with Insulin-Dependent Diabetes Mellitus", *The New England Journal of Medicine* 333:1726-1732, doi:10.1056/NEJM199512283332602 (1995).
Boyle et al., "Amylin—Its role in the homeostatic and hedonic control of eating and recent developments of amylin analogs to treat obesity", *Molecular Metabolism* 8:203-210, doi: 10.1016/j.molmet.2017.11.009 (2018).
Brod et al., "The Impact of Non-Severe Hypoglycemic Events on Work Productivity and Diabetes Management", *Value in Health* 14(5):665-671, doi:10.1016/j.jval.2011.02.001 (2011).
Brown et al., "All-Cause Mortality in the Canterbury (New Zealand) Insulin-Treated Diabetic Registry Population", *Diabetes Care* 24(1):56-63, doi.org/10.2337/diacare.24.1.56 (Jan. 2001).
Chan et al., "It Takes Two to Tango: Combined Amylin/Leptin Agonism as a Potential Approach to Obesity Drug Development", *Journal of Investigative Medicine* 57(7):777-783, doi: 10.2310/JIM.0b013e3181b91911 (Oct. 2009).
Chapman et al., "Effect of pramlintide on satiety and food intake in obese subjects and subjects with type 2 diabetes", *Diabetologia* 48:838-848; doi: 10.1007/s00125-005-1732-4 (Apr. 2005).
Chase et al., "Pramlintide Lowered Glucose Excursions and Was Well-Tolerated in Adolescents with Type 1 Diabetes: Results from a Randomized, Single-Blind, Placebo-Controlled, Crossover Study", The Journal of Pediatrics 155(3):369-373, doi: 10.1016/j.jpeds.2009.03.012 (Sep. 2009).
Chaturvedula et al., "In vivo iontophoretic delivery and pharmacokinetics of salmon calcitonin", *International Journal of Pharmaceutics* 297(1-2):190-196, doi: 10.1016/j.ijpharm.2005.03.019 (2005).
Cheng et al., "Coffee Components Inhibit Amyloid Formation of Human Islet Amyloid Polypeptide in Vitro: Possible Link between Coffee Consumption and Diabetes Mellitus", *Journal of Agricultural and Food Chemistry* 59(24):13147-13155, doi.org/10.1021/jf201702h (2011).
Cheng et al., "Calcitonin Receptor Neurons in the Mouse Nucleus Tractus Solitarius Control Energy Balance via the Non-aversive Suppression of Feeding", *Cell Metabolism* 31:1-12.e1-e5 (2020).
Chiang et al., "Type 1 Diabetes Through the Life Span: A Position Statement of the American Diabetes Association", *Diabetes Care* 37:2034-2054, doi: 10.2337/dc14-1140 (2014).
Childs B., "Pramlintide Use in Type 1 Diabetes Resulting in Less Hypoglycemia", *Diabetes Spectrum* 19(1):50-52, doi.org/10.2337/diaspect.19.1.50 (2006).

(56) References Cited

OTHER PUBLICATIONS

Christopoulos et al., "Multiple Amylin Receptors Arise from Receptor Activity-Modifying Protein Interaction with the Calcitonin Receptor Gene Product", *Molecular Pharmacology* 56:235-242 (1999).

Clodi et al., "Distribution and kinetics of amylin in humans", *American Journal of Physiology* 274(5):E903-E908, doi: 10.1152/ajpendo.1998.274.5.E903 (May 1998).

Coester et al., "RAMP1 and RAMP3 differentially control amylin's effects on food intake, glucose and energy balance in male and female mice", *Neuroscience* 447:74-93, doi.org/10.1016/j.neuroscience.2019.11.036 (Nov. 2019).

Colburn et al., "Pharmacokinetics and Pharmacodynamics of AC137 (25,28,29 Tripro-Amylin, Human) After Intravenous Bolus and Infusion Doses in Patients with Insulin-Dependent Diabetes", *Journal of Clinical Pharmacology* 36(1):13-24, doi: 10.1002/j.1552-4604.1996.tb04147.x (Jan. 1996).

Cowie et al., "Disparities in incidence of diabetic end-stage renal disease according to race and type of diabetes", *The New England Journal of Medicine* 321(16):1074-1079 (Oct. 19, 1989).

Cryer P.E., "Hypoglycaemia: The limiting factor in the glycaemic management of Type I and Type II Diabetes", *Diabetologia* 45:937-948, doi: 10.1007/s00125-002-0822-9 (2002).

Cryer P.E., "Glycemic Goals in Diabetes: Trade-off Between Glycemic Control and Iatrogenic Hypoglycemia", *Diabetes* 63(7):2188-2195, doi.org/10.2337/db14-0059 (Jul. 2014).

Cummins et al., "Clinical effectiveness and cost-effectiveness of continuous subcutaneous insulin infusion for diabetes: systematic review and economic evaluation", *Health Technology Assessment* 14(11):iii-iv, xi-xvi, 1-181, doi: 10.3310/hta14110 (Feb. 2010).

Curkendall et al., "Incidence and Cost of Hypoglycemia Among Patients with Type 2 Diabetes in the United States: Analysis of a Health Insurance Database", *JCOM* 18(10):455-462 (Oct. 2011).

Dagogo-Jack et al., "Hypoglycemia-associated Autonomic Failure in Insulin-dependent Diabetes Mellitus", *J Clin Invest.* 91(3):819-828, doi: 10.1172/JCI116302 (Mar. 1993).

Dal Maso et al., "Extracellular loops 2 and 3 of the calcitonin receptor selectively modify agonist binding and efficacy", *Biochemical Pharmacology* 150:214-244 (2018).

Davis et al., "Hypoglycemia—The Major Barrier to Good Glycemic Control", *US Endocrinology* (1):2-9, doi.org/10.17925/USE.2006.00.1.2f (2006).

Deems et al., "Amylin Activates Glycogen Phosphorylase and Inactivates Glycogen Synthase via a CAMP-Independent Mechanism", *Biochemical and Biophysical Research Communications* 174(2):716-720, doi: 10.1016/0006-291x(91)91476-s (Jan. 31, 1991).

Defronzo et al., "Effects of Exenatide (Exendin-4) on Glycemic Control and Weight Over 30 Weeks in Metformin-Treated Patients With Type 2 Diabetes", *Diabetes Care* 28(5):1092-1100, doi: 10.2337/diacare.28.5.1092. (May 2005).

Devendra et al., "Type 1 diabetes: recent developments", *BMJ* 328(7442):750-754, doi: 10.1136/bmj.328.7442.750 (Mar. 27, 2004).

Edelman et al., "A Double-Blind, Placebo-Controlled Trial Assessing Pramlintide Treatment in the Setting of Intensive Insulin Therapy in Type 1 Diabetes", *Diabetes Care* 29(10):2189-2195, doi: 10.2337/dc06-0042 (Oct. 2006).

Edelman et al., "Pramlintide in the Treatment of Diabetes Mellitus", *Biodrugs* 22(6):375-386 (2008).

El-Khatib et al., "A Bihormonal Closed-Loop Artificial Pancreas for Type 1 Diabetes", *Science Translation Medicine* 2(27), 27ra27, doi: 10.1126/scitranslmed.3000619 (Apr. 2010).

El-Khatib et al., "Autonomous and Continuous Adaptation of a Bihormonal Bionic Pancreas in Adults and Adolescents With Type 1 Diabetes", *J Clin Endocrinol Metab* 99(5):1701-1711, doi: 10.1210/jc.2013-4151 (2014).

Engelgau et al., "The Evolving Diabetes Burden in the United States", *Annals of Internal Medicine* 140(11):945-950 (Jun. 2004).

Ettaro et al., "Cost-of-Illness Studies in Diabetes Mellitus", *Pharmacoeconomics* 22(3):149-164, doi: 10.2165/00019053-200422030-00002 (2004).

Fanelli et al., "Meticulous Prevention of Hypoglycemia Normalizes the Glycemic Thresholds and Magnitude of Most of Neuroendocrine Responses to, Symptoms of, and Cognitive Function During Hypoglycemia in intensively Treated Patients With Short-Term IDDM", *Diabetes* 42(11):1683-1689, doi: 10.2337/diab.42.11.1683 (Nov. 1993).

Fang et al., "Study Reanalysis Using a Mechanism-Based Pharmacokinetic/Pharmacodynamic Model of Pramlintide in Subjects with Type 1 Diabetes", *The AAPS Journal* 15(1):15-29, doi: 10.1208/s12248-012-9409-7 (Jan. 2013).

Farhy et al., "Pancreatic Network Control of Glucagon Secretion and Counterregulation", *Methods of Enzymology* 467:547-581, doi: 10.1016/S0076-6879(09)67021-X (2009).

Farhy et al., "Models of Glucagon Secretion, Their Application to the Analysis of the Defects in Glucagon Counterregulation and Potential Extension to Approximate Glucagon Action", *Journal of Diabetes Science and Technology* 4(6):1345-1356, doi: 10.1177/193229681000400608 (Nov. 2010).

Feigh et al., "A novel oral form of salmon calcitonin improves glucose homeostasis and reduces body weight in diet-induced obese rats", *Diabetes, Obesity and Metabolism* 13(10):911-920, doi: 10.1111/j.1463-1326.2011.01425.x (Oct. 2011).

Feigh et al., "Oral salmon calcitonin attenuates hyperglycemia and preserves pancreatic beta-cell area and function in Zucker diabetic fatty acids", *British Journal of Pharmacology* 167(1):151-163, doi: 10.1111/j.1476-5381.2012.01979.x (2012).

Feigh et al., "Oral Salmon Calcitonin Improves Fasting and Postprandial Glycemic Control in Lean Healthy Rats", *Horm Metab Res.* 44(2):130-134, doi: 10.1055/s-0031-1298027 (2012).

Feigh et al., "Oral salmon calcitonin enhances insulin action and glucose metabolism in diet-induced obese streptozotocin-diabetic rats", *European Journal of Pharmacology* 737:91-96, doi: 10.1016/j.ejphar.2014.05.016 (2014).

Fernandes-Santos et al., "Amylin Acts in the Central Nervous System to Increase Sympathetic Nerve Activity", *Endocrinology* 154(7):2481-2488, doi.org/10.1210/en.2012-2172 (2013).

Fidler et al., "Hypoglycemia: An overview of fear of hypoglycemia, quality-of-life, and impact on costs", *Journal of Medical Economics* 14(5):646-655, doi: 10.3111/13696998.2011.610852 (2011).

Fineman et al., "The Human Amylin Analog, Pramlintide, Corrects Postprandial Hyperglucagonemia in Patients With Type 1 Diabetes", *Metabolism* 51(5):636-641 (May 2002).

Flores et al., "Intestinal transport of 3-O-methyl-D-glucose in the normal and alloxan-diabetic rat", *The American Journal of Physiology* 214(4):725-729, doi: 10.1152/ajplegacy.168.214.4.725 (1968).

Fu et al., "Amylin receptor: a common pathophysiological target in Alzheimer's disease and diabetes mellitus", *Frontiers in Aging Neuroscience* 5:42, doi: 10.3389/fnagi.2013.00042 (2013).

Fukuda et al., "Electrophysiologically identified presynaptic mechanisms underlying amylinergic modulation of area postrema neuronal excitability in rat brain slices", *Brain Research* 1494:9-16, doi: 10.1016/j.brainres.2012.11.051 (2013).

Gedulin et al., "Dose-Response for Glucagonostatic Effect of Amylin in Rats", *Metabolism* 46(1):67-70 (1997).

Gedulin et al., "Hypoglycemia Overrides Amylin-Mediated Regulation of Gastric Emptying in Rats", *Diabetes* 47(1):93-97, doi: 10.2337/diab.47.1.93 (Jan. 1998).

Greenway et al., "Combination Drugs for Treating Obesity", *Curr Diab Rep* 10:108-115, doi: 10.1007/s11892-010-0096-4 (2010).

Gromada et al., "α-Cells of the Endocrine Pancreas: 35 Years of Research but the Enigma Remains", *Endocrine Reviews* 28(1):84-116, doi: 10.1210/er.2006-0007 (2007).

Guerreiro et al., "Preparation and Characterization of PEGylated Amylin", *AAPS PharmSciTech*, 14(3):1083-1097 (Sep. 2013).

Guidobono et al., "Amylin Given by Central and Peripheral Routes Inhibits Acid Gastric Secretion", *Peptides* 15(4):699-702 (1994).

Gydesen et al., "Optimization of tolerability and efficacy of the novel dual amylin and calcitonin receptor agonist KBP-089 through dose escalation and combination with a GLP-1 analog", *Am J Physiol Endocrinol Metab* 313:E598-E607 (2017).

Harris et al., "Prevalence of Adult-Onset IDDM in the U.S. Population", *Diabetes Care* 17(11):1337-1340, doi: 10.2337/diacare.17.11.1337 (Nov. 1994).

(56) References Cited

OTHER PUBLICATIONS

Hassan et al., "Reducing postprandial hyperglycemia with adjuvant premeal pramlintide and postmeal insulin in children with type 1 diabetes mellitus", *Pediatric Diabetes* 10:264-268, doi: 10.1111/j.1399-5448.2008.00490.x (2009).
Hauber et al., "Risking health to avoid injections; preferences of Canadians with type 2 diabetes", *Diabetes Care* 28(9):2243-2245, doi.org/10.2337/diacare.28.9.2243 (Sep. 2005).
Hay, "Amylin Receptor" Elsevier Inc. (2007) 14 pages.
Hay et al., "Amylin: Pharmacology, Physiology, and Clinical Potential", *Pharmacology Review* 67:564-600, doi: 10.1124/pr.115.010629 (Jul. 2015).
Hay et al., "Receptor-Activity Modifying Proteins (RAMPs): New Insights and Roles", *The Annual Review of Pharmacology and Toxicology* 56:469-487, doi: 10.1146/annurev-pharmtox-010715-103120 (2016).
Heptulla et al., "The Role of Amylin and Glucagon in the Dampening of Glycemic Excursions in Children With Type 1 Diabetes", *Diabetes* 54(4):1100-1107, doi: 10.2337/diabetes.54.4.1100 (Apr. 2005).
Heptulla et al., "Gastric emptying and postprandial glucose excursions in adolescents with type 1 diabetes", *Pediatric Diabetes* 9:561-566, doi: 10.1111/j.1399-5448.2008.00430.x (2008).
Heptulla et al., "Twenty-Four-Hour Simultaneous Subcutaneous Basal-Bolus Administration of Insulin and Amylin in Adolescents with Type 1 Diabetes Decreases Postprandial Hyperglycemia", *Journal of Clinical Endocrinology Metabolism* 94(5):1608-1611 (May 2009).
Heymsfield et al., "Recombinant Leptin for Weight Loss in Obese and Lean Adults; A Randomized, Controlled, Dose-Escalation Trial", *JAMA* 282(16):1568-1575 (Oct. 1999).
Hilton et al., "Identification of key components in the irreversibility of salmon calcitonin binding to calcitonin receptors", *Journal of Endocrinology* 166:213-226 (2000).
Hollander et al., "Pramlintide as an Adjunct to Insulin Therapy Improves Long-Term Glycemic and Weight Control in Patients with Type 2 Diabetes: A 1-year randomized controlled trial", *Diabetes Care* 26(3):784-790, doi: 10.2337/diacare.26.3.784 (Mar. 2003).
Hollander et al., "Effect of Pramlintide on Weight in Overweight and Obese Insulin-Treated Type 2 Diabetes Patients", *Obesity Research* 12(4):661-668 doi: 10.1038/oby.2004.76 (Apr. 2004).
Hoogwerf et al., "Pramlintide, the synthetic analogue of amylin: physiology, pathophysiology, and effects on glycemic control, body weight, and selected biomarkers of vascular risk", *Vascular Health and Risk Management* 4(2):355-362, doi: 10.2147/vhrm.s1978 (2008).
Hovorka et al., "Nonlinear model predictive control of glucose concentration in subjects with type 1 diabetes", *Physiological Measurement* 25:905-920, doi:10.1088/0967-3334/25/4/010 (2004).
Hovorka R., "Closed-loop insulin delivery: from bench to clinical practice", *Nature Reviews Endocrinology* 7:385-395 (2011).
Huffman et al., "Continuous Subcutaneous Pramlintide Infusion Therapy in Patients with Type 1 Diabetes: Observations from a Pilot Study", *Endocrine Practice* 15(7):689-695, doi: 10.4158/EP09044.ORR1 (Nov.-Dec. 2009).
International Search Report and Written Opinion for PCT International Patent Application No. PCT/US2019/055696, dated Jan. 20, 2020, 12 pages.
Israelian et al., "Increasing the Decrement in Insulin Secretion Improves Glucagon Responses to Hypoglycemia in Advanced Type 2 Diabetes", *Diabetes Care* 28(11):2691-2696 (Nov. 2005).
Johnson et al., "Increasing incidence of serious hypoglycemia in insulin users", *Journal of Clinical Epidemiology* 55:253-259 (2002).
Jönsson et al., "Cost of Hypoglycemia in Patients with Type 2 Diabetes in Sweden", *Value in Health* 9(3):193-198. doi: 10.1111/j.1524-4733.2006.00100.x (2006).
Kang et al., "Preparation, In Vitro Release, In Vivo Absorption and Biocompatibility Studies of Insulin-loaded Microspheres in Rabbits", *AAPS PharmSciTech* 6 (3) Article 61 (2005).
Karl et al., "Pramlintide as an Adjunct to Insulin in Patients with Type 2 Diabetes in a Clinical Practice Setting Reduced A1C, Postprandial Glucose Excursions, and Weight", *Diabetes Technology & Therapeutics* 9(2):191-199, doi: 10.1089/dia.2006.0013 (2007).
Karvonen et al., "Incidence of Childhood Type 1 Diabetes Worldwide", *Diabetes Care* 23(10):1516-1526. doi: 10.2337/diacare.23.10.1516 (Oct. 2000).
Kawamori et al., "Insulin Signaling in a Cells Modulates Glucagon Secretion In Vivo", *Cell Metabolism* 9, 350-361 (Apr. 8, 2009).
Kimura et al., "Beta Amyloid-Induced Depression of Hippocampal Long-Term Potentiation Is Mediated through the Amylin Receptor", *The Journal of Neuroscience* 32(48):17401-17406 doi:10.1523/JNEUROSCI.3028-12.2012 (Nov. 28, 2012).
King A.B., "Comparison of the Post-Meal Glucose Response to Different Insulin Bolus Waveforms in Insulin Pump- and Pre-Meal Pramlintide-Treated Type 1 Diabetes Patients", *Diabetes Technology & Therapeutics* 12(2):105-108. doi: 10.1089/dia.2009.0096 (Feb. 2010).
Kishiyama et al., "A Pilot Trial of Pramlintide Home Usage in Adolescents With Type 1 Diabetes", *Pediatrics* 124(5):1344-1347, doi: 10.1542/peds.2008-3750 (2009).
Kodl et al., "Practical Strategies to Normalize Hyperglycemia Without Undue Hypoglycemia in Type 2 Diabetes Mellitus", *Current Diabetes Report* 8(5):375-382, doi: 10.1007/s11892-008-0065-3 (Oct. 2008).
Kong et al., "Infusion of pramlintide, a human amylin analogue, delays gastric emptying in men with IDDM", *Diabetologia* 40(1):82-88, doi: 10.1007/s001250050646 (1997).
Kovatchev et al., "Algorithmic Evaluation of Metabolic Control and Risk of Severe Hypoglycemia in Type 1 and Type 2 Diabetes Using Self-Monitoring Blood Glucose Data", *Diabetes Technology & Therapeutics* 5(5):817-828. doi: 10.1089/152091503322527021 (2003).
Kovatchev et al., "Quantifying Temporal Glucose Variability in Diabetes via Continuous Glucose Monitoring: Mathematical Methods and Clinical Application", *Diabetes Technology & Therapeutics* 7(6):849-862, doi: 10.1089/dia.2005.7.849 (2005).
Kovatchev et al., "Pramlintide Reduces the Risks Associated with Glucose Variability in Type 1 Diabetes", *Diabetes Technology & Therapeutics* 10(5):391-396. doi: 10.1089/dia.2007.0295 (2008).
Kowalczyk et al., "Convergent chemoenzymatic synthesis of a library of glycosylated analogues of pramlintide: structure-activity relationships for amylin receptor agonism", *Organic & Biomolecular Chemistry* 12:8142-8151 (2014).
Kraenzlin et al., "Infusion of a novel peptide, calcitonin gene-related peptide (CGRP) in man. Pharmacokinetics and effects on gastric acid secretion and on gastrointestinal hormones", *Regulatory Peptides* 10:189-197 (1985).
Kreymann et al., "Glucagon-Like Peptide-1 7-36: A Physiological Incretin In Man", *The Lancet* 2(8571):1300-1304, doi: 10.1016/s0140-6736(87)91194-9 (1987).
Kuwasako et al., "β-arrestins negatively control human adrenomedullin type 1-receptor internalization", *Biochemical and Biophysical Research Communications* 487(2):438-443, doi: 10.1016/j.bbrc.2017.04.083 (2017).
Laporte et al., "Prevalence and Incidence of Insulin-Dependent Diabetes", *Diabetes In America*, Chapter 3, pp. 37-46.
Lebovitz H.E., "Adjunct therapy for type 1 diabetes mellitus", *Nature Reviews Endocrinology* 6:326-334, doi: 10.1038/nrendo.2010.49 (Jun. 2010).
Lebovitz H.E., "Pramlintide: profile of an amylin analog", *Expert Reviews Endocrinology Metabolism* 7(6):599-609 (2012).
Lee et al., "in vivo assessment of salmon calcitonin sustained release from biodegradable microspheres", *Journal of Controlled Release* 17(2):199-205, doi.org/10.1016/0168-3659(91)90059-M (1991).
Lee et al., "Oral delivery of salmon calcitonin", *Advanced Drug Delivery Reviews* 42:225-238 (2000).
Lee et al., "Efficacy and Harms of the Hypoglycemic Agent Pramlintide in Diabetes Mellitus", *Annals of Family Medicine* 8(6):542-549, doi: 10.1370/afm.1174 (Nov./Dec. 2010).
Lee et al., "How Type II Diabetes-Related Islet Amyloid Polypeptide Damages Lipid Bilayers", *Biophysical Journal* 102(5):1059-1068, doi: 10.1016/j.bpj.2012.01.039 (Mar. 2012).

(56) References Cited

OTHER PUBLICATIONS

Leese et al., "Frequency of Severe Hypoglycemia Requiring Emergency Treatment in Type 1 and Type 2 Diabetes; A population-based study of health service resource use", *Diabetes Care* 26(4):1176-1180 (Apr. 2003).
Leichter S.B., "The Business of Insulin: A Relationship Between Innovation and Economics", *Clinical Diabetes* 21(1):40-42, doi.org/10.2337/diaclin.21.1.40 (2003).
Levetan et al., "Impact of Pramlintide on Glucose Fluctuations and Postprandial Glucose, Glucagon, and Triglyceride Excursions Among Patients With Type 1 Diabetes Intensively Treated With Insulin Pumps", *Diabetes Care* 26(1):1-8, doi: 10.2337/diacare.26.1.1 (Jan. 2003).
Levy et al., "Novel Exenatide Analogs with Peptidic Albumin Binding Domains: Potent Anti-Diabetic Agents with Extended Duration of Action", *PLOS One* 9(2):e87704, doi: 10.1371/journal.pone.0087704 (Feb. 2014),.
Liese et al., "The Burden of Diabetes Mellitus Among US Youth: Prevalence Estimates From the Search for Diabetes in Youth Study", *Pediatrics* 118(4):1510-1518, doi: 10.1542/peds.2006-0690 (2006).
Lillioja et al., "In Vivo Insulin Action Is Familial Characteristic in Nondiabetic Pima Indians", *Diabetes* 36(11):1329-1335, doi: 10.2337/diab.36.11.1329, (Nov. 1987).
Ludvik et al., "Inverse relation between amylin and glucagon secretion in healthy and diabetic human subjects", *European Journal of Clinical Investigation* 33(4):316-322, doi: 10.1046/j.1365-2362.2003.01142.x (Apr. 2003).
Mack et al., "Pharmacological actions of the peptide hormone amylin in the long-term regulation of food intake, food preference, and body weight", *Am J Physiol Regul Integr Comp Physiol*, 293:R1855-R1863, doi: 10.1152/ajpregu.00297.2007 (2007).
Mack et al., "Davalintide (AC2307), a novel amylin-mimetic peptide: enhanced pharmacological properties over native amylin to reduce food intake and body weight", *International Journal of Obesity* 34, 385-395 (2010).
Mack et al., "Glucoregulatory effects and prolonged duration of action of davalintide: a novel amylinomimetic peptide", *Diabetes, Obesity and Metabolism* 13(12):1105-1113, (Dec. 2011).
Maggs et al., "Pramlintide reduces postprandial glucose excursions when added to insulin lispro in subjects with type 2 diabetes: a dose-timing study", *Diabetes/Metabolism Research and Reviews* 20:55-60, doi: 10.1002/dmrr.419 (2004).
Maianti et al., "Anti-diabetic activity of insulin-degrading enzyme inhibitors mediated by multiple hormones", *Nature* 511:94-98, doi: 10.1038/nature13297 (2014).
Makita et al., "Biased agonism: a novel paradigm in G protein-coupled receptor signaling observed in acquired hypocalciuric hypercalcemia", *Endocrine Journal* 61(4):303-309, doi: 10.1507/endocrj.ej13-0453 (2014).
Marks et al., "Gastric acid secretion in diabetes mellitus", *Annals of Internal Medicine*, 51(2):227-237 (Aug. 1959).
Marrero et al., "Effect of Adjunctive Pramlintide Treatment on Treatment Satisfaction in Patients With Type 1 Diabetes", *Diabetes Care* 30(2):210-216, doi.org/10.2337/dc06-1026 (Feb. 2007).
McCall et al., "A Novel Analytical Method for Assessing Glucose Variability: Using CGMS in Type 1 Diabetes Mellitus", *Diabetes Technology & Therapeutics* 8(6):644-653, doi: 10.1089/dia.2006.8.644 (2006).
McCrimmon et al., "Hypoglycemia in Type 1 Diabetes", *Diabetes* 59(10):2333-2339, doi.org/10.2337/db10-0103 (Oct. 2010).
Mehta N., "Clinical Development Case Study: Optimizing a Solid Dosage Formulation for the Oral Delivery of Peptides", TIDES, Boston (May 25, 2011).
Mehta et al., "Preclinical Studies with UGP281, a Potent, Orally Delivered, Anorexigenic Peptide", Unigene ADA Poster 2011.
Micheletto et al., "In Silico Design of Optimal Ratio for Co-Administration of Pramlintide and Insulin in Type 1 Diabetes", *Diabetes Technology & Therapeutics* 15(10):802-809, doi: 10.1089/dia.2013.0054 (2013).

Miller et al., "Current State of Type 1 Diabetes Treatment in the U.S.: Updated Data From the T1D Exchange Clinic Registry", *Diabetes Care* 38:971-978, doi: 10.2337/dc15-0078 (Jun. 2015).
Miyazaki et al., "Estimation of Bioavailability of Salmon Calcitonin from the Hypocalcemic Effects in Rats (I): Pharmacokinetic-Pharmacodynamic Modeling Based on the Endogenous Ca Regulatory System", *Drug Metabolism and Pharamcokinetics* 18(6):350-357 (2003).
Miyazaki et al., "Estimation of Bioavailability of Salmon Calcitonin from the Hypocalcemic Effect in Rats (II): Effect of Protease Inhibitor on the Pharmacokinetic-Pharmacodynamic Relationship after Intranasal Administration", *Drug Metabolism and Pharmacokinetics* 18(6):358-364, doi.org/10.2133/dmpk.18.358 (2003).
Morfis et al., "Receptor Activity-Modifying Proteins Differentially Modulate the G Protein-Coupling Efficiency of Amylin Receptors", *Endocrinology* 149(11):5423-5431, doi: 10.1210/en.2007-1735 (2008).
Nordfeldt et al., "Short-term effects of severe hypoglycaemia in children and adolescents with type 1 diabetes. A cost-of-illness study", *Acta Paediatrica* 90(2):137-42, doi: 10.1080/080352501300049244 (2001).
Notkins et al., "Autoimmune type 1 diabetes: resolved and unresolved issues", *Journal of Clinical Investigation* 108:1247-1252, doi: 10.1172/JCI200114257 (2001).
Nyholm et al., "The Amylin Analog Pramlintide Improves Glycemic Control and Reduces Postprandial Glucagon Concentrations in Patients With Type 1 Diabetes Mellitus", *Metabolism* 48(7):935-941 (Jul. 1999).
Onkamo et al., "Worldwide increase in incidence of Type I diabetes—the analysis of the data on published incidence trends", *Diabetologia*, 42:1395-1403 (1999).
Osuga et al., "Derivation of Functional Antagonists Using N-Terminal Extracellular Domain of Gonadotropin and Thyrotropin Receptors", *Molecular Endocrinology*, 11(11):1659-1668 (1997).
Overman et al., "Salmon Calcitonin Use and Associated Cancer Risk", *Annals of Pharmacotherapy* 47(12):1675-1684, doi: 10.1177/1060028013509233 (2013).
Palerm C.C., "Physiologic insulin delivery with insulin feedback: A control systems perspective", *Computer Methods and Programs in Biomedicine* 102(2):130-137, doi: 10.1016/j.cmpb.2010.06.007 (2011).
Palmer et al., "The Core Diabetes Model: Projecting Long-term Clinical Outcomes, Costs and Cost-effectiveness of Interventions in Diabetes Mellitus (Types 1 and 2) to Support Clinical and Reimbursement Decision-making", *Current Medical Research and Opinions* 20(Suppl 1):S5-S26, doi: 10.1185/030079904X1980 (Aug. 2004).
Pambianco et al., "The 30-Year Natural History of Type 1 Diabetes Complications; The Pittsburgh Epidemiology of Diabetes Complications Study Experience", *Diabetes* 55(5):1463-1469, doi: 10.2337/db05-1423 (May 2006).
Pawaskar et al., "Medication utilization patterns among type 2 diabetes patients initiating Exenatide BID or insulin glargine: a retrospective database study", *BMC Endocrine Disorders* 13:20 (2013).
Pencek et al., "Safety of pramlintide added to mealtime insulin in patients with type 1 or type 2 diabetes: a large observational study", *Diabetes, Obesity and Metabolism* 12(6):548-551 (2010).
Peyser et al., "The artificial pancreas: current status and future prospects in the management of diabetes", *Annals of the New York Academy of Sciences* 1311:102-123, doi: 10.1111/nyas.12431 (2014).
Pickup et al., "Severe hypoglycaemia and glycaemic control in Type 1 diabetes: meta-analysis of multiple daily insulin injections compared with continuous subcutaneous insulin infusion", *Diabetic Medicine* 25(7):765-774, doi: 10.1111/j.1464-5491.2008.02486.x (2008).
Pittner et al., "Molecular Physiology of Amylin", *Journal of Cellular Biochemistry* 55S:19-28 (1994).
Portuese et al., "Mortality in Insulin-Dependent Diabetes", *Diabetes In America*, Chapter 10 (2013).
Potes et al., "Brainstem mechanisms of amylin-induced anorexia", *Physiology & Behavior* 100:511-518 (2010).
Potter et al., "Islet amyloid deposition limits the viability of human islet grafts but not porcine islet grafts", *PNAS* 107(9):4305-4310, doi.org/10.1073/pnas.0909024107 (Mar. 2, 2010).

(56) References Cited

OTHER PUBLICATIONS

Pullman et al., "Pramlintide in the management of insulin-using patients with type 2 and type 1 diabetes", *Vascular Health and Risk Management* 2(3):203-212 (2006).
Purnell et al., "Patient Preferences for Noninsulin Diabetes Medications: A Systematic Review", *Diabetes Care* 37:2055-2062, doi: 10.2337/dc13-2527 (Jul. 2014).
Raman et al., "The Role of Adjunctive Exenatide Therapy in Pediatric Type 1 Diabetes", *Diabetes Care* 33(6):1294-1296 (Jun. 2010).
Ramkissoon et al., "A Model of Glucose-Insulin-Pramlintide Pharmacokinetics and Pharmacodynamics in Type I Diabetes", *Journal of Diabetes Science and Technology* 8(3):529-542, doi: 10.1177/1932296813517323 (May 2014).
Ratner et al., "Adjunctive Therapy with Pramlintide Lowers HbA1c without Concomitant Weight Gain and Increased Risk of Severe Hypoglycemia in Patients with Type 1 Diabetes Approaching Glycemic Targets", *Exp Clin Endocrinol Diabetes* 113(4):199-204 (Apr. 2005).
Ravussin et al., "Enhanced Weight Loss With Pramlintide/ Metreleptin: An Integrated Neurohormonal Approach to Obesity Pharmacotherapy", *Obesity* (Silver Spring) 17(9):1736-1743, doi:10. 1038/oby.2009.184 (Sep. 2009).
Rhoads et al., "Contribution of Hypoglycemia to Medical Care Expenditures and Short-Term Disability in Employees With Diabetes", *J Occupational and Environmental Medicine* 47(5):447-452, doi: 10.1097/01.jom.0000161727.03431.3e (May 2005).
Riddle et al., "Pramlintide Improved Glycemic Control and Reduced Weight in Patients With Type 2 Diabetes Using Basal Insulin", *Diabetes Care* 30(11):2794-2799, (Nov. 2007).
Riddle et al., "Control of Postprandial Hyperglycemia in Type 1 Diabetes by 24-Hour Fixed-Dose Coadministration of Pramlintide and Regular Human Insulin: A Randomized, Two-Way Crossover Study", *Diabetes Care* 41(11):2346-2352, doi: 10.2337/dc18-1091 (2018).
Riediger et al., "Actions of amylin on subfornical organ neurons and on drinking behavior in rats", *The American Journal of Physiology (Regulatory Integrative Comp. Physiol.* 276:R514-R521, doi: 10.1152/ ajpregu.1999.276.2.R514 (Feb. 1999).
Roberson S.W., "The Islet Amyloid Polypeptide hormone Amylin: Its function, effects and uses in medicine", Loyola Marymount University (Nov. 5, 2012).
Rodriguez et al., "The Role of Prandial Pramlintide in the Treatment of Adolescents With Type 1 Diabetes", *Pediatric Research* 62(6):746- 749, doi: 10.1203/PDR.0b013e318159af8c (2007).
Rosenstock et al., "Effects of Exenatide and Lifestyle Modification on Body Weight and Glucose Tolerance in Obese Subjects With and Without Pre-Diabetes", *Diabetes Care* 33(6):1173-1175, doi: 10.2337/ dc09-1203 (Jun. 2010).
Roth et al., "Antiobesity Effects of the β-Cell Hormone Amylin in Diet-Induced Obese Rats: Effects on Food Intake, Body Weight, Composition, Energy Expenditure, and Gene Expression", *Endocrinology* 147(12):5855-5864 (Dec. 2006).
Roth et al., "Leptin responsiveness restored by amylin agonism in diet-induced obesity: Evidence from nonclinical and clinical studies", *PNAS USA* 105(20):7257-7262, doi: 10.1073/pnas. 0706473105 (May 20, 2008).
Roth et al., "Antiobesity effects of the β-cell hormone amylin in combination with phentermine or sibutramine in diet-induced obese rats", *International Journal of Obesity* 32(8):1201-1210, doi: 10.1038/ ijo.2008.91 (Jun. 17, 2008).
Roth et al., "'Weighing in' on synergy: Preclinical research on neurohormonal anti-obesity combinations", *Brain Research* 1350:86- 94, doi: 10.1016/j.brainres.2010.01.027 (2010).
Roth et al., "GLP-1R and amylin agonism in metabolic disease: complementary mechanisms and future opportunities", *British Journal of Pharmacology* 166:121-136 (2012).
Roth J.D., "Amylin and the regulation of appetite and adiposity: recent advances in receptor signaling, neurobiology and pharmacology", *Current Opinion Endocrinology Diabetes Obes.* 20(1):8- 13, doi: 10.1097/MED.0b013e32835b896f (Feb. 2013).
Routledge et al., "The effects of RAMPs upon cell signalling", *Molecular and Cellular Endocrinology* 449:12-20, doi: 10.1016/j. mce.2017.03.033 (2017).
Ruiz et al., "Effect of Insulin Feedback on Closed-Loop Glucose Control: A Crossover Study", *Journal of Diabetes Science and Technology* 6(5):1123-1130, doi: 10.1177/193229681200600517 (Sep. 2012).
Russell et al., "Blood Glucose Control in Type 1 Diabetes With a Bihormonal Bionic Endocrine Pancreas", *Diabetes Care* 35(11):2148- 2155, doi: 10.2337/dc12-0071 (2012).
Russell-Jones et al., "Efficacy and Safety of Exenatide Once Weekly Versus Metformin, Pioglitazone, and Sitagliptin Used as Monotherapy in Drug-Naive Patients With Type 2 Diabetes (Duration-4)", *Diabetes Care* 35:252-258, doi: 10.2337/dc11-1107 (Feb. 2012).
Ryan et al., "Review of pramlintide as adjunctive therapy in treatment of type 1 and type 2 diabetes", *Drug, Design, Development and Therapy* 2:203-214, doi: 10.2147/dddt.s3225 (2008).
Schmitz et al., "Effects of Amylin and the Amylin Agonist Pramlintide on Glucose Metabolism", *Diabetic Medicine* 14(Suppl 2):S19-S23, doi: 10.1002/(sici) 1096-9136(199706)14:2+<s19::aid-dia400>3.3. co;2-w (Jun. 1997).
Schorr et al., "Simultaneous Use of Two External Subcutaneous Pumps Delivering Insulin and SYMLIN: Use of a Double-Pump System", *J Diabetes Sci Technology Letter to the Editor* 6(6):1507- 1508, doi: 10.1177/193229681200600633 (Nov. 2012).
Schvarcz et al., "Physiological Hyperglycemia Slows Gastric Emptying in Normal Subjects and Patients With Insulin-Dependent Diabetes Mellitus", *Gastroenterology* 113(1):60-66, doi: 10.1016/ s0016-5085(97)70080-5 (Jul. 1997).
Schwartz et al., "Glycemic Control and Weight Reduction Without Causing Hypoglycemia: The Case for Continued Safe Aggressive Care of Patients With Type 2 Diabetes Mellitus and Avoidance of Therapeutic Inertia", *Mayo Clin Proc.*; 85(12)(suppl):S15-S26 (2010).
Seth et al., "Combined amylin-leptin treatment lowers blood pressure and adiposity in lean and obese rats", *International Journal of Obesity (Lond.)* 35(9):1183-1192, doi: 10.1038/ijo.2010.262 (2011).
Sexton et al., "Modulating receptor function through RAMPs: can they represent drug targets in themselves?", *Drug Discovery Today*, 14(7/8):413-419 (Apr. 2009).
Shaw et al., "Global estimates of the prevalence of diabetes for 2010 and 2030", *Diabetes Research and Clinical Practice* 87:4-14, doi: 10.1016/j.diabres.2009.10.007 (2010).
Sherr et al., "Reduced Hypoglycemia and Increased Time in Target Using Closed-Loop Insulin Delivery During Nights With or Without Antecedent Afternoon Exercise in Type 1 Diabetes", *Diabetes Care* 36:2909-2914 (Oct. 2013).
Sherr et al., "Evolution of Abnormal Plasma Glucagon Responses to Mixed-Meal Feedings in Youth With Type 1 Diabetes During the First 2 Years After Diagnosis", *Diabetes Care* 37(6):1741-1744, doi.org/10.2337/dc13-2612 (Jun. 2014).
Sherr et al., "Evolution of Abnormal Plasma Glucagon Responses to Mixed-Meal Feedings in Youth With Type 1 Diabetes During the First 2 Years After Diagnosis—Supplemental Data", *Diabetes Care* 37(6):1741-1744. doi.org/10.2337/dc13-2612 (Jun. 2014).
Silverstein et al., "Care of Children and Adolescents With Type 1 Diabetes—A statement of the American Diabetes Association", *Diabetes Care* 28(1):186-212, doi.org/10.2337/diacare.28.1.186 (Jan. 2005).
Silvestre et al., "Influence of glucose concentration on the inhibitory effect of amylin on insulin secretion. Study in the perfused rat pancreas", *Regulatory Peptides* 68:31-35, doi: 10.1016/s0167- 0115(96)00139-5 (1997).
Silvestre et al., "Selective amylin inhibition of the glucagon response to arginine is extrinsic to the pancreas", *American Journal of Physiological Endocrinology Metabolism* 280:E443-E449 (2001).
Smith et al., "Pramlintide treatment reduces 24-h caloric intake and meal sizes and improves control of eating in obese subjects: a 6-wk translational research study", *American Journal of Physiological Endocrinology Metabolism* 293:E620-E627, doi:10.1152/ajpendo. 00217.2007 (2007).
Smith et al., "Sustained Weight Loss Following 12-Month Pramlintide Treatment as an Adjunct to Lifestyle Intervention in Obesity", *Diabetes Care* 31(9):1816-1823, doi: 10.2337/dc08-0029 (Sep. 2008).

(56) References Cited

OTHER PUBLICATIONS

Smith et al., "Sustained Weight Loss Following 12-Month Pramlintide Treatment as an Adjunct to Lifestyle Intervention in Obesity—Supplemental Information", *Diabetes Care* 31(9):1816-1823, doi: 10.2337/dc08-0029 (Sep. 2008).

Soedamah-Muthu et al., "Predicting major outcomes in type 1 diabetes: a model development and validation study", *Diabetologia* 57(11):2304-2314, doi: 10.1007/s00125-014-3358-x (Sep. 4, 2014).

Steil et al., "Modeling β-Cell Insulin Secretion—Implications for Closed-Loop Glucose Homeostasis", *Diabetes Technology & Therapeutics* 5(6):953-964, doi: 10.1089/152091503322640999 (2003).

Steil et al., "The Effect of Insulin Feedback on Closed Loop Glucose Control", *Journal of Clinical Endocrinology Metabolism* 96(5):1402-1408, doi: 10.1210/jc.2010-2578 (Mar. 2, 2011).

Sun et al., "Bifunctional PEGylated Exenatide-Amylinomimetic Hybrids to Treat Metabolic Disorders: An Example of Long-Acting Dual Hormonal Therapeutics", *Journal of Medicinal Chemistry* 56(22):9328-9341, doi.org/10.1021/jm401418s (2013).

Sun et al., "Calcitonin Nasal Spray and Increased Cancer Risk: A Population-Based Nested Case-Control Study", *The Journal of Clinical Endocrinology & Metabolism* 99(11):4259-4264 (Nov. 2014).

Taborsky, Jr. et al., "Autonomic Mediation of Glucagon Secretion During Hypoglycemia—Implications for Impaired α-Cell Responses in Type 1 Diabetes", *Diabetes* 47:995-1005 (Jul. 1998).

Thompson et al., "Pramlintide: A Human Amylin Analogue Reduced Postprandial Plasma Glucose, Insulin, and C-peptide Concentrations in Patients with Type 2 Diabetes", *Diabetic Medicine* 14(7):547-555, doi: 10.1002/(SICI)1096-9136(199707)14:7<547:AID-DIA390>3.0.CO;2-U (1997).

Thorogood et al., "The Effects of Pancreatectomy on Glycosuria and Ketosis in Dogs made Diabetic by Alloxan", *Endocrinology* 37(3):191-200 (1945).

Trevaskis et al., "Amylin-Mediated Restoration of Leptin Responsiveness in Diet-Induced Obesity: Magnitude and Mechanisms", *Endocrinology* 149(11):5679-5687 doi: 10.1210/en.2008-0770 (2008).

Trevaskis et al., "Interaction of Leptin and Amylin in the Long-term Maintenance of Weight Loss in Diet-induced Obese Rats", *Obesity* (Silver Spring) 18(1):21-26, doi: 10.1038/oby.2009.187 (Jan. 2010).

Trevaskis et al., "Insights into amylin-leptin synergy", *Trends in Endocrinology and Metabolism* 21(8):473-479, doi: 10.1016/j.tem.2010.03.006 (2010).

Trevaskis et al., "Improved Glucose Control and Reduced Body Weight in Rodents with Dual Mechanism of Action Peptide Hybrids", *PLOS One* 8(10):e78154 (Oct. 2013).

Tucker M.E., "Liraglutide Benefits Patients With Type 1 Diabetes", *Medscape* (May 27, 2014).

Uhing et al., "Active Transport of 3-O-Methyl-Glucose by the Small Intestine in Chronically Catheterized Rats", *The Journal of Clinical Investigation* 95(6):2799-2805, doi: 10.1172/JCI117984 (Jun. 1995).

Unger et al., "Recognition, Prevention, and Proactive Management of Hypoglycemia in Patients with Type I Diabetes Mellitus", *Postgraduate Medicine* 123(4):71-80, doi: 10.3810/pgm.2011.07.2306 (Jul. 2011).

Unger et al., "Glucagonocentric restructuring of diabetes: a pathophysiologic and therapeutic makeover", *The Journal of Clinical Investigation* 122(1):4-12, doi: 10.1172/JCI60016 (Jan. 2012).

Van Witteloostujin et al., "Neoglycolipids for Prolonging the Effects of Peptides: Self-Assembling Glucagon-like Peptide 1 Analogues with Albumin Binding Properties and Potent in Vivo Efficacy", *Molecular Pharmaceutics* 14:193-205 (2017).

Van Witteloostujin et al., "Neoglycolipids for Prolonging the Effects of Peptides: Self-Assembling Glucagon-like Peptide 1 Analogues with Albumin Binding Properties and Potent in Vivo Efficacy—Supplemental Data", *Molecular Pharmaceutics* 14:193-205 (2017).

Vine et al., "Comparison of the in vitro and in vivo pharmacology of adrenomedullin, calcitonin gene-related peptide and amylin in rats", *European Journal of Pharmacology* 314(1-2):115-121, doi: 10.1016/s0014-2999(96)00544 (1996).

Vine et al., "Effects of Rat Amylin on Renal Function in the Rat", *Horm Metab Res* 30:518-522 (1998).

Wagner J.G., "Pharmacokinetic Absorption Plots from Oral Data Alone or Oral/Intravenous Data and An Exact Loo-Riegelman Equation", *Journal of Pharmaceutical Sciences* 72(7):838-842 (Jul. 1983).

Walker et al., "Mice Lacking the Neuropeptide α-Calcitonin Gene-Related Peptide Are Protected Against Diet-Induced Obesity", *Endocrinology* 151(9):4257-4269, doi: 10.1210/en.2010-0284 (Sep. 2010).

Walker T.C., "Use of continuous glucose monitoring to introduce adjunctive pramlintide therapy in a patient with type 1 diabetes: A case study", *Journal of the American Academy of Nurse Practitioners* 23:521-524 (2011).

Watson et al., "The Use of Stimulus-Biased Assay Systems to Detect Agonist-Specific Receptor Active States: Implications for the Trafficking of Receptor Stimulus by Agonists", *Molecular Pharmacology* 58(6):1230-1238, doi: 10.1124/mol.58.6.1230 (2000).

Weinzimer et al., "Fully Automated Closed-Loop Insulin Delivery Versus Semiautomated Hybrid Control in Pediatric Patients with Type 1 Diabetes Using an Artificial Pancreas", *Diabetes Care* 31(5):934-939, doi: 10.2337/dc07-1967 (May 2008).

Weinzimer et al., "Effect of Pramlintide on Prandial Glycemic Excursions During Closed-Loop Control in Adolescents and Young Adults With Type 1 Diabetes", *Diabetes Care* 35:1994-1999 (Oct. 2012).

Werle et al., "Strategies to improve plasma half life time of peptide and protein drugs", *Amino Acids* 30:351-367, doi: 10.1007/s00726-005-0289-3 (2006).

Weyer et al., "Amylin Replacement With Pramlintide as an Adjunct to Insulin Therapy in Type 1 and Type 2 Diabetes Mellitus: A Physiological Approach Toward Improved Metabolic Control", *Current Pharmaceutical Design* 7:1353-1373 (2001).

Weyer et al., "Properties of pramlintide and insulin upon mixing", *Am J Health Syst Pharm* 62(8):816-822, doi: 10.1093/ajhp/62.8.816 (Apr. 15, 2005).

Whitehouse et al., "A Randomized Study and Open-Label Extension Evaluating the Long-Term Efficacy of Pramlintide as an Adjunct to Insulin Therapy in Type 1 Diabetes", *Diabetes Care* 25(4):724-730, doi: 10.2337/diacare.25.4.724 (Apr. 2002).

Wild et al., "Global Prevalence of Diabetes—Estimates for the year 2000 and projections for 2030", *Diabetes Care* 27(5):1047-1053, doi: 10.2337/diacare.27.5.1047 (May 2004).

Wilinska et al., "Insulin Kinetics in Type-1 Diabetes: Continuous and Bolus Delivery of Rapid Acting Insulin", *IEEE Transactions on Biomedical Engineering* 52(1):3-12, doi: 10.1109/TBME.2004.839639 (Jan. 2005).

Withycombe S.E., "A 4-month Randomized Controlled Clinical Trial of Adjuvant Exenatide or Pramlintide Versus Insulin Alone in Pediatric Type 1 Diabetes Mellitus: Effect on Glycemic Control", The University of Texas Medical Branch Thesis (Aug. 2010).

Wood et al., "Incretins and amylin in pediatric diabetes: new tools for management of diabetes in youth", *Current Opinion Pediatrics* 25(4):502-508, doi:10.1097/MOP.0b013e328362fdfb (Aug. 2013).

Woods et al., "Pancreatic signals controlling food intake; insulin, glucagon and amylin", *Philosophical Transactions of The Royal Society B*, 361:1219-1235, doi:10.1098/rstb.2006.1858 (2006).

Woolley et al., "Receptor activity-modifying protein dependent and independent activation mechanisms in the coupling of calcitonin gene-related peptide and adrenomedullin receptors to Gs", *Biochemical Pharmacology* 142:96-110, doi: 10.1016/j.bcp.2017.07.005 (Jul. 2017).

Xu et al., "Prevalence of diagnosed type 1 and type 2 diabetes among US adults in 2016 and 2017: population based study", *BMJ* 3621k1497, doi: 10.1136/bmj.k1497 (2018).

Yki-Jarvinen et al., "Regulation of Glycogen Synthase and Phosphorylase Activities by Glucose and Insulin in Human Skeletal Muscle", *The Journal of Clinical Investigation* 80:95-100, doi: 10.1172/JCI113069 (Jul. 1987).

Young et al., "Insulin response of components of whole-body and muscle carbohydrate metabolism in humans", *The American Journal of Physiology* 254:E231-E236, doi: 10.1152/ajpendo.1988.254.2.E231 (1988).

(56) References Cited

OTHER PUBLICATIONS

Young et al., "Muscle Glycogen Synthesis and Disposition of Infused Glucose in Humans With Reduced Rates of Insulin-Mediated Carbohydrate Storage", *Diabetes* 37(3):303-308, doi: 10.2337/diab.37.3.303 (Mar. 1988).

Young et al., "Amylin activates glycogen phosphorylase in the isolated soleus muscle of the rat", *FEBS Letters* 281(1,2):149-151, doi: 10.1016/0014-5793(91)80380-I (Apr. 1991).

Young et al., "Amylin and insulin in rat soleus muscle: dose responses for cosecreted noncompetitive antagonists", *The American Journal of Physiology* 263:E274-E281, doi: 10.1152/ajpendo.1992.263.2.E274 (1992).

Young et al., "Dose Response Characteristics for the Hyperglycemic, Hyperlactemic, Hypotensive and Hypocalcemic Actions of Amylin and Calcitonin Gene-Related Peptide-I (CGRPα) in the Fasted, Anaesthetized Rat", *Life Sciences* 52(21):1717-1726 (1993).

Young et al., "Amylin and Syndrome-X", *Drug Development Research* 32:90-99 (1994).

Young et al., "Amylin regulation of carbohydrate metabolism", *Biochem Soc Trans.* 23(2):325-331, doi: 10.1042/bst0230325 (May 1995).

Young et al., "Gastric emptying is accelerated in diabetic BB rats and is slowed by subcutaneous injections of amylin", *Diabetologia* 38:642-648 (1995).

Young et al., "Diabetogenic Effects of Salmon Calcitonin Are Attributable to Amylin-Like Activity", *Metabolism* 44(12):1581-1589 (Dec. 1995).

Young et al., "Dose-Responses for the Slowing of Gastric Emptying in a Rodent Model by Glucagon-Like Peptide (7-36)NH$_2$, Amylin, Cholecystokinin, and Other Possible Regulators of Nutrient Uptake", *Metabolism* 45(1):1-3 (Jan. 1996).

Young et al., "Preclinical Pharmacology of Pramlintide in the Rat: Comparisons With Human and Rat Amylin", *Drug Development Research* 37:231-248 (1996).

Young et al., "Dose-response for inhibition by amylin of cholecystokinin-stimulated secretion of amylase and lipase in rats", *Regulatory Peptides* 130:19-26 (2005).

Young A.A., "Brainstem sensing of meal-related signals in energy homeostasis", *Neuropharmacology* 63:31-45, doi: 10.1016/j.neuropharm.2012.03.019 (2012).

Younk et al., "Pramlintide and the treatment of diabetes: a review of the data since its introduction", *Expert Opinion Pharmacother* 12(9):1439-1451, doi: 10.1517/14656566.2011.581663 (2011).

Zelissen et al., "Effect of three treatment schedules of recombinant methionyl human leptin on body weight in obese adults: a randomized, placebo-controlled trial", *Diabetes, Obesity and Metabolism* 7(6):755-761, doi: 10.1111/j.1463-1326.2005.00468.x (2005).

Zhang et al., "The Burden of Hypoglycemia in Type 2 diabetes: A Systematic Review of Patient and Economic Perspectives", *JCOM*, 17(12):547-557 (Dec. 2010).

Zhang et al., "Porcine islet amyloid polypeptide fragments are refractory to amyloid formation", *FEBS Letters* 585:71-77, doi: 10.1016/j.febslet.2010.11.050 (2011).

Zhou et al., "Understanding the GPCR biased signaling through G protein and arrestin complex structures", *Current Opinion in Structural Biology* 45:150-159 (2017).

\* cited by examiner

FIG 1

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | |
|---|---|---|---|---|---|---|---|---|---|---|---|---|---|---|---|---|---|---|---|---|---|---|---|---|---|---|---|---|---|---|---|---|---|---|---|---|---|---|
| Human-amylin | K | C* | N | T | A | T | C* | A | T | Q | R | L | A | N | F | L | V | H | S | S | N | N | F | G | A | I | L | S | S | T | N | V | G | S | N | T | Y | NH2 |
| Rat-amylin | K | C* | N | T | A | T | C* | A | T | Q | R | L | A | N | F | L | V | R | S | S | N | N | L | G | P | V | L | P | P | T | N | V | G | S | N | T | Y | NH2 |
| Pramlintide | K | C* | N | T | A | T | C* | A | T | Q | R | L | A | N | F | L | V | H | S | S | N | N | F | G | P | I | L | P | P | T | N | V | G | S | N | T | Y | NH2 |
| Davalintide | K | C* | N | T | A | T | C* | V | L | G | R | L | S | Q | E | L | H | R | | | | | Y | | Q | T | Y | P | R | T | N | T | G | S | N | T | Y | NH2 |
| Human calcitonin | | C* | G | N | L | S | C* | M | L | G | T | Y | T | Q | D | F | N | K | | | | | F | | H | T | F | P | Q | T | A | I | G | V | G | A | P | NH2 |
| Salmon calcitonin | | C* | S | L | S | T | C* | V | L | G | K | L | S | Q | E | L | H | K | | | | | L | | Q | T | Y | P | R | T | N | T | G | S | G | T | P | NH2 |
| β-CGRP | A | C* | N | T | A | T | C* | V | T | H | R | L | A | G | L | L | S | R | S | G | G | M | V | K | S | N | F | V | P | T | N | V | G | S | K | A | F | NH2 |

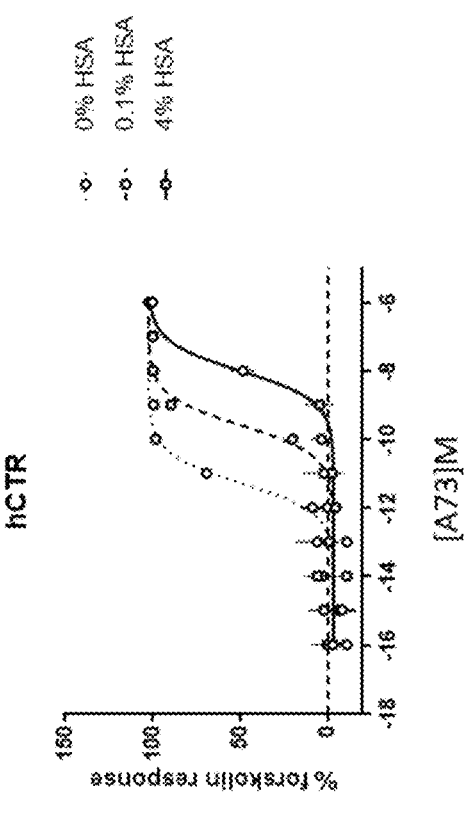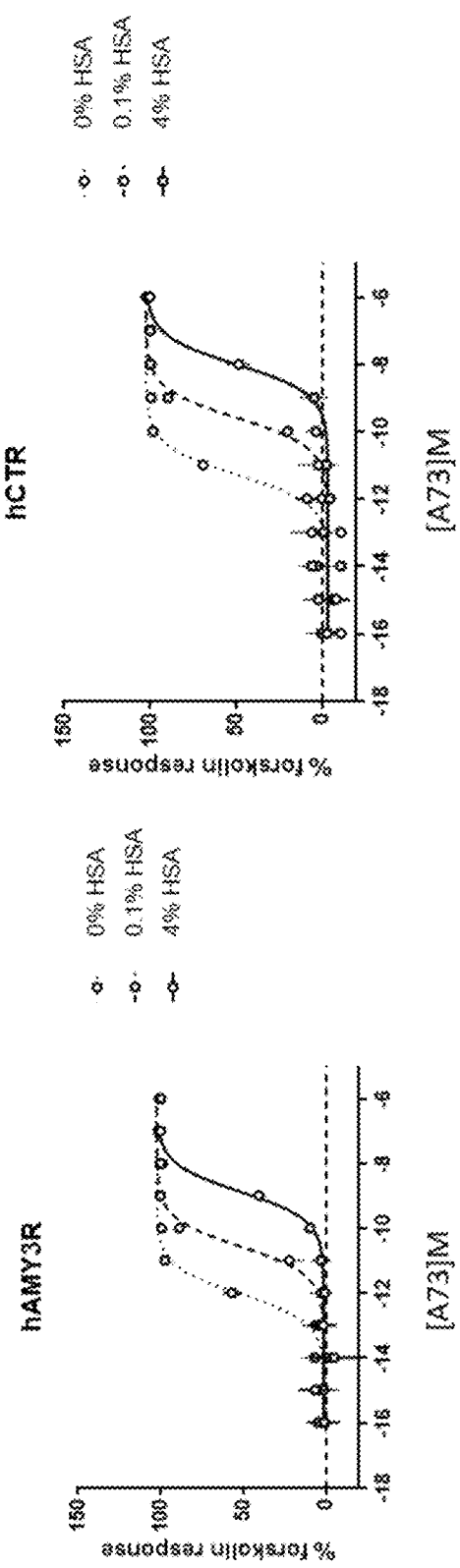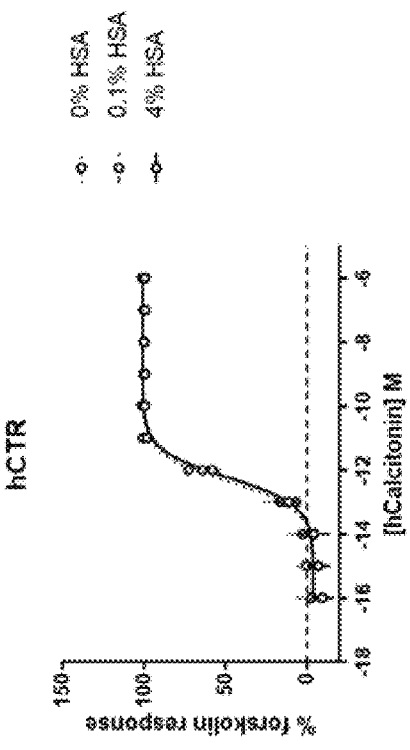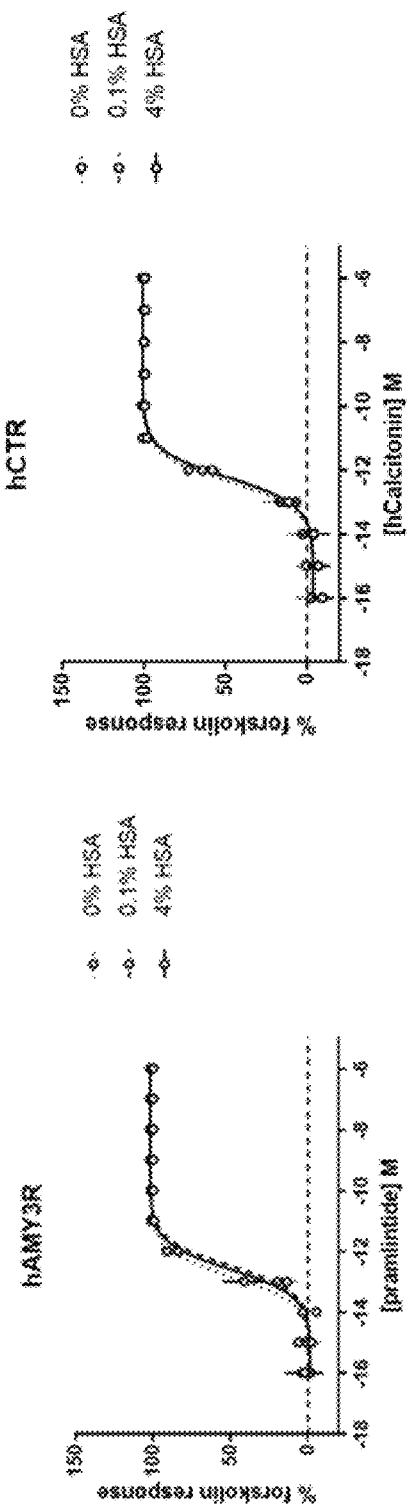

SEQUENCE LISTING

```
<160> NUMBER OF SEQ ID NOS: 318

<210> SEQ ID NO 1
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

His Cys Asn Thr Ser Thr Cys Ala Thr Gln Arg Leu Ala Asn Phe Leu
1               5                   10                  15

Val Lys Ser Ser Asn Glu Phe Gly Pro Ile Leu Pro Pro Thr Lys Val
            20                  25                  30

Gly Ser Glu Thr Tyr
        35

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2
```

```
Ile Cys Asn Thr Ser Thr Cys Ala Thr Gln Arg Leu Ala Asn Phe Leu
1               5                   10                  15

Val Lys Ser Ser Asn Glu Phe Gly Pro Ile Leu Pro Pro Thr Lys Val
                20                  25                  30

Gly Ser Glu Thr Tyr
            35
```

<210> SEQ ID NO 3
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Lys(CO(CH2)4CO2H)

<400> SEQUENCE: 3

```
Ser Cys Asn Thr Ser Thr Cys Ala Thr Gln Arg Leu Ala Asn Lys Leu
1               5                   10                  15

His Lys Ser Ser Asn Asn Phe Gly Pro Ile Leu Pro Pro Thr Lys Val
                20                  25                  30

Gly Ser Glu Thr Tyr
            35
```

<210> SEQ ID NO 4
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Ser Cys Asn Thr Ser Thr Cys Ala Thr Gln Arg Leu Ser Asn Phe Leu
1               5                   10                  15

Val Lys Ser Ser Asn Glu Phe Gly Pro Ile Leu Pro Pro Thr Lys Val
                20                  25                  30

Gly Ser Glu Thr Tyr
            35
```

<210> SEQ ID NO 5
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys(gammaGlu-dpeg-dpeg-(gammaGlu)4-CO(CH2)
      14CH3)

<400> SEQUENCE: 5

```
Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
                20                  25                  30

Gly Ser Glu Thr Tyr
            35
```

```
<210> SEQ ID NO 6
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Leu

<400> SEQUENCE: 6

Ser Cys Asn Thr Ser Thr Cys Ala Thr Gln Arg Leu Ala Asn Phe Leu
1               5                   10                  15

Val Lys Ser Ser Asn Glu Phe Gly Pro Ile Leu Pro Pro Thr Lys Val
            20                  25                  30

Gly Ser Glu Thr Tyr
        35

<210> SEQ ID NO 7
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ser Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Lys Thr Lys Val
            20                  25                  30

Gly Ser Asn Thr Tyr
        35

<210> SEQ ID NO 8
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ser Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
            20                  25                  30

Gly Ser Lys Thr Tyr
        35

<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ser Cys Asn Thr Ala Ser Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30
```

Gly Ser Asn Thr Tyr
        35

<210> SEQ ID NO 10
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Lys(gammaGlu-CO(CH2)14CH3)

<400> SEQUENCE: 10

Ser Cys Asn Thr Ser Thr Cys Ala Thr Gln Arg Leu Ala Asn Glu Leu
1               5                   10                  15

Lys Lys Ser Ser Asn Asn Phe Gly Pro Ile Leu Pro Pro Thr Lys Val
            20                  25                  30

Gly Ser Glu Thr Tyr
        35

<210> SEQ ID NO 11
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ser Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Arg Thr Lys Val
            20                  25                  30

Gly Ser Asn Thr Tyr
        35

<210> SEQ ID NO 12
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(dpeg-dpeg-gammaGlu-CO(CH2)14CH3)

<400> SEQUENCE: 12

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 13
<211> LENGTH: 37
<212> TYPE: PRT
<213> ORGANISM: Artificial Sequence
<220> FEATURE:
<223> OTHER INFORMATION: Description of Artificial Sequence: Synthetic

```
        polypeptide
<220> FEATURE:
<221> NAME/KEY: MOD_RES
<222> LOCATION: (16)..(16)
<223> OTHER INFORMATION: D-Lys((gammaGlu)3-CO(CH2)16CH3)

<400> SEQUENCE: 13

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 14
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys((gammaGlu)5-CO(CH2)14CH3)

<400> SEQUENCE: 14

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 15
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ser Cys Asn Thr Ser Thr Cys Ala Thr Gln Arg Leu Ala Asn Tyr Leu
1               5                   10                  15

Val Lys Ser Ser Asn Glu Phe Gly Pro Ile Leu Pro Pro Thr Lys Val
            20                  25                  30

Gly Ser Glu Thr Tyr
        35

<210> SEQ ID NO 16
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(dpeg-dpeg-gammaGlu-CO(CH2)14CH3)

<400> SEQUENCE: 16

Ser Cys Asn Thr Ser Thr Cys Ala Thr Gln Arg Leu Ala Asn Glu Lys
1               5                   10                  15
```

His Lys Ser Ser Asn Asn Phe Gly Pro Ile Leu Pro Pro Thr Lys Val
            20                  25                  30

Gly Ser Gly Thr Tyr
        35

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
            20                  25                  30

Gly Ser Asn Thr Tyr
        35

<210> SEQ ID NO 18
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Lys(CO(CH2)6CO2H)

<400> SEQUENCE: 18

Ser Cys Asn Thr Ser Thr Cys Ala Thr Gln Arg Leu Ala Asn Lys Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 19
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys(gammaGlu-dpeg-dpeg-(gammaGlu)3-CO(CH2)
      14CH3)

<400> SEQUENCE: 19

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 20
<211> LENGTH: 37
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(dpeg-dpeg-gammaGlu-CO(CH2)14CH3)

<400> SEQUENCE: 20

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Ala Thr Tyr
        35

<210> SEQ ID NO 21
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys((gammaGlu)4-CO(CH2)14CH3)

<400> SEQUENCE: 21

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 22
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser Cys Asn Thr Ser Thr Cys Ala Thr Ser Arg Leu Ala Asn Tyr Leu
1               5                   10                  15

Val Lys Ser Ser Asn Glu Phe Gly Pro Ile Leu Pro Pro Thr Lys Val
            20                  25                  30

Gly Ser Glu Thr Tyr
        35

<210> SEQ ID NO 23
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser Cys Ser Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
```

Gly Ser Asn Thr Tyr
        35

<210> SEQ ID NO 24
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ser Cys Asn Thr Ser Thr Cys Ala Thr Gln Arg Leu Ala Asn Ile Leu
1               5                   10                  15

Val Lys Ser Ser Asn Glu Phe Gly Pro Ile Leu Pro Pro Thr Lys Val
            20                  25                  30

Gly Ser Glu Thr Tyr
        35

<210> SEQ ID NO 25
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(gammaGlu-dpeg-dpeg-(gammaGlu)-CO(CH2)
      14CH3)

<400> SEQUENCE: 25

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 26
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys(gammaGlu-dpeg-dpeg-(gammaGlu)2-CO(CH2)
      14CH3)

<400> SEQUENCE: 26

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 27
<211> LENGTH: 37
<212> TYPE: PRT

<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (16)..(16)
<223> OTHER INFORMATION: D-Lys((gammaGlu)2-CO(CH2)14CH3)

<400> SEQUENCE: 27

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 28
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (16)..(16)
<223> OTHER INFORMATION: D-Lys((gammaGlu)2-CO(CH2)14CH3)

<400> SEQUENCE: 28

Ser Cys Asn Thr Ser Thr Cys Ala Thr Gln Arg Leu Ala Gln Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 29
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (16)..(16)
<223> OTHER INFORMATION: Lys((gammaGlu)3-CO(CH2)14CH3)

<400> SEQUENCE: 29

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 30
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Ser Cys Asn Thr Ser Thr Cys Ala Thr Gln Arg Leu Glu Asn Phe Leu
1               5                   10                  15

Val Lys Ser Ser Asn Glu Phe Gly Pro Ile Leu Pro Pro Thr Lys Val
            20                  25                  30

Gly Ser Glu Thr Tyr
        35
```

<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Lys(CO(CH2)11CO2H)

<400> SEQUENCE: 31

```
Ser Cys Asn Thr Ser Thr Cys Ala Thr Gln Arg Leu Ala Asn Lys Leu
1               5                   10                  15

His Lys Ser Ser Asn Asn Phe Gly Pro Ile Leu Pro Pro Thr Lys Val
            20                  25                  30

Gly Ser Glu Thr Tyr
        35
```

<210> SEQ ID NO 32
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Ser Cys Asn Thr Ser Thr Cys Ala Thr Ser Arg Leu Ala Asn Glu Leu
1               5                   10                  15

Val His Ser Ser Asn Asn Phe Gly Pro Ile Leu Pro Pro Thr Asn Val
            20                  25                  30

Gly Ser Asn Thr Tyr
        35
```

<210> SEQ ID NO 33
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Ser Cys Asn Thr Ser Thr Cys Ala Thr Ser Arg Leu Ser Asn Glu Leu
1               5                   10                  15

His Arg Ser Ser Asn Asn Phe Gly Pro Ile Leu Pro Pro Thr Lys Val
            20                  25                  30

Gly Ser Glu Thr Tyr
        35
```

<210> SEQ ID NO 34
<211> LENGTH: 37
<212> TYPE: PRT
<213> ORGANISM: Artificial Sequence
<220> FEATURE:

-continued

<223> OTHER INFORMATION: Description of Artificial Sequence: Synthetic
     polypeptide

<400> SEQUENCE: 34

Ser Cys Asn Thr Ser Thr Cys Ala Thr Gln Arg Leu Ser Asn Glu Leu
1               5                   10                  15

His Arg Ser Ser Asn Asn Phe Gly Pro Ile Leu Pro Pro Thr Lys Val
            20                  25                  30

Gly Ser Glu Thr Tyr
        35

<210> SEQ ID NO 35
<211> LENGTH: 37
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (16)..(16)
<223> OTHER INFORMATION: D-Leu

<400> SEQUENCE: 35

Ser Cys Asn Thr Ser Thr Cys Ala Thr Gln Arg Leu Ala Asn Phe Leu
1               5                   10                  15

Val Lys Ser Ser Asn Glu Phe Gly Pro Ile Leu Pro Pro Thr Asn Val
            20                  25                  30

Gly Ser Asn Thr Tyr
        35

<210> SEQ ID NO 36
<211> LENGTH: 37
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (16)..(16)
<223> OTHER INFORMATION: D-Lys(gammaGlu-CO(CH2)14CH3)

<400> SEQUENCE: 36

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 37
<211> LENGTH: 37
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 37

Ser Cys Asn Thr Ala Ser Cys Ala Thr Gln Arg Leu Ala Asn Tyr Leu
1               5                   10                  15

Val His Ser Ser Asn Asn Phe Gly Pro Ile Leu Pro Pro Thr Asn Val
            20                  25                  30

-continued

Gly Ser Asn Thr Tyr
        35

<210> SEQ ID NO 38
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ser Cys Asn Thr Ser Thr Cys Ala Thr Gln Arg Leu Ala Asn Glu Leu
1               5                   10                  15

His Lys Ser Ser Asn Glu Phe Gly Pro Ile Leu Pro Pro Thr Lys Val
            20                  25                  30

Gly Ser Asn Thr Tyr
        35

<210> SEQ ID NO 39
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys((gammaGlu)2-Gly-CO(CH2)14CH3)

<400> SEQUENCE: 39

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 40
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ser Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr His Val
            20                  25                  30

Gly Ser Glu Thr Tyr
        35

<210> SEQ ID NO 41
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ser Cys Asn Thr Ser Thr Cys Ala Thr Gln Arg Leu Ala Asn Glu Leu

```
                1               5                  10                 15
His Arg Ser Ser Asn Glu Phe Gly Pro Ile Leu Pro Pro Thr Asn Val
            20                  25                 30

Gly Ser Asn Thr Tyr
            35

<210> SEQ ID NO 42
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Lys(gammaGlu-CO(CH2)14CH3)

<400> SEQUENCE: 42

Ser Cys Asn Thr Ser Thr Cys Ala Thr Gln Arg Leu Ala Asn Lys Leu
1               5                  10                 15

His Lys Ser Ser Asn Asn Phe Gly Pro Ile Leu Pro Pro Thr Lys Val
            20                  25                 30

Gly Ser Glu Thr Tyr
            35

<210> SEQ ID NO 43
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ser Cys Asn Thr Ser Thr Cys Ala Thr Gln Arg Leu Ala Asn Phe Leu
1               5                  10                 15

Val Lys Ser Ser Asn Glu Phe Gly Pro Ile Leu Pro Pro Thr Lys Val
            20                  25                 30

Gly Ser Glu Thr Tyr
            35

<210> SEQ ID NO 44
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ser Cys Asn Thr Ser Thr Cys Ala Thr Gln Arg Leu Ala Asn Glu Leu
1               5                  10                 15

Val His Ser Ser Asn Asn Phe Gly Pro Ile Leu Pro Pro Thr Asn Val
            20                  25                 30

Gly Ser Asn Thr Tyr
            35

<210> SEQ ID NO 45
<211> LENGTH: 37
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 45

Ser Cys Asn Thr Ser Thr Cys Ala Thr Gln Arg Leu Ala Asn Glu Leu
1               5                   10                  15

His Arg Ser Ser Asn Asn Phe Gly Pro Ile Leu Pro Pro Thr Asn Val
            20                  25                  30

Gly Ser Asn Thr Tyr
        35

<210> SEQ ID NO 46
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Leu

<400> SEQUENCE: 46

Ser Cys Asn Thr Ser Thr Cys Ala Thr Gln Arg Leu Ala Asn Phe Leu
1               5                   10                  15

Val Lys Ser Ser Asn Asn Phe Gly Pro Ile Leu Pro Pro Thr Asn Val
            20                  25                  30

Gly Ser Asn Thr Tyr
        35

<210> SEQ ID NO 47
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(gammaGlu-CO(CH2)14CH3)

<400> SEQUENCE: 47

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 48
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(dpeg-dpeg-gammaGlu-(CO(CH2)16CO2H))

<400> SEQUENCE: 48

Lys Cys Asn Thr Ser Thr Cys Ala Thr Ser Arg Leu Ala Gln Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
        35

<210> SEQ ID NO 49
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ser Cys Ser Thr Ala Thr Cys Ala Thr Gln Arg Leu Ala Asn Tyr Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 50
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Leu

<400> SEQUENCE: 50

Ser Cys Asn Thr Ser Thr Cys Ala Thr Gln Arg Leu Ala Asn Phe Leu
1               5                   10                  15

Val Lys Ser Ser Asn Glu Phe Gly Pro Ile Leu Pro Pro Thr Lys Val
            20                  25                  30

Gly Ser Asn Thr Tyr
        35

<210> SEQ ID NO 51
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ser Cys Asn Thr Ser Thr Cys Ala Thr Ser Arg Leu Ala Asn Glu Leu
1               5                   10                  15

Val Arg Ser Ser Asn Asn Phe Gly Pro Ile Leu Pro Pro Thr Lys Val
            20                  25                  30

Gly Ser Glu Thr Tyr
        35

<210> SEQ ID NO 52
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 52

Ser Cys Asn Thr Ser Thr Cys Ala Thr Gln Arg Leu Ser Asn Glu Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 53
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys((gammaGlu)3-CO(CH2)14CH3)

<400> SEQUENCE: 53

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 54
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Ser Cys Asn Thr Ser Thr Cys Ala Thr Ser Arg Leu Ala Asn Glu Leu
1               5                   10                  15

His Arg Ser Ser Asn Glu Phe Gly Pro Ile Leu Pro Pro Thr Lys Val
            20                  25                  30

Gly Ser Glu Thr Tyr
        35

<210> SEQ ID NO 55
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(CO(CH2)16CO2H))

<400> SEQUENCE: 55

Lys Cys Asn Thr Ser Thr Cys Ala Thr Ser Arg Leu Ala Asn Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
        35
```

```
<210> SEQ ID NO 56
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys((gammaGlu)2-CO(CH2)16CH3)

<400> SEQUENCE: 56

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 57
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Ser Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 58
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Ser Cys Asn Thr Ser Thr Cys Ala Thr Ser Arg Leu Ala Asn Phe Leu
1               5                   10                  15

Gln Lys Ser Ser Asn Glu Phe Gly Pro Ile Leu Pro Pro Thr Lys Val
            20                  25                  30

Gly Ser Glu Thr Tyr
        35

<210> SEQ ID NO 59
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Ser Cys Asn Thr Ser Thr Cys Ala Thr Ser Arg Leu Ala Asn Tyr Leu
1               5                   10                  15

Gln Lys Ser Ser Asn Glu Phe Gly Pro Ile Leu Pro Pro Thr Lys Val
```

```
            20                  25                  30

Gly Ser Glu Thr Tyr
        35

<210> SEQ ID NO 60
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: D-Phe

<400> SEQUENCE: 60

Ser Cys Asn Thr Ser Thr Cys Ala Thr Gln Arg Leu Ala Asn Phe Leu
1               5                   10                  15

Val Lys Ser Ser Asn Glu Phe Gly Pro Ile Leu Pro Pro Thr Lys Val
            20                  25                  30

Gly Ser Glu Thr Tyr
        35

<210> SEQ ID NO 61
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ser Cys Asn Thr Ala Ser Cys Ala Thr Gln Arg Leu Ala Asn Tyr Leu
1               5                   10                  15

His Arg Ser Ser Asn Asn Phe Gly Pro Ile Leu Pro Pro Thr Asn Val
            20                  25                  30

Gly Ser Asn Thr Tyr
        35

<210> SEQ ID NO 62
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ser Cys Asn Thr Ser Thr Cys Ala Thr Ser Arg Leu Ala Asn Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
        35

<210> SEQ ID NO 63
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (16)..(16)
<223> OTHER INFORMATION: Lys(gammaGlu-dpeg-dpeg-gammaGlu-CO(CH2)14CH3)

<400> SEQUENCE: 63

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 64
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys((gammaGlu)2(CO(CH2)18CO2H))

<400> SEQUENCE: 64

Lys Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 65
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys((gammaGlu)2(CO(CH2)16CO2H))

<400> SEQUENCE: 65

Lys Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 66
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys((gammaGlu)4-CO(CH2)14CH3)

<400> SEQUENCE: 66

Ser Cys Asn Thr Ser Thr Cys Ala Thr Gln Arg Leu Ala Asn Glu Lys
1               5                   10                  15
```

His Lys Ser Ser Asn Asn Phe Gly Pro Ile Leu Pro Pro Thr Lys Val
            20                  25                  30

Gly Ser Glu Thr Tyr
        35

<210> SEQ ID NO 67
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys((gammaGlu)3-CO(CH2)14CH3)

<400> SEQUENCE: 67

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Asn Thr Tyr
        35

<210> SEQ ID NO 68
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Lys((gammaGlu)2-CO(CH2)14CH3)
<220> FEATURE:
<221> NAME/KEY: MOD_RES
<222> LOCATION: (16)..(16)
<223> OTHER INFORMATION: D-Lys(2(gammaGlu)-CO(CH2)14CH3)

<400> SEQUENCE: 68

Ser Cys Asn Thr Ser Thr Cys Ala Thr Gln Arg Leu Ala Asn Lys Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 69
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(dpeg-dpeg-gammaGlu-CO(CH2)14CH3)

<400> SEQUENCE: 69

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Tyr Thr Tyr
        35

<210> SEQ ID NO 70
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys((gammaGlu)2-CO(CH2)14CH3)

<400> SEQUENCE: 70

Ser Cys Asn Thr Ser Thr Cys Ala Thr Gln Arg Leu Ala Asn Phe Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 71
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys((gammaGlu)2-dpeg-dpeg-gammaGlu-CO(CH2)
      14CH3)

<400> SEQUENCE: 71

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 72
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Lys(CO(CH2)14CO2H)

<400> SEQUENCE: 72

Ser Cys Asn Thr Ser Thr Cys Ala Thr Gln Arg Leu Ala Asn Lys Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 73

```
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys(gammaGlu-CO(CH2)18CO2H)

<400> SEQUENCE: 73

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 74
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys(CO(CH2)10CO2H))

<400> SEQUENCE: 74

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 75
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys(CO(CH2)18CO2H)

<400> SEQUENCE: 75

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 76
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (16)..(16)
<223> OTHER INFORMATION: Lys(gammaGlu-CO(CH2)16CO2H)

<400> SEQUENCE: 76

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 77
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys((gammaGlu)3-Gly-CO(CH2)14CH3)

<400> SEQUENCE: 77

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 78
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(dpeg-dpeg-gammaGlu-CO(CH2)14CH3)

<400> SEQUENCE: 78

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Pro Thr Tyr
        35

<210> SEQ ID NO 79
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys(CO(CH2)15CO2H)

<400> SEQUENCE: 79

Ser Cys Asn Thr Ser Thr Cys Ala Thr Gln Arg Leu Ala Asn Glu Lys
```

```
1               5                   10                  15

His Lys Ser Ser Asn Asn Phe Gly Pro Ile Leu Pro Pro Thr Lys Val
            20                  25                  30

Gly Ser Glu Thr Tyr
            35

<210> SEQ ID NO 80
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys(gammaGlu-CO(CH2)15CO2H)

<400> SEQUENCE: 80

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
            35

<210> SEQ ID NO 81
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys(CO(CH2)12CO2H)

<400> SEQUENCE: 81

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
            35

<210> SEQ ID NO 82
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Lys((gammaGlu)2-CO(CH2)14CO2H)

<400> SEQUENCE: 82

Ser Cys Asn Thr Ser Thr Cys Ala Thr Gln Arg Leu Ala Asn Lys Leu
1               5                   10                  15

His Lys Ser Ser Asn Asn Phe Gly Pro Ile Leu Pro Pro Thr Lys Val
            20                  25                  30

Gly Ser Glu Thr Tyr
            35
```

<210> SEQ ID NO 83
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Lys(CO(CH2)16CO2H)

<400> SEQUENCE: 83

Ser Cys Asn Thr Ser Thr Cys Ala Thr Gln Arg Leu Ala Asn Lys Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 84
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys(CO(CH2)8CO2H)

<400> SEQUENCE: 84

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 85
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Lys((gammaGlu)2-dpeg-dpeg-gammaGlu-CO(CH2)
      18CO2H)

<400> SEQUENCE: 85

Ser Cys Asn Thr Ser Thr Cys Ala Thr Gln Arg Leu Ala Tyr Lys Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 86
<211> LENGTH: 37
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys(CO(CH2)14CO2H)

<400> SEQUENCE: 86

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 87
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Lys((gammaGlu)2-CO(CH2)16CO2H)

<400> SEQUENCE: 87

Ser Cys Asn Thr Ser Thr Cys Ala Thr Gln Arg Leu Ala Asn Lys Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 88
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys(gammaGlu-CO(CH2)14CO2H)

<400> SEQUENCE: 88

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 89
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Lys(CO(CH2)18CO2H)
```

```
<400> SEQUENCE: 89

Ser Cys Asn Thr Ser Thr Cys Ala Thr Gln Arg Leu Ala Asn Lys Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 90
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys(CO(CH2)6CO2H)

<400> SEQUENCE: 90

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 91
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys((gammaGlu)5-CO(CH2)14CH3)

<400> SEQUENCE: 91

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 92
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Lys((gammaGlu)2-CO(CH2)18CO2H)

<400> SEQUENCE: 92

Ser Cys Asn Thr Ser Thr Cys Ala Thr Gln Arg Leu Ala Asn Lys Leu
1               5                   10                  15

His Lys Ser Ser Asn Asn Phe Gly Pro Ile Leu Pro Pro Thr Lys Val
```

```
                    20                  25                  30

Gly Ser Glu Thr Tyr
        35

<210> SEQ ID NO 93
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys(CO(CH2)16CO2H)

<400> SEQUENCE: 93

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
                20                  25                  30

Gly Ser Glu Thr Tyr
        35

<210> SEQ ID NO 94
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Lys((gammaGlu)2-dpeg-dpeg-gammaGlu-CO(CH2)
      18CO2H)

<400> SEQUENCE: 94

Ser Cys Asn Thr Ser Thr Cys Ala Thr Gln Arg Leu Ala Asn Lys Leu
1               5                   10                  15

His Lys Ser Ser Asn Asn Phe Gly Pro Ile Leu Pro Pro Thr Lys Val
                20                  25                  30

Gly Ser Glu Thr Tyr
        35

<210> SEQ ID NO 95
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: D-Lys(CO(CH2)18CO2H)

<400> SEQUENCE: 95

Ser Cys Asn Thr Ser Thr Cys Ala Thr Gln Arg Leu Ala Asn Lys Leu
1               5                   10                  15

His Lys Ser Ser Asn Asn Phe Gly Pro Ile Leu Pro Pro Thr Lys Val
                20                  25                  30

Gly Ser Glu Thr Tyr
        35
```

```
<210> SEQ ID NO 96
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: D-Lys((gammaGlu)2-dpeg-CO(CH2)18CO2H)

<400> SEQUENCE: 96

Ser Cys Asn Thr Ser Thr Cys Ala Thr Gln Arg Leu Ala Asn Lys Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 97
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: D-Lys((gammaGlu)2-CO(CH2)18CO2H)

<400> SEQUENCE: 97

Ser Cys Asn Thr Ser Thr Cys Ala Thr Gln Arg Leu Ala Asn Lys Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 98
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Lys(dpeg-dpeg-gammaGlu-CO(CH2)16CO2H)

<400> SEQUENCE: 98

Ser Cys Asn Thr Ser Thr Cys Ala Thr Gln Arg Leu Ala Asn Lys Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 99
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (17)..(17)
<223> OTHER INFORMATION: Lys(dpeg-dpeg-gammaGlu-CO(CH2)16CO2H)

<400> SEQUENCE: 99
```

Ser Cys Asn Thr Ser Thr Cys Ala Thr Gln Arg Leu Ala Asn Glu Leu
1               5                   10                  15

Lys Lys Ser Ser Asn Asn Phe Gly Pro Ile Leu Pro Pro Thr Lys Val
            20                  25                  30

Gly Ser Glu Thr Tyr
        35

```
<210> SEQ ID NO 100
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: D-Lys((gammaGlu)2-dpeg-gammaGlu-CO(CH2)18CO2H)

<400> SEQUENCE: 100
```

Ser Cys Asn Thr Ser Thr Cys Ala Thr Gln Arg Leu Ala Asn Lys Leu
1               5                   10                  15

His Lys Ser Ser Asn Asn Phe Gly Pro Ile Leu Pro Pro Thr Lys Val
            20                  25                  30

Gly Ser Glu Thr Tyr
        35

```
<210> SEQ ID NO 101
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: D-Lys((gammaGlu)2-dpeg-dpeg-gammaGlu-CO(CH2)
      18CO2H)

<400> SEQUENCE: 101
```

Ser Cys Asn Thr Ser Thr Cys Ala Thr Gln Arg Leu Ala Asn Lys Leu
1               5                   10                  15

His Lys Ser Ser Asn Asn Phe Gly Pro Ile Leu Pro Pro Thr Lys Val
            20                  25                  30

Gly Ser Glu Thr Tyr
        35

```
<210> SEQ ID NO 102
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(dpeg-dpeg-gammaGlu-CO(CH2)16CO2H)

<400> SEQUENCE: 102
```

```
Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
            35
```

<210> SEQ ID NO 103
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys((gammaGlu)2-dpeg-dpeg-gammaGlu-CO(CH2)
      18CO2H)

<400> SEQUENCE: 103

```
Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
            35
```

<210> SEQ ID NO 104
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys((gammaGlu)3-CO(CH2)16CO2H)

<400> SEQUENCE: 104

```
Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
            35
```

<210> SEQ ID NO 105
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(dpeg-gammaGlu-CO(CH2)16CO2H)

<400> SEQUENCE: 105

```
Lys Cys Asn Thr Ser Thr Cys Ala Thr Ser Arg Leu Ala Gln Phe Leu
1               5                   10                  15

Gln Lys Ser Ser Asn Asn Phe Gly Pro Ile Leu Pro Pro Thr Lys Val
            20                  25                  30
```

Gly Ser Glu Thr Tyr
        35

<210> SEQ ID NO 106
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(gammaGlu-CO(CH2)16CO2H)

<400> SEQUENCE: 106

Lys Cys Asn Thr Ser Thr Cys Ala Thr Ser Arg Leu Ala Gln Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
        35

<210> SEQ ID NO 107
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Lys(gammaGlu-CO(CH2)14CH3)

<400> SEQUENCE: 107

Ser Cys Asn Thr Ser Thr Cys Ala Thr Gln Arg Leu Lys Asn Glu Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 108
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Lys(gammaGlu-CO(CH2)14CH3)

<400> SEQUENCE: 108

Ser Cys Asn Thr Ser Thr Cys Lys Thr Gln Arg Leu Ala Asn Glu Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 109
<211> LENGTH: 37

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(gammaGlu-CO(CH2)16CO2H)

<400> SEQUENCE: 109

Lys Cys Asn Thr Ser Thr Cys Ala Thr Ser Arg Leu Ala Asn Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
            35

<210> SEQ ID NO 110
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(gammaGlu-CO(CH2)16CO2H)

<400> SEQUENCE: 110

Lys Cys Asn Thr Ser Thr Cys Ala Thr Ser Arg Leu Ala Asn Tyr Leu
1               5                   10                  15

Val His Ser Ser Asn Asn Phe Gly Pro Ile Leu Pro Pro Thr Lys Val
            20                  25                  30

Gly Ser Glu Thr Tyr
            35

<210> SEQ ID NO 111
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Ser Cys Asn Thr Ser Thr Cys Ala Thr Ser Arg Leu Ala Asn Tyr Leu
1               5                   10                  15

Val His Ser Ser Asn Asn Phe Gly Pro Ile Leu Pro Pro Thr Lys Val
            20                  25                  30

Gly Ser Glu Thr Tyr
            35

<210> SEQ ID NO 112
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys((gammaGlu)2-dpeg-dpeg-gammaGlu-CO(CH2)
      18CO2H)
```

```
<400> SEQUENCE: 112

Lys Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
            20                  25                  30

Gly Ser Glu Thr Tyr
            35

<210> SEQ ID NO 113
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(dpeg-dpeg-gammaGlu-CO(CH2)16CO2H)

<400> SEQUENCE: 113

Lys Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
            20                  25                  30

Gly Ser Glu Thr Tyr
            35

<210> SEQ ID NO 114
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys((gammaGlu)2-CO(CH2)18CO2H)

<400> SEQUENCE: 114

Lys Cys Asn Thr Ser Thr Cys Ala Thr Ser Arg Leu Ala Asn Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
            35

<210> SEQ ID NO 115
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(CO(CH2)18CO2H)

<400> SEQUENCE: 115

Lys Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
            20                  25                  30
```

Gly Ser Glu Thr Tyr
        35

<210> SEQ ID NO 116
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(gammaGlu-CO(CH2)18CO2H)

<400> SEQUENCE: 116

Lys Cys Asn Thr Ser Thr Cys Ala Thr Ser Arg Leu Ala Asn Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
        35

<210> SEQ ID NO 117
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys((gammaGlu)2-CO(CH2)10CO2H)

<400> SEQUENCE: 117

Lys Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 118
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys((gammaGlu)2-CO(CH2)6CO2H)

<400> SEQUENCE: 118

Lys Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 119
<211> LENGTH: 37

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(gammaGlu)-CO(CH2)18CO2H

<400> SEQUENCE: 119

Lys Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 120
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(CO(CH2)16CO2H)

<400> SEQUENCE: 120

Lys Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 121
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Lys(gammaGlu)-CO(CH2)14CH3)

<400> SEQUENCE: 121

Ser Cys Asn Thr Ser Thr Cys Ala Thr Gln Arg Lys Ala Asn Glu Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 122
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

<222> LOCATION: (16)..(16)
<223> OTHER INFORMATION: Lys((gammaGlu)2-dpeg-dpeg-gammaGlu-CO(CH2)
     14CH3)

<400> SEQUENCE: 122

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 123
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys((gammaGlu)2-CO(CH2)14CH3)

<400> SEQUENCE: 123

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 124
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys((gammaGlu)2-CO(CH2)20CH3)

<400> SEQUENCE: 124

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 125
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Lys(gammaGlu-CO(CH2)14CH3)

<400> SEQUENCE: 125

Ser Cys Asn Thr Ser Thr Cys Ala Thr Gln Arg Leu Ala Asn Glu Lys

```
                1               5                  10                 15
His Lys Ser Ser Asn Asn Phe Gly Pro Ile Leu Pro Pro Thr Lys Val
            20                  25                 30

Gly Ser Glu Thr Tyr
        35

<210> SEQ ID NO 126
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(dpeg-dpeg-gammaGlu-CO(CH2)16CO2H)

<400> SEQUENCE: 126

Lys Cys Asn Thr Ser Thr Cys Ala Thr Ser Arg Leu Ala Asn Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
        35

<210> SEQ ID NO 127
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys

<400> SEQUENCE: 127

Ser Cys Asn Thr Ser Thr Cys Ala Thr Gln Arg Leu Ala Asn Phe Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 128
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 129
<211> LENGTH: 37
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys

<400> SEQUENCE: 129

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 130
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Lys Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 131
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Lys Cys Asn Thr Ser Thr Cys Ala Thr Gln Arg Leu Ala Asn Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
        35

<210> SEQ ID NO 132
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Aib

<400> SEQUENCE: 132

Ser Cys Asn Thr Ser Thr Cys Ala Thr Gln Arg Leu Ala Asn Xaa Leu
1               5                   10                  15
```

Val Lys Ser Ser Asn Glu Phe Gly Pro Ile Leu Pro Pro Thr Lys Val
            20                  25                  30

Gly Ser Glu Thr Tyr
        35

<210> SEQ ID NO 133
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (19)..(19)
<223> OTHER INFORMATION: Aib

<400> SEQUENCE: 133

Ser Cys Asn Thr Ser Thr Cys Ala Thr Gln Arg Leu Ala Asn Phe Leu
1               5                   10                  15

Val Lys Xaa Ser Asn Glu Phe Gly Pro Ile Leu Pro Pro Thr Lys Val
            20                  25                  30

Gly Ser Glu Thr Tyr
        35

<210> SEQ ID NO 134
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Aib

<400> SEQUENCE: 134

Ser Cys Asn Thr Ser Thr Cys Ala Thr Gln Arg Leu Ala Asn Phe Xaa
1               5                   10                  15

Val Lys Ser Ser Asn Glu Phe Gly Pro Ile Leu Pro Pro Thr Lys Val
            20                  25                  30

Gly Ser Glu Thr Tyr
        35

<210> SEQ ID NO 135
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Aib

<400> SEQUENCE: 135

Ser Cys Asn Thr Ser Thr Cys Ala Thr Gln Arg Leu Ala Asn Phe Leu
1               5                   10                  15

Xaa Lys Ser Ser Asn Glu Phe Gly Pro Ile Leu Pro Pro Thr Lys Val
            20                  25                  30

Gly Ser Glu Thr Tyr
        35

-continued

```
<210> SEQ ID NO 136
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: N-MeLeu

<400> SEQUENCE: 136

Ser Cys Asn Thr Ser Thr Cys Ala Thr Gln Arg Leu Ser Asn Phe Leu
1               5                   10                  15

Val Lys Ser Ser Asn Glu Phe Gly Pro Ile Leu Pro Pro Thr Lys Val
            20                  25                  30

Gly Ser Glu Thr Tyr
            35

<210> SEQ ID NO 137
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: N-MeLeu

<400> SEQUENCE: 137

Ser Cys Asn Thr Ser Thr Cys Ala Thr Gln Arg Leu Ala Asn Phe Leu
1               5                   10                  15

Val Lys Ser Ser Asn Glu Phe Gly Pro Ile Leu Pro Pro Thr Lys Val
            20                  25                  30

Gly Ser Glu Thr Tyr
            35

<210> SEQ ID NO 138
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: D-Asn
<220> FEATURE:
<221> NAME/KEY: MOD_RES
<222> LOCATION: (16)..(16)
<223> OTHER INFORMATION: Lys((gammaGlu)5-(CO(CH2)14CH3)

<400> SEQUENCE: 138

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Gly Thr Pro
            35

<210> SEQ ID NO 139
<211> LENGTH: 37
<212> TYPE: PRT
```

<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys((gammaGlu)2-(CO(CH2)18CO2H)

<400> SEQUENCE: 139

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Pro
        35

<210> SEQ ID NO 140
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys((gammaGlu)2-(CO(CH2)16CO2H)
<220> FEATURE:
<221> NAME/KEY: MOD_RES
<222> LOCATION: (14)..(14)
<223> OTHER INFORMATION: D-Asn

<400> SEQUENCE: 140

Lys Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
            20                  25                  30

Gly Ser Gly Thr Pro
        35

<210> SEQ ID NO 141
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys((gammaGlu)2-(CO(CH2)16CO2H)
<220> FEATURE:
<221> NAME/KEY: MOD_RES
<222> LOCATION: (14)..(14)
<223> OTHER INFORMATION: D-Asp

<400> SEQUENCE: 141

Lys Cys Asn Thr Ser Thr Cys Ala Thr Gln Arg Leu Ala Asp Glu Leu
1               5                   10                  15

His Lys Ser Ser Asn Asn Phe Gly Pro Ile Leu Pro Pro Thr Lys Val
            20                  25                  30

Gly Ser Gly Thr Pro
        35

<210> SEQ ID NO 142
<211> LENGTH: 37

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys((gammaGlu)2-(CO(CH2)16CO2H)
<220> FEATURE:
<221> NAME/KEY: MOD_RES
<222> LOCATION: (14)..(14)
<223> OTHER INFORMATION: D-Asp

<400> SEQUENCE: 142

Lys Cys Asn Thr Ser Thr Cys Ala Thr Gln Arg Leu Ala Asp Glu Leu
1               5                   10                  15

Arg His Ser Ser Asn Asn Phe Gly Pro Ile Leu Pro Pro Thr Lys Val
                20                  25                  30

Gly Ser Gly Thr Pro
        35

<210> SEQ ID NO 143
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys((gammaGlu)2-(CO(CH2)14CO2H)

<400> SEQUENCE: 143

Lys Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
                20                  25                  30

Gly Ser Glu Thr Tyr
        35

<210> SEQ ID NO 144
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(acetyl)

<400> SEQUENCE: 144

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
                20                  25                  30

Gly Ser Glu Thr Tyr
        35

<210> SEQ ID NO 145
<211> LENGTH: 37
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(allyloxycarbonyl)

<400> SEQUENCE: 145

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 146
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys((dimethyl-2,6-dioxocyclohex-1-ylidene)
      ethyl)

<400> SEQUENCE: 146

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 147
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(gammaGlu)

<400> SEQUENCE: 147

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 148
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(gammaGlu-acetyl)
```

<400> SEQUENCE: 148

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 149
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(gammaGlu-trityl)

<400> SEQUENCE: 149

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 150
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(gammaGlu-tert-butyl)

<400> SEQUENCE: 150

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 151
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(gammaGlu-gammaGlu)

<400> SEQUENCE: 151

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val

```
                20                  25                  30

Gly Ser Glu Thr Tyr
        35

<210> SEQ ID NO 152
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(gammaGlu-gammaGlu-acetyl)

<400> SEQUENCE: 152

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 153
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(gammaGlu-gammaGlu-trityl)

<400> SEQUENCE: 153

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 154
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: D-Lys(gammaGlu-gammaGlu-tert-butyl)

<400> SEQUENCE: 154

Ser Cys Asn Thr Ser Thr Cys Ala Thr Gln Arg Leu Ala Asn Glu Lys
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 155
```

```
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Lys Cys Asn Thr Ser Thr Cys Ala Thr Ser Arg Leu Ala Asn Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
        35

<210> SEQ ID NO 156
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(Fmoc)

<400> SEQUENCE: 156

Lys Cys Asn Thr Ser Thr Cys Ala Thr Ser Arg Leu Ala Asn Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
        35

<210> SEQ ID NO 157
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(gammaGlu)

<400> SEQUENCE: 157

Lys Cys Asn Thr Ser Thr Cys Ala Thr Ser Arg Leu Ala Asn Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
        35

<210> SEQ ID NO 158
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(gammaGlu-acetyl)
```

```
<400> SEQUENCE: 158

Lys Cys Asn Thr Ser Thr Cys Ala Thr Ser Arg Leu Ala Asn Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
            35

<210> SEQ ID NO 159
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(gammaGlu-trityl)

<400> SEQUENCE: 159

Lys Cys Asn Thr Ser Thr Cys Ala Thr Ser Arg Leu Ala Asn Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
            35

<210> SEQ ID NO 160
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(gammaGlu-tert-butyl)

<400> SEQUENCE: 160

Lys Cys Asn Thr Ser Thr Cys Ala Thr Ser Arg Leu Ala Asn Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
            35

<210> SEQ ID NO 161
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(gammaGlu-gammaGlu)

<400> SEQUENCE: 161

Lys Cys Asn Thr Ser Thr Cys Ala Thr Ser Arg Leu Ala Asn Phe Leu
1               5                   10                  15

Gln Lys Ser Ser Asn Asn Phe Gly Pro Ile Leu Pro Pro Thr Lys Val
            20                  25                  30
```

Gly Ser Glu Thr Tyr
        35

<210> SEQ ID NO 162
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(gammaGlu-gammaGlu-acetyl)

<400> SEQUENCE: 162

Lys Cys Asn Thr Ser Thr Cys Ala Thr Ser Arg Leu Ala Asn Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
        35

<210> SEQ ID NO 163
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(gammaGlu-gammaGlu-trityl)

<400> SEQUENCE: 163

Lys Cys Asn Thr Ser Thr Cys Ala Thr Ser Arg Leu Ala Asn Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
        35

<210> SEQ ID NO 164
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(gammaGlu-gammaGlu-tert-butyl)

<400> SEQUENCE: 164

Lys Cys Asn Thr Ser Thr Cys Ala Thr Ser Arg Leu Ala Asn Phe Leu
1               5                   10                  15

Gln Lys Ser Ser Asn Asn Phe Gly Pro Ile Leu Pro Pro Thr Lys Val
            20                  25                  30

Gly Ser Glu Thr Tyr
        35

<210> SEQ ID NO 165
<211> LENGTH: 37

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(gammaGlu)

<400> SEQUENCE: 165

Lys Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 166
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Lys(gammaGlu-gammaGlu)

<400> SEQUENCE: 166

Lys Cys Asn Thr Ser Thr Cys Ala Thr Gln Arg Leu Ala Asn Glu Leu
1               5                   10                  15

His Lys Ser Ser Asn Asn Phe Gly Pro Ile Leu Pro Pro Thr Lys Val
            20                  25                  30

Gly Ser Glu Thr Tyr
        35

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000
```

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

```
<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194
```

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser, Lys, D-Lys, His or Ile
<220> FEATURE:
<221> NAME/KEY: MOD_RES
<222> LOCATION: (3)..(3)
<223> OTHER INFORMATION: Asn or Ser
<220> FEATURE:
<221> NAME/KEY: MOD_RES
<222> LOCATION: (5)..(5)
<223> OTHER INFORMATION: Ser or Ala
<220> FEATURE:
<221> NAME/KEY: MOD_RES
<222> LOCATION: (6)..(6)
<223> OTHER INFORMATION: Thr or Ser
<220> FEATURE:
<221> NAME/KEY: MOD_RES
<222> LOCATION: (8)..(8)
<223> OTHER INFORMATION: Ala or Lys
<220> FEATURE:
<221> NAME/KEY: MOD_RES
<222> LOCATION: (10)..(10)
<223> OTHER INFORMATION: Gln or Ser
<220> FEATURE:
<221> NAME/KEY: MOD_RES
<222> LOCATION: (12)..(12)
<223> OTHER INFORMATION: Leu or Lys
<220> FEATURE:
<221> NAME/KEY: MOD_RES
<222> LOCATION: (13)..(13)
<223> OTHER INFORMATION: Ala, Ser, Glu or Lys
<220> FEATURE:
<221> NAME/KEY: MOD_RES
<222> LOCATION: (14)..(14)
<223> OTHER INFORMATION: Asn, D-Asn, D-Asp, Tyr or Gln
<220> FEATURE:
<221> NAME/KEY: MOD_RES
<222> LOCATION: (15)..(15)

<223> OTHER INFORMATION: Glu, Phe, D-Phe, Tyr, Ile, D-Lys, Lys or
      alpha-aminoisobutyric acid (Aib)
<220> FEATURE:
<221> NAME/KEY: MOD_RES
<222> LOCATION: (16)..(16)
<223> OTHER INFORMATION: Lys, D-Lys, Leu, Aib, N-methyl leucine (N-MeL)
      or D-Leu
<220> FEATURE:
<221> NAME/KEY: MOD_RES
<222> LOCATION: (17)..(17)
<223> OTHER INFORMATION: His, Val, Gln, Arg, D-Lys, Lys or Aib
<220> FEATURE:
<221> NAME/KEY: MOD_RES
<222> LOCATION: (18)..(18)
<223> OTHER INFORMATION: Lys, His or Arg
<220> FEATURE:
<221> NAME/KEY: MOD_RES
<222> LOCATION: (19)..(19)
<223> OTHER INFORMATION: Ser or Aib
<220> FEATURE:
<221> NAME/KEY: MOD_RES
<222> LOCATION: (20)..(20)
<223> OTHER INFORMATION: Ser or Aib
<220> FEATURE:
<221> NAME/KEY: MOD_RES
<222> LOCATION: (22)..(22)
<223> OTHER INFORMATION: Asn or Glu
<220> FEATURE:
<221> NAME/KEY: MOD_RES
<222> LOCATION: (29)..(29)
<223> OTHER INFORMATION: Pro, Arg or Lys
<220> FEATURE:
<221> NAME/KEY: MOD_RES
<222> LOCATION: (31)..(31)
<223> OTHER INFORMATION: Lys, D-Lys, Asn, or His
<220> FEATURE:
<221> NAME/KEY: MOD_RES
<222> LOCATION: (35)..(35)
<223> OTHER INFORMATION: Glu, D-Glu, Asn, Lys, Gly, Ala, Tyr, or Pro
<220> FEATURE:
<221> NAME/KEY: MOD_RES
<222> LOCATION: (37)..(37)
<223> OTHER INFORMATION: Tyr or Pro

<400> SEQUENCE: 199

Xaa Cys Xaa Thr Xaa Xaa Cys Xaa Thr Xaa Arg Xaa Xaa Xaa Xaa
1               5                   10                  15

Xaa Xaa Xaa Xaa Asn Xaa Phe Gly Pro Ile Leu Pro Xaa Thr Xaa Val
            20                  25                  30

Gly Ser Xaa Thr Xaa
        35

<210> SEQ ID NO 200
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser, Lys, D-Lys, His or Ile
<220> FEATURE:
<221> NAME/KEY: MOD_RES
<222> LOCATION: (3)..(3)
<223> OTHER INFORMATION: Asn or Ser
<220> FEATURE:
<221> NAME/KEY: MOD_RES
<222> LOCATION: (5)..(5)
<223> OTHER INFORMATION: Ser or Ala
<220> FEATURE:
<221> NAME/KEY: MOD_RES
<222> LOCATION: (6)..(6)
<223> OTHER INFORMATION: Thr or Ser

```
<220> FEATURE:
<221> NAME/KEY: MOD_RES
<222> LOCATION: (8)..(8)
<223> OTHER INFORMATION: Ala or Lys
<220> FEATURE:
<221> NAME/KEY: MOD_RES
<222> LOCATION: (10)..(10)
<223> OTHER INFORMATION: Gln or Ser
<220> FEATURE:
<221> NAME/KEY: MOD_RES
<222> LOCATION: (12)..(12)
<223> OTHER INFORMATION: Leu or Lys
<220> FEATURE:
<221> NAME/KEY: MOD_RES
<222> LOCATION: (13)..(13)
<223> OTHER INFORMATION: Ala, Ser, Glu or Lys
<220> FEATURE:
<221> NAME/KEY: MOD_RES
<222> LOCATION: (14)..(14)
<223> OTHER INFORMATION: Asn, D-Asn, D-Asp, Tyr or Gln
<220> FEATURE:
<221> NAME/KEY: MOD_RES
<222> LOCATION: (15)..(15)
<223> OTHER INFORMATION: Glu, Phe, D-Phe, Tyr, Ile, D-Lys, Lys or
      alpha-aminoisobutyric acid (Aib)
<220> FEATURE:
<221> NAME/KEY: MOD_RES
<222> LOCATION: (16)..(16)
<223> OTHER INFORMATION: Lys, D-Lys, Leu, Aib, N-methyl leucine (N-MeL)
      or D-Leu
<220> FEATURE:
<221> NAME/KEY: MOD_RES
<222> LOCATION: (17)..(17)
<223> OTHER INFORMATION: His, Val, Gln, Arg, D-Lys, Lys or Aib
<220> FEATURE:
<221> NAME/KEY: MOD_RES
<222> LOCATION: (18)..(18)
<223> OTHER INFORMATION: Lys, His or Arg
<220> FEATURE:
<221> NAME/KEY: MOD_RES
<222> LOCATION: (19)..(19)
<223> OTHER INFORMATION: Ser or Aib
<220> FEATURE:
<221> NAME/KEY: MOD_RES
<222> LOCATION: (20)..(20)
<223> OTHER INFORMATION: Ser or Aib
<220> FEATURE:
<221> NAME/KEY: MOD_RES
<222> LOCATION: (22)..(22)
<223> OTHER INFORMATION: Asn or Glu
<220> FEATURE:
<221> NAME/KEY: MOD_RES
<222> LOCATION: (29)..(29)
<223> OTHER INFORMATION: Pro, Arg or Lys
<220> FEATURE:
<221> NAME/KEY: MOD_RES
<222> LOCATION: (31)..(31)
<223> OTHER INFORMATION: Lys, D-Lys or Asn
<220> FEATURE:
<221> NAME/KEY: MOD_RES
<222> LOCATION: (35)..(35)
<223> OTHER INFORMATION: Glu, D-Glu or Asn

<400> SEQUENCE: 200

Xaa Cys Xaa Thr Xaa Xaa Cys Xaa Thr Xaa Arg Xaa Xaa Xaa Xaa Xaa
1               5                   10                  15

Xaa Xaa Xaa Xaa Asn Xaa Phe Gly Pro Ile Leu Pro Xaa Thr Xaa Val
            20                  25                  30

Gly Ser Xaa Thr Tyr
        35

<210> SEQ ID NO 201
<211> LENGTH: 37
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser, Lys, D-Lys, His or Ile
<220> FEATURE:
<221> NAME/KEY: MOD_RES
<222> LOCATION: (3)..(3)
<223> OTHER INFORMATION: Asn or Ser
<220> FEATURE:
<221> NAME/KEY: MOD_RES
<222> LOCATION: (5)..(5)
<223> OTHER INFORMATION: Ser or Ala
<220> FEATURE:
<221> NAME/KEY: MOD_RES
<222> LOCATION: (6)..(6)
<223> OTHER INFORMATION: Thr or Ser
<220> FEATURE:
<221> NAME/KEY: MOD_RES
<222> LOCATION: (8)..(8)
<223> OTHER INFORMATION: Ala or Lys
<220> FEATURE:
<221> NAME/KEY: MOD_RES
<222> LOCATION: (10)..(10)
<223> OTHER INFORMATION: Gln or Ser
<220> FEATURE:
<221> NAME/KEY: MOD_RES
<222> LOCATION: (12)..(12)
<223> OTHER INFORMATION: Leu or Lys
<220> FEATURE:
<221> NAME/KEY: MOD_RES
<222> LOCATION: (13)..(13)
<223> OTHER INFORMATION: Ala, Ser, Glu or Lys
<220> FEATURE:
<221> NAME/KEY: MOD_RES
<222> LOCATION: (14)..(14)
<223> OTHER INFORMATION: Asn, D-Asn, D-Asp, Tyr or Gln
<220> FEATURE:
<221> NAME/KEY: MOD_RES
<222> LOCATION: (15)..(15)
<223> OTHER INFORMATION: Glu, Phe, D-Phe, Tyr, Ile, D-Lys, Lys or Aib
<220> FEATURE:
<221> NAME/KEY: MOD_RES
<222> LOCATION: (16)..(16)
<223> OTHER INFORMATION: Lys, D-Lys, Leu, Aib, N-MeL or D-Leu
<220> FEATURE:
<221> NAME/KEY: MOD_RES
<222> LOCATION: (17)..(17)
<223> OTHER INFORMATION: His, Val, Gln, Arg, D-Lys, Lys or Aib
<220> FEATURE:
<221> NAME/KEY: MOD_RES
<222> LOCATION: (18)..(18)
<223> OTHER INFORMATION: Lys, His or Arg
<220> FEATURE:
<221> NAME/KEY: MOD_RES
<222> LOCATION: (19)..(19)
<223> OTHER INFORMATION: Ser or Aib
<220> FEATURE:
<221> NAME/KEY: MOD_RES
<222> LOCATION: (20)..(20)
<223> OTHER INFORMATION: Ser or Aib
<220> FEATURE:
<221> NAME/KEY: MOD_RES
<222> LOCATION: (22)..(22)
<223> OTHER INFORMATION: Asn or Glu
<220> FEATURE:
<221> NAME/KEY: MOD_RES
<222> LOCATION: (29)..(29)
<223> OTHER INFORMATION: Pro, Arg or Lys

<400> SEQUENCE: 201

Xaa Cys Xaa Thr Xaa Xaa Cys Xaa Thr Xaa Arg Xaa Xaa Xaa Xaa Xaa
1               5                   10                  15

Xaa Xaa Xaa Xaa Asn Xaa Phe Gly Pro Ile Leu Pro Xaa Thr Lys Val
            20                  25                  30
```

Gly Ser Glu Thr Tyr
        35

<210> SEQ ID NO 202
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser, D-Lys or Lys
<220> FEATURE:
<221> NAME/KEY: MOD_RES
<222> LOCATION: (5)..(5)
<223> OTHER INFORMATION: Ser or Ala
<220> FEATURE:
<221> NAME/KEY: MOD_RES
<222> LOCATION: (10)..(10)
<223> OTHER INFORMATION: Gln or Ser
<220> FEATURE:
<221> NAME/KEY: MOD_RES
<222> LOCATION: (15)..(15)
<223> OTHER INFORMATION: Glu or Phe
<220> FEATURE:
<221> NAME/KEY: MOD_RES
<222> LOCATION: (16)..(16)
<223> OTHER INFORMATION: Lys, D-Lys or Leu
<220> FEATURE:
<221> NAME/KEY: MOD_RES
<222> LOCATION: (17)..(17)
<223> OTHER INFORMATION: His, Val or Gln
<220> FEATURE:
<221> NAME/KEY: MOD_RES
<222> LOCATION: (18)..(18)
<223> OTHER INFORMATION: Lys, His or Arg
<220> FEATURE:
<221> NAME/KEY: MOD_RES
<222> LOCATION: (31)..(31)
<223> OTHER INFORMATION: Lys or Asn
<220> FEATURE:
<221> NAME/KEY: MOD_RES
<222> LOCATION: (35)..(35)
<223> OTHER INFORMATION: Glu or Asn

<400> SEQUENCE: 202

Xaa Cys Asn Thr Xaa Thr Cys Ala Thr Xaa Arg Leu Ala Asn Xaa Xaa
1               5                   10                  15

Xaa Xaa Ser Ser Asn Asn Phe Gly Pro Ile Leu Pro Pro Thr Xaa Val
            20                  25                  30

Gly Ser Xaa Thr Tyr
        35

<210> SEQ ID NO 203
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser, D-Lys or Lys
<220> FEATURE:
<221> NAME/KEY: MOD_RES
<222> LOCATION: (5)..(5)
<223> OTHER INFORMATION: Ser or Ala
<220> FEATURE:
<221> NAME/KEY: MOD_RES
<222> LOCATION: (10)..(10)

```
<223> OTHER INFORMATION: Gln or Ser
<220> FEATURE:
<221> NAME/KEY: MOD_RES
<222> LOCATION: (15)..(15)
<223> OTHER INFORMATION: Glu or Phe
<220> FEATURE:
<221> NAME/KEY: MOD_RES
<222> LOCATION: (16)..(16)
<223> OTHER INFORMATION: Lys, D-Lys or Leu
<220> FEATURE:
<221> NAME/KEY: MOD_RES
<222> LOCATION: (17)..(17)
<223> OTHER INFORMATION: His, Val or Gln
<220> FEATURE:
<221> NAME/KEY: MOD_RES
<222> LOCATION: (18)..(18)
<223> OTHER INFORMATION: Lys, His or Arg

<400> SEQUENCE: 203

Xaa Cys Asn Thr Xaa Thr Cys Ala Thr Xaa Arg Leu Ala Asn Xaa Xaa
1               5                   10                  15

Xaa Xaa Ser Ser Asn Asn Phe Gly Pro Ile Leu Pro Pro Thr Lys Val
            20                  25                  30

Gly Ser Glu Thr Tyr
        35

<210> SEQ ID NO 204
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser, Lys or D-Lys
<220> FEATURE:
<221> NAME/KEY: MOD_RES
<222> LOCATION: (10)..(10)
<223> OTHER INFORMATION: Gln or Ser
<220> FEATURE:
<221> NAME/KEY: MOD_RES
<222> LOCATION: (15)..(15)
<223> OTHER INFORMATION: Glu or Phe
<220> FEATURE:
<221> NAME/KEY: MOD_RES
<222> LOCATION: (16)..(16)
<223> OTHER INFORMATION: Leu, Lys or D-Lys
<220> FEATURE:
<221> NAME/KEY: MOD_RES
<222> LOCATION: (17)..(17)
<223> OTHER INFORMATION: His, Val or Gln
<220> FEATURE:
<221> NAME/KEY: MOD_RES
<222> LOCATION: (35)..(35)
<223> OTHER INFORMATION: Glu or Asn

<400> SEQUENCE: 204

Xaa Cys Asn Thr Ser Thr Cys Ala Thr Xaa Arg Leu Ala Asn Xaa Xaa
1               5                   10                  15

Xaa Lys Ser Ser Asn Asn Phe Gly Pro Ile Leu Pro Pro Thr Lys Val
            20                  25                  30

Gly Ser Xaa Thr Tyr
        35

<210> SEQ ID NO 205
<211> LENGTH: 37
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser, Lys or D-Lys
<220> FEATURE:
<221> NAME/KEY: MOD_RES
<222> LOCATION: (10)..(10)
<223> OTHER INFORMATION: Gln or Ser
<220> FEATURE:
<221> NAME/KEY: MOD_RES
<222> LOCATION: (15)..(15)
<223> OTHER INFORMATION: Glu or Phe
<220> FEATURE:
<221> NAME/KEY: MOD_RES
<222> LOCATION: (16)..(16)
<223> OTHER INFORMATION: Leu, Lys or D-Lys
<220> FEATURE:
<221> NAME/KEY: MOD_RES
<222> LOCATION: (17)..(17)
<223> OTHER INFORMATION: His, Val or Gln

<400> SEQUENCE: 205

Xaa Cys Asn Thr Ser Thr Cys Ala Thr Xaa Arg Leu Ala Asn Xaa Xaa
1               5                   10                  15

Xaa Lys Ser Ser Asn Asn Phe Gly Pro Ile Leu Pro Pro Thr Lys Val
            20                  25                  30

Gly Ser Glu Thr Tyr
        35

<210> SEQ ID NO 206
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Glu or Phe
<220> FEATURE:
<221> NAME/KEY: MOD_RES
<222> LOCATION: (16)..(16)
<223> OTHER INFORMATION: Leu, Lys or D-Lys
<220> FEATURE:
<221> NAME/KEY: MOD_RES
<222> LOCATION: (17)..(17)
<223> OTHER INFORMATION: His, Val or Gln
<220> FEATURE:
<221> NAME/KEY: MOD_RES
<222> LOCATION: (35)..(35)
<223> OTHER INFORMATION: Glu or Asn

<400> SEQUENCE: 206

Ser Cys Asn Thr Ser Thr Cys Ala Thr Gln Arg Leu Ala Asn Xaa Xaa
1               5                   10                  15

Xaa Lys Ser Ser Asn Asn Phe Gly Pro Ile Leu Pro Pro Thr Lys Val
            20                  25                  30

Gly Ser Xaa Thr Tyr
        35

<210> SEQ ID NO 207
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (15)..(15)
<223> OTHER INFORMATION: Glu or Phe
<220> FEATURE:
<221> NAME/KEY: MOD_RES
<222> LOCATION: (16)..(16)
<223> OTHER INFORMATION: Leu, Lys or D-Lys
<220> FEATURE:
<221> NAME/KEY: MOD_RES
<222> LOCATION: (17)..(17)
<223> OTHER INFORMATION: His, Val or Gln

<400> SEQUENCE: 207

Ser Cys Asn Thr Ser Thr Cys Ala Thr Gln Arg Leu Ala Asn Xaa Xaa
1               5                   10                  15

Xaa Lys Ser Ser Asn Asn Phe Gly Pro Ile Leu Pro Pro Thr Lys Val
            20                  25                  30

Gly Ser Glu Thr Tyr
        35

<210> SEQ ID NO 208
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(1)
<223> OTHER INFORMATION: L- or D- configuration
<220> FEATURE:
<221> NAME/KEY: MOD_RES
<222> LOCATION: (10)..(10)
<223> OTHER INFORMATION: Gln or Ser
<220> FEATURE:
<221> NAME/KEY: MOD_RES
<222> LOCATION: (15)..(15)
<223> OTHER INFORMATION: Glu or Phe
<220> FEATURE:
<221> NAME/KEY: MOD_RES
<222> LOCATION: (16)..(16)
<223> OTHER INFORMATION: Leu, Lys or D-Lys
<220> FEATURE:
<221> NAME/KEY: MOD_RES
<222> LOCATION: (17)..(17)
<223> OTHER INFORMATION: His, Val or Gln
<220> FEATURE:
<221> NAME/KEY: MOD_RES
<222> LOCATION: (35)..(35)
<223> OTHER INFORMATION: Glu or Asn

<400> SEQUENCE: 208

Lys Cys Asn Thr Ser Thr Cys Ala Thr Xaa Arg Leu Ala Asn Xaa Xaa
1               5                   10                  15

Xaa Lys Ser Ser Asn Asn Phe Gly Pro Ile Leu Pro Pro Thr Lys Val
            20                  25                  30

Gly Ser Xaa Thr Tyr
        35

<210> SEQ ID NO 209
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(1)
<223> OTHER INFORMATION: L- or D- configuration
```

```
<220> FEATURE:
<221> NAME/KEY: MOD_RES
<222> LOCATION: (10)..(10)
<223> OTHER INFORMATION: Gln or Ser
<220> FEATURE:
<221> NAME/KEY: MOD_RES
<222> LOCATION: (15)..(15)
<223> OTHER INFORMATION: Glu or Phe
<220> FEATURE:
<221> NAME/KEY: MOD_RES
<222> LOCATION: (16)..(16)
<223> OTHER INFORMATION: Leu, Lys or D-Lys
<220> FEATURE:
<221> NAME/KEY: MOD_RES
<222> LOCATION: (17)..(17)
<223> OTHER INFORMATION: His, Val or Gln

<400> SEQUENCE: 209

Lys Cys Asn Thr Ser Thr Cys Ala Thr Xaa Arg Leu Ala Asn Xaa Xaa
1               5                   10                  15

Xaa Lys Ser Ser Asn Asn Phe Gly Pro Ile Leu Pro Pro Thr Lys Val
            20                  25                  30

Gly Ser Glu Thr Tyr
        35

<210> SEQ ID NO 210
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser, Lys, D-Lys, His or Ile
<220> FEATURE:
<221> NAME/KEY: MOD_RES
<222> LOCATION: (3)..(3)
<223> OTHER INFORMATION: Asn or Ser
<220> FEATURE:
<221> NAME/KEY: MOD_RES
<222> LOCATION: (5)..(5)
<223> OTHER INFORMATION: Ser or Ala
<220> FEATURE:
<221> NAME/KEY: MOD_RES
<222> LOCATION: (6)..(6)
<223> OTHER INFORMATION: Thr or Ser
<220> FEATURE:
<221> NAME/KEY: MOD_RES
<222> LOCATION: (8)..(8)
<223> OTHER INFORMATION: Ala or Lys
<220> FEATURE:
<221> NAME/KEY: MOD_RES
<222> LOCATION: (10)..(10)
<223> OTHER INFORMATION: Gln or Ser
<220> FEATURE:
<221> NAME/KEY: MOD_RES
<222> LOCATION: (12)..(12)
<223> OTHER INFORMATION: Leu or Lys
<220> FEATURE:
<221> NAME/KEY: MOD_RES
<222> LOCATION: (13)..(13)
<223> OTHER INFORMATION: Ala, Ser, Glu or Lys
<220> FEATURE:
<221> NAME/KEY: MOD_RES
<222> LOCATION: (14)..(14)
<223> OTHER INFORMATION: Asn, D-Asn, D-Asp, Tyr or Gln
<220> FEATURE:
<221> NAME/KEY: MOD_RES
<222> LOCATION: (15)..(15)
<223> OTHER INFORMATION: Glu, Phe, D-Phe, Tyr, Ile, D-Lys, Lys or
      alpha-aminoisobutyric acid (Aib)
<220> FEATURE:
<221> NAME/KEY: MOD_RES
```

-continued

```
<222> LOCATION: (16)..(16)
<223> OTHER INFORMATION: Lys, D-Lys, Leu, Aib, N-methyl leucine (N-MeL)
      or D-Leu
<220> FEATURE:
<221> NAME/KEY: MOD_RES
<222> LOCATION: (17)..(17)
<223> OTHER INFORMATION: His, Val, Gln, Arg, D-Lys, Lys or Aib
<220> FEATURE:
<221> NAME/KEY: MOD_RES
<222> LOCATION: (18)..(18)
<223> OTHER INFORMATION: Lys, His or Arg
<220> FEATURE:
<221> NAME/KEY: MOD_RES
<222> LOCATION: (19)..(19)
<223> OTHER INFORMATION: Ser or Aib
<220> FEATURE:
<221> NAME/KEY: MOD_RES
<222> LOCATION: (20)..(20)
<223> OTHER INFORMATION: Ser or Aib
<220> FEATURE:
<221> NAME/KEY: MOD_RES
<222> LOCATION: (22)..(22)
<223> OTHER INFORMATION: Asn or Glu
<220> FEATURE:
<221> NAME/KEY: MOD_RES
<222> LOCATION: (29)..(29)
<223> OTHER INFORMATION: Pro, Arg or Lys
<220> FEATURE:
<221> NAME/KEY: MOD_RES
<222> LOCATION: (31)..(31)
<223> OTHER INFORMATION: Lys, D-Lys or Asn
<220> FEATURE:
<221> NAME/KEY: MOD_RES
<222> LOCATION: (35)..(35)
<223> OTHER INFORMATION: Glu, D-Glu or Asn

<400> SEQUENCE: 210

Xaa Cys Xaa Thr Xaa Xaa Cys Xaa Thr Xaa Arg Xaa Xaa Xaa Xaa Xaa
1               5                   10                  15

Xaa Xaa Xaa Xaa Asn Xaa Phe Gly Pro Ile Leu Pro Xaa Thr Xaa Val
            20                  25                  30

Gly Ser Xaa Thr Tyr
        35

<210> SEQ ID NO 211
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser, Lys or D-Lys
<220> FEATURE:
<221> NAME/KEY: MOD_RES
<222> LOCATION: (10)..(10)
<223> OTHER INFORMATION: Gln or Ser
<220> FEATURE:
<221> NAME/KEY: MOD_RES
<222> LOCATION: (15)..(15)
<223> OTHER INFORMATION: Glu or Phe
<220> FEATURE:
<221> NAME/KEY: MOD_RES
<222> LOCATION: (16)..(16)
<223> OTHER INFORMATION: Leu, Lys or D-Lys
<220> FEATURE:
<221> NAME/KEY: MOD_RES
<222> LOCATION: (17)..(17)
<223> OTHER INFORMATION: His, Val or Gln
<220> FEATURE:
<221> NAME/KEY: MOD_RES
<222> LOCATION: (35)..(35)
<223> OTHER INFORMATION: Glu or Asn
```

```
<400> SEQUENCE: 211

Xaa Cys Asn Thr Ser Thr Cys Ala Thr Xaa Arg Leu Ala Asn Xaa Xaa
1               5                   10                  15

Xaa Lys Ser Ser Asn Asn Phe Gly Pro Ile Leu Pro Pro Thr Lys Val
            20                  25                  30

Gly Ser Xaa Thr Tyr
        35

<210> SEQ ID NO 212
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Glu or Phe
<220> FEATURE:
<221> NAME/KEY: MOD_RES
<222> LOCATION: (16)..(16)
<223> OTHER INFORMATION: Leu, Lys or D-Lys
<220> FEATURE:
<221> NAME/KEY: MOD_RES
<222> LOCATION: (17)..(17)
<223> OTHER INFORMATION: His, Val or Gln
<220> FEATURE:
<221> NAME/KEY: MOD_RES
<222> LOCATION: (35)..(35)
<223> OTHER INFORMATION: Glu or Asn

<400> SEQUENCE: 212

Ser Cys Asn Thr Ser Thr Cys Ala Thr Gln Arg Leu Ala Asn Xaa Xaa
1               5                   10                  15

Xaa Lys Ser Ser Asn Asn Phe Gly Pro Ile Leu Pro Pro Thr Lys Val
            20                  25                  30

Gly Ser Xaa Thr Tyr
        35

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217
```

<400> SEQUENCE: 217

000

<210> SEQ ID NO 218
<400> SEQUENCE: 218

000

<210> SEQ ID NO 219
<400> SEQUENCE: 219

000

<210> SEQ ID NO 220
<400> SEQUENCE: 220

000

<210> SEQ ID NO 221
<400> SEQUENCE: 221

000

<210> SEQ ID NO 222
<400> SEQUENCE: 222

000

<210> SEQ ID NO 223
<400> SEQUENCE: 223

000

<210> SEQ ID NO 224
<400> SEQUENCE: 224

000

<210> SEQ ID NO 225
<400> SEQUENCE: 225

000

<210> SEQ ID NO 226
<400> SEQUENCE: 226

000

<210> SEQ ID NO 227
<400> SEQUENCE: 227

000

<210> SEQ ID NO 228
<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

```
<210> SEQ ID NO 240
<400> SEQUENCE: 240
000

<210> SEQ ID NO 241
<400> SEQUENCE: 241
000

<210> SEQ ID NO 242
<400> SEQUENCE: 242
000

<210> SEQ ID NO 243
<400> SEQUENCE: 243
000

<210> SEQ ID NO 244
<400> SEQUENCE: 244
000

<210> SEQ ID NO 245
<400> SEQUENCE: 245
000

<210> SEQ ID NO 246
<400> SEQUENCE: 246
000

<210> SEQ ID NO 247
<400> SEQUENCE: 247
000

<210> SEQ ID NO 248
<400> SEQUENCE: 248
000

<210> SEQ ID NO 249
<400> SEQUENCE: 249
000

<210> SEQ ID NO 250
<400> SEQUENCE: 250
000

<210> SEQ ID NO 251
```

```
<400> SEQUENCE: 251
000

<210> SEQ ID NO 252
<400> SEQUENCE: 252
000

<210> SEQ ID NO 253
<400> SEQUENCE: 253
000

<210> SEQ ID NO 254
<400> SEQUENCE: 254
000

<210> SEQ ID NO 255
<400> SEQUENCE: 255
000

<210> SEQ ID NO 256
<400> SEQUENCE: 256
000

<210> SEQ ID NO 257
<400> SEQUENCE: 257
000

<210> SEQ ID NO 258
<400> SEQUENCE: 258
000

<210> SEQ ID NO 259
<400> SEQUENCE: 259
000

<210> SEQ ID NO 260
<400> SEQUENCE: 260
000

<210> SEQ ID NO 261
<400> SEQUENCE: 261
000

<210> SEQ ID NO 262
<400> SEQUENCE: 262
```

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

```
<210> SEQ ID NO 285
<400> SEQUENCE: 285
000

<210> SEQ ID NO 286
<400> SEQUENCE: 286
000

<210> SEQ ID NO 287
<400> SEQUENCE: 287
000

<210> SEQ ID NO 288
<400> SEQUENCE: 288
000

<210> SEQ ID NO 289
<400> SEQUENCE: 289
000

<210> SEQ ID NO 290
<400> SEQUENCE: 290
000

<210> SEQ ID NO 291
<400> SEQUENCE: 291
000

<210> SEQ ID NO 292
<400> SEQUENCE: 292
000

<210> SEQ ID NO 293
<400> SEQUENCE: 293
000

<210> SEQ ID NO 294
<400> SEQUENCE: 294
000

<210> SEQ ID NO 295
<400> SEQUENCE: 295
000

<210> SEQ ID NO 296
```

```
<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300
<211> LENGTH: 37
<212> TYPE: PRT
<213> ORGANISM: Homo sapiens

<400> SEQUENCE: 300

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
                20                  25                  30

Gly Ser Asn Thr Tyr
        35

<210> SEQ ID NO 301
<211> LENGTH: 37
<212> TYPE: PRT
<213> ORGANISM: Rattus sp.

<400> SEQUENCE: 301

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
                20                  25                  30

Gly Ser Asn Thr Tyr
        35

<210> SEQ ID NO 302
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
                20                  25                  30

Gly Ser Asn Thr Tyr
        35
```

<210> SEQ ID NO 303
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 304
<211> LENGTH: 32
<212> TYPE: PRT
<213> ORGANISM: Homo sapiens

<400> SEQUENCE: 304

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 305
<211> LENGTH: 32
<212> TYPE: PRT
<213> ORGANISM: Unknown
<220> FEATURE:
<223> OTHER INFORMATION: Description of Unknown:
      salmon calcitonin

<400> SEQUENCE: 305

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 306
<211> LENGTH: 37
<212> TYPE: PRT
<213> ORGANISM: Unknown
<220> FEATURE:
<223> OTHER INFORMATION: Description of Unknown:
      beta-calcitonin-gene-related peptide

<400> SEQUENCE: 306

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
        35

<210> SEQ ID NO 307
<211> LENGTH: 39
<212> TYPE: PRT
<213> ORGANISM: Unknown
<220> FEATURE:
<223> OTHER INFORMATION: Description of Unknown:
      exenatide sequence

<400> SEQUENCE: 307

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 308
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, D-Lys or Lys
<220> FEATURE:
<221> NAME/KEY: MOD_RES
<222> LOCATION: (5)..(5)
<223> OTHER INFORMATION: Ser or Ala

<400> SEQUENCE: 308

Xaa Cys Asn Thr Xaa Thr Cys
1               5

<210> SEQ ID NO 309
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Lys or D-Lys

<400> SEQUENCE: 309

Xaa Cys Asn Thr Ser Thr Cys
1               5

<210> SEQ ID NO 310
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Ser Cys Asn Thr Ser Thr Cys
1               5

<210> SEQ ID NO 311
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: gammaGlu
<220> FEATURE:
<221> NAME/KEY: MISC_FEATURE
<222> LOCATION: (1)..(10)
<223> OTHER INFORMATION: This sequence may encompass 1-10 residues

<400> SEQUENCE: 311

Glu Glu Glu Glu Glu Glu Glu Glu Glu Glu
1               5                   10

<210> SEQ ID NO 312
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: gammaGlu
<220> FEATURE:
<221> NAME/KEY: MISC_FEATURE
<222> LOCATION: (1)..(10)
<223> OTHER INFORMATION: This region may encompass 1-10 residues

<400> SEQUENCE: 312

Glu Glu Glu Glu Glu Glu Glu Glu Glu Glu Gly
1               5                   10

<210> SEQ ID NO 313
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: gammaGlu

<400> SEQUENCE: 313

Glu Glu Glu Glu
1

<210> SEQ ID NO 314
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: gammaGlu

<400> SEQUENCE: 314

Glu Glu Glu Glu Glu
1               5

<210> SEQ ID NO 315
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: gammaGlu

<400> SEQUENCE: 315

```
<210> SEQ ID NO 316
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(11)
<223> OTHER INFORMATION: gammaGlu
<220> FEATURE:
<221> NAME/KEY: MISC_FEATURE
<222> LOCATION: (2)..(11)
<223> OTHER INFORMATION: This region may encompass 1-10 residues

<400> SEQUENCE: 316

Gly Glu Glu Glu Glu Glu Glu Glu Glu Glu Glu
1               5                   10

<210> SEQ ID NO 317
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Glu Glu Glu Glu
1

<210> SEQ ID NO 318
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: L- or D- configuration

<400> SEQUENCE: 318

Lys Cys Asn Thr Ser Thr Cys
1               5
```

Glu Glu Glu Gly
1

HUMAN AMYLIN ANALOG POLYPEPTIDES AND METHODS OF USE

This application claims priority to and benefit of U.S. Provisional Application No. 62/744,236, filed Oct. 11, 2018, which application is herein incorporated by reference in its entirety.

SEQUENCE LISTING

The instant application contains a Sequence Listing which has been submitted electronically in ASCII format and is hereby incorporated by reference in its entirety. Said ASCII copy, created on Oct. 10, 2019, is named 617097_102487-055_SL-10-10-2019.txt and is 115,055 bytes in size.

FIELD

This invention relates to isolated polypeptides that are analogs of human amylin. The disclosed amylin analog polypeptides have beneficial physicochemical properties relative to endogenous amylin, such as longer elimination half-lives ($t_{1/2}$) and improved solubility and thermal stability. This invention also relates to methods of using the presently disclosed amylin analog polypeptides in a variety of therapeutic indications, as well as methods of producing the same. As explained in greater detail below, the disclosed amylin analog polypeptides are particularly useful in methods of treating metabolic diseases or disorders, such as types 1 and 2 diabetes, and providing weight loss.

BACKGROUND

Human amylin, or islet amyloid polypeptide (IAPP), is a 37-residue polypeptide hormone. Amylin is co-secreted with insulin from pancreatic β-cells in the ratio of approximately 100:1 (insulin:amylin). Pro-islet amyloid polypeptide (i.e., pro-IAPP) is produced in the pancreatic β-cells as a 67 amino acid, 7404 Dalton pro-peptide that undergoes post-translational modifications including protease cleavage to produce the 37-residue amylin. Loss of β-cell function that occurs early in type 1 diabetics and can occur late in type 2 diabetics leads to deficiencies in the secretion of insulin and amylin.

Amylin functions as part of the endocrine pancreas, those cells within the pancreas that synthesize and secrete hormones. Amylin contributes to glycemic control; it is secreted from the pancreatic islets into the blood circulation and is cleared by peptidases in the kidney. Amylin's metabolic function is well-characterized as an inhibitor of the appearance of nutrients, such as glucose, in the plasma. It thus functions as a synergistic partner to insulin, a peptide that regulates blood glucose levels and coordinates the body's distribution and uptake of glucose.

Insulin's role in the body is, among other things, to prevent blood glucose levels from rising too high, particularly after a meal.

Amylin is believed to play a role in glycemic regulation by slowing gastric emptying and promoting satiety (i.e., feeling of fullness), thereby preventing post-prandial (i.e., after-meal) spikes in blood glucose levels. The overall effect is to slow the rate of appearance of glucose in the blood after eating. Amylin also lowers the secretion of glucagon by the pancreas. Glucagon's role in the body is, among other things, to prevent blood glucose levels dropping too low. This is significant because certain type 1 diabetics, for example, are prone to secrete excess amounts of the blood glucose-raising glucagon just after meals.

For numerous reasons, human amylin, having a half-life in serum of about 13 minutes, is not amenable for use as a therapeutic agent. Rather, pramlintide (Symlin®, developed by Amylin Pharmaceuticals, Inc., San Diego, CA, USA and marketed by AstraZeneca plc, Cambridge, UK) was developed as a synthetic analogue of human amylin for the treatment of patients with types 1 or 2 diabetes, who use meal-time insulin but cannot achieve desired glycemic control despite optimal insulin therapy. Pramlintide differs from human amylin in 3 of its 37 amino acids. These modifications provide pramlintide a longer half-life of approximately 48 minutes in humans and reduce its propensity to aggregate, a characteristic found of human amylin.

For treatment of type 1 diabetics, pramlintide is administered up to four times per day, via subcutaneous injection before meals, as an adjunct to insulin therapy administered after meals. Pramlintide cannot be mixed with insulin; separate syringes are used. Reported side effects of pramlintide include nausea and vomiting. Adverse reactions can include severe hypoglycemia, particularly for type 1 diabetics. Consequently, dosage of meal-time insulin is reduced for patients who initiate administration of pramlintide.

For treatment of type 2 diabetics, pramlintide is administered before each meal via subcutaneous injection at a recommended starting dose that is gradually increased to a target maintenance dose. Another investigational analog of human amylin, davalintide (AC2307; also developed by Amylin Pharmaceuticals, Inc.), has a half-life of about 26 minutes.

Accordingly, there exists a need for improved amylin analog polypeptides that mimic amylin activity yet have greater therapeutic potential than both endogenous human amylin and existing amylin analogs such as pramlintide and davalintide.

SUMMARY

It has now been discovered that polypeptides of this invention, and pharmaceutically acceptable compositions thereof, are effective as amylin analogs. Such polypeptides have the general formula of SEQ ID NO: 199: $X_1CX_3TX_5X_6CX_8TX_{10}RX_{12}X_{13}X_{14}X_{15}X_{16}X_{17}X_{18}X_{19}X_{20}NX_{22}FGPILPX_{29}TX_{31}VGSX_{35}TX_{37}$-(OH/NH$_2$) (SEQ ID NO: 199), or a pharmaceutically acceptable salt thereof, wherein:

$X_1$ is S, K, k, H or I; $X_3$ is N or S; $X_5$ is S or A; $X_6$ is T or S; $X_8$ is A or K; $X_{10}$ is Q or S; $X_{12}$ is L or K; $X_{13}$ is A, S, E or K; $X_{14}$ is N, n, d, Y or Q; $X_{15}$ is E, F, f, Y, I, k, K or ca-aminoisobutyric acid (Aib); $X_{16}$ is k, K, L, Aib, N-methyl leucine (N-MeL), or l; $X_{17}$ is H, V, Q, R, k, K or Aib; $X_{18}$ is K, H, or R; $X_{19}$ is S or Aib; $X_{20}$ is S or Aib; $X_{22}$ is N or E; $X_{29}$ is P, R or K; $X_{31}$ is k, K, N, or H; $X_{35}$ is e, E, N, K, G, A, Y, or P; and $X_{37}$ is Y or P;

each K independently represents an L-lysine optionally covalently bound to a lipophilic substituent, optionally via a spacer;

each k independently represents a D-lysine optionally covalently bound to a lipophilic substituent, optionally via a spacer;

wherein the two cysteine residues of $X_1CX_3TX_5X_6C$ are optionally further bound by a disulfide bridge;

with the proviso that if $X_{31}$ is N, then $X_{35}$ is E, or if $X_{35}$ is N, then $X_{31}$ is K.

BRIEF DESCRIPTION OF THE DRAWINGS

FIG. 1 is a table illustrating comparative sequence alignments for certain reference polypeptides: human amylin, SEQ ID NO: 300; rat amylin, SEQ ID NO: 301; pramlintide, SEQ ID NO: 302; davalintide, SEQ ID NO: 303; hCT (human calcitonin), SEQ ID NO: 304; sCT (salmon calcitonin), SEQ ID NO: 305; and beta-calcitonin-gene-related peptide (β-CGRP), SEQ ID NO: 306.

FIGS. 2A, 2B, 2C and 2D depict dose-response curves for an acylated amylin analog A73 at hAMY3R (FIG. 2A), the acylated amylin analog A73 at hCTR (FIG. 2B), pramlintide at hAMY3R (FIG. 2C), and human calcitonin (hCalcitonin) at hCTR (FIG. 2D). The term "acylated" as used herein, in relation to disclosed polypeptides, means the disclosed polypeptide is substituted with one or more lipophilic substituents each optionally via a spacer, wherein "lipophilic substituent" and "spacer" are defined herein.

DETAILED DESCRIPTION

Figure 3A:
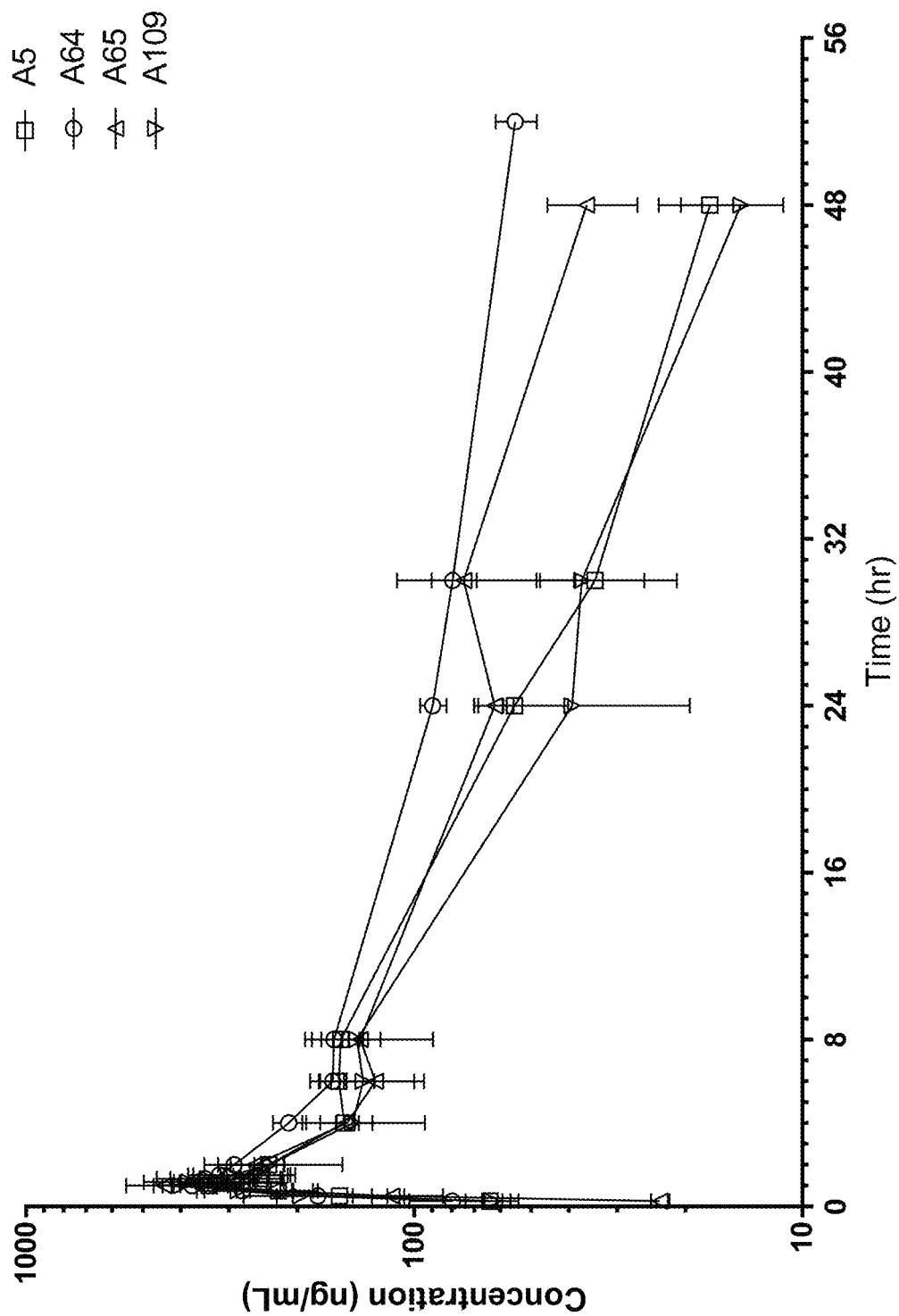
FIGS. 3A and 3B depict data from pharmacokinetic studies to assess polypeptide clearance from the kidney (CL) following intravenous infusion of linear, i.e. non-acylated, polypeptides (FIG. 3A) and conjugated, i.e. acylated, polypeptides (FIG. 3B).

1. General Description of Certain Embodiments of the Invention

This invention relates to isolated polypeptides that are amylin analogs as well as pharmaceutical compositions comprising these polypeptides. This invention also relates to methods of producing and using such amylin analog polypeptides. These amylin analog polypeptides are particularly useful in methods of treating metabolic diseases or disorders, such as types 1 and 2 diabetes, obesity, and methods of providing weight loss.

2. Definitions

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a solvent" includes a combination of two or more such solvents, reference to "a peptide" includes one or more peptides, or mixtures of peptides, reference to "a drug" includes one or more drugs, reference to "an osmotic delivery device" includes one or more osmotic delivery devices, and the like. Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the term "substantially" is understood as within a narrow range of variation or otherwise normal tolerance in the art. Substantially can be understood as within 5%, 4%, 3%, 2%, 1%, 0.5%, 0.1%, 0.05%, 0.01% or 0.001% of the stated value.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The terms "drug," "therapeutic agent," and "beneficial agent" are used interchangeably to refer to any therapeutically active substance that is delivered to a subject to produce a desired beneficial effect. In one embodiment of the present invention, the drug is a polypeptide. In another embodiment of the present invention, the drug is a small molecule, for example, hormones such as androgens or estrogens. The devices and methods of the present invention are well suited for the delivery of proteins, small molecules and combinations thereof.

The terms "peptide," "polypeptide," and "protein" are used interchangeably herein and typically refer to a molecule comprising a chain of two or more amino acids (e.g., most typically L-amino acids, but also including, e.g., D-amino acids, modified amino acids, amino acid analogs, and amino acid mimetics).

In some embodiments, naturally-occurring L-amino acids, are represented by either conventional three-letter, or capitalized one-letter, amino acid designations of Table 1. In other embodiments, naturally-occurring L-amino acids and D-amino acids, are both represented by either conventional three-letter, or capitalized one-letter, amino acid designations of Table 1. In still other embodiments, D-amino acids, are represented by lower-case one-letter amino acid designations corresponding to one-letter designations of Table 1, i.e., g, a, l, m, f, w, k, q, e, s, p, v, i, c, y, h, r, n, d, and t.

TABLE 1

| Naturally-occurring amino acids | | | | | |
|---|---|---|---|---|---|
| G | Glycine | Gly | P | Proline | Pro |
| A | Alanine | Ala | V | Valine | Val |
| L | Leucine | Leu | I | Isoleucine | Ile |
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

Peptides may be naturally occurring, synthetically produced, or recombinantly expressed. Peptides may also comprise additional groups modifying the amino acid chain, for example, functional groups added via post-translational modification. Examples of post-translation modifications include, but are not limited to, acetylation, alkylation (including, methylation), biotinylation, glutamylation, glycylation, glycosylation, isoprenylation, lipoylation, phosphopantetheinylation, phosphorylation, selenation, and C-terminal amidation. The term peptide also includes peptides comprising modifications of the amino terminus and/or the carboxy terminus. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is C1-C4 alkyl). The term peptide also includes modifications, such as but not limited to those described above, of amino acids falling between the amino and carboxy termini. In one embodiment, a peptide may be modified by addition of a small-molecule drug.

The terminal amino acid at one end of the peptide chain typically has a free amino group (i.e., the amino terminus). The terminal amino acid at the other end of the chain typically has a free carboxyl group (i.e., the carboxy terminus). Typically, the amino acids making up a peptide are numbered in order, starting at the amino terminus and increasing in the direction of the carboxy terminus of the peptide.

The phrase "amino acid residue" as used herein refers to an amino acid that is incorporated into a peptide by an amide bond or an amide bond mimetic.

The term "insulinotropic" as used herein typically refers to the ability of a compound, e.g., a peptide, to stimulate or affect the production and/or activity of insulin (e.g., an insulinotropic hormone). Such compounds typically stimulate or otherwise affect the secretion or biosynthesis of insulin in a subject. Thus, an "insulinotropic peptide" is an amino acid-containing molecule capable of stimulating or otherwise affecting secretion or biosynthesis of insulin.

The term "insulinotropic peptide" as used herein includes, but is not limited to, glucagon-like peptide 1 (GLP-1), as well as derivatives and analogues thereof, GLP-1 receptor agonists, such as exenatide, exenatide having the amino acid sequence of SEQ ID NO; 307, as well as derivatives and analogues thereof.

The term "acylated" as used herein, in relation to disclosed polypeptides, means the disclosed polypeptide is substituted with one or more lipophilic substituents each optionally via a spacer, wherein "lipophilic substituent" and "spacer" are defined herein. Certain lipophilic substituents, each optionally via a spacer, can bind albumin and confer affinity to albumin to the resulting acylated polypeptide. The extent is variable, and depending on numerous factors, to which lipophilic substituents, each optionally via a spacer, bind albumin and confer affinity to albumin to the resulting acylated polypeptide. Numerous factors include identities of the lipophilic substituent, optional spacer, polypeptide, and the site of covalent attachment to the polypeptide.

The terms "linear" or "liner polypeptide" as used herein, refer to a "non-acylated" polypeptide, in other words, a disclosed amylin analog polypeptide without a lipophilic substituents each optionally via a spacer, wherein "lipophilic substituent" and "spacer" are defined herein.

The terms "conjugated" or conjugated polypeptide" as used herein, refer to an "acylated" polypeptide, in other words, a disclosed amylin analog polypeptide having one or more lipophilic substituents each optionally via a spacer, wherein "lipophilic substituent" and "spacer" are defined herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid (TFA), oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N+(C1-4alkyl)4 salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The phrase "incretin mimetics" as used herein includes, but is not limited to GLP-1 peptide, GLP-1 receptor agonists, peptide derivatives of GLP-1, peptide analogs of GLP-1; exenatide, exenatide having the amino acid sequence of SEQ ID NO: 307, exenatide peptide, peptide derivatives of exenatide, and peptide analogs of exenatide. Examples of preferred incretin mimetics include exenatide, exenatide having the amino acid sequence of exendin-4 (the naturally-occurring form of exenatide, exenatide-LAR, lixisenatide, GLP-1 (7-36), liraglutide, semaglutide, dulaglutide, albiglutide, and taspoglutide. Incretin mimetics are also referred to herein as "insulinotropic peptides." Incretin mimetics which target the GLP-1 receptor are also known in the literature as "GLP-1 receptor agonists" or "GLP-1 agonists," with both terms being used interchangeably herein.

The term "an exenatide" as used herein includes, but is not limited to exenatide, exenatide having the amino acid sequence of (HGEGTFTSDLSKQMEEEAVRLFIEW-LKNGGPSSGAPPPS-NH$_2$), SEQ ID NO: 307, native exendin-4, exenatide peptides, exenatide peptide analogs, and exenatide peptide derivatives.

The term "GLP-1" refers to a polypeptide that is produced by the L-cell located mainly in the ileum and colon, and to a lesser extent by L-cells in the duodenum and jejunum. GLP-1 is a regulatory peptide that binds to the extracellular region of the GLP-1 receptor (GLP-1R), a G-coupled protein receptor on 3 cell and via adenyl cyclase activity and production of cAMP stimulates the insulin response to the nutrients that are absorbed from the gut [Baggio 2007, "Biology of incretins: GLP-1 and GIP," Gastroenterology, vol. 132(6):2131-57; Holst 2008, "The incretin system and its role in type 2 diabetes mellitus," Mol Cell Endocrinology, vol. 297(1-2):127-36]. The effects of GLP-1R agonism are multiple. GLP-1 maintains glucose homeostasis by enhancing endogenous glucose dependent insulin secretion, rendering the β cells glucose competent and sensitive to GLP-1, suppressing glucagon release, restoring first and second phase insulin secretion, slowing gastric emptying, decreasing food intake, and increasing satiety [Holst 2008 Mol. Cell Endocrinology; Kjems 2003 "The influence of GLP-1 on glucose-stimulated insulin secretion: effects on beta-cell sensitivity in type 2 and nondiabetic subjects," Diabetes, vol. 52(2): 380-86; Holst 2013 "Incretin hormones and the satiation signal," Int J Obes (Lond), vol. 37(9):1161-69; Seufert 2014, "The extra-pancreatic effects of GLP-1 receptor agonists: a focus on the cardiovascular, gastrointestinal and central nervous systems," Diabetes Obes Metab, vol. 16(8): 673-88]. The risk of hypoglycemia is minimal given the mode of action of GLP-1.

As described in greater detail below, in some embodiments, the amylin analog polypeptides disclosed herein are provided in methods for treatment of type 1 diabetes, as an adjunct to treatment with insulin. The term "insulin," as used herein, refers to human insulin or any insulin analogs. Exemplary non-limiting insulin analogs include those listed in Table 2:

TABLE 2

Exemplary insulin analogs

| Type of Insulin & Brand Name | Onset | Peak | Duration | Role in Blood Sugar Management |
|---|---|---|---|---|
| "Ultra Fast" Rapid-Acting | | | | |
| Fiasp ® (aspart) | about 5 mins sooner than Rapid Acting Insulins | 1-3 hours | 3-5 hours | |
| Rapid-Acting (enter the bloodstream within minutes, for injection within 5 to 10 minutes of eating; peak action period of 60-120 minutes, and clears after about four hours; used in continuous subcutaneous insulin infusion) | | | | |
| Lilly's Humalog ® (lispro) | 15-30 min. | 30-90 min | 3-5 hours | Rapid-acting insulins cover insulin needs for meals eaten at the same time as the injection. This type of insulin is often used with longer-acting insulin. |
| Novo's Novolog ® (aspart) | 10-20 min. | 40-50 min. | 3-5 hours | |
| Sanofi's Apidra ® (glulisine) | 20-30 min. | 30-90 min. | 1-2½ hours | |
| Sanofi's Admelog ® (lispro) | 15-30 min. | 30-90 min | 3-5 hours | |
| Short-Acting | | | | |
| Novo's Novolin ® (recombinant insulin) | 30 min.-1 hour | 2-5 hours | 5-8 hours | Short-acting insulins cover insulin needs for meals eaten within 30-60 minutes. |
| velosulin (human insulin for use in an insulin pump) | 30 min.-1 hour | 1-2 hours | 2-3 hours | |
| Intermediate-Acting | | | | |
| neutral protamine hagedorn (NPH) insulin | 1-2 hours | 4-12 hours | 18-24 hours | Intermediate-acting insulin covers insulin needs for about half the day or overnight. This type of insulin is often combined with a rapid- or short-acting type. |
| Long-Acting (suitable for background or basal insulin replacement) | | | | |
| Lilly's Basaglar ® (100 units/mL); Sanofi's Lantus ® (100 units/mL) & Toujeo ® (300 units/mL) (insulin glargine) Usually injected once daily, but may be given twice daily. Insulin glargine aggregates into clusters when injected. Individual insulin units detach from the cluster, for absorption into the blood stream. Slow break-up of these clusters contribute to insulin glargine's long action. | 1-1½ hours | No peak time. Delivered at a steady level. | 20-24 hours | Long-acting insulins cover insulin needs for about one full day. This type is often combined, when needed, with rapid- or short-acting insulin. |

TABLE 2-continued

Exemplary insulin analogs

| Type of Insulin & Brand Name | Onset | Peak | Duration | Role in Blood Sugar Management |
|---|---|---|---|---|
| Novo's Levemir ® (insulin detemir) Suitable for twice daily injection. Insulin detemir is absorbed into the blood stream, binds human serum albumin (HSA), and provides relatively steady concentrations, over 12 to 24 hours, of low levels of unbound or "free" detemir. | 1-2 hours | 6-8 hours | Up to 24 hours | |
| Novo's Tresiba ® (insulin degludec) | 30-90 min. | No peak time | 42 hours *** | |

Pre-Mixed* Insulins

| | | | | |
|---|---|---|---|---|
| Lilly's Humulin ® 70/30 | 30 min. | 2-4 hours | 14-24 hours | These products are |
| Novo's Novolin ® 70/30 | 30 min. | 2-12 hours | Up to 24 hours | generally taken |
| Novo's Novolog ® 70/30 | 10-20 min. | 1-4 hours | Up to 24 hours | two or three times |
| Lilly's Humulin ® 50/50 | 30 min. | 2-5 hours | 18-24 hours | a day before |
| Lilly's Humalog ® mix 75/25 | 15 min. | 30 min.-2½ hours | 16-20 hours | mealtime. |

*Premixed insulins combine specific amounts of intermediate-acting and short-acting insulin in one unit or insulin pen. (The numbers following the brand name indicate the percentage of each type of insulin.)

Insulin/GLP-1 receptor agonist combinations

| | | | | |
|---|---|---|---|---|
| Novo's Xultophy ®) (insulin degludec 100 units/mL & liraglutide 3.6 mg/mL) | 30-90 min. | No peak time | 42 hours | |
| Sanofi's Soliqua ® (insulin glargine 100 units/mL & lixisenatide 33 mcg/mL) | 1-1½ hours | No peak time | 20-24 hours | |

The term "meal-time insulin" as used herein refers to a fast-acting insulin formulation that reaches peak blood concentration in approximately 45-90 minutes and peak activity approximately 1 to 3 hours after administration and is administered at or around mealtime.

The term "vehicle" as used herein refers to a medium used to carry a compound, e.g., a drug or a particle containing a drug. Vehicles of the present invention typically comprise components such as polymers and solvents. The suspension vehicles of the present invention typically comprise solvents and polymers that are used to prepare suspension formulations further comprising drug particle formulations.

The phrase "phase separation" as used herein refers to the formation of multiple phases (e.g., liquid and gel phases) in the suspension vehicle, such as when the suspension vehicle contacts the aqueous environment. In some embodiments of the present invention, the suspension vehicle is formulated to exhibit phase separation upon contact with an aqueous environment having less than approximately 10% water.

The phrase "single-phase" as used herein refers to a solid, semisolid, or liquid homogeneous system that is physically and chemically uniform throughout.

The term "dispersed" as used herein refers to dissolving, dispersing, suspending, or otherwise distributing a compound, for example, a drug particle formulation, in a suspension vehicle.

The phrase "chemically stable" as used herein refers to formation in a formulation of an acceptable percentage of degradation products produced over a defined period of time by chemical pathways, such as deamidation (usually by hydrolysis), aggregation, or oxidation.

The phrase "physically stable" as used herein refers to formation in a formulation of an acceptable percentage of aggregates (e.g., dimers and other higher molecular weight products). Further, a physically stable formulation does not change its physical state as, for example, from liquid to solid, or from amorphous to crystal form.

The term "viscosity" as used herein typically refers to a value determined from the ratio of shear stress to shear rate (see, e.g., Considine, D. M. & Considine, G. D., Encyclopedia of Chemistry, 4th Edition, Van Nostrand, Reinhold, N.Y., 1984) essentially as follows:

$$F/A = \mu * V/L \qquad \text{(Equation 1)}$$

where F/A=shear stress (force per unit area),
μ=a proportionality constant (viscosity), and
V/L=the velocity per layer thickness (shear rate).

From this relationship, the ratio of shear stress to shear rate defines viscosity. Measurements of shear stress and shear rate are typically determined using parallel plate rheometry performed under selected conditions (for example, a temperature of about 37° C.). Other methods for the determination of viscosity include, measurement of a kinematic viscosity using viscometers, for example, a Cannon-Fenske viscometer, an Ubbelohde viscometer for the Cannon-Fenske opaque solution, or a Ostwald viscometer. Generally, suspension vehicles of the present invention have a viscosity sufficient to prevent a particle formulation suspended therein from settling during storage and use in a method of delivery, for example, in an implantable, drug delivery device.

The term "non-aqueous" as used herein refers to an overall moisture content, for example, of a suspension formulation, typically of less than or equal to about 10 wt %, for example, less than or equal to about 7 wt %, less than or equal to about 5 wt %, and/or less than about 4 wt %. Also, a particle formulation of the present invention comprises less than about 10 wt %, for example, less than about 5 wt %, residual moisture.

The term "subject" as used herein refers to any member of the subphylum Chordata, including, without limitation, humans and other primates, including non-human primates such as rhesus macaques and other monkey species and chimpanzees and other ape species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age or gender. Thus, both adult and newborn individuals are intended to be covered.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "osmotic delivery device" as used herein typically refers to a device used for delivery of a drug (e.g., a disclosed amylin analog polypeptide) to a subject, wherein the device comprises, for example, a reservoir (made, e.g., from a titanium alloy) having a lumen that contains a suspension formulation comprising a drug (e.g., a disclosed amylin analog polypeptide) and an osmotic agent formulation. A piston assembly positioned in the lumen isolates the suspension formulation from the osmotic agent formulation. A semi-permeable membrane is positioned at a first distal end of the reservoir adjacent the osmotic agent formulation and a diffusion moderator (which defines a delivery orifice through which the suspension formulation exits the device) is positioned at a second distal end of the reservoir adjacent the suspension formulation. Typically, the osmotic delivery device is implanted within the subject, for example, subdermally or subcutaneously (e.g., in the inside, outside, or back of the upper arm and in the abdominal area). An exemplary osmotic delivery device is the DUROS® (ALZA Corporation, Mountain View, Calif.) delivery device. Examples of terms synonymous to "osmotic delivery device" include but are not limited to "osmotic drug delivery device", "osmotic drug delivery system", "osmotic device", "osmotic delivery device", "osmotic delivery system", "osmotic pump", "implantable drug delivery device", "drug delivery system", "drug delivery device", "implantable osmotic pump", "implantable drug delivery system", and "implantable delivery system". Other terms for "osmotic delivery device" are known in the art.

The term "continuous delivery" as used herein typically refers to a substantially continuous release of drug from an osmotic delivery device and into tissues near the implantation site, e.g., subdermal and subcutaneous tissues. For example, an osmotic delivery device releases drug essentially at a predetermined rate based on the principle of osmosis. Extracellular fluid enters the osmotic delivery device through the semi-permeable membrane directly into the osmotic engine that expands to drive the piston at a slow and consistent rate of travel. Movement of the piston forces the drug formulation to be released through the orifice of the diffusion moderator. Thus release of the drug from the osmotic delivery device is at a slow, controlled, consistent rate.

The term "substantial steady-state delivery" as used herein typically refers to delivery of a drug at or near a target concentration over a defined period of time, wherein the amount of the drug being delivered from an osmotic delivery device is substantially zero-order delivery. Substantial zero-order delivery of an active agent (e.g., a disclosed amylin analog polypeptide) means that the rate of drug delivered is constant and is independent of the drug available in the delivery system; for example, for zero-order delivery, if the rate of drug delivered is graphed against time and a line is fitted to the data the line has a slope of approximately zero, as determined by standard methods (e.g., linear regression).

The phrase "drug half-life" as used herein refers how long it takes a drug to be eliminated from blood plasma by one half of its concentration. A drug's half-life is usually measured by monitoring how a drug degrades when it is administered via injection or intravenously. A drug is usually detected using, for example, a radioimmunoassay (RIA), a chromatographic method, an electrochemiluminescent (ECL) assay, an enzyme linked immunosorbent assay (ELISA) or an immunoenzymatic sandwich assay (IEMA).

The terms "µg" and "mcg" and "ug" are understood to mean "micrograms". Similarly, the terms "µl" and "uL" are understood to mean "microliter", and the terms "µM" and "uM" are understood to mean "micromolar".

The term "serum" is meant to mean any blood product from which a substance can be detected. Thus, the term serum includes at least whole blood, serum, and plasma. For example, "an amount of [a substance] in a subject's serum" would cover "an amount of [the substance] in a subject's plasma".

Baseline is defined as the last assessment on or before the day of the initial placement of an osmotic delivery device (containing drug or placebo).

3. Endogenous Amylin, Related Peptides and Amylin Receptors

Human amylin, a 37-residue polypeptide hormone, is co-secreted with insulin from the pancreatic β-cells. Loss of β-cell function that occurs early in type 1 diabetics and can occur late in type 2 diabetics leads to deficiencies in the secretion of insulin and amylin. Amylin is believed to play a role in glycemic regulation by slowing gastric emptying and promoting satiety, thereby preventing post-prandial spikes in blood glucose levels. The overall effect is to slow the rate of appearance of glucose in the blood after eating.

Amylin's amino acid sequence is most closely related to that of calcitonin gene-related peptide (CGRP). CGRP also shares a similarly positioned disulfide bond and an amidated C-terminus. This is also the case for calcitonin, adrenomedullin, and adrenomedullin 2. Together, these peptides form a small family, united by these characteristic features. Consequently, there is a degree of overlap in binding the cognate receptors for each peptide and pharmacological activity. The table of FIG. 1 illustrates comparative sequence alignments for amylin and certain related reference polypeptides.

The peptides typically designated as calcitonin (CT) peptide family members include; calcitonin gene-related peptide (CGRP), calcitonin (CT), amylin (AMY), adrenomedullin 1, and adrenomedullin 2/intermedin (ADM1, ADM2 respectively). Two G protein-coupled receptor proteins (calcitonin receptor; CTR, and calcitonin-receptor-like receptor;

CALCRL) and three receptor activity-modifying proteins, (RAMP1, RAMP2, RAMP3) make up the pharmacologically distinct receptors for the entire peptide family (CTR, AMY1, AMY2, AMY3, CGRPR, AM1, AM2). There appear to be at least five distinct receptors to which amylin binds with significant affinity (AMY1, AMY2, AMY3, CTR, CGRPR). CTR dimerizes with RAMPs 1, 2, or 3 to reconstitute the AMY1, AMY2, or AMY3 receptors with pharmacology selective for amylin over calcitonin. In the absence of a RAMP, CTR pharmacology becomes calcitonin selective versus amylin. CALCRL dimerized with RAMP1 generates CGRPR with high affinity for CGRP and reduced affinities for all other peptide family members including amylin. CALCRL and RAMP2, or RAMP3, reconstitute the pharmacology of AM1, and AM2 respectively with very low to no affinity for amylin.

Amylin analog polypeptides, having binding affinity to amylin receptor complexes, have been developed. Pramlintide, for example, was developed by Amylin Pharmaceuticals, and approved by the U.S. Food and Drug Administration (FDA), as a synthetic analogue of human amylin for the treatment of types 1 and 2 diabetics, who use meal-time insulin but cannot achieve desired glycemic control despite optimal insulin therapy. Pramlintide is an amylinomimetic agent that is at least as potent as human amylin. It is also a 37-amino-acid polypeptide and differs in amino acid sequence from human amylin by replacement of amino acids with proline at positions 25 (alanine), 28 (serine), and 29 (serine). As a result of these substitutions, pramlintide is soluble, non-adhesive, and nonaggregating, thereby overcoming a number of the physicochemical liabilities of native human amylin. The half-life of pramlintide is approximately 48 minutes in humans, longer than that of native human amylin (about 13 minutes). Pramlintide requires frequent and inconvenient administration.

For treatment of type 1 diabetics, pramlintide is administered up to four times per day, via subcutaneous injection in the thigh or abdomen before meals, as an adjunct to insulin therapy administered after meals. Pramlintide cannot be mixed with insulin; separate syringes are used. Pramlintide is administered with or prior to each meal or snack that consists of at least 250 calories or 30 g of carbohydrate. The typical starting dose for type 1 diabetics is 15 µg subcutaneous pramlintide before each meal, with subsequent titration to a target dose of 60 µg before each meal. Reported side effects of pramlintide include nausea and vomiting. Adverse reactions, particularly for type 1 diabetics, can include severe hypoglycemia. Consequently, dosage of meal-time insulin is reduced for diabetic patients who initiate administration of pramlintide.

For treatment of type 2 diabetics, pramlintide is administered via subcutaneous injection at a recommended starting dose of 60 µg, with a target maintenance dose of 120 µg before each meal.

Davalintide (AC2307) is another analog of human amylin. Davalintide is an investigational compound with a half-life of about 26 minutes. Like pramlintide, davalintide would likewise require frequent administration via injection.

Certain disclosed amylin analog polypeptides, including those of Table 3 below, exhibit one or more of: excellent solubility, stability, biological activity and specificity, and longer half-lives than those for endogenous human amylin and known synthetic amylin analog polypeptides. Certain disclosed amylin analog polypeptides were developed to accommodate less frequent administration than is required for pramlintide. Certain disclosed amylin analog polypeptides were developed for administration via weekly or monthly injections. Certain disclosed amylin analog polypeptides were developed for administration via implantation of a delivery device comprising the amylin analog polypeptide, where the delivery device comprises a dose of the amylin analog polypeptide of up to 3 months, 6 months, 9 months, one year, 18 months or two years.

4. Description of Exemplary Embodiments

In certain embodiments, the present invention relates to isolated polypeptides that are amylin analogs.

In some embodiments, an isolated polypeptide of the disclosure comprises an amino acid sequence, or a pharmaceutically acceptable salt thereof, selected from the group consisting of amino acid sequences represented by the consensus sequence of SEQ ID NO: 199: $X_1CX_3TX_5X_6CX_8TX_{10}RX_{12}X_{13}X_{14}X_{15}X_{16}X_{17}X_{18}X_{19}X_{20}NX_{22}FGPILPX_{29}TX_{31}VGSX_{35}TX_{37}$-(OH/NH$_2$) (SEQ ID NO: 199), or a pharmaceutically acceptable salt thereof, wherein:

$X_1$ is S, K, k, H or I;
$X_3$ is N or S;
$X_5$ is S or A;
$X_6$ is T or S;
$X_8$ is A or K;
$X_{10}$ is Q or S;
$X_{12}$ is L or K;
$X_{13}$ is A, S, E or K;
$X_{14}$ is N, n, d, Y or Q;
$X_{15}$ is E, F, f, Y, I, k, K or α-aminoisobutyric acid (Aib);
$X_{16}$ is k, K, L, Aib, N-methyl leucine (N-MeL), or l;
$X_{17}$ is H, V, Q, R, k, K or Aib;
$X_{18}$ is K, H, or R;
$X_{19}$ is S or Aib;
$X_{20}$ is S or Aib;
$X_{22}$ is N or E;
$X_{29}$ is P, R or K;
$X_{31}$ is k, K, N, or H;
$X_{35}$ is e, E, N, K, G, A, Y, or P; and
$X_{37}$ is Y or P;

each K independently represents an L-lysine optionally covalently bound to a lipophilic substituent, optionally via a spacer;

each k independently represents a D-lysine optionally covalently bound to a lipophilic substituent, optionally via a spacer;

wherein the two cysteine residues of $X_1CX_3TX_5X_6C$ are optionally further bound by a disulfide bridge;

with the proviso that if $X_{31}$ is N, then $X_{35}$ is E, or if $X_{35}$ is N, then $X_{31}$ is K.

In some embodiments, $X_{31}$ is K. In some embodiments, $X_{31}$ is N.

In some embodiments, $X_{35}$ is E. In some embodiments, $X_{35}$ is N.

In some embodiments, certain amino acids represented by the consensus sequence of SEQ ID NO: 199 include the following:

In some embodiments, carboxy terminal $X_{37}$ is Y—(NH$_2$). In some embodiments, carboxy terminal $X_{37}$ is Y—(OH). In some embodiments, carboxy terminal $X_{37}$ is P—(NH$_2$). In some embodiments, carboxy terminal $X_{37}$ is P—(OH).

In some embodiments, $X_1$ is S. In some embodiments, $X_1$ is K. In some embodiments, $X_1$ is k. In some embodiments, $X_1$ is H. In some embodiments, $X_1$ is I.

As used herein, k refers to D-lysine.

In some embodiments, $X_3$ is N. In some embodiments, $X_3$ is S.

In some embodiments, $X_5$ is S. In some embodiments, $X_5$ is A.

In some embodiments, $X_6$ is T. In some embodiments, $X_6$ is S.

In some embodiments, $X_8$ is A. In some embodiments, $X_8$ is K.

In some embodiments, $X_{10}$ is Q. In some embodiments, $X_{10}$ is S.

In some embodiments, $X_{12}$ is L. In some embodiments, $X_{12}$ is K.

In some embodiments, $X_{13}$ is A. In some embodiments, $X_{13}$ is S. In some embodiments, $X_{13}$ is E. In some embodiments, $X_{13}$ is K.

In some embodiments, $X_{14}$ is N. In some embodiments, $X_{14}$ is n. In some embodiments, $X_{14}$ is d. In some embodiments, $X_{14}$ is Y. In some embodiments, $X_{14}$ is Q.

As used herein, n refers to D-asparagine.

As used herein, d refers to D-aspartic acid.

In some embodiments, $X_{15}$ is E. In some embodiments, $X_{15}$ is F. In some embodiments, $X_{15}$ is f. In some embodiments, $X_{15}$ is Y. In some embodiments, $X_{15}$ is I. In some embodiments, $X_{15}$ is K. In some embodiments, $X_{15}$ is k. In some embodiments, $X_{15}$ is Aib.

As used herein, f refers to D-phenylalanine.

As used herein, Aib refers alternatively to 2-aminoisobutyric acid, α-aminoisobutyric acid, α-methylalanine or 2-methylalanine.

In some embodiments, $X_{16}$ is L. In some embodiments, $X_{16}$ is 1. In some embodiments, $X_{16}$ is K. In some embodiments, $X_{16}$ is k. In some embodiments, $X_{16}$ is Aib. In some embodiments, $X_{16}$ is N-MeL.

As used herein, 1 refers to D-leucine.

As used herein, N-MeL refers to N-methyl leucine.

In some embodiments, $X_{17}$ is H. In some embodiments, $X_{17}$ is V. In some embodiments, $X_{17}$ is Q. In some embodiments, $X_{17}$ is R. In some embodiments, $X_{17}$ is K. In some embodiments, $X_{17}$ is k. In some embodiments, $X_{17}$ is Aib.

In some embodiments, $X_{18}$ is K. In some embodiments, $X_{18}$ is H. In some embodiments, $X_{18}$ is R.

In some embodiments, $X_{19}$ is S. In some embodiments, $X_{19}$ is Aib.

In some embodiments, $X_{20}$ is S. In some embodiments, $X_{20}$ is Aib.

In some embodiments, $X_{22}$ is N. In some embodiments, $X_{22}$ is E.

In some embodiments, $X_{29}$ is P. In some embodiments, $X_{29}$ is R. In some embodiments, $X_{29}$ is K.

In some embodiments, $X_{31}$ is k. In some embodiments, $X_{31}$ is K. In some embodiments, $X_{31}$ is N. In some embodiments, $X_{31}$ is H.

In some embodiments, $X_{35}$ is e. In some embodiments, $X_{35}$ is E. In some embodiments, $X_{35}$ is N. In some embodiments, $X_{35}$ is K. In some embodiments, $X_{35}$ is G. In some embodiments, $X_{35}$ is A. In some embodiments, $X_{35}$ is Y. In some embodiments, $X_{35}$ is P.

As used herein, e refers to D-glutamic acid.

In some embodiments, certain amino acids represented by the consensus sequence of SEQ ID NO: 199 include the following:

In some embodiments, $X_1$ is S and $X_5$ is S. In some embodiments, $X_1$ is S and $X_{10}$ is Q. In some embodiments, $X_1$ is S and $X_{15}$ is E. In some embodiments, $X_1$ is S and $X_{16}$ is L. In some embodiments, $X_1$ is S and $X_{16}$ is k. In some embodiments, $X_1$ is S and $X_{17}$ is H. In some embodiments, $X_1$ is S and $X_{18}$ is K. In some embodiments, $X_1$ is S and $X_{31}$ is K. In some embodiments, $X_1$ is S and $X_{35}$ is E. In some embodiments, $X_1$ is S and $X_{37}$ is Y.

In some embodiments, $X_1$ is K and $X_5$ is S. In some embodiments, $X_1$ is K and $X_{10}$ is Q. In some embodiments, $X_1$ is K and $X_{15}$ is E. In some embodiments, $X_1$ is K and $X_{16}$ is L. In some embodiments, $X_1$ is K and $X_{16}$ is k. In some embodiments, $X_1$ is K and $X_{17}$ is H. In some embodiments, $X_1$ is K and $X_{18}$ is K. In some embodiments, $X_1$ is K and $X_{31}$ is K. In some embodiments, $X_1$ is K and $X_{35}$ is E. In some embodiments, $X_1$ is K and $X_{37}$ is Y.

In some embodiments, $X_1$ is k and $X_5$ is S. In some embodiments, $X_1$ is k and $X_{10}$ is Q. In some embodiments, $X_1$ is k and $X_{15}$ is E. In some embodiments, $X_1$ is k and $X_{16}$ is L. In some embodiments, $X_1$ is k and $X_{16}$ is k. In some embodiments, $X_1$ is k and $X_{17}$ is H. In some embodiments, $X_1$ is k and $X_{18}$ is K. In some embodiments, $X_1$ is k and $X_{31}$ is K. In some embodiments, $X_1$ is k and $X_{35}$ is E. In some embodiments, $X_1$ is k and $X_{37}$ is Y.

In some embodiments, $X_5$ is S and $X_{15}$ is E. In some embodiments, $X_5$ is S and $X_{10}$ is Q. In some embodiments, $X_5$ is S and $X_{16}$ is L. In some embodiments, $X_5$ is S and $X_{16}$ is k. In some embodiments, $X_5$ is S and $X_{17}$ is H. In some embodiments, $X_5$ is S and $X_{18}$ is K. In some embodiments, $X_5$ is S and $X_{31}$ is K. In some embodiments, $X_5$ is S and $X_{35}$ is E. In some embodiments, $X_5$ is S and $X_{37}$ is Y.

In some embodiments, $X_{10}$ is Q and $X_{15}$ is E. In some embodiments, $X_{10}$ is Q and $X_{16}$ is L. In some embodiments, $X_{10}$ is Q and $X_{16}$ is k. In some embodiments, $X_{10}$ is Q and $X_{17}$ is H. In some embodiments, $X_{10}$ is Q and $X_{18}$ is K. In some embodiments, $X_{10}$ is Q and $X_{31}$ is K. In some embodiments, $X_{10}$ is Q and $X_{35}$ is E. In some embodiments, $X_{10}$ is Q and $X_{37}$ is Y.

In some embodiments, $X_{15}$ is E and $X_{16}$ is L. In some embodiments, $X_{15}$ is E and $X_{16}$ is k. In some embodiments, $X_{15}$ is E and $X_{17}$ is H. In some embodiments, $X_{15}$ is E and $X_{18}$ is K. In some embodiments, $X_{15}$ is E and $X_{31}$ is K. In some embodiments, $X_{15}$ is E and $X_{35}$ is E. In some embodiments, $X_{15}$ is E and $X_{37}$ is Y.

In some embodiments, $X_{16}$ is L and $X_{17}$ is H. In some embodiments, $X_{16}$ is L and $X_{18}$ is K. In some embodiments, $X_{16}$ is L and $X_{31}$ is K. In some embodiments, $X_{16}$ is L and $X_{35}$ is E. In some embodiments, $X_{16}$ is L and $X_{37}$ is Y.

In some embodiments, $X_{16}$ is k and $X_{17}$ is H. In some embodiments, $X_{16}$ is k and $X_{18}$ is K. In some embodiments, $X_{16}$ is k and $X_{31}$ is K. In some embodiments, $X_{16}$ is k and $X_{35}$ is E. In some embodiments, $X_{16}$ is k and $X_{37}$ is Y.

In some embodiments, $X_{17}$ is H and $X_{18}$ is K. In some embodiments, $X_{17}$ is H and $X_{31}$ is K. In some embodiments, $X_{17}$ is H and $X_{35}$ is E. In some embodiments, $X_{17}$ is H and $X_{37}$ is Y.

In some embodiments, $X_{18}$ is K and $X_{31}$ is K. In some embodiments, $X_{18}$ is K and $X_{35}$ is E. In some embodiments, $X_{18}$ is K and $X_{37}$ is Y.

In some embodiments, $X_{31}$ is K and $X_{35}$ is E. In some embodiments, $X_{31}$ is K and $X_{37}$ is Y.

In some embodiments, $X_{35}$ is E and $X_{37}$ is Y.

In some embodiments, certain amino acids represented by the consensus sequence of SEQ ID NO: 199 include the following:

In some embodiments, $X_1$ is S, $X_5$ is S, and $X_{15}$ is E. In some embodiments, $X_1$ is S, $X_5$ is S, and $X_{16}$ is L. In some embodiments, $X_1$ is S, $X_5$ is S, and $X_{16}$ is k. In some embodiments, $X_1$ is S, $X_5$ is S, and $X_{17}$ is H. In some embodiments, $X_1$ is S, $X_5$ is S, and $X_{18}$ is K. In some embodiments, $X_1$ is S, $X_5$ is S, and $X_{31}$ is K. In some embodiments, $X_1$ is S and $X_{35}$ is E. In some embodiments, $X_1$ is S, $X_5$ is S, and $X_{37}$ is Y.

In some embodiments, $X_1$ is K, $X_5$ is S, and $X_{15}$ is E. In some embodiments, $X_1$ is K, $X_5$ is S, and $X_{16}$ is L. In some embodiments, $X_1$ is K, $X_5$ is S, and $X_{16}$ is k. In some embodiments, $X_1$ is K, $X_5$ is S, and $X_{17}$ is H. In some embodiments, $X_1$ is K, $X_5$ is S, and $X_{18}$ is K. In some embodiments, $X_1$ is K, $X_5$ is S, and $X_{31}$ is K. In some embodiments, $X_1$ is K, $X_5$ is S, and $X_{35}$ is E. In some embodiments, $X_1$ is K, $X_5$ is S, and $X_{37}$ is Y.

In some embodiments, $X_1$ is k, $X_5$ is S, and $X_{15}$ is E. In some embodiments, $X_1$ is k, $X_5$ is S, and $X_{16}$ is L. In some embodiments, $X_1$ is k, $X_5$ is S, and $X_{16}$ is k. In some embodiments, $X_1$ is k, $X_5$ is S, and $X_{17}$ is H. In some embodiments, $X_1$ is k, $X_5$ is S, and $X_{18}$ is K. In some embodiments, $X_1$ is k, $X_5$ is S, and $X_{31}$ is K. In some embodiments, $X_1$ is k, $X_5$ is S, and $X_{35}$ is E. In some embodiments, $X_1$ is k, $X_5$ is S, and $X_{37}$ is Y.

In some embodiments, $X_5$ is S, $X_{15}$ is E, and $X_{16}$ is L. In some embodiments, $X_5$ is S, $X_{15}$ is E, and $X_{16}$ is k. In some embodiments, $X_5$ is S, $X_{15}$ is E, and $X_{17}$ is H. In some embodiments, $X_5$ is S, $X_{15}$ is E, and $X_{18}$ is K. In some embodiments, $X_5$ is S, $X_{15}$ is E, and $X_{31}$ is K. In some embodiments, $X_5$ is S, $X_{15}$ is E, and $X_{35}$ is E. In some embodiments, $X_5$ is S, $X_{15}$ is E, and $X_{37}$ is Y.

In some embodiments, $X_{10}$ is Q, $X_{15}$ is E and $X_{16}$ is L. In some embodiments, $X_{10}$ is Q, and $X_{16}$ is k and $X_{17}$ is H. In some embodiments, $X_{10}$ is Q, $X_{18}$ is K, and $X_{31}$ is K. In some embodiments, $X_{10}$ is Q, $X_{31}$ is K and $X_{35}$ is E. In some embodiments, $X_{10}$ is Q, $X_{31}$ is K and $X_{37}$ is Y.

In some embodiments, $X_{15}$ is E, $X_{16}$ is L, and $X_{17}$ is H. In some embodiments, $X_{15}$ is E, $X_{16}$ is L, and $X_{18}$ is K. In some embodiments, $X_{15}$ is E, $X_{16}$ is L, and $X_{31}$ is K. In some embodiments, $X_{15}$ is E, $X_{16}$ is L, and $X_{35}$ is E. In some embodiments, $X_{15}$ is E, $X_{16}$ is L, and $X_{37}$ is Y.

In some embodiments, $X_{15}$ is E, $X_{16}$ is k, and $X_{17}$ is H. In some embodiments, $X_{15}$ is E, $X_{16}$ is k, and $X_{18}$ is K. In some embodiments, $X_{15}$ is E, $X_{16}$ is k, and $X_{31}$ is K. In some embodiments, $X_{15}$ is E, $X_{16}$ is k, and $X_{35}$ is E. In some embodiments, $X_{15}$ is E, $X_{16}$ is k, and $X_{37}$ is Y.

In some embodiments, $X_{16}$ is L, $X_{17}$ is H, and $X_{18}$ is K. In some embodiments, $X_{16}$ is L, $X_{17}$ is H, and $X_{31}$ is K. In some embodiments, $X_{16}$ is L, $X_{17}$ is H, and $X_{35}$ is E. In some embodiments, $X_{16}$ is L, $X_{17}$ is H, and $X_{37}$ is Y.

In some embodiments, $X_{16}$ is k, $X_{17}$ is H, and $X_{18}$ is K. In some embodiments, $X_{16}$ is k, $X_{17}$ is H, and $X_{31}$ is K. In some embodiments, $X_{16}$ is k, $X_{17}$ is H, and $X_{35}$ is E. In some embodiments, $X_{16}$ is k, $X_{17}$ is H, and $X_{37}$ is Y.

In some embodiments, $X_{17}$ is H, $X_{18}$ is K, and $X_{31}$ is K. In some embodiments, $X_{17}$ is H, $X_{18}$ is K, and $X_{35}$ is E. In some embodiments, $X_{17}$ is H, $X_{18}$ is K, and $X_{37}$ is Y.

In some embodiments, $X_{18}$ is K, $X_{31}$ is K, and $X_{35}$ is E. In some embodiments, $X_{18}$ is K, $X_{31}$ is K, and $X_{37}$ is Y.

In some embodiments, $X_{31}$ is K, $X_{35}$ is E, and $X_{37}$ is Y.

In some embodiments, carboxy terminal amino acid 37 is Y—($NH_2$). In some embodiments, carboxy terminal amino acid 37 is Y—(OH). In some embodiments, carboxy terminal amino acid 37 is P—($NH_2$). In some embodiments, carboxy terminal amino acid 37 is P—(OH).

In some embodiments, an isolated polypeptide of the disclosure comprises an amino acid sequence, or a pharmaceutically acceptable salt thereof, selected from the group consisting of amino acid sequences represented by the consensus sequence of SEQ ID NO: 200: $X_1CX_3TX_5X_6CX_8TX_{10}RX_{12}X_{13}X_{14}X_{15}X_{16}X_{17}X_{18}X_{19}X_{20}NX_{22}FGPILPX_{29}TX_{31}VGSX_{35}TY$-(OH/$NH_2$) (SEQ ID NO: 200), or a pharmaceutically acceptable salt thereof, wherein:

$X_1$ is S, K, k, H or I;
$X_3$ is N or S;
$X_5$ is S or A;
$X_6$ is T or S;
$X_8$ is A or K;
$X_{10}$ is Q or S;
$X_{12}$ is L or K;
$X_{13}$ is A, S, E or K;
$X_{14}$ is N, n, d, Y or Q;
$X_{15}$ is E, F, f, Y, I, k, K or α-aminoisobutyric acid (Aib);
$X_{16}$ is k, K, L, Aib, N-methyl leucine (N-MeL), or l;
$X_{17}$ is H, V, Q, R, k, K or Aib;
$X_{18}$ is K, H, or R;
$X_{19}$ is S or Aib;
$X_{20}$ is S or Aib;
$X_{22}$ is N or E;
$X_{29}$ is P, R or K;
$X_{31}$ is k, K or N; and
$X_{35}$ is e, E or N;
each K independently represents an L-lysine optionally covalently bound to a lipophilic substituent, optionally via a spacer;
each k independently represents a D-lysine optionally covalently bound to a lipophilic substituent, optionally via a spacer;
wherein the two cysteine residues of $X_1CX_3TX_5X_6C$ are optionally further bound by a disulfide bridge;
with the proviso that if $X_{31}$ is N, then $X_{35}$ is E, or if $X_{35}$ is N, then $X_{31}$ is K.

In some embodiments, $X_{31}$ is K. In some embodiments, $X_{31}$ is N.

In some embodiments, $X_{35}$ is E. In some embodiments, $X_{35}$ is N.

In some embodiments, an isolated polypeptide of the disclosure comprises an amino acid sequence, or a pharmaceutically acceptable salt thereof, selected from the group consisting of amino acid sequences represented by the consensus sequence of SEQ ID NO: 201: $X_1CX_3TX_5X_6CX_8TX_{10}RX_{12}X_{13}X_{14}X_{15}X_{16}X_{17}X_{18}X_{19}X_{20}NX_{22}FGPILPX_{29}TKVGSETY$-(OH/$NH_2$) (SEQ ID NO: 201), wherein:

$X_1$ is S, K, k, H or I;
$X_3$ is N or S;
$X_8$ is S or A;
$X_6$ is T or S;
$X_8$ is A or K;
$X_{10}$ is Q or S;
$X_{12}$ is L or K;
$X_{13}$ is A, S, E or K;
$X_{14}$ is N, n, d, Y or Q;
$X_{15}$ is E, F, f, Y, I, k, K or Aib;
$X_{16}$ is k, K, L, Aib, N-MeL or l;
$X_{17}$ is H, V, Q, R, k, K or Aib;
$X_{18}$ is K, H, or R;
$X_{19}$ is S or Aib;
$X_{20}$ is S or Aib;
$X_{22}$ is N or E; and
$X_{29}$ is P, R or K;
each K independently represents an L-lysine optionally covalently bound to a lipophilic substituent, optionally via a spacer;
each k independently represents a D-lysine optionally covalently bound to a lipophilic substituent, optionally via a spacer;
wherein the two cysteine residues of $X_1CX_3TX_5X_6C$ are optionally further bound by a disulfide bridge.

In some embodiments, certain amino acids represented by the consensus sequence of SEQ ID NO: 200 or SEQ ID NO: 201 include the following:

In some embodiments, carboxy terminal amino acid 37 is Y—($NH_2$). In some embodiments, carboxy terminal amino acid 37 is Y—(OH).

In some embodiments, $X_1$ is S. In some embodiments, $X_1$ is K. In some embodiments, $X_1$ is k. In some embodiments, $X_1$ is H. In some embodiments, $X_1$ is I.

As used herein, k refers to D-lysine.

In some embodiments, $X_3$ is N. In some embodiments, $X_3$ is S.

In some embodiments, $X_5$ is S. In some embodiments, $X_5$ is A.

In some embodiments, $X_6$ is T. In some embodiments, $X_6$ is S.

In some embodiments, $X_8$ is A. In some embodiments, $X_8$ is K.

In some embodiments, $X_{10}$ is Q. In some embodiments, $X_{10}$ is S.

In some embodiments, $X_{12}$ is L. In some embodiments, $X_{12}$ is K.

In some embodiments, $X_{13}$ is A. In some embodiments, $X_{13}$ is S. In some embodiments, $X_{13}$ is E. In some embodiments, $X_{13}$ is K.

In some embodiments, $X_{14}$ is N. In some embodiments, $X_{14}$ is n. In some embodiments, $X_{14}$ is d. In some embodiments, $X_{14}$ is Y. In some embodiments, $X_{14}$ is Q.

As used herein, n refers to D-asparagine.

As used herein, d refers to D-aspartic acid.

In some embodiments, $X_{15}$ is E. In some embodiments, $X_{15}$ is F. In some embodiments, $X_{15}$ is f. In some embodiments, $X_{15}$ is Y. In some embodiments, $X_{15}$ is I. In some embodiments, $X_{15}$ is K. In some embodiments, $X_{15}$ is k. In some embodiments, $X_{15}$ is Aib.

As used herein, f refers to D-phenylalanine.

As used herein, Aib refers alternatively to 2-aminoisobutyric acid, α-aminoisobutyric acid, α-methylalanine or 2-methylalanine.

In some embodiments, $X_{16}$ is L. In some embodiments, $X_{16}$ is 1. In some embodiments, $X_{16}$ is K. In some embodiments, $X_{16}$ is k. In some embodiments, $X_{16}$ is Aib. In some embodiments, $X_{16}$ is N-MeL.

As used herein, 1 refers to D-leucine.

As used herein, N-MeL refers to N-methyl leucine.

In some embodiments, $X_{17}$ is H. In some embodiments, $X_{17}$ is V. In some embodiments, $X_{17}$ is Q. In some embodiments, $X_{17}$ is R. In some embodiments, $X_{17}$ is K. In some embodiments, $X_{17}$ is k. In some embodiments, $X_{17}$ is Aib.

In some embodiments, $X_{18}$ is K. In some embodiments, $X_{18}$ is H. In some embodiments, $X_{18}$ is R.

In some embodiments, $X_{19}$ is S. In some embodiments, $X_{19}$ is Aib.

In some embodiments, $X_{20}$ is S. In some embodiments, $X_{20}$ is Aib.

In some embodiments, $X_{22}$ is N. In some embodiments, $X_{22}$ is E.

In some embodiments, $X_{29}$ is P. In some embodiments, $X_{29}$ is R. In some embodiments, $X_{29}$ is K.

In some embodiments, $X_{31}$ is k. In some embodiments, $X_{31}$ is K. In some embodiments, $X_{31}$ is N.

In some embodiments, $X_{35}$ is e. In some embodiments, $X_{35}$ is E. In some embodiments, $X_{35}$ is N.

As used herein, e refers to D-glutamic acid.

In some embodiments, certain amino acids represented by the consensus sequence of SEQ ID NO: 200 or SEQ ID NO: 201 include the following:

In some embodiments, $X_1$ is S and $X_5$ is S. In some embodiments, $X_1$ is S and $X_{10}$ is Q. In some embodiments, $X_1$ is S and $X_{15}$ is E. In some embodiments, $X_1$ is S and $X_{16}$ is L. In some embodiments, $X_1$ is S and $X_{16}$ is k. In some embodiments, $X_1$ is S and $X_{17}$ is H. In some embodiments, $X_1$ is S and $X_{15}$ is K. In some embodiments, $X_1$ is S and $X_{31}$ is K. In some embodiments, $X_1$ is S and $X_{35}$ is E.

In some embodiments, $X_1$ is K and $X_5$ is S. In some embodiments, $X_1$ is K and $X_{10}$ is Q. In some embodiments, $X_1$ is K and $X_{15}$ is E. In some embodiments, $X_1$ is K and $X_{16}$ is L. In some embodiments, $X_1$ is K and $X_{16}$ is k. In some embodiments, $X_1$ is K and $X_{17}$ is H. In some embodiments, $X_1$ is K and $X_{18}$ is K. In some embodiments, $X_1$ is K and $X_{31}$ is K. In some embodiments, $X_1$ is K and $X_{35}$ is E.

In some embodiments, $X_1$ is k and $X_5$ is S. In some embodiments, $X_1$ is k and $X_{10}$ is Q. In some embodiments, $X_1$ is k and $X_{15}$ is E. In some embodiments, $X_1$ is k and $X_{16}$ is L. In some embodiments, $X_1$ is k and $X_{16}$ is k. In some embodiments, $X_1$ is k and $X_{17}$ is H. In some embodiments, $X_1$ is k and $X_{18}$ is K. In some embodiments, $X_1$ is k and $X_{31}$ is K. In some embodiments, $X_1$ is k and $X_{35}$ is E.

In some embodiments, $X_5$ is S and $X_{15}$ is E. In some embodiments, $X_5$ is S and $X_{10}$ is Q. In some embodiments, $X_5$ is S and $X_{16}$ is L. In some embodiments, $X_5$ is S and $X_{16}$ is k. In some embodiments, $X_5$ is S and $X_{17}$ is H. In some embodiments, $X_5$ is S and $X_{18}$ is K. In some embodiments, $X_5$ is S and $X_{31}$ is K. In some embodiments, $X_5$ is S and $X_{35}$ is E.

In some embodiments, $X_{10}$ is Q and $X_{15}$ is E. In some embodiments, $X_{10}$ is Q and $X_{16}$ is L. In some embodiments, $X_{10}$ is Q and $X_{16}$ is k. In some embodiments, $X_{10}$ is Q and $X_{17}$ is H. In some embodiments, $X_{10}$ is Q and $X_{18}$ is K. In some embodiments, $X_{10}$ is Q and $X_{31}$ is K. In some embodiments, $X_{10}$ is Q and $X_{35}$ is E.

In some embodiments, $X_{15}$ is E and $X_{16}$ is L. In some embodiments, $X_{15}$ is E and $X_{16}$ is k. In some embodiments, $X_{15}$ is E and $X_{17}$ is H. In some embodiments, $X_{15}$ is E and $X_{18}$ is K. In some embodiments, $X_{15}$ is E and $X_{31}$ is K. In some embodiments, $X_{15}$ is E and $X_{35}$ is E.

In some embodiments, $X_{16}$ is L and $X_{17}$ is H. In some embodiments, $X_{16}$ is L and $X_{18}$ is K. In some embodiments, $X_{16}$ is L and $X_{31}$ is K. In some embodiments, $X_{16}$ is L and $X_{35}$ is E.

In some embodiments, $X_{16}$ is k and $X_{17}$ is H. In some embodiments, $X_{16}$ is k and $X_{18}$ is K. In some embodiments, $X_{16}$ is k and $X_{31}$ is K. In some embodiments, $X_{16}$ is k and $X_{35}$ is E.

In some embodiments, $X_{17}$ is H and $X_{18}$ is K. In some embodiments, $X_{17}$ is H and $X_{31}$ is K. In some embodiments, $X_{17}$ is H and $X_{35}$ is E.

In some embodiments, $X_{18}$ is K and $X_{31}$ is K. In some embodiments, $X_{18}$ is K and $X_{35}$ is E.

In some embodiments, $X_{31}$ is K and $X_{35}$ is E.

In some embodiments, certain amino acids represented by the consensus sequence of SEQ ID NO: 200 or SEQ ID NO: 201 include the following:

In some embodiments, $X_1$ is S, $X_5$ is S, and $X_{15}$ is E. In some embodiments, $X_1$ is S, $X_5$ is S, and $X_{16}$ is L. In some embodiments, $X_1$ is S, $X_5$ is S, and $X_{16}$ is k. In some embodiments, $X_1$ is S, $X_5$ is S, and $X_{17}$ is H. In some embodiments, $X_1$ is S, $X_5$ is S, and $X_{15}$ is K. In some embodiments, $X_1$ is S, $X_5$ is S, and $X_{31}$ is K. In some embodiments, $X_1$ is S and $X_{35}$ is E.

In some embodiments, $X_1$ is K, $X_5$ is S, and $X_{15}$ is E. In some embodiments, $X_1$ is K, $X_5$ is S, and $X_{16}$ is L. In some embodiments, $X_1$ is K, $X_5$ is S, and $X_{16}$ is k. In some embodiments, $X_1$ is K, $X_5$ is S, and $X_{17}$ is H. In some embodiments, $X_1$ is K, $X_5$ is S, and $X_{18}$ is K. In some embodiments, $X_1$ is K, $X_5$ is S, and $X_{31}$ is K. In some embodiments, $X_1$ is K, $X_5$ is S, and $X_{35}$ is E.

In some embodiments, $X_1$ is k, $X_5$ is S, and $X_{15}$ is E. In some embodiments, $X_1$ is k, $X_5$ is S, and $X_{16}$ is L. In some embodiments, $X_1$ is k, $X_5$ is S, and $X_{16}$ is k. In some embodiments, $X_1$ is k, $X_5$ is S, and $X_{17}$ is H. In some embodiments, $X_1$ is k, $X_5$ is S, and $X_{15}$ is K. In some embodiments, $X_1$ is k, $X_5$ is S, and $X_{31}$ is K. In some embodiments, $X_1$ is k, $X_5$ is S, and $X_{35}$ is E.

In some embodiments, $X_5$ is S, $X_{15}$ is E, and $X_{16}$ is L. In some embodiments, $X_5$ is S, $X_{15}$ is E, and $X_{16}$ is k. In some embodiments, $X_5$ is S, $X_{15}$ is E, and $X_{17}$ is H. In some embodiments, $X_5$ is S, $X_{15}$ is E, and $X_{18}$ is K. In some embodiments, $X_5$ is S, $X_{15}$ is E, and $X_{31}$ is K. In some embodiments, $X_5$ is S, $X_{15}$ is E, and $X_{35}$ is E.

In some embodiments, $X_{10}$ is Q, $X_{15}$ is E and $X_{16}$ is L. In some embodiments, $X_{10}$ is Q, and $X_{16}$ is k and $X_{17}$ is H. In some embodiments, $X_{10}$ is Q, $X_{18}$ is K, and $X_{31}$ is K. In some embodiments, $X_{10}$ is Q, $X_{31}$ is K and $X_{35}$ is E.

In some embodiments, $X_{15}$ is E, $X_{16}$ is L, and $X_{17}$ is H. In some embodiments, $X_{15}$ is E, $X_{16}$ is L, and $X_{18}$ is K. In some embodiments, $X_{15}$ is E, $X_{16}$ is L, and $X_{31}$ is K. In some embodiments, $X_{15}$ is E, $X_{16}$ is L, and $X_{35}$ is E.

In some embodiments, $X_{15}$ is E, $X_{16}$ is k, and $X_{17}$ is H. In some embodiments, $X_{15}$ is E, $X_{16}$ is k, and $X_{18}$ is K. In some embodiments, $X_{15}$ is E, $X_{16}$ is k, and $X_{31}$ is K. In some embodiments, $X_{15}$ is E, $X_{16}$ is k, and $X_{35}$ is E.

In some embodiments, $X_{16}$ is L, $X_{17}$ is H, and $X_{18}$ is K. In some embodiments, $X_{16}$ is L, $X_{17}$ is H, and $X_{31}$ is K. In some embodiments, $X_{16}$ is L, $X_{17}$ is H, and $X_{35}$ is E.

In some embodiments, $X_{16}$ is k, $X_{17}$ is H, and $X_{18}$ is K. In some embodiments, $X_{16}$ is k, $X_{17}$ is H, and $X_{31}$ is K. In some embodiments, $X_{16}$ is k, $X_{17}$ is H, and $X_{35}$ is E.

In some embodiments, $X_{17}$ is H, $X_{18}$ is K, and $X_{31}$ is K. In some embodiments, $X_{17}$ is H, $X_{18}$ is K, and $X_{35}$ is E.

In some embodiments, $X_{18}$ is K, $X_{31}$ is K, and $X_{35}$ is E.

In some embodiments, an isolated polypeptide of the disclosure comprises an amino acid sequence, or a pharmaceutically acceptable salt thereof, selected from the group consisting of amino acid sequences represented by the consensus sequence of SEQ ID NO: 202 $X_1$CNTX$_5$TCATX$_{10}$RLANX$_{15}$X$_{16}$X$_{17}$X$_{18}$SSNNFGPILPPTX$_{31}$VGSX$_{35}$TY-(OH/NH$_2$) (SEQ ID NO: 202), wherein:

$X_1$ is S, k, or K;
$X_8$ is S or A;
$X_{10}$ is Q or S;
$X_{15}$ is E or F;
$X_{16}$ is k, K or L;
$X_{17}$ is H, V, and Q;
$X_{18}$ is K, H, or R;
$X_{31}$ is K or N; and
$X_{35}$ is E or N;
each K independently represents an L-lysine optionally covalently bound to a lipophilic substituent, optionally via a spacer;
each k independently represents a D-lysine optionally covalently bound to a lipophilic substituent, optionally via a spacer;
wherein the two cysteine residues of $X_1$CNTX$_5$TC (SEQ ID NO: 308) are optionally further bound by a disulfide bridge; and
with the proviso that if $X_{31}$ is N, then $X_{35}$ is E, or if $X_{35}$ is N, then $X_{31}$ is K.

In some embodiments, $X_{31}$ is K. In some embodiments, $X_{31}$ is N.

In some embodiments, $X_{35}$ is E. In some embodiments, $X_{35}$ is N.

In some embodiments, an isolated polypeptide of the disclosure comprises an amino acid sequence, or a pharmaceutically acceptable salt thereof, selected from the group consisting of amino acid sequences represented by the consensus sequence of SEQ ID NO: 203: $X_1$CNTX$_5$TCATX$_{10}$RLANX$_{15}$X$_{16}$X$_{17}$X$_{18}$SSNNFGPILPPTKVGSETY-(OH/NH$_2$) (SEQ ID NO: 203), wherein:

$X_1$ is S, k, or K;
$X_8$ is S or A;
$X_{10}$ is Q or S;
$X_{15}$ is E or F;
$X_{16}$ is k, K or L;
$X_{17}$ is H, V, and Q; and
$X_{18}$ is K, H, or R;
each K independently represents an L-lysine optionally covalently bound to a lipophilic substituent, optionally via a spacer;
each k independently represents a D-lysine optionally covalently bound to a lipophilic substituent, optionally via a spacer;
wherein the two cysteine residues of $X_1$CNTX$_5$TC (SEQ ID NO: 308) are optionally further bound by a disulfide bridge.

In some embodiments, certain amino acids represented by the consensus sequence of SEQ ID NO: 202 or SEQ ID NO: 203 include the following:

In some embodiments, carboxy terminal amino acid 37 is Y—(NH$_2$). In some embodiments, carboxy terminal amino acid 37 is Y—(OH).

In some embodiments, $X_1$ is S. In some embodiments, $X_1$ is K. In some embodiments, $X_1$ is k.

In some embodiments, $X_5$ is S. In some embodiments, $X_8$ is A.

In some embodiments, $X_{10}$ is Q. In some embodiments, $X_{10}$ is S.

In some embodiments, $X_{15}$ is E. In some embodiments, $X_{15}$ is F.

In some embodiments, $X_{16}$ is L. In some embodiments, $X_{16}$ is K. In some embodiments, $X_{16}$ is k.

In some embodiments, $X_{17}$ is H. In some embodiments, $X_{17}$ is V. In some embodiments, $X_{17}$ is Q.

In some embodiments, $X_{18}$ is K. In some embodiments, $X_{18}$ is H. In some embodiments, $X_{18}$ is R.

In some embodiments, $X_{31}$ is K. In some embodiments, $X_{31}$ is N.

In some embodiments, $X_{35}$ is E. In some embodiments, $X_{35}$ is N.

In some embodiments, certain amino acids represented by the consensus sequence of SEQ ID NO: 202 or SEQ ID NO: 203 include the following:

In some embodiments, $X_1$ is S and $X_5$ is S. In some embodiments, $X_1$ is S and $X_{10}$ is E. In some embodiments, $X_1$ is S and $X_{16}$ is L. In some embodiments, $X_1$ is S and $X_{16}$ is k. In some embodiments, $X_1$ is S and $X_{17}$ is H. In some embodiments, $X_1$ is S and $X_{18}$ is K. In some embodiments, $X_1$ is S and $X_{31}$ is K. In some embodiments, $X_1$ is S and $X_{35}$ is E.

In some embodiments, $X_1$ is K and $X_5$ is S. In some embodiments, $X_1$ is K and $X_{15}$ is E. In some embodiments, $X_1$ is K and $X_{16}$ is L. In some embodiments, $X_1$ is K and $X_{16}$ is k. In some embodiments, $X_1$ is K and $X_{17}$ is H. In some embodiments, $X_1$ is K and $X_{18}$ is K. In some embodiments, $X_1$ is K and $X_{31}$ is K. In some embodiments, $X_1$ is K and $X_{35}$ is E.

In some embodiments, $X_5$ is S and $X_{15}$ is E. In some embodiments, $X_5$ is S and $X_{16}$ is L. In some embodiments, $X_5$ is S and $X_{16}$ is k. In some embodiments, $X_5$ is S and $X_{17}$ is H. In some embodiments, $X_5$ is S and $X_{18}$ is K. In some embodiments, $X_5$ is S and $X_{31}$ is K. In some embodiments, $X_5$ is S and $X_{35}$ is E.

In some embodiments, $X_{10}$ is Q and $X_{15}$ is E. In some embodiments, $X_{10}$ is Q and $X_{16}$ is L. In some embodiments, $X_{10}$ is Q and $X_{16}$ is k. In some embodiments, $X_{10}$ is Q and $X_{17}$ is H. In some embodiments, $X_{10}$ is Q and $X_{18}$ is K. In some embodiments, $X_{10}$ is Q and $X_{31}$ is K. In some embodiments, $X_{10}$ is Q and $X_{35}$ is E.

In some embodiments, $X_{15}$ is E and $X_{16}$ is L. In some embodiments, $X_{15}$ is E and $X_{16}$ is k. In some embodiments, $X_{15}$ is E and $X_{17}$ is H. In some embodiments, $X_{15}$ is E and $X_{18}$ is K. In some embodiments, $X_{15}$ is E and $X_{31}$ is K. In some embodiments, $X_{15}$ is E and $X_{35}$ is E.

In some embodiments, $X_{16}$ is L and $X_{17}$ is H. In some embodiments, $X_{16}$ is L and $X_{18}$ is K. In some embodiments, $X_{16}$ is L and $X_{31}$ is K. In some embodiments, $X_{16}$ is L and $X_{35}$ is E.

In some embodiments, $X_{16}$ is k and $X_{17}$ is H. In some embodiments, $X_{16}$ is k and $X_{18}$ is K. In some embodiments, $X_{16}$ is k and $X_{31}$ is K. In some embodiments, $X_{16}$ is k and $X_{35}$ is E.

In some embodiments, $X_{17}$ is H and $X_{18}$ is K. In some embodiments, $X_{17}$ is H and $X_{31}$ is K. In some embodiments, $X_{17}$ is H and $X_{35}$ is E.

In some embodiments, $X_{18}$ is K and $X_{31}$ is K. In some embodiments, $X_{18}$ is K and $X_{35}$ is E.

In some embodiments, $X_{31}$ is K and $X_{35}$ is E.

In some embodiments, certain amino acids represented by the consensus sequence of SEQ ID NO: 202 or SEQ ID NO: 203 include the following:

In some embodiments, $X_1$ is S, $X_5$ is S, and $X_{10}$ is Q. In some embodiments, $X_1$ is S, $X_5$ is S, and $X_{15}$ is E. In some embodiments, $X_1$ is S, $X_5$ is S, and $X_{16}$ is L. In some embodiments, $X_1$ is S, $X_5$ is S, and $X_{16}$ is k. In some embodiments, $X_1$ is S, $X_5$ is S, and $X_{17}$ is H. In some embodiments, $X_1$ is S, $X_5$ is S, and $X_{18}$ is K. In some embodiments, $X_1$ is S, $X_5$ is S, and $X_{31}$ is K. In some embodiments, $X_1$ is S and $X_{35}$ is E.

In some embodiments, $X_1$ is K, $X_5$ is S, and $X_{10}$ is Q. In some embodiments, $X_1$ is K, $X_5$ is S, and $X_{15}$ is E. In some embodiments, $X_1$ is K, $X_5$ is S, and $X_{16}$ is L. In some embodiments, $X_1$ is K, $X_5$ is S, and $X_{16}$ is k. In some embodiments, $X_1$ is K, $X_5$ is S, and $X_{17}$ is H. In some embodiments, $X_1$ is K, $X_5$ is S, and $X_{18}$ is K. In some embodiments, $X_1$ is K, $X_5$ is S, and $X_{31}$ is K. In some embodiments, $X_1$ is K, $X_5$ is S, and $X_{35}$ is E.

In some embodiments, $X_5$ is S, $X_{10}$ is Q, and $X_{15}$ is E. In some embodiments, $X_5$ is S, $X_{10}$ is Q, and $X_{16}$ is L. In some embodiments, $X_5$ is S, $X_{10}$ is Q, and $X_{16}$ is k. In some embodiments, $X_5$ is S, $X_{10}$ is Q, and $X_{17}$ is H. In some embodiments, $X_5$ is S, $X_{10}$ is Q, and $X_{18}$ is K. In some embodiments, $X_5$ is S, $X_{10}$ is Q, and $X_{31}$ is K. In some embodiments, $X_5$ is S, $X_{10}$ is Q, and $X_{35}$ is E.

In some embodiments, $X_{10}$ is Q, $X_{15}$ is E, and $X_{16}$ is L. In some embodiments, $X_{10}$ is Q, $X_{15}$ is E, and $X_{16}$ is k. In some embodiments, $X_{10}$ is Q, $X_{15}$ is E, and $X_{17}$ is H. In some embodiments, $X_{10}$ is Q, $X_{15}$ is E, and $X_{18}$ is K. In some embodiments, $X_{10}$ is Q, $X_{15}$ is E, and $X_{31}$ is K. In some embodiments, $X_{10}$ is Q, $X_{15}$ is E, and $X_{35}$ is E.

In some embodiments, $X_{15}$ is E, $X_{16}$ is L and $X_{17}$ is H. In some embodiments, $X_{15}$ is E, $X_{16}$ is L, and $X_{18}$ is K. In some embodiments, $X_{15}$ is E, $X_{16}$ is L, and $X_{31}$ is K. In some embodiments, $X_{15}$ is E, $X_{16}$ is L, and $X_{35}$ is E.

In some embodiments, $X_{15}$ is E, $X_{16}$ is k and $X_{17}$ is H. In some embodiments, $X_{15}$ is E, $X_{16}$ is k, and $X_{18}$ is K. In some embodiments, $X_{15}$ is E, $X_{16}$ is k, and $X_{31}$ is K. In some embodiments, $X_{15}$ is E, $X_{16}$ is k, and $X_{35}$ is E.

In some embodiments, $X_{16}$ is L, $X_{17}$ is H, and $X_{18}$ is K. In some embodiments, $X_{16}$ is L, $X_{17}$ is H, and $X_{31}$ is K. In some embodiments, $X_{16}$ is L, $X_{17}$ is H, and $X_{35}$ is E.

In some embodiments, $X_{16}$ is k, $X_{17}$ is H, and $X_{18}$ is K. In some embodiments, $X_{16}$ is k, $X_{17}$ is H, and $X_{31}$ is K. In some embodiments, $X_{16}$ is k, $X_{17}$ is H, and $X_{35}$ is E.

In some embodiments, $X_{17}$ is H, $X_{18}$ is K, and $X_{31}$ is K. In some embodiments, $X_{17}$ is H, $X_{18}$ is K, and $X_{35}$ is E.

In some embodiments, $X_{18}$ is K, $X_{31}$ is K, and $X_{35}$ is E.

In some embodiments, an isolated polypeptide of the disclosure comprises an amino acid sequence, or a pharmaceutically acceptable salt thereof, selected from the group consisting of amino acid sequences represented by the consensus sequence of SEQ ID NO: 204: $X_1$CNTSTCAT$X_{10}$RLAN$X_{15}X_{16}X_{17}$XKSSNNFGPILPPTKVGS$X_{35}$TY-(OH/NH$_2$) (SEQ ID NO: 204), wherein:
$X_1$ is S, K or k;
$X_{10}$ is Q or S;
$X_{15}$ is E or F;
$X_{16}$ is L, K or k;
$X_{17}$ is H, V or Q; and
$X_{35}$ is E or N;
each K independently represents an L-lysine optionally covalently bound to a lipophilic substituent, optionally via a spacer;
each k independently represents a D-lysine optionally covalently bound to a lipophilic substituent, optionally via a spacer;
wherein the two cysteine residues of $X_1$CNTSTC (SEQ ID NO: 309) are optionally further bound by a disulfide bridge.

In some embodiments, $X_{35}$ is E. In some embodiments, $X_{35}$ is N.

In some embodiments, an isolated polypeptide of the disclosure comprises an amino acid sequence, or a pharmaceutically acceptable salt thereof, selected from the group consisting of amino acid sequences represented by the consensus sequence of SEQ ID NO: 205: $X_1$CNTSTCAT$X_{10}$RLAN$X_{15}X_{16}X_{17}$KSSNNFGPILPPTKVGSETY-(OH/NH$_2$) (SEQ ID NO: 205), wherein:
$X_1$ is S, K or k;
$X_{10}$ is Q or S;
$X_{15}$ is E or F;
$X_{16}$ is L, K or k; and
$X_{17}$ is H, V or Q;
each K independently represents an L-lysine optionally covalently bound to a lipophilic substituent, optionally via a spacer;
each k independently represents a D-lysine optionally covalently bound to a lipophilic substituent, optionally via a spacer; and
wherein the two cysteine residues of $X_1$CNTSTC (SEQ ID NO: 309) are optionally further bound by a disulfide bridge.

In some embodiments, certain amino acids represented by the consensus sequence of SEQ ID NO: 204 or SEQ ID NO: 205 include the following:

In some embodiments, carboxy terminal amino acid 37 is Y—(NH$_2$). In some embodiments, carboxy terminal amino acid 37 is Y—(OH).

In some embodiments, $X_1$ is S. In some embodiments, $X_1$ is K. In some embodiments, $X_1$ is k.

In some embodiments, $X_{10}$ is Q. In some embodiments, $X_{10}$ is S.

In some embodiments, $X_{15}$ is E. In some embodiments, $X_{15}$ is F.

In some embodiments, $X_{16}$ is L. In some embodiments, $X_{16}$ is K. In some embodiments, $X_{16}$ is k.

In some embodiments, $X_{17}$ is H. In some embodiments, $X_{17}$ is V. In some embodiments, $X_{17}$ is Q.

In some embodiments, $X_{35}$ is E. In some embodiments, $X_{35}$ is N.

In some embodiments, certain amino acids represented by the consensus sequence of SEQ ID NO: 204 or SEQ ID NO: 205 include the following:

In some embodiments, $X_1$ is S and $X_{10}$ is Q. In some embodiments, $X_1$ is S and $X_{10}$ is S. In some embodiments, $X_1$ is S and $X_{15}$ is E. In some embodiments, $X_1$ is S and $X_{15}$ is F. In some embodiments, $X_1$ is S and $X_{16}$ is L. In some embodiments, $X_1$ is S and $X_{16}$ is K. In some embodiments, $X_1$ is S and $X_{16}$ is k. In some embodiments, $X_1$ is S and $X_{17}$ is H. In some embodiments, $X_1$ is S and $X_{17}$ is V. In some embodiments, $X_1$ is S and $X_{17}$ is Q. In some embodiments, $X_1$ is S and $X_{35}$ is E. In some embodiments, $X_1$ is S and $X_{35}$ is N.

In some embodiments, $X_1$ is K and $X_{10}$ is Q. In some embodiments, $X_1$ is K and $X_{10}$ is S. In some embodiments, $X_1$ is K and $X_{15}$ is E. In some embodiments, $X_1$ is K and $X_{15}$ is F. In some embodiments, $X_1$ is K and $X_{16}$ is L. In some embodiments, $X_1$ is K and $X_{16}$ is K. In some embodiments, $X_1$ is K and $X_{16}$ is k. In some embodiments, $X_1$ is K and $X_{17}$ is H. In some embodiments, $X_1$ is K and $X_{17}$ is V. In some embodiments, $X_1$ is K and $X_{17}$ is Q. In some embodiments, $X_1$ is K and $X_{35}$ is E. In some embodiments, $X_1$ is K and $X_{35}$ is N.

In some embodiments, $X_1$ is k and $X_{10}$ is Q. In some embodiments, $X_1$ is k and $X_{10}$ is S. In some embodiments, $X_1$ is k and $X_{15}$ is E. In some embodiments, $X_1$ is k and $X_{15}$ is F. In some embodiments, $X_1$ is k and $X_{16}$ is L. In some embodiments, $X_1$ is k and $X_{16}$ is K. In some embodiments, $X_1$ is k and $X_{16}$ is k. In some embodiments, $X_1$ is k and $X_{17}$ is H. In some embodiments, $X_1$ is k and $X_{17}$ is V. In some embodiments, $X_1$ is k and $X_{17}$ is Q. In some embodiments, $X_1$ is k and $X_{35}$ is E. In some embodiments, $X_1$ is k and $X_{35}$ is N.

In some embodiments, $X_{10}$ is Q and $X_{15}$ is E. In some embodiments, $X_{10}$ is Q and $X_{15}$ is F. In some embodiments, $X_{10}$ is Q and $X_{16}$ is L. In some embodiments, $X_{10}$ is Q and $X_{16}$ is K. In some embodiments, $X_{10}$ is Q and $X_{16}$ is k. In some embodiments, $X_{10}$ is Q and $X_{17}$ is H. In some embodiments, $X_{10}$ is Q and $X_{17}$ is V. In some embodiments, $X_{10}$ is Q and $X_{17}$ is Q. In some embodiments, $X_{10}$ is Q and $X_{35}$ is E. In some embodiments, $X_{10}$ is Q and $X_{35}$ is N.

In some embodiments, $X_{10}$ is S and $X_{15}$ is E. In some embodiments, $X_{10}$ is S and $X_{15}$ is F. In some embodiments, $X_{10}$ is S and $X_{16}$ is L. In some embodiments, $X_{10}$ is S and $X_{16}$ is K. In some embodiments, $X_{10}$ is S and $X_{16}$ is k. In some embodiments, $X_{10}$ is S and $X_{17}$ is H. In some embodiments, $X_{10}$ is S and $X_{17}$ is V. In some embodiments, $X_{10}$ is S and $X_{17}$ is Q. In some embodiments, $X_{10}$ is S and $X_{35}$ is E. In some embodiments, $X_{10}$ is S and $X_{35}$ is N.

In some embodiments, $X_{15}$ is E and $X_{16}$ is L. In some embodiments, $X_{15}$ is E and $X_{16}$ is K. In some embodiments, $X_{15}$ is E and $X_{16}$ is k. In some embodiments, $X_{15}$ is E and $X_{17}$ is H. In some embodiments, $X_{15}$ is E and $X_{17}$ is V. In some embodiments, $X_{15}$ is E and $X_{17}$ is Q. In some embodiments, $X_{15}$ is E and $X_{35}$ is E. In some embodiments, $X_{15}$ is E and $X_{35}$ is N.

In some embodiments, $X_{15}$ is F and $X_{16}$ is L. In some embodiments, $X_{15}$ is F and $X_{16}$ is K. In some embodiments, $X_{15}$ is F and $X_{16}$ is k. In some embodiments, $X_{15}$ is F and $X_{17}$ is H. In some embodiments, $X_{15}$ is F and $X_{17}$ is V. In some embodiments, $X_{15}$ is F and $X_{17}$ is Q. In some embodiments, $X_{15}$ is F and $X_{35}$ is E. In some embodiments, $X_{15}$ is F and $X_{35}$ is N.

In some embodiments, $X_{16}$ is L and $X_{17}$ is H. In some embodiments, $X_{16}$ is L and $X_{17}$ is V. In some embodiments, $X_{16}$ is L and $X_{17}$ is Q. In some embodiments, $X_{16}$ is L and $X_{35}$ is E. In some embodiments, $X_{16}$ is L and $X_{35}$ is N.

In some embodiments, $X_{16}$ is K and $X_{17}$ is H. In some embodiments, $X_{16}$ is K and $X_{17}$ is V. In some embodiments, $X_{16}$ is K and $X_{17}$ is Q. In some embodiments, $X_{16}$ is K and $X_{35}$ is E. In some embodiments, $X_{16}$ is K and $X_{35}$ is N.

In some embodiments, $X_{16}$ is k and $X_{17}$ is H. In some embodiments, $X_{16}$ is k and $X_{17}$ is V. In some embodiments, $X_{16}$ is k and $X_{17}$ is Q. In some embodiments, $X_{16}$ is k and $X_{35}$ is E. In some embodiments, $X_{16}$ is k and $X_{35}$ is N.

In some embodiments, $X_{17}$ is H and $X_{35}$ is E. In some embodiments, $X_{17}$ is H and $X_{35}$ is N.

In some embodiments, $X_{17}$ is V and $X_{35}$ is E. In some embodiments, $X_{17}$ is V and $X_{35}$ is N.

In some embodiments, $X_{17}$ is Q and $X_{35}$ is E. In some embodiments, $X_{17}$ is Q and $X_{35}$ is N.

In some embodiments, an isolated polypeptide of the disclosure comprises an amino acid sequence, or a pharmaceutically acceptable salt thereof, selected from the group consisting of amino acid sequences represented by the consensus sequence of SEQ ID NO: 206: SCNTSTCATQRLANX$_{15}$X$_{16}$X$_{17}$KSSNNFGPILPPTKVG-SX$_{35}$TY-(OH/NH$_2$) (SEQ ID NO: 206), wherein:

$X_{15}$ is E or F;
$X_{16}$ is L, K or k;
$X_{17}$ is H, V or Q; and
$X_{35}$ is E or N;
each K independently represents an L-lysine optionally covalently bound to a lipophilic substituent, optionally via a spacer;
each k independently represents a D-lysine optionally covalently bound to a lipophilic substituent, optionally via a spacer; and
wherein the two cysteine residues of SCNTSTC (SEQ ID NO: 310) are optionally further bound by a disulfide bridge.

In some embodiments, $X_{35}$ is E. In some embodiments, $X_{35}$ is N.

In some embodiments, an isolated polypeptide of the disclosure comprises an amino acid sequence, or a pharmaceutically acceptable salt thereof, selected from the group consisting of amino acid sequences represented by the consensus sequence of SEQ ID NO: 207:

(SEQ ID NO: 207)
SCNTSTCATQRLANX$_{15}$X$_{16}$X$_{17}$KSSNNFGPILPPTKVGSETY-(OH/NH$_2$), wherein:
$X_{15}$ is E or F;
$X_{16}$ is L, K or k; and
$X_{17}$ is H, V or Q;
each K independently represents an L-lysine optionally covalently bound to a lipophilic substituent, optionally via a spacer;
each k independently represents a D-lysine optionally covalently bound to a lipophilic substituent, optionally via a spacer; and
wherein the two cysteine residues of SC*NTSTC* are optionally further bound by a disulfide bridge.

In some embodiments, certain amino acids represented by the consensus sequence of SEQ ID NO:206 or SEQ ID NO:207 include the following:

In some embodiments, carboxy terminal amino acid 37 is Y—(NH$_2$). In some embodiments, carboxy terminal amino acid 37 is Y—(OH).

In some embodiments, $X_{15}$ is E. In some embodiments, $X_{15}$ is F.

In some embodiments, $X_{16}$ is L. In some embodiments, $X_{16}$ is K. In some embodiments, $X_{16}$ is k.

In some embodiments, $X_{17}$ is H. In some embodiments, $X_{17}$ is V. In some embodiments, $X_{17}$ is Q.

In some embodiments, $X_{15}$ is E and $X_{16}$ is L. In some embodiments, $X_{15}$ is E and $X_{16}$ is K. In some embodiments, $X_{15}$ is E and $X_{16}$ is k. In some embodiments, $X_{15}$ is E and $X_{17}$ is H. In some embodiments, $X_{15}$ is E and $X_{17}$ is V. In some embodiments, $X_{15}$ is E and $X_{17}$ is Q. In some embodiments, $X_{15}$ is E and $X_{35}$ is E. In some embodiments, $X_{15}$ is E and $X_{35}$ is N.

In some embodiments, $X_{15}$ is F and $X_{16}$ is L. In some embodiments, $X_{15}$ is F and $X_{16}$ is K. In some embodiments, $X_{15}$ is F and $X_{16}$ is k. In some embodiments, $X_{15}$ is F and $X_{17}$ is H. In some embodiments, $X_{15}$ is F and $X_{17}$ is V. In some embodiments, $X_{15}$ is F and $X_{17}$ is Q. In some embodiments, $X_{15}$ is F and $X_{35}$ is E. In some embodiments, $X_{15}$ is F and $X_{35}$ is N.

In some embodiments, $X_{16}$ is L and $X_{17}$ is H. In some embodiments, $X_{16}$ is L and $X_{17}$ is V. In some embodiments, $X_{16}$ is L and $X_{17}$ is Q. In some embodiments, $X_{16}$ is L and $X_{35}$ is E. In some embodiments, $X_{16}$ is L and $X_{35}$ is N.

In some embodiments, $X_{16}$ is K and $X_{17}$ is H. In some embodiments, $X_{16}$ is K and $X_{17}$ is V. In some embodiments, $X_{16}$ is K and $X_{17}$ is Q. In some embodiments, $X_{16}$ is K and $X_{35}$ is E. In some embodiments, $X_{16}$ is K and $X_{35}$ is N.

In some embodiments, $X_{16}$ is k and $X_{17}$ is H. In some embodiments, $X_{16}$ is k and $X_{17}$ is V. In some embodiments, $X_{16}$ is k and $X_{17}$ is Q. In some embodiments, $X_{16}$ is k and $X_{35}$ is E. In some embodiments, $X_{16}$ is k and $X_{35}$ is N.

In some embodiments, $X_{17}$ is H and $X_{35}$ is E. In some embodiments, $X_{17}$ is H and $X_{35}$ is N.

In some embodiments, $X_{17}$ is V and $X_{35}$ is E. In some embodiments, $X_{17}$ is V and $X_{35}$ is N.

In some embodiments, $X_{17}$ is Q and $X_{35}$ is E. In some embodiments, $X_{17}$ is Q and $X_{35}$ is N.

In some embodiments, an isolated polypeptide of the disclosure comprises an amino acid sequence selected from the group consisting of:

```
                                    (SEQ ID NO: 127)
SC*NTSTC*ATQRLANFkHKSSNNFGPILPPTKVGSETY-(NH2),
``` which is also referred to herein as Compound A127;

```
                                    (SEQ ID NO: 57)
SC*NTSTC*ATQRLANELHKSSNNFGPILPPTKVGSETY-(NH2),
``` which is also referred to herein as Compound A57;

```
                                    (SEQ ID NO: 128)
SC*NTSTC*ATQRLANEKHKSSNNFGPILPPTKVGSETY-(NH2),
``` which is also referred to herein as Compound A128;

```
                                    (SEQ ID NO: 129)
SC*NTSTC*ATQRLANEkHKSSNNFGPILPPTKVGSETY-(NH2),
``` which is also referred to herein as Compound A129; and

```
                                    (SEQ ID NO: 43)
SC*NTSTC*ATQRLANFLVKSSNEFGPILPPTKVGSETY-(NH2),
``` which is also referred to herein as Compound A43.

In some embodiments, an isolated polypeptide of the disclosure comprises an amino acid sequence: SC*NTSTC*ATQRLANELHKSSNNFGPILPPTKVGSETY-(NH$_2$) (SEQ ID NO: 57), which is also referred to herein as Compound A57.

In some embodiments, an isolated polypeptide of the disclosure comprises an amino acid sequence: SC*NTSTC*ATQRLANFkHKSSNNFGPILPPTKVGSETY-(NH$_2$) (SEQ ID NO: 127), which is also referred to herein as Compound A127.

In some embodiments, an isolated polypeptide of the disclosure comprises an amino acid sequence: SC*NTSTC*ATQRLANEk*((γGlu)$_2$-CO(CH$_2$)$_{14}$CH$_3$) HKSSNNFGPILPP TKVGSETY-NH$_2$ (SEQ ID NO: 27), which is also referred to herein as Compound A27.

In some embodiments, an isolated polypeptide of the disclosure comprises an amino acid sequence, or a pharmaceutically acceptable salt thereof, selected from the group consisting of amino acid sequences represented by the consensus sequence of SEQ ID NO:208: $X_1$CNTSTCATX$_{10}$RLANX$_{15}$X$_{16}$X$_{17}$XKSSNNFGPILPP-TKVGSX$_{35}$TY-(OH/NH$_2$) (SEQ ID NO:208), wherein:

$X_1$ is K or k;

$X_{10}$ is Q or S;

$X_{15}$ is E or F;

$X_{16}$ is L, K or k;

$X_{17}$ is H, V or Q; and $X_{35}$ is E or N;

each K independently represents an L-lysine optionally covalently bound to a lipophilic substituent, optionally via a spacer;

each k independently represents a D-lysine optionally covalently bound to a lipophilic substituent, optionally via a spacer; and wherein the two cysteine residues of $X_1$CNTSTC (SEQ ID NO: 318) are optionally further bound by a disulfide bridge.

In some embodiments, $X_{35}$ is E. In some embodiments, $X_{35}$ is N.

In some embodiments, an isolated polypeptide of the disclosure comprises an amino acid sequence, or a pharmaceutically acceptable salt thereof, selected from the group consisting of amino acid sequences represented by the consensus sequence of SEQ ID NO:209: $X_1$CNTSTCATX$_{10}$RLANX$_{15}$X$_{16}$X$_{17}$XKSSNNFGPILPP-TKVGSETY-(OH/NH$_2$) (SEQ ID NO:209), wherein:

$X_1$ is K or k;

$X_{10}$ is Q or S;

$X_{15}$ is E or F;

$X_{16}$ is L, K or k; and $X_{17}$ is H, V or Q;

each K independently represents an L-lysine optionally covalently bound to a lipophilic substituent, optionally via a spacer;

each k independently represents a D-lysine optionally covalently bound to a lipophilic substituent, optionally via a spacer; and wherein the two cysteine residues of $X_1$CNTSTC (SEQ ID NO: 318) are optionally further bound by a disulfide bridge.

In some embodiments, certain amino acids represented by the consensus sequence of SEQ ID NO:208 or SEQ ID NO:209 include the following:

In some embodiments, carboxy terminal amino acid 37 is Y—(NH$_2$). In some embodiments, carboxy terminal amino acid 37 is Y—(OH).

In some embodiments, $X_1$ is K. In some embodiments, $X_1$ is k.

In some embodiments, $X_{10}$ is Q. In some embodiments, $X_{10}$ is S.

In some embodiments, $X_{15}$ is E. In some embodiments, $X_{15}$ is F.

In some embodiments, $X_{16}$ is L. In some embodiments, $X_{16}$ is K. In some embodiments, $X_{16}$ is k.

In some embodiments, $X_{17}$ is H. In some embodiments, $X_{17}$ is V. In some embodiments, $X_{17}$ is Q.

In some embodiments, $X_1$ is K and $X_{10}$ is Q. In some embodiments, $X_1$ is K and $X_{10}$ is S. In some embodiments, $X_1$ is K and $X_{15}$ is E. In some embodiments, $X_1$ is K and $X_{15}$ is F. In some embodiments, $X_1$ is K and $X_{16}$ is L. In some embodiments, $X_1$ is K and $X_{16}$ is K. In some embodiments, $X_1$ is K and $X_{16}$ is k. In some embodiments, $X_1$ is K and $X_{17}$ is H. In some embodiments, $X_1$ is K and $X_{17}$ is V. In some embodiments, $X_1$ is K and $X_{17}$ is Q. In some embodiments, $X_1$ is K and $X_{35}$ is E. In some embodiments, $X_1$ is K and $X_{35}$ is N.

In some embodiments, $X_1$ is k and $X_{10}$ is Q. In some embodiments, $X_1$ is k and $X_{10}$ is S. In some embodiments, $X_1$ is k and $X_{15}$ is E. In some embodiments, $X_1$ is k and $X_{15}$ is F. In some embodiments, $X_1$ is k and $X_{16}$ is L. In some embodiments, $X_1$ is k and $X_{16}$ is K. In some embodiments, $X_1$ is k and $X_{16}$ is k. In some embodiments, $X_1$ is k and $X_{17}$ is H. In some embodiments, $X_1$ is k and $X_{17}$ is V. In some embodiments, $X_1$ is k and $X_{17}$ is Q. In some embodiments, $X_1$ is k and $X_{35}$ is E. In some embodiments, $X_1$ is k and $X_{35}$ is N.

In some embodiments, $X_{10}$ is Q and $X_{15}$ is E. In some embodiments, $X_{10}$ is Q and $X_{15}$ is F. In some embodiments, $X_{10}$ is Q and $X_{16}$ is L. In some embodiments, $X_{10}$ is Q and $X_{16}$ is K. In some embodiments, $X_{10}$ is Q and $X_{16}$ is k. In some embodiments, $X_{10}$ is Q and $X_{17}$ is H. In some embodiments, $X_{10}$ is Q and $X_{17}$ is V. In some embodiments, $X_{10}$ is Q and $X_{17}$ is Q. In some embodiments, $X_{10}$ is Q and $X_{35}$ is E. In some embodiments, $X_{10}$ is Q and $X_{35}$ is N.

In some embodiments, $X_{10}$ is S and $X_{15}$ is E. In some embodiments, $X_{10}$ is S and $X_{15}$ is F. In some embodiments, $X_{10}$ is S and $X_{16}$ is L. In some embodiments, $X_{10}$ is S and $X_{16}$ is K. In some embodiments, $X_{10}$ is S and $X_{16}$ is k. In some embodiments, $X_{10}$ is S and $X_{17}$ is H. In some embodiments, $X_{10}$ is S and $X_{17}$ is V. In some embodiments, $X_{10}$ is S and $X_{17}$ is Q. In some embodiments, $X_{10}$ is S and $X_{35}$ is E. In some embodiments, $X_{10}$ is S and $X_{35}$ is N.

In some embodiments, $X_{15}$ is E and $X_{16}$ is L. In some embodiments, $X_{15}$ is E and $X_{16}$ is K. In some embodiments, $X_{15}$ is E and $X_{16}$ is k. In some embodiments, $X_{15}$ is E and $X_{17}$ is H. In some embodiments, $X_{15}$ is E and $X_{17}$ is V. In some embodiments, $X_{15}$ is E and $X_{17}$ is Q. In some embodiments, $X_{15}$ is E and $X_{35}$ is E. In some embodiments, $X_{15}$ is E and $X_{35}$ is N.

In some embodiments, $X_{15}$ is F and $X_{16}$ is L. In some embodiments, $X_{15}$ is F and $X_{16}$ is K. In some embodiments, $X_{15}$ is F and $X_{16}$ is k. In some embodiments, $X_{15}$ is F and $X_{17}$ is H. In some embodiments, $X_{15}$ is F and $X_{17}$ is V. In some embodiments, $X_{15}$ is F and $X_{17}$ is Q. In some embodiments, $X_{15}$ is F and $X_{35}$ is E. In some embodiments, $X_{15}$ is F and $X_{35}$ is N.

In some embodiments, $X_{16}$ is L and $X_{17}$ is H. In some embodiments, $X_{16}$ is L and $X_{17}$ is V. In some embodiments, $X_{16}$ is L and $X_{17}$ is Q. In some embodiments, $X_{16}$ is L and $X_{35}$ is E. In some embodiments, $X_{16}$ is L and $X_{35}$ is N.

In some embodiments, $X_{16}$ is K and $X_{17}$ is H. In some embodiments, $X_{16}$ is K and $X_{17}$ is V. In some embodiments, $X_{16}$ is K and $X_{17}$ is Q. In some embodiments, $X_{16}$ is K and $X_{35}$ is E. In some embodiments, $X_{16}$ is K and $X_{35}$ is N.

In some embodiments, $X_{16}$ is K and $X_{17}$ is H. In some embodiments, $X_{16}$ is K and $X_{17}$ is V. In some embodiments, $X_{16}$ is K and $X_{17}$ is Q. In some embodiments, $X_{16}$ is K and $X_{35}$ is E. In some embodiments, $X_{16}$ is K and $X_{35}$ is N.

In some embodiments, $X_{17}$ is H and $X_{35}$ is E. In some embodiments, $X_{17}$ is H and $X_{35}$ is N.

In some embodiments, $X_{17}$ is V and $X_{35}$ is E. In some embodiments, $X_{17}$ is V and $X_{35}$ is N.

In some embodiments, $X_{17}$ is Q and $X_{35}$ is E. In some embodiments, $X_{17}$ is Q and $X_{35}$ is N.

In some embodiments, an isolated polypeptide of the disclosure comprises an amino acid sequence selected from the group consisting of:

```
                                        (SEQ ID NO: 130)
KC*NTSTC*ATQRLANELHKSSNNFGPILPPTKVGSETY-(NH2),
``` which is also referred to herein as Compound A130; and

```
                                        (SEQ ID NO: 131)
KC*NTSTC*ATQRLANFLQKSSNNFGPILPPTKVGSETY-(NH2),
``` which is also referred to herein as Compound A131.

In some embodiments, $X_{31}$ is K. In some embodiments, $X_{31}$ is N.

In some embodiments, $X_{35}$ is E. In some embodiments, $X_{35}$ is N.

5. Conjugation of a Lipophilic Substituent to any of the Peptides, Optionally Via a Spacer In some embodiments, any of the disclosed polypeptides is optionally substituted with one or more lipophilic substituents each optionally via a spacer, wherein "lipophilic substituent" and "spacer" are defined herein. In some embodiments, any of the disclosed polypeptides, comprising an amino acid sequence selected from the group consisting of amino acid sequences represented by any of the consensus sequences of SEQ ID NO: 1 through SEQ ID NO: 143, either comprises one or more lipophilic substituents each optionally via a spacer, or can be modified, or further modified, by covalent attachment of one or more lipophilic substituents each optionally via a spacer. In some embodiments, the lipophilic substituent may be attached to an amino group of the polypeptide (e.g., an ε-amino group of a lysine residue) by means of a carboxyl group of the lipophilic substituent, or optionally an amino group of the spacer, wherein a carboxyl group of the spacer forms an amide bond with an ε-amino group of a lysine residue.

Lipophilic Substituent

Conjugation of one or more "lipophilic substituents", each optionally via a "spacer," to any of the disclosed polypeptides of this invention is intended to prolong the action of the polypeptide by facilitating binding to serum albumin and delayed renal clearance of the conjugated polypeptide. As used herein, a "lipophilic substituent" comprises a substituent comprising 4 to 40 carbon atoms, 8 to 25 carbon atoms, 12 to 22 carbon atoms, or 6 to 20 carbon atoms. The lipophilic substituent may be attached to an amino group of the polypeptide (e.g., an ε-amino group of a lysine residue) by means of a carboxyl group of the lipophilic substituent, or optionally an amino group of the spacer, which carboxyl group of the spacer in turn forms an amide bond with an amino group of the amino acid (e.g., lysine) residue to which it is attached. In some embodiments, the polypeptide comprises three, two, or preferably one lipophilic substituent each with or without an optional spacer, which is defined in greater detail below.

In some embodiments, the lipophilic substituent comprises a straight-chain or branched alkyl group. In some embodiments, the lipophilic substituent is an acyl group of a straight-chain or branched fatty acid. In some embodiments, the lipophilic substituent is an acyl group of a straight-chain or branched fatty acid, further substituted with one or more carboxylic acid and/or hydroxamic acid groups.

In some embodiments, the polypeptide comprises three, two, or preferably one lipophilic substituents each without an optional spacer. In some embodiments, the lipophilic substituent is a monovalent group of Formula I:

—CO—(CH$_2$)$_m$—Z      Formula I wherein
Z is —CH$_3$ or —CO$_2$H; and
m is from 4 to 24,
which lipophilic substituent forms an amide bond between an amino group (e.g., ε-amino group of a lysine) of the disclosed polypeptide and a CO— group of the lipophilic substituent.

In some embodiments, m is selected from the group consisting of 4-20, 8-20, 12-20, 14-20, 16-20, 14, 16, 18, and 20.

In some embodiments, Z is —CO$_2$H, and the lipophilic substituent has the formula —CO—(CH$_2$)$_m$—CO$_2$H. In some embodiments, —CO—(CH$_2$)$_m$—Z is selected from the group consisting of —CO—(CH$_2$)$_4$—CO$_2$H, —CO—(CH$_2$)$_5$—CO$_2$H, —CO—(CH$_2$)$_6$—CO$_2$H, —CO—(CH$_2$)$_7$—CO$_2$H, —CO—(CH$_2$)$_8$—CO$_2$H, —CO—(CH$_2$)$_9$—CO$_2$H, —CO—(CH$_2$)$_{10}$—CO$_2$H, —CO—(CH$_2$)$_{11}$—CO$_2$H, —CO—(CH$_2$)$_{12}$—CO$_2$H, —CO—(CH$_2$)$_{13}$—CO$_2$H, —CO—(CH$_2$)$_{14}$—CO$_2$H, —CO—(CH$_2$)$_{15}$—CO$_2$H, —CO—(CH$_2$)$_{16}$—CO$_2$H, —CO—(CH$_2$)$_{17}$—CO$_2$H, —CO—(CH$_2$)$_{18}$—CO$_2$H, —CO—(CH$_2$)$_{19}$—CO$_2$H, —CO—(CH$_2$)$_{20}$—CO$_2$H.

In some embodiments, the lipophilic substituent is —CO—(CH$_2$)$_{18}$—CO$_2$H.

In some embodiments, Z is —CH$_3$, and the lipophilic substituent has the formula —CO—(CH$_2$)$_m$—CH$_3$. In some embodiments, —CO—(CH$_2$)$_m$—Z is selected from the group consisting of —CO—(CH$_2$)$_4$—CH$_3$, —CO—(CH$_2$)$_5$—CH$_3$, —CO—(CH$_2$)$_6$—CH$_3$, —CO—(CH$_2$)$_7$—CH$_3$, —CO—(CH$_2$)$_8$—CH$_3$, —CO—(CH$_2$)$_9$—CH$_3$, —CO—(CH$_2$)$_{10}$—CH$_3$, —CO—(CH$_2$)$_{11}$—CH$_3$, —CO—(CH$_2$)$_{12}$—CH$_3$, —CO—(CH$_2$)$_{13}$—CH$_3$, —CO—(CH$_2$)$_{14}$—CH$_3$, —CO—(CH$_2$)$_{15}$—CH$_3$, —CO—(CH$_2$)$_{16}$—CH$_3$, —CO—(CH$_2$)$_{17}$—CH$_3$, —CO—(CH$_2$)$_{18}$—CH$_3$, —CO—(CH$_2$)$_{19}$—CH$_3$, and —CO—(CH$_2$)$_{20}$—CH$_3$.

Spacer

In some embodiments, the lipophilic substituent is attached to the parent peptide by means of a "spacer." In some embodiments, provided herein is any of the disclosed polypeptides, comprising an amino acid sequence selected from the group consisting of amino acid sequences represented by any of the consensus sequences of SEQ ID NO: 1 through SEQ ID NO: 143, comprising a lipophilic substituent, wherein the lipophilic substituent is linked to the ε-amino group of a lysine via a spacer, which spacer forms a bridge between an amino group of the disclosed polypeptide and a CO— group of the lipophilic substituent.

In some embodiments, the spacer comprises one or more amino acids, for example, single amino acid such as Glu, Asp, Gly or Lys, dipeptide such as 2(Glu), Glu-Gly, or polypeptide such as 3(Glu), 4(Glu) (SEQ ID NO: 317), 2(Glu)-Gly etc. In some embodiments, when the spacer comprises one or more amino acids, e.g., Glu, Asp, Gly or Lys, one carboxyl group of the spacer may form an amide bond with an amino group of the disclosed polypeptide, and an amino group of the spacer may form an amide bond with a carboxyl group of the lipophilic substituent.

In some embodiments, when the spacer comprises Glu or Asp, that further include a carboxylic acid-terminating sidechain, the terminal carboxyl group of the sidechain of the Glu or Asp-containing spacer may form an amide bond with an amino group of the disclosed polypeptide, and an amino group of the Glu or Asp-containing spacer may form an amide bond with a carboxyl group of the lipophilic substituent, i.e., γGlu or βAsp. In some embodiments, the spacer is γGlu. In some embodiments, the spacer is 2(γGlu). In some embodiments, the spacer is 3(γGlu).

In some embodiments, the polypeptide comprises three, two, or preferably one lipophilic substituent each with a spacer. In some embodiments, the lipophilic substituent and spacer are a monovalent group of Formula II:

—(Y)$_n$—CO—(CH$_2$)$_m$—Z      Formula II wherein
Y is selected from the group consisting of γGlu, Asp, Lys and Gly;
Z is —CH$_3$ or —CO$_2$H;
m is from 4 to 24; and
n is from 1 to 10.

In some embodiments, Y is selected from the group consisting of γGlu and Gly. In some embodiments, Y is γGlu. In some embodiments, Y is Gly.

In some embodiments, the polypeptide comprises three, two, or preferably one lipophilic substituent each with a spacer. In some embodiments, the lipophilic substituent and spacer are a monovalent group of Formula III:

-(γGlu)$_n$-CO—(CH$_2$)$_m$—Z("(γGlu)$_n$" disclosed as SEQ ID NO:311)      Formula III wherein
Z is —CH$_3$ or —CO$_2$H;
m is from 4 to 24; and
n is from 1 to 10.

In some embodiments, Z is —CH$_3$. In some embodiments, Z is —CO$_2$H.

In some embodiments, m is selected from the group consisting of 4-20, 8-20, 12-20, 14-20, 16-20, 14, 16, 18, and 20.

In some embodiments, n is selected from the group consisting of 1, 2, 3, 4, 5, 6, 7, 8, 9 and 10. In some embodiments, n is 1. In some embodiments, n is 2. In some embodiments, n is 3. In some embodiments, n is 4. In some embodiments, n is 5.

In some embodiments, the polypeptide comprises three, two, or preferably one lipophilic substituent each with a spacer. In some embodiments, the lipophilic substituent and spacer are a monovalent group of Formula IV:

-(γGlu)$_n$-(Gly)-CO—(CH$_2$)$_m$—Z("(γGlu)$_n$-(Gly)" disclosed as SEQ ID NO:312)      Formula IV wherein Z is —CH$_3$ or —CO$_2$H;

m is from 4 to 24; and n is from 1 to 10.

In some embodiments, (γGlu)$_n$ is selected from the group consisting of γGlu; 2(γGlu); 3(γGlu); 4(γGlu) (SEQ ID NO: 313); and 5(γGlu) (SEQ ID NO: 314). In some embodiments, -(γGlu)$_n$-(Gly)-("(γGlu)$_n$-(Gly)" disclosed as SEQ ID NO: 312) is selected from the group consisting of 2(γGlu), Gly; and 3(γGlu),Gly (SEQ ID NO: 315).

In some embodiments, the polypeptide comprises three, two, or preferably one lipophilic substituent each with a spacer. In some embodiments, the lipophilic substituent and spacer are a monovalent group of Formula V:

-(Gly)-(γGlu)$_n$-(CO—(CH$_2$)$_m$—Z("(Gly)-(γGlu)$_n$" disclosed as SEQ ID NO:316)    Formula V wherein Z is —CH$_3$ or —CO$_2$H;

m is from 4 to 24; and n is from 1 to 10.

In some embodiments, certain variables represented in Formula II, Formula III, Formula IV, or Formula V include the following:

In some embodiments, Z is —CH$_3$. In some embodiments, Z is —CO$_2$H.

In some embodiments, m is selected from the group consisting of 4-20, 8-20, 12-20, 14-20, 16-20, 14, 16, 18, and 20.

In some embodiments, n is selected from the group consisting of 1, 2, 3, 4, 5, 6, 7, 8, 9 and 10. In some embodiments, n is 1. In some embodiments, n is 2. In some embodiments, n is 3. In some embodiments, n is 4. In some embodiments, n is 5.

In some embodiments, n is 1 and Z is —CO$_2$H. In some embodiments, n is 1 and Z is —CH$_3$. In some embodiments, n is 2 and Z is —CO$_2$H. In some embodiments, n is 2 and Z is —CH$_3$. In some embodiments, n is 3 and Z is —CO$_2$H. In some embodiments, n is 3 and Z is —CH$_3$. In some embodiments, n is 4 and Z is —CO$_2$H. In some embodiments, n is 4 and Z is —CH$_3$. In some embodiments, n is 5 and Z is —CO$_2$H. In some embodiments, n is 5 and Z is —CH$_3$.

In some embodiments, n is 1, Z is —CO$_2$H, and m is 14-20. In some embodiments, n is 1, Z is —CO$_2$H, and m is 14. In some embodiments, n is 1, Z is —CO$_2$H, and m is 16. In some embodiments, n is 1, Z is —CO$_2$H, and m is 18.

In some embodiments, n is 1, Z is —CH$_3$, and m is 14-20. In some embodiments, n is 1, Z is —CH$_3$ and m is 14. In some embodiments, n is 1, Z is —CH$_3$, and m is 16. In some embodiments, n is 1, Z is —CH$_3$, and m is 18.

In some embodiments, n is 2, Z is —CO$_2$H, and m is 14-20. In some embodiments, n is 2, Z is —CO$_2$H, and m is 14. In some embodiments, n is 2, Z is —CO$_2$H, and m is 16. In some embodiments, n is 2, Z is —CO$_2$H, and m is 18.

In some embodiments, n is 2, Z is —CH$_3$, and m is 14-20. In some embodiments, n is 2, Z is —CH$_3$ and m is 14. In some embodiments, n is 2, Z is —CH$_3$, and m is 16. In some embodiments, n is 2, Z is —CH$_3$, and m is 18.

In some embodiments, n is 3, Z is —CO$_2$H, and m is 14-20. In some embodiments, n is 3, Z is —CO$_2$H, and m is 14. In some embodiments, n is 3, Z is —CO$_2$H, and m is 16. In some embodiments, n is 3, Z is —CO$_2$H, and m is 18.

In some embodiments, n is 3, Z is —CH$_3$, and m is 14-20. In some embodiments, n is 3, Z is —CH$_3$ and m is 14. In some embodiments, n is 3, Z is —CH$_3$, and m is 16. In some embodiments, n is 3, Z is —CH$_3$, and m is 18.

In some embodiments, n is 4, Z is —CO$_2$H, and m is 14-20. In some embodiments, n is 4, Z is —CO$_2$H, and m is 14. In some embodiments, n is 4, Z is —CO$_2$H, and m is 16. In some embodiments, n is 4, Z is —CO$_2$H, and m is 18.

In some embodiments, n is 4, Z is —CH$_3$, and m is 14-20. In some embodiments, n is 4, Z is —CH$_3$ and m is 14. In some embodiments, n is 4, Z is —CH$_3$, and m is 16. In some embodiments, n is 4, Z is —CH$_3$, and m is 18.

In some embodiments, n is 5, Z is —CO$_2$H, and m is 14-20. In some embodiments, n is 5, Z is —CO$_2$H, and m is 14. In some embodiments, n is 5, Z is —CO$_2$H, and m is 16. In some embodiments, n is 5, Z is —CO$_2$H, and m is 18.

In some embodiments, n is 5, Z is —CH$_3$, and m is 14-20. In some embodiments, n is 5, Z is —CH$_3$ and m is 14. In some embodiments, n is 5, Z is —CH$_3$, and m is 16. In some embodiments, n is 5, Z is —CH$_3$, and m is 18.

In some embodiments, the polypeptide comprises three, two, or preferably one lipophilic substituent each with a spacer. In some embodiments, the lipophilic substituent and spacer are a monovalent group of Formula VI:

—(Y1)$_{n1}$—(V)$_r$—(Y2)$_{n2}$—CO—(CH$_2$)$_m$—Z    Formula VI wherein

Z is —CH$_3$ or —CO$_2$H;

m is from 4 to 24;

Y1 is selected from the group consisting of γGlu, Asp, and Gly;

Y2 is selected from the group consisting of γGlu, Asp, and Gly;

V is —[COCH$_2$(O(CH$_2$)$_2$)$_t$OCH$_2$NH]—, and t is from 1 to 8;

r is from 1 to 8;

n1 is from 0 to 10; and n2 is from 0 to 10.

In some embodiments, the polypeptide comprises three, two, or preferably one lipophilic substituent each with a spacer. In some embodiments, the lipophilic substituent and spacer are a monovalent group of Formula VII:

—(Y1)$_{n1}$-(dpeg)$_r$-(Y2)$_{n2}$—CO—(CH$_2$)$_m$—Z    Formula VII wherein

Z is —CH$_3$ or —CO$_2$H;

m is from 4 to 24;

Y1 is selected from the group consisting of γGlu, Asp, and Gly;

Y2 is selected from the group consisting of γGlu, Asp, and Gly;

dpeg is —[CO(CH$_2$)O(CH$_2$)$_2$O(CH$_2$)NH]—;

r is from 1 to 8;

n1 is from 0 to 10; and n2 is from 0 to 10.

In some embodiments, —(Y1)$_{n1}$-(dpeg)$_r$-(Y2)$_{n2}$— is selected from the group consisting of γGlu,dpeg,dpeg,γGlu; γGlu,dpeg,dpeg,2(γGlu); γGlu,dpeg,dpeg,3(γGlu); γGlu,dpeg,dpeg,4(γGlu); 2(γGlu),dpeg,dpeg,γGlu; and 2(γGlu),dpeg,γGlu.

In some embodiments, the polypeptide comprises three, two, or preferably one lipophilic substituent each with a spacer. In some embodiments, the lipophilic substituent and spacer are a monovalent group of Formula VIII:

—(V)$_r$—(Y2)$_{n2}$—CO—(CH$_2$)$_m$—Z    Formula VIII wherein

Z is —CH$_3$ or —CO$_2$H;

m is from 4 to 24;

Y2 is selected from the group consisting of γGlu, Asp, and Gly;

V is —[COCH$_2$(O(CH$_2$)$_2$)$_t$OCH$_2$NH]—, and t is from 1 to 8;
r is from 1 to 8; and
n2 is from 0 to 10.

In some embodiments, the polypeptide comprises three, two, or preferably one lipophilic substituent each with a spacer. In some embodiments, the lipophilic substituent and spacer are a monovalent group of Formula IX:

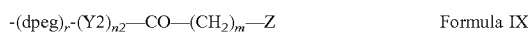
-(dpeg)$_r$-(Y2)$_{n2}$—CO—(CH$_2$)$_m$—Z    Formula IX wherein
Z is —CH$_3$ or —CO$_2$H;
m is from 4 to 24;
dpeg is —[CO(CH$_2$)O(CH$_2$)$_2$O(CH$_2$)NH]—;
Y2 is selected from the group consisting of γGlu, Asp, and Gly;
r is from 1 to 8; and
n2 is from 0 to 10.

In some embodiments, -(dpeg)$_r$-(Y2)$_{n2}$— is selected from the group consisting of dpeg,γGlu; and dpeg,dpeg,γGlu.

In some embodiments, the polypeptide comprises three, two, or preferably one lipophilic substituent each with a spacer. In some embodiments, the lipophilic substituent and spacer are a monovalent group of Formula X:

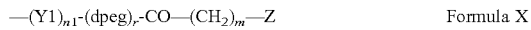
—(Y1)$_{n1}$-(dpeg)$_r$-CO—(CH$_2$)$_m$—Z    Formula X wherein
Z is —CH$_3$ or —CO$_2$H;
m is from 4 to 24;
Y1 is selected from the group consisting of γGlu, Asp, and Gly;
dpeg is —[CO(CH$_2$)O(CH$_2$)$_2$O(CH$_2$)NH]—;
r is from 1 to 8; and
n1 is from 0 to 10.

In some embodiments, —(Y1)$_{n1}$-(dpeg)$_r$- is 2(γGlu), dpeg.

In some embodiments, the spacer comprises a bivalent group of Formula XI:

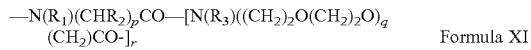
—N(R$_1$)(CHR$_2$)$_p$CO—[N(R$_3$)((CH$_2$)$_2$O(CH$_2$)$_2$O)$_q$(CH$_2$)CO-]$_r$    Formula XI wherein
each R$_1$ and R$_3$ is hydrogen or C$_1$-C$_4$ alkyl;
each R$_2$ is H or CO$_2$H;
p is 1, 2, 3, 4, 5 or 6;
q is 1, 2 or 3;
r is 0 or 1.
which spacer forms a bridge between an amino group of the disclosed polypeptide and a CO— group of the lipophilic substituent.

In some embodiments, the spacer comprises a bivalent group of Formula XII:

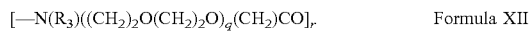
[—N(R$_3$)((CH$_2$)$_2$O(CH$_2$)$_2$O)$_q$(CH$_2$)CO]$_r$    Formula XII wherein
each R$_3$ is hydrogen or C$_1$-C$_4$ alkyl;
q is 1, 2 or 3;
r is 0 or 1.
which spacer forms a bridge between an amino group of the disclosed polypeptide and a CO— group of the lipophilic substituent.

In some embodiments, certain variables represented in Formula XI or Formula XII include the following:

In some embodiments, each R$_1$ is hydrogen. In some embodiments, each R$_3$ is hydrogen. In some embodiments, each R$_1$ and each R$_3$ are hydrogen.

In some embodiments, at least one R$_2$ is CO$_2$H. In some embodiments, one R$_2$ is CO$_2$H.

In some embodiments, p is 1. In some embodiments, p is 2. In some embodiments, p is 3. In some embodiments, p is 4. In some embodiments, p is 5. In some embodiments, p is 6.

In some embodiments, q is 1. In some embodiments, q is 2. In some embodiments, q is 3.

In some embodiments, r is 0. In some embodiments, r is 1.

In some embodiments, the spacer is γ-glutamyl, i.e., —NH(CHCO$_2$H)(CH$_2$)$_2$CO—. In some embodiments, the spacer is γ-aminobutanoyl, i.e., —NH(CH$_2$)$_3$CO—. In some embodiments, the spacer is β-asparagyl, i.e., —NH(CHCO$_2$H)(CH$_2$)CO—. In some embodiments, the spacer is —NH(CH$_2$)$_2$CO—. In some embodiments, the spacer is glycyl. In some embodiments, the spacer is 3-alanyl.

In some embodiments, the spacer is —NHCH(CO$_2$H)(CH$_2$)$_2$CO—[N(R$_3$)((CH$_2$)$_2$O(CH$_2$)$_2$O)$_q$(CH$_2$)CO-]$_r$. In some embodiments, the spacer is —NH(CH$_2$)$_3$CO—[N(R$_3$)((CH$_2$)$_2$O(CH$_2$)$_2$O)$_q$(CH$_2$)CO-]$_r$. In some embodiments, the spacer is —NHCH(CO$_2$H)(CH$_2$)$_2$CO—NH((CH$_2$)$_2$O(CH$_2$)$_2$O)$_2$(CH$_2$)CO—. In some embodiments, the spacer is —NH(CH$_2$)$_3$CO—NH((CH$_2$)$_2$O(CH$_2$)$_2$O)$_2$(CH$_2$)CO—. In some embodiments, the spacer is —NHCH(CO$_2$H)CH$_2$CO—[N(R$_3$)((CH$_2$)$_2$O(CH$_2$)$_2$O)$_q$(CH$_2$)CO-]$_r$. In some embodiments, the spacer is —NH(CH$_2$)$_2$CO—[N(R$_3$)((CH$_2$)$_2$O(CH$_2$)$_2$O)$_q$(CH$_2$)CO-]$_r$.

In some embodiments, the spacer comprises a bivalent group of Formula XIII:

—(Y)$_n$—    Formula XIII wherein
Y is selected from the group consisting of γGlu, Asp, Lys and Gly;
n is from 1 to 10.

In some embodiments, Y is selected from the group consisting of γGlu and Gly. In some embodiments, Y is γGlu. In some embodiments, Y is Gly.

In some embodiments, the spacer forms a bridge between an amino group of the disclosed polypeptide and a CO— group of a lipophilic substituent. In some embodiments, one end of the spacer forms a covalent bond with an amino group of the disclosed polypeptide and the other end of the spacer forms a covalent bond with a hydrogen atom or a protecting group.

In some embodiments, the spacer comprises a bivalent group of Formula XIV:

-(γGlu)$_n$-("(γGlu)$_n$" disclosed as SEQ ID NO:311)    Formula XIV wherein
n is from 1 to 10.

In some embodiments, n is selected from the group consisting of 1, 2, 3, 4, 5, 6, 7, 8, 9 and 10. In some embodiments, n is 1. In some embodiments, n is 2. In some embodiments, n is 3. In some embodiments, n is 4. In some embodiments, n is 5.

In some embodiments, the spacer forms a bridge between an amino group of the disclosed polypeptide and a CO— group of a lipophilic substituent. In some embodiments, one end of the spacer forms a covalent bond with an amino group of the disclosed polypeptide and the other end of the spacer forms a covalent bond with a hydrogen atom or a protecting group.

In some embodiments, the spacer comprises a bivalent group of Formula XV:

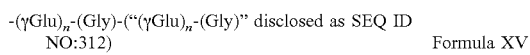
-(γGlu)$_n$-(Gly)-("(γGlu)$_n$-(Gly)" disclosed as SEQ ID NO:312)    Formula XV wherein n is from 1 to 10.

In some embodiments, (γGlu)$_n$ is selected from the group consisting of γGlu; 2(γGlu); 3(γGlu); 4(γGlu) (SEQ ID NO: 313); and 5(γGlu) (SEQ ID NO: 314). In some embodiments, -(γGlu)$_n$-(Gly)-("(γGlu)$_n$-(Gly)" disclosed as SEQ ID NO: 312) is selected from the group consisting of 2(γGlu),Gly; and 3(γGlu),Gly (SEQ ID NO: 315).

In some embodiments, the spacer forms a bridge between an amino group of the disclosed polypeptide and a CO— group of a lipophilic substituent. In some embodiments, one end of the spacer forms a covalent bond with an amino group of the disclosed polypeptide and the other end of the spacer forms a covalent bond with a hydrogen atom or a protecting group.

In some embodiments, the spacer comprises a bivalent group of Formula XVI:

-(Gly)-(γGlu)$_n$-("(Gly)-(γGlu)$_n$" disclosed as SEQ ID NO:316)  Formula XVI wherein n is from 1 to 10.

In some embodiments, the spacer forms a bridge between an amino group of the disclosed polypeptide and a CO— group of a lipophilic substituent. In some embodiments, one end of the spacer forms a covalent bond with an amino group of the disclosed polypeptide and the other end of the spacer forms a covalent bond with a hydrogen atom or a protecting group.

In some embodiments of Formula XIII, Formula XIV, Formula XV, or Formula XVI, n is selected from the group consisting of 1, 2, 3, 4, 5, 6, 7, 8, 9 and 10. In some embodiments, n is 1. In some embodiments, n is 2. In some embodiments, n is 3. In some embodiments, n is 4. In some embodiments, n is 5.

In some embodiments, the spacer comprises a bivalent group of Formula XVII:

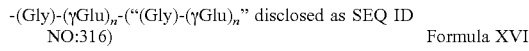

—(Y1)$_{n1}$—(V)$_r$—(Y2)$_{n2}$—  Formula XVII wherein

Y1 is selected from the group consisting of γGlu, Asp, and Gly;

Y2 is selected from the group consisting of γGlu, Asp, and Gly;

V is —[COCH$_2$(O(CH$_2$)$_2$)$_t$OCH$_2$NH]—, and t is from 1 to 8;

r is from 1 to 8;

n1 is from 0 to 10; and n2 is from 0 to 10.

In some embodiments, the spacer forms a bridge between an amino group of the disclosed polypeptide and a CO— group of a lipophilic substituent. In some embodiments, one end of the spacer forms a covalent bond with an amino group of the disclosed polypeptide and the other end of the spacer forms a covalent bond with a hydrogen atom or a protecting group.

In some embodiments, the spacer comprises a bivalent group of Formula XVIII:

—(Y1)$_{n1}$-(dpeg)$_r$-(Y2)$_{n2}$—  Formula XVIII wherein

Y1 is selected from the group consisting of γGlu, Asp, and Gly;

Y2 is selected from the group consisting of γGlu, Asp, and Gly;

dpeg is —[CO(CH$_2$)O(CH$_2$)$_2$O(CH$_2$)NH]—;

r is from 1 to 8;

n1 is from 0 to 10; and n2 is from 0 to 10.

In some embodiments,  —(Y1)$_{n1}$-(dpeg)$_r$-(Y2)$_{n2}$— is selected from the group consisting of γGlu,dpeg,dpeg,γGlu; γGlu,dpeg,dpeg,2(γGlu); γGlu,dpeg,dpeg,3(γGlu); γGlu, dpeg,dpeg,4(γGlu); 2(γGlu),dpeg,dpeg,γGlu; and 2(γGlu), dpeg,γGlu.

In some embodiments, the spacer forms a bridge between an amino group of the disclosed polypeptide and a CO— group of a lipophilic substituent. In some embodiments, one end of the spacer forms a covalent bond with an amino group of the disclosed polypeptide and the other end of the spacer forms a covalent bond with a hydrogen atom or a protecting group.

Accordingly, in some embodiments, an isolated polypeptide provided herein comprises an amino acid sequence, or a pharmaceutically acceptable salt thereof, selected from the group consisting of amino acid sequences represented by a consensus sequence selected from the group consisting of SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, and SEQ ID NO: 209, wherein the isolated peptide further comprises a lipophilic substituent, and optionally comprises a spacer.

In an embodiment the isolated polypeptide comprises an amino acid sequence of SEQ ID NO: 199, or a pharmaceutically acceptable salt thereof, further comprising a lipophilic substituent of Formula I. In an embodiment the isolated polypeptide comprises an amino acid sequence of SEQ ID NO: 199, or a pharmaceutically acceptable salt thereof, further comprising a lipophilic substituent and spacer selected from the group consisting of Formula II, Formula III, Formula IV, Formula V, Formula VI, Formula VII, Formula VIII, Formula IX, and Formula X. In an embodiment the isolated polypeptide comprises an amino acid sequence of SEQ ID NO: 199, or a pharmaceutically acceptable salt thereof, further comprising a lipophilic substituent and spacer of Formula III. In an embodiment the isolated polypeptide comprises an amino acid sequence of SEQ ID NO: 199, or a pharmaceutically acceptable salt thereof, further comprising a lipophilic substituent and spacer of Formula VI. In an embodiment the isolated polypeptide comprises an amino acid sequence of SEQ ID NO: 199, or a pharmaceutically acceptable salt thereof, further comprising a lipophilic substituent and spacer of Formula VII.

In an embodiment the isolated polypeptide comprises an amino acid sequence of SEQ ID NO: 200, or a pharmaceutically acceptable salt thereof, further comprising a lipophilic substituent of Formula I. In an embodiment the isolated polypeptide comprises an amino acid sequence of SEQ ID NO: 200, or a pharmaceutically acceptable salt thereof, further comprising a lipophilic substituent and spacer selected from the group consisting of Formula II, Formula III, Formula IV, Formula V, Formula VI, Formula VII, Formula VIII, Formula IX, and Formula X. In an embodiment the isolated polypeptide comprises an amino acid sequence of SEQ ID NO: 200, or a pharmaceutically acceptable salt thereof, further comprising a lipophilic substituent and spacer of Formula III. In an embodiment the isolated polypeptide comprises an amino acid sequence of SEQ ID NO: 200, or a pharmaceutically acceptable salt thereof, further comprising a lipophilic substituent and spacer of Formula VI. In an embodiment the isolated polypeptide comprises an amino acid sequence of SEQ ID NO:

200, or a pharmaceutically acceptable salt thereof, further comprising a lipophilic substituent and spacer of Formula VII.

In an embodiment the isolated polypeptide comprises an amino acid sequence of SEQ ID NO: 204, or a pharmaceutically acceptable salt thereof, further comprising a lipophilic substituent of Formula I. In an embodiment the isolated polypeptide comprises an amino acid sequence of SEQ ID NO: 204, or a pharmaceutically acceptable salt thereof, further comprising a lipophilic substituent and spacer selected from the group consisting of Formula II, Formula III, Formula IV, Formula V, Formula VI, Formula VII, Formula VIII, Formula IX, and Formula X. In an embodiment the isolated polypeptide comprises an amino acid sequence of SEQ ID NO: 204, or a pharmaceutically acceptable salt thereof, further comprising a lipophilic substituent and spacer of Formula III. In an embodiment the isolated polypeptide comprises an amino acid sequence of SEQ ID NO: 204, or a pharmaceutically acceptable salt thereof, further comprising a lipophilic substituent and spacer of Formula VI. In an embodiment the isolated polypeptide comprises an amino acid sequence of SEQ ID NO: 204, or a pharmaceutically acceptable salt thereof, further comprising a lipophilic substituent and spacer of Formula VII.

In an embodiment the isolated polypeptide comprises an amino acid sequence of SEQ ID NO: 206, or a pharmaceutically acceptable salt thereof, further comprising a lipophilic substituent of Formula I. In an embodiment the isolated polypeptide comprises an amino acid sequence of SEQ ID NO: 206, or a pharmaceutically acceptable salt thereof, further comprising a lipophilic substituent and spacer selected from the group consisting of Formula II, Formula III, Formula IV, Formula V, Formula VI, Formula VII, Formula VIII, Formula IX, and Formula X. In an embodiment the isolated polypeptide comprises an amino acid sequence of SEQ ID NO: 206, or a pharmaceutically acceptable salt thereof, further comprising a lipophilic substituent and spacer of Formula III. In an embodiment the isolated polypeptide comprises an amino acid sequence of SEQ ID NO: 206, or a pharmaceutically acceptable salt thereof, further comprising a lipophilic substituent and spacer of Formula VI. In an embodiment the isolated polypeptide comprises an amino acid sequence of SEQ ID NO: 206, or a pharmaceutically acceptable salt thereof, further comprising a lipophilic substituent and spacer of Formula VII.

In an embodiment the isolated polypeptide comprises an amino acid sequence of SEQ ID NO: 208, or a pharmaceutically acceptable salt thereof, further comprising a lipophilic substituent of Formula I. In an embodiment the isolated polypeptide comprises an amino acid sequence of SEQ ID NO: 208, or a pharmaceutically acceptable salt thereof, further comprising a lipophilic substituent and spacer selected from the group consisting of Formula II, Formula III, Formula IV, Formula V, Formula VI, Formula VII, Formula VIII, Formula IX, and Formula X. In an embodiment the isolated polypeptide comprises an amino acid sequence of SEQ ID NO: 208, or a pharmaceutically acceptable salt thereof, further comprising a lipophilic substituent and spacer of Formula III. In an embodiment the isolated polypeptide comprises an amino acid sequence of SEQ ID NO: 208, or a pharmaceutically acceptable salt thereof, further comprising a lipophilic substituent and spacer of Formula VI. In an embodiment the isolated polypeptide comprises an amino acid sequence of SEQ ID NO: 208, or a pharmaceutically acceptable salt thereof, further comprising a lipophilic substituent and spacer of Formula VII.

In some embodiments, an isolated polypeptide provided herein comprises an amino acid sequence, or a pharmaceutically acceptable salt thereof, selected from the group consisting of amino acid sequences represented by the consensus sequence of SEQ ID NO: 200: $X_1CX_3TX_5X_6CX_8TX_{10}RX_{12}X_{13}X_{14}X_{15}X_{16}X_{17}X_{18}X_{19}X_{20}NX_{22}FGPILPX_{29}TX_{31}VGSX_{35}TY\text{-}(OH/NH_2)$ (SEQ ID NO: 200), or a pharmaceutically acceptable salt thereof, wherein: $X_1$ is S, K, k, H or I; $X_3$ is N or S; $X_5$ is S or A; $X_6$ is T or S; $X_8$ is A or K; $X_{10}$ is Q or S; $X_{12}$ is L or K; $X_{13}$ is A, S, E or K; $X_{14}$ is N, n, d, Y or Q; $X_{15}$ is E, F, f, Y, I, k, K or Aib; $X_{16}$ is k, K, L, Aib, N-MeL or 1; $X_{17}$ is H, V, Q, R, k, K or Aib; $X_{18}$ is K, H, or R; $X_{19}$ is S or Aib; $X_{20}$ is S or Aib; $X_{22}$ is N or E; $X_{29}$ is P, R or K; $X_{31}$ is k, K or N; and $X_{35}$ is e, E or N; each K independently represents an L-lysine optionally covalently bound to a lipophilic substituent, optionally via a spacer; each k independently represents a D-lysine optionally covalently bound to a lipophilic substituent, optionally via a spacer; wherein the two cysteine residues of $X_1CX_3TX_5X_6C$ are optionally further bound by a disulfide bridge; and with the proviso that if $X_{31}$ is N, then $X_{35}$ is E, or if $X_{35}$ is N, then $X_{31}$ is K; and wherein the isolated peptide further comprises a lipophilic substituent of Formula I:

$$-CO-(CH_2)_m-Z \qquad \text{Formula I}$$

wherein
Z is $-CH_3$ or $-CO_2H$; and
m is from 4 to 24.

In some embodiments, an isolated polypeptide provided herein comprises an amino acid sequence, or a pharmaceutically acceptable salt thereof, selected from the group consisting of amino acid sequences represented by the consensus sequence of SEQ ID NO: 200: $X_1CX_3TX_5X_6CX_8TX_{10}RX_{12}X_{13}X_{14}X_{15}X_{16}X_{17}X_{18}X_{19}X_{20}NX_{22}FGPILPX_{29}TX_{31}VGSX_{35}TY\text{-}(OH/NH_2)$ (SEQ ID NO: 200), or a pharmaceutically acceptable salt thereof, wherein:

$X_1$ is S, K, k, H or I; $X_3$ is N or S; $X_5$ is S or A; $X_6$ is T or S; $X_8$ is A or K; $X_{10}$ is Q or S; $X_{12}$ is L or K; $X_{13}$ is A, S, E or K; $X_{14}$ is N, n, d, Y or Q; $X_{15}$ is E, F, f, Y, I, k, K or Aib; $X_{16}$ is k, K, L, Aib, N-MeL or 1; $X_{17}$ is H, V, Q, R, k, K or Aib; $X_{18}$ is K, H, or R; $X_{19}$ is S or Aib; $X_{20}$ is S or Aib; $X_{22}$ is N or E; $X_{29}$ is P, R or K; $X_{31}$ is k, K or N; and $X_{35}$ is e, E or N; each K independently represents an L-lysine optionally covalently bound to a lipophilic substituent, optionally via a spacer; each k independently represents a D-lysine optionally covalently bound to a lipophilic substituent, optionally via a spacer; wherein the two cysteine residues of $X_1CX_3TX_5X_6C$ are optionally further bound by a disulfide bridge; and with the proviso that if $X_{31}$ is N, then $X_{35}$ is E, or if $X_{35}$ is N, then $X_{31}$ is K; and wherein the isolated peptide further comprises a lipophilic substituent and spacer of Formula III:

$$-(\gamma Glu)_n\text{-}CO-(CH_2)_m-Z(\text{``}(\gamma Glu)_n\text{''ʼ disclosed as SEQ ID NO:311}) \qquad \text{Formula III}$$

wherein
Z is $-CH_3$ or $-CO_2H$;
m is from 4 to 24; and
n is from 1 to 10.

In some embodiments, an isolated polypeptide provided herein comprises an amino acid sequence, or a pharmaceutically acceptable salt thereof, selected from the group consisting of amino acid sequences represented by the consensus sequence of SEQ ID NO: 200: $X_1CX_3TX_5X_6CX_8TX_{10}RX_{12}X_{13}X_{14}X_{15}X_{16}X_{17}X_{18}X_{19}X_{20}NX_{22}FGPILPX_{29}TX_{31}VGSX_{35}TY$-(OH/NH$_2$) (SEQ ID NO: 200), or a pharmaceutically acceptable salt thereof, wherein:

$X_1$ is S, K, k, H or I; $X_3$ is N or S; $X_5$ is S or A; $X_6$ is T or S; $X_8$ is A or K; $X_{10}$ is Q or S;

$X_{12}$ is L or K; $X_{13}$ is A, S, E or K; $X_{14}$ is N, n, d, Y or Q; $X_{15}$ is E, F, f, Y, I, k, K or Aib;

$X_{16}$ is k, K, L, Aib, N-MeL or l; $X_{17}$ is H, V, Q, R, k, K or Aib; $X_{18}$ is K, H, or R; $X_{19}$ is S or Aib; $X_{20}$ is S or Aib; $X_{22}$ is N or E; $X_{29}$ is P, R or K; $X_{31}$ is k, K or N; and $X_{35}$ is e, E or N; each K independently represents an L-lysine optionally covalently bound to a lipophilic substituent, optionally via a spacer; each k independently represents a D-lysine optionally covalently bound to a lipophilic substituent, optionally via a spacer; wherein the two cysteine residues of $X_1CX_3TX_5X_6C$ are optionally further bound by a disulfide bridge; and with the proviso that if $X_{31}$ is N, then $X_{35}$ is E, or if $X_{35}$ is N, then $X_{31}$ is K; and wherein the isolated peptide further comprises a lipophilic substituent and spacer of Formula VI:

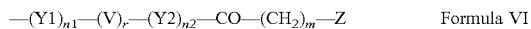
—(Y1)$_{n1}$—(V)$_r$—(Y2)$_{n2}$—CO—(CH$_2$)$_m$—Z                Formula VI wherein Z is —CH$_3$ or —CO$_2$H;

m is from 4 to 24;

Y1 is selected from the group consisting of γGlu, Asp, and Gly;

Y2 is selected from the group consisting of γGlu, Asp, and Gly;

V is —[COCH$_2$(O(CH$_2$)$_2$)$_t$OCH$_2$NH]—, and t is from 1 to 8;

r is from 1 to 8;

n1 is from 0 to 10; and n2 is from 0 to 10.

In some embodiments, an isolated polypeptide provided herein comprises an amino acid sequence, or a pharmaceutically acceptable salt thereof, selected from the group consisting of amino acid sequences represented by the consensus sequence of SEQ ID NO: 200: $X_1CX_3TX_5X_6CX_8TX_{10}RX_{12}X_{13}X_{14}X_{15}X_{16}X_{17}X_{18}X_{19}X_{20}NX_{22}FGPILPX_{29}TX_{31}VGSX_{35}TY$-(OH/NH$_2$) (SEQ ID NO: 200), or a pharmaceutically acceptable salt thereof, wherein:

$X_1$ is S, K, k, H or I; $X_3$ is N or S; $X_5$ is S or A; $X_6$ is T or S; $X_8$ is A or K; $X_{10}$ is Q or S;

$X_{12}$ is L or K; $X_{13}$ is A, S, E or K; $X_{14}$ is N, n, d, Y or Q; $X_{15}$ is E, F, f, Y, I, k, K or Aib;

$X_{16}$ is k, K, L, Aib, N-MeL or l; $X_{17}$ is H, V, Q, R, k, K or Aib; $X_{18}$ is K, H, or R; $X_{19}$ is S or Aib; $X_{20}$ is S or Aib; $X_{22}$ is N or E; $X_{29}$ is P, R or K; $X_{31}$ is k, K or N; and $X_{35}$ is e, E or N; each K independently represents an L-lysine optionally covalently bound to a lipophilic substituent, optionally via a spacer; each k independently represents a D-lysine optionally covalently bound to a lipophilic substituent, optionally via a spacer; wherein the two cysteine residues of $X_1CX_3TX_5X_6C$ are optionally further bound by a disulfide bridge; and with the proviso that if $X_{31}$ is N, then $X_{35}$ is E, or if $X_{35}$ is N, then $X_{31}$ is K; and wherein the isolated peptide further comprises a lipophilic substituent and spacer of Formula VII:

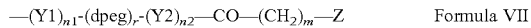
—(Y1)$_{n1}$-(dpeg)$_r$-(Y2)$_{n2}$—CO—(CH$_2$)$_m$—Z                Formula VII wherein Z is —CH$_3$ or —CO$_2$H;

m is from 4 to 24;

Y1 is selected from the group consisting of γGlu, Asp, and Gly;

Y2 is selected from the group consisting of γGlu, Asp, and Gly;

dpeg is —[CO(CH$_2$)O(CH$_2$)$_2$O(CH$_2$)NH]—;

r is from 1 to 8;

n1 is from 0 to 10; and n2 is from 0 to 10.

In some embodiments, the isolated polypeptide comprises a lipophilic substituent at position $X_1$, $X_{15}$, or $X_{16}$.

In some embodiments, the isolated polypeptide comprising a lipophilic substituent at position $X_1$, $X_{15}$, or $X_{16}$ is conjugated via a lysine at that position.

In some embodiments, the isolated polypeptide comprises a lipophilic substituent at position $X_1$.

In some embodiments, the isolated polypeptide comprises a lipophilic substituent at position $X_{15}$.

In some embodiments, the isolated polypeptide comprises a lipophilic substituent at position $X_{16}$.

In some embodiments, the isolated polypeptide comprising a lipophilic substituent at position $X_1$ is conjugated via a lysine at that position.

In some embodiments, the isolated polypeptide comprising a lipophilic substituent at position $X_{15}$ is conjugated via a lysine at that position.

In some embodiments, the isolated polypeptide comprising a lipophilic substituent at position $X_{16}$ is conjugated via a lysine at that position.

In some embodiments, an isolated polypeptide of the disclosure comprises an amino acid sequence: SC*NTSTC*ATQRLANEk*((γGlu)$_2$-CO(CH$_2$)$_{14}$CH$_3$)HKSSNNFGPILPP TKVGSETY-NH$_2$ (SEQ ID NO: 27), which is also referred to herein as Compound A27.

In some embodiments, an isolated polypeptide of the disclosure comprises an amino acid sequence: K*((γGlu)$_2$(CO(CH$_2$)$_{18}$CO$_2$H))C*NTSTC*ATQRLANELHKSSNNFGPILPPTKVGSETY-(NH$_2$) (SEQ ID NO: 64), which is also referred to herein as Compound A64.

In some embodiments, an isolated polypeptide of the disclosure comprises an amino acid sequence: K*((γGlu)$_2$(CO(CH$_2$)$_{16}$CO$_2$H))C*NTSTC*ATQRLANELHKSSNNFGPILPPTKVGSETY-(NH$_2$) (SEQ ID NO: 65), which is also referred to herein as Compound A65.

In some embodiments, an isolated polypeptide of the disclosure comprises an amino acid sequence: K*(γGlu-CO(CH$_2$)$_{16}$CO$_2$H)C*NTSTC*ATSRLANFLQKSSNNFGPILPPTKVGSETY-NH$_2$ (SEQ ID NO: 109), which is also referred to herein as Compound A109.

6. Exemplary Compounds: Amylin Analog Polypeptides

In some embodiments, an isolated polypeptide of the disclosure comprises an amino acid sequence selected from the group consisting of the following peptides listed in Table 3:

TABLE 3

Exemplary compounds: amylin analog polypeptides

| Compound No. | Sequence | SEQ ID NO |
|---|---|---|
| A1 | HC*NTSTC*ATQRLANFLVKSSNEFGPILPPTKVGSETY-NH2 | SEQ ID NO: 1 |
| A2 | IC*NTSTC*ATQRLANFLVKSSNEFGPILPPTKVGSETY-NH2 | SEQ ID NO: 2 |
| A3 | SC*NTSTC*ATQRLANK*(CO(CH$_2$)$_4$CO$_2$H)LHKSSNNFGPILPPTKVGSETY-NH2 | SEQ ID NO: 3 |
| A4 | SC*NTSTC*ATQRLSNFLVKSSNEFGPILPPTKVGSETY-NH2 | SEQ ID NO: 4 |
| A5 | SC*NTSTC*ATQRLANEK*(γGlu-dpeg-dpeg-(γGlu)$_4$-CO(CH$_2$)$_{14}$CH$_3$)HKSSNNFGPILPPTKVGSETY-NH2 | SEQ ID NO: 5 |
| A6 | SC*NTSTC*ATQRLANFIVKSSNEFGPILPPTKVGSETY-NH2 | SEQ ID NO: 6 |
| A7 | SC*NTSTC*ATQRLANELHKSSNNFGPILPKTKVGSNTY-NH2 | SEQ ID NO: 7 |
| A8 | SC*NTSTC*ATQRLANELHKSSNNFGPILPPTKVGSKTY-NH2 | SEQ ID NO: 8 |
| A9 | SC*NTASC*ATQRLANFLVHSSNNFGPILPPTNVGSNTY-NH2 | SEQ ID NO: 9 |
| A10 | SC*NTSTC*ATQRLANELK*(γGlu-CO(CH$_2$)$_{14}$CH$_3$)KSSNNFGPILPPTKVGSETY-NH2 | SEQ ID NO: 10 |
| A11 | SC*NTSTC*ATQRLANELHKSSNNFGPILPRTKVGSNTY-NH2 | SEQ ID NO: 11 |
| A12 | SC*NTSTC*ATQRLANEk*(dpeg-dpeg-γGlu-CO(CH$_2$)$_{14}$CH$_3$)HKSSNNFGPILPPTKVGSETY-NH2 | SEQ ID NO: 12 |
| A13 | SC*NTSTC*ATQRLANEk*((γGlu)$_3$-CO(CH$_2$)$_{16}$CH$_3$)HKSSNNFGPILPPTKVGSETY-NH2 | SEQ ID NO: 13 |
| A14 | SC*NTSTC*ATQRLANEK*((γGlu)$_5$-CO(CH$_2$)$_{14}$CH$_3$)HKSSNNFGPILPPTKVGSETY-NH2 | SEQ ID NO: 14 |
| A15 | SC*NTSTC*ATQRLANYLVKSSNEFGPILPPTKVGSETY-NH2 | SEQ ID NO: 15 |
| A16 | SC*NTSTC*ATQRLANEk*(dpeg-dpeg-γGlu-CO(CH$_2$)$_{14}$CH$_3$)HKSSNNFGPILPPTKVGSGTY-NH2 | SEQ ID NO: 16 |
| A17 | SC*NTSTC*ATQRLANELHKSSNNFGPILPPTKVGSNTY-NH2 | SEQ ID NO: 17 |
| A18 | SC*NTSTC*ATQRLANK*(CO(CH$_2$)$_6$CO$_2$H)LHKSSNNFGPILPPTKVGSETY-NH2 | SEQ ID NO: 18 |
| A19 | SC*NTSTC*ATQRLANEK*(γGlu-dpeg-dpeg-(γGlu)$_3$-CO(CH$_2$)$_{14}$CH$_3$)HKSSNNFGPILPPTKVGSETY-NH2 | SEQ ID NO: 19 |
| A20 | SC*NTSTC*ATQRLANEk*(dpeg-dpeg-γGlu-CO(CH$_2$)$_{14}$CH$_3$)HKSSNNFGPILPPTKVGSATY-NH2 | SEQ ID NO: 20 |
| A21 | SC*NTSTC*ATQRLANEK*-((γGlu)$_4$-CO(CH$_2$)$_{14}$CH$_3$)HKSSNNFGPILPPTKVGSETY-NH2 | SEQ ID NO: 21 |
| A22 | SC*NTSTC*ATSRLANYLVKSSNEFGPILPPTKVGSETY-NH2 | SEQ ID NO: 22 |
| A23 | SC*STATC*ATQRLANFLVHSSNNFGPILPPTNVGSNTY-NH2 | SEQ ID NO: 23 |
| A24 | SC*NTSTC*ATQRLANILVKSSNEFGPILPPTKVGSETY-NH2 | SEQ ID NO: 24 |
| A25 | SC*NTSTC*ATQRLANEk*(γGlu-dpeg-dpeg-(γGlu)-CO(CH$_2$)$_{14}$CH$_3$)HKSSNNFGPILPPTKVGSETY-NH2 | SEQ ID NO: 25 |
| A26 | SC*NTSTC*ATQRLANEK*(γGlu-dpeg-dpeg-(γGlu)$_2$-CO(CH$_2$)$_{14}$CH$_3$)HKSSNNFGPILPPTKVGSETY-NH2 | SEQ ID NO: 26 |
| A27 | SC*NTSTC*ATQRLANEk*((γGlu)$_2$-CO(CH$_2$)$_{14}$CH$_3$)HKSSNNFGPILPPTKVGSETY-NH2 | SEQ ID NO: 27 |
| A28 | SC*NTSTC*ATQRLAQEk*((γGlu)$_2$-CO(CH$_2$)$_{14}$CH$_3$)HKSSNNFGPILPPTKVGSETY-NH2 | SEQ ID NO: 28 |
| A29 | SC*NTSTC*ATQRLANEK*((γGlu)$_3$-CO(CH$_2$)$_{14}$CH$_3$)HKSSNNFGPILPPTKVGSETY-NH2 | SEQ ID NO: 29 |
| A30 | SC*NTSTC*ATQRLENFLVKSSNEFGPILPPTKVGSETY-NH2 | SEQ ID NO: 30 |
| A31 | SC*NTSTC*ATQRLANK*(CO(CH$_2$)$_{11}$CO$_2$H)LHKSSNNFGPILPPTKVGSETY-NH2 | SEQ ID NO: 31 |

TABLE 3-continued

Exemplary compounds: amylin analog polypeptides

| Compound No. | Sequence | SEQ ID NO |
|---|---|---|
| A32 | SC*NTSTC*ATSRLANELVHSSNNFGPILPPTNVGSNTY-NH2 | SEQ ID NO: 32 |
| A33 | SC*NTSTC*ATSRLSNELHRSSNNFGPILPPTKVGSETY-NH2 | SEQ ID NO: 33 |
| A34 | SC*NTSTC*ATQRLSNELHRSSNNFGPILPPTKVGSETY-NH2 | SEQ ID NO: 34 |
| A35 | SC*NTSTC*ATQRLANFIVKSSNEFGPILPPTNVGSNTY-NH2 | SEQ ID NO: 35 |
| A36 | SC*NTSTC*ATQRLANEk*(γGlu-CO(CH$_2$)$_{14}$CH$_3$)HKSSNNFGPILPPTKVGSETY-NH2 | SEQ ID NO: 36 |
| A37 | SC*NTASC*ATQRLANYLVHSSNNFGPILPPTNVGSNTY-NH2 | SEQ ID NO: 37 |
| A38 | SC*NTSTC*ATQRLANELHKSSNEFGPILPPTNVGSNTY-NH2 | SEQ ID NO: 38 |
| A39 | SC*NTSTC*ATQRLANEk*((γGlu)$_2$-Gly-CO(CH$_2$)$_{14}$CH$_3$)HKSSNNFGPILPPTKVGSETY-NH2 | SEQ ID NO: 39 |
| A40 | SC*NTSTC*ATQRLANELHKSSNNFGPILPPTHVGSETY-NH2 | SEQ ID NO: 40 |
| A41 | SC*NTSTC*ATQRLANELHRSSNEFGPILPPTNVGSNTY-NH2 | SEQ ID NO: 41 |
| A42 | SC*NTSTC*ATQRLANK*(γGlu-CO(CH$_2$)$_{14}$CH$_3$)LHKSSNNFGPILPPTKVGSETY-NH2 | SEQ ID NO: 42 |
| A43 | SC*NTSTC*ATQRLANFLVKSSNEFGPILPPTKVGSETY-NH2 | SEQ ID NO: 43 |
| A44 | SC*NTSTC*ATQRLANELVHSSNNFGPILPPTNVGSNTY-NH2 | SEQ ID NO: 44 |
| A45 | SC*NTSTC*ATQRLANELHRSSNNFGPILPPTNVGSNTY-NH2 | SEQ ID NO: 45 |
| A46 | SC*NTSTC*ATQRLANFIVKSSNNFGPILPPTNVGSNTY-NH2 | SEQ ID NO: 46 |
| A47 | SC*NTSTC*ATQRLANEk*(γGlu-CO(CH$_2$)$_{14}$CH$_3$)HKSSNNFGPILPPTKVGSETY-NH2 | SEQ ID NO: 47 |
| A48 | K*(dpeg-dpeg-γGlu-(CO(CH$_2$)$_{16}$CO$_2$H))C*NTSTC*ATSRLAQFLQKSSNNFGPILPPTKVGSETY-NH2 | SEQ ID NO: 48 |
| A49 | SC*STATC*ATQRLANYLVHSSNNFGPILPPTNVGSNTY-NH2 | SEQ ID NO: 49 |
| A50 | SC*NTSTC*ATQRLANFIVKSSNEFGPILPPTNVGSNTY-NH2 | SEQ ID NO: 50 |
| A51 | SC*NTSTC*ATSRLANELVRSSNNFGPILPPTKVGSETY-NH2 | SEQ ID NO: 51 |
| A52 | SC*NTSTC*ATQRLSNELHKSSNNFGPILPPTKVGSETY-NH2 | SEQ ID NO: 52 |
| A53 | SC*NTSTC*ATQRLANEk*((γGlu)$_3$-CO(CH$_2$)$_{14}$CH$_3$)HKSSNNFGPILPPTKVGSETY-NH2 | SEQ ID NO: 53 |
| A54 | SC*NTSTC*ATSRLANELHRSSNEFGPILPPTKVGSETY-NH2 | SEQ ID NO: 54 |
| A55 | K*(CO(CH$_2$)$_{16}$CO$_2$H))C*NTSTC*ATSRLANFLQKSSNNFGPILPPTKVGSETY-NH2 | SEQ ID NO: 55 |
| A56 | SC*NTSTC*ATQRLANEk*((γGlu)$_2$-CO(CH$_2$)$_{16}$CH$_3$)HKSSNNFGPILPPTKVGSETY-NH2 | SEQ ID NO: 56 |
| A57 | SC*NTSTC*ATQRLANELHKSSNNFGPILPPTKVGSETY-NH2 | SEQ ID NO: 57 |
| A58 | SC*NTSTC*ATSRLANFLQKSSNEFGPILPPTKVGSETY-NH2 | SEQ ID NO: 58 |
| A59 | SC*NTSTC*ATSRLANYLQKSSNEFGPILPPTKVGSETY-NH2 | SEQ ID NO: 59 |
| A60 | SC*NTSTC*ATQRLANfLVKSSNEFGPILPPTKVGSETY-NH2 | SEQ ID NO: 60 |
| A61 | SC*NTASC*ATQRLANYLHRSSNNFGPILPPTNVGSNTY-NH2 | SEQ ID NO: 61 |
| A62 | SC*NTSTC*ATSRLANFLQKSSNNFGPILPPTKVGSETY-NH2 | SEQ ID NO: 62 |
| A63 | SC*NTSTC*ATQRLANEK*(γGlu-dpeg-dpeg-γGlu-CO(CH$_2$)$_{14}$CH$_3$)HKSSNNFGPILPPTKVGSETY-NH2 | SEQ ID NO: 63 |

TABLE 3-continued

Exemplary compounds: amylin analog polypeptides

| Compound No. | Sequence | SEQ ID NO |
|---|---|---|
| A64 | K*((γGlu)$_2$-(CO(CH$_2$)$_{18}$CO$_2$H))C*NTSTC*ATQRLANELHKSSNNFGPILPPTKV GSETY-NH2 | SEQ ID NO: 64 |
| A65 | K*((γGlu)$_2$-(CO(CH$_2$)$_{16}$CO$_2$H))C*NTSTC*ATQRLANELHKSSNNFGPILPPTKV GSETY-NH2 | SEQ ID NO: 65 |
| A66 | SC*NTSTC*ATQRLANEk*((γGlu)$_4$-CO(CH$_2$)$_{14}$CH$_3$)HKSSNNFGPILPPTKVGSETY-NH2 | SEQ ID NO: 66 |
| A67 | SC*NTSTC*ATQRLANEk*((γGlu)$_3$-CO(CH$_2$)$_{14}$CH$_3$)HKSSNNFGPILPPTKVGSNTY-NH2 | SEQ ID NO: 67 |
| A68 | SC*NTSTC*ATQRLANK*((γGlu)$_2$-CO(CH$_2$)$_{14}$CH$_3$)k*(2(γGlu)-CO(CH$_2$)$_{14}$CH$_3$)HKSSNNFGPILPPTKVGSETY-NH2 | SEQ ID NO: 68 |
| A69 | SC*NTSTC*ATQRLANEk*(dpeg-dpeg-γGlu-CO(CH$_2$)$_{14}$CH$_3$)HKSSNNFGPILPPTKVGSYTY-NH2 | SEQ ID NO: 69 |
| A70 | SC*NTSTC*ATQRLANFk*((γGlu)$_2$-CO(CH$_2$)$_{14}$CH$_3$)HKSSNNFGPILPPTKVGSETY-NH2 | SEQ ID NO: 70 |
| A71 | SC*NTSTC*ATQRLANEk*((γGlu)$_2$-dpeg-dpeg-γGlu-CO(CH$_2$)$_{14}$CH$_3$)HKSSNNFGPILPPTKVGSETY-NH2 | SEQ ID NO: 71 |
| A72 | SC*NTSTC*ATQRLANK*(CO(CH$_2$)$_{14}$CO$_2$H))LHKSSNNFGPILPPTKVGSETY-NH2 | SEQ ID NO: 72 |
| A73 | SC*NTSTC*ATQRLANEK*(γGlu-CO(CH$_2$)$_{18}$CO$_2$H)HKSSNNFGPILPPTKVGSETY-NH2 | SEQ ID NO: 73 |
| A74 | SC*NTSTC*ATQRLANEK*(CO(CH$_2$)$_{10}$CO$_2$H))HKSSNNFGPILPPTKVGSETY-NH2 | SEQ ID NO: 74 |
| A75 | SC*NTSTC*ATQRLANEK*(CO(CH$_2$)$_{18}$CO$_2$H)HKSSNNFGPILPPTKVGSETY-NH2 | SEQ ID NO: 75 |
| A76 | SC*NTSTC*ATQRLANEK*(γGlu-CO(CH$_2$)$_{16}$CO$_2$H)HKSSNNFGPILPPTKVGSETY-NH2 | SEQ ID NO: 76 |
| A77 | SC*NTSTC*ATQRLANEk*((γGlu)$_3$-Gly-CO(CH$_2$)$_{14}$CH$_3$)HKSSNNFGPILPPTKVGSETY-NH2 | SEQ ID NO: 77 |
| A78 | SC*NTSTC*ATQRLANEk*(dpeg-dpeg-γGlu-CO(CH$_2$)$_{14}$CH$_3$)HKSSNNFGPILPPTKVGSPTY-NH2 | SEQ ID NO: 78 |
| A79 | SC*NTSTC*ATQRLANEK*(CO(CH$_2$)$_{15}$CO$_2$H)HKSSNNFGPILPPTKVGSETY-NH2 | SEQ ID NO: 79 |
| A80 | SC*NTSTC*ATQRLANEK*(γGlu-CO(CH$_2$)$_{15}$CO$_2$H)HKSSNNFGPILPPTKVGSETY-NH2 | SEQ ID NO: 80 |
| A81 | SC*NTSTC*ATQRLANEK*(CO(CH$_2$)$_{12}$CO$_2$H)HKSSNNFGPILPPTKVGSETY-NH2 | SEQ ID NO: 81 |
| A82 | SC*NTSTC*ATQRLANK*((γGlu)$_2$-CO(CH$_2$)$_{14}$CO$_2$H)LHKSSNNFGPILPPTKVGSETY-NH2 | SEQ ID NO: 82 |
| A83 | SC*NTSTC*ATQRLANK*(CO(CH$_2$)$_{16}$CO$_2$H)LHKSSNNFGPILPPTKVGSETY-NH2 | SEQ ID NO: 83 |
| A84 | SC*NTSTC*ATQRLANEK*(CO(CH$_2$)$_{8}$CO$_2$H)HKSSNNFGPILPPTKVGSETY-NH2 | SEQ ID NO: 84 |
| A85 | SC*NTSTC*ATQRLAYK*((γGlu)$_2$-dpeg-dpeg-γGlu-CO(CH$_2$)$_{18}$CO$_2$H)LHKSSNNFGPILPPTKVGSETY-NH2 | SEQ ID NO: 85 |
| A86 | SC*NTSTC*ATQRLANEK*(CO(CH$_2$)$_{14}$CO$_2$H)HKSSNNFGPILPPTKVGSETY-NH2 | SEQ ID NO: 86 |
| A87 | SC*NTSTC*ATQRLANK*((γGlu)$_2$-CO(CH$_2$)$_{16}$CO$_2$H)LHKSSNNFGPILPPTKVGSETY-NH2 | EQ ID NO: 87 |
| A88 | SC*NTSTC*ATQRLANEK*(γGlu-CO(CH$_2$)$_{14}$CO$_2$H)HKSSNNFGPILPPTKVGSETY-NH2 | SEQ ID NO: 88 |
| A89 | SC*NTSTC*ATQRLANK*(CO(CH$_2$)$_{18}$CO$_2$H)LHKSSNNFGPILPPTKVGSETY-NH2 | SEQ ID NO: 89 |
| A90 | SC*NTSTC*ATQRLANEK*(CO(CH$_2$)$_{6}$CO$_2$H)HKSSNNFGPILPPTKVGSETY-NH2 | SEQ ID NO: 90 |

TABLE 3-continued

Exemplary compounds: amylin analog polypeptides

| Compound No. | Sequence | SEQ ID NO |
|---|---|---|
| A91 | SC*NTSTC*ATQRLANEk*((γGlu)$_5$-CO(CH$_2$)$_{14}$CH$_3$)HKSSNNFGPILPPTKVGSETY-NH2 | SEQ ID NO: 91 |
| A92 | SC*NTSTC*ATQRLANK*((γGlu)$_2$-CO(CH$_2$)$_{18}$CO$_2$H)LHKSSNNFGPILPPTKVGSETY-NH2 | SEQ ID NO: 92 |
| A93 | SC*NTSTC*ATQRLANEK*(CO(CH$_2$)$_{16}$CO$_2$H)HKSSNNFGPILPPTKVGSETY-NH2 | SEQ ID NO: 93 |
| A94 | SC*NTSTC*ATQRLANK*((γGlu)$_2$-dpeg-dpeg-γGlu-CO(CH$_2$)$_{18}$CO$_2$H)LHKSSNNFGPILPPTKVGSETY-NH2 | SEQ ID NO: 94 |
| A95 | SC*NTSTC*ATQRLANk*(CO(CH$_2$)$_{18}$CO$_2$H)LHKSSNNFGPILPPTKVGSETY-NH2 | SEQ ID NO: 95 |
| A96 | SC*NTSTC*ATQRLANk*((γGlu)$_2$-dpeg-CO(CH$_2$)$_{18}$CO$_2$H)LHKSSNNFGPILPPTKVGSETY-NH2 | SEQ ID NO: 96 |
| A97 | SC*NTSTC*ATQRLANk*((γGlu)$_2$-CO(CH$_2$)$_{18}$CO$_2$H)LHKSSNNFGPILPPTKVGSETY-NH2 | SEQ ID NO: 97 |
| A98 | SC*NTSTC*ATQRLANK*(dpeg-dpeg-γGlu-CO(CH$_2$)$_{16}$CO$_2$H)LHKSSNNFGPILPPTKVGSETY-NH2 | SEQ ID NO: 98 |
| A99 | SC*NTSTC*ATQRLANELK*(dpeg-dpeg-γGlu-CO(CH$_2$)$_{16}$CO$_2$H)KSSNNFGPILPPTKVGSETY-NH2 | SEQ ID NO: 99 |
| A100 | SC*NTSTC*ATQRLANk*((γGlu)$_2$-dpeg-γGlu-CO(CH$_2$)$_{18}$CO$_2$H)LHKSSNNFGPILPPTKVGSETY-NH2 | SEQ ID NO: 100 |
| A101 | SC*NTSTC*ATQRLANk*((γGlu)$_2$-dpeg-dpeg-γGlu-CO(CH$_2$)$_{18}$CO$_2$H)LHKSSNNFGPILPPTKVGSETY-NH2 | SEQ ID NO: 101 |
| A102 | SC*NTSTC*ATQRLANEk*(dpeg-dpeg-γGlu-CO(CH$_2$)$_{16}$CO$_2$H)HKSSNNFGPILPPTKVGSETY-NH2 | SEQ ID NO: 102 |
| A103 | SC*NTSTC*ATQRLANEk*((γGlu)$_2$-dpeg-dpeg-γGlu-CO(CH$_2$)$_{18}$CO$_2$H)HKSSNNFGPILPPTKVGSETY-NH2 | SEQ ID NO: 103 |
| A104 | SC*NTSTC*ATQRLANEk*((γGlu)$_3$-CO(CH$_2$)$_{16}$CO$_2$H)HKSSNNFGPILPPTKVGSETY-NH2 | SEQ ID NO: 104 |
| A105 | K*(dpeg-γGlu-CO(CH$_2$)$_{16}$CO$_2$H)C*NTSTC*ATSRLAQFLQKSSNNFGPILPPTKVGSETY-NH2 | SEQ ID NO: 105 |
| A106 | K*(γGlu-CO(CH$_2$)$_{16}$CO$_2$H)C*NTSTC*ATSRLAQFLQKSSNNFGPILPPTKVGSETY-NH2 | SEQ ID NO: 106 |
| A107 | SC*NTSTC*ATQRLK*(γGlu-CO(CH$_2$)$_{14}$CH$_3$)NELHKSSNNFGPILPPTKVGSETY-NH2 | SEQ ID NO: 107 |
| A108 | SC*NTSTC*K*(γGlu-CO(CH$_2$)$_{14}$CH$_3$)TQRLANELHKSSNNFGPILPPTKVGSETY-NH2 | SEQ ID NO: 108 |
| A109 | K*(γGlu-CO(CH$_2$)$_{16}$CO$_2$H)C*NTSTC*ATSRLANFLQKSSNNFGPILPPTKVGSETY-NH2 | SEQ ID NO: 109 |
| A110 | K*(γGlu-CO(CH$_2$)$_{16}$CO$_2$H)C*NTSTC*ATSRLANYLVHSSNNFGPILPPTKVGSETY-NH2 | SEQ ID NO: 110 |
| A111 | SC*NTSTC*ATSRLANYLVHSSNNFGPILPPTKVGSETY-NH2 | SEQ ID NO: 111 |
| A112 | K*((γGlu)$_2$-dpeg-dpeg-γGlu-CO(CH$_2$)$_{18}$CO$_2$H)C*NTSTC*ATQRLANELHKSSNNFGPILPPTKVGSETY-NH2 | SEQ ID NO: 112 |
| A113 | K*(dpeg-dpeg-γGlu-CO(CH$_2$)$_{16}$CO$_2$H)C*NTSTC*ATQRLANELHKSSNNFGPILPPTKVGSETY-NH2 | SEQ ID NO: 113 |
| A114 | K*((γGlu)$_2$-CO(CH$_2$)$_{18}$CO$_2$H)C*NTSTC*ATSRLANFLQKSSNNFGPILPPTKVGSETY-NH2 | SEQ ID NO: 114 |
| A115 | K*(CO(CH2)$_{18}$CO$_2$H)C*NTSTC*ATQRLANELHKSSNNFGPILPPTKVGSETY-NH2 | SEQ ID NO: 115 |
| A116 | K*(γGlu-CO(CH$_2$)$_{18}$CO$_2$H)C*NTSTC*ATSRLANFLQKSSNNFGPILPPTKVGSETY-NH2 | SEQ ID NO: 116 |

TABLE 3-continued

Exemplary compounds: amylin analog polypeptides

| Compound No. | Sequence | SEQ ID NO |
|---|---|---|
| A117 | K*((γGlu)$_2$-CO(CH$_2$)$_{10}$CO$_2$H)C*NTSTC*ATQRLANELHKSSNNFGPILPPTKVGSETY-NH2 | SEQ ID NO: 117 |
| A118 | K*((γGlu)$_2$-CO(CH2)$_6$CO$_2$H)C*NTSTC*ATQRLANELHKSSNNFGPILPPTKVGSETY-NH2 | SEQ ID NO: 118 |
| A119 | K*(γGlu)-CO(CH$_2$)$_{18}$CO$_2$H)C*NTSTC*ATQRLANELHKSSNNFGPILPPTKVGSETY-NH2 | SEQ ID NO: 119 |
| A120 | K*(CO(CH$_2$)$_{16}$CO$_2$H)C*NTSTC*ATQRLANELHKSSNNFGPILPPTKVGSETY-NH2 | SEQ ID NO: 120 |
| A121 | SC*NTSTC*ATQRK*(γGlu)-CO(CH$_2$)$_{14}$CH$_3$)ANELHKSSNNFGPILPPTKVGSETY-NH2 | SEQ ID NO: 121 |
| A122 | SC*NTSTC*ATQRLANEK*((γGlu)$_2$-dpeg-dpeg-γGlu-CO(CH$_2$)$_{14}$CH$_3$)HKSSNNFGPILPPTKVGSETY-NH2 | SEQ ID NO: 122 |
| A123 | SC*NTSTC*ATQRLANEK((γGlu)$_2$-CO(CH$_2$)$_{14}$CH$_3$)HKSSNNFGPILPPTKVGSETY-NH2 | SEQ ID NO: 123 |
| A124 | SC*NTSTC*ATQRLANEk*((γGlu)$_2$-CO(CH$_2$)$_{20}$CH$_3$)HKSSNNFGPILPPTKVGSETY-NH2 | SEQ ID NO: 124 |
| A125 | SC*NTSTC*ATQRLANEK*(γGlu-CO(CH$_2$)$_{14}$CH$_3$)HKSSNNFGPILPPTKVGSETY-NH2 | SEQ ID NO: 125 |
| A126 | K*(dpeg-dpeg-γGlu-CO(CH$_2$)$_{16}$CO$_2$H)C*NTSTC*ATSRLANFLQKSSNNFGPILPPTKVGSETY-NH2 | SEQ ID NO: 126 |
| A127 | SC*NTSTC*ATQRLANFIdIKSSNNFGPILPPTKVGSETY-NH2 | SEQ ID NO: 127 |
| A128 | SC*NTSTC*ATQRLANEKHKSSNNFGPILPPTKVGSETY-NH2 | SEQ ID NO: 128 |
| A129 | SC*NTSTC*ATQRLANEkHKSSNNFGPILPPTKVGSETY-NH2 | SEQ ID NO: 129 |
| A130 | KC*NTSTC*ATQRLANELHKSSNNFGPILPPTKVGSETY-NH2 | SEQ ID NO: 130 |
| A131 | KC*NTSTC*ATQRLANFLQKSSNNFGPILPPTKVGSETY-(NH2) | SEQ ID NO: 131 |
| A132 | SC*NTSTC*ATQRLAN(Aib)LVKSSNEFGPILPPTKVGSETY-NH2 | SEQ ID NO: 132 |
| A133 | SC*NTSTC*ATQRLANFLVK(Aib)SNEFGPILPPTKVGSETY-NH2 | SEQ ID NO: 133 |
| A134 | SC*NTSTC*ATQRLANF(Aib)VKSSNEFGPILPPTKVGSETY-NH2 | SEQ ID NO: 134 |
| A135 | SC*NTSTC*ATQRLANFL(Aib)KSSNEFGPILPPTKVGSETY-NH2 | SEQ ID NO: 135 |
| A136 | SC*NTSTC*ATQRLSNF(N-MeLeu)VKSSNEFGPILPPTKVGSETY-NH2 | SEQ ID NO: 136 |
| A137 | SC*NTSTC*ATQRLANF(N-MeLeu)VKSSNEFGPILPPTKVGSETY-NH2 | SEQ ID NO: 137 |
| A138 | SC*NTSTC*ATQRLAnEK*((γGlu)$_5$-(CO(CH$_2$)$_{14}$CH$_3$)HKSSNNFGPILPPTKVGSTP-NH2 | SEQ ID NO: 138 |
| A139 | SC*NTSTC*ATQRLANEk*((γGlu)$_2$-(CO(CH$_2$)$_{18}$CO$_2$H)HKSSNNFGPILPPTKVGSETP-NH2 | SEQ ID NO: 139 |
| A140 | K*((γGlu)$_2$-(CO(CH$_2$)$_{16}$CO$_2$H)-C*NTSTC*ATQRLAnELHKSSNNFGPILPPTKVGSGTP-NH2 | SEQ ID NO: 140 |
| A141 | K*((γGlu)$_2$-(CO(CH$_2$)$_{16}$CO$_2$H)C*NTSTC*ATQRLAdELHKSSNNFGPILPPTKVGSGTP-NH2 | SEQ ID NO: 141 |
| A142 | K*((γGlu)$_2$-(CO(CH$_2$)$_{16}$CO$_2$H)C*NTSTC*ATQRLAdELRHSSNNFGPILPPTKVGSGTP-NH2 | SEQ ID NO: 142 |

TABLE 3-continued

Exemplary compounds: amylin analog polypeptides

| Compound No. | Sequence | SEQ ID NO |
|---|---|---|
| A143 | K*((γGlu)$_2$-(CO(CH$_2$)$_{14}$CO$_2$H) C*NTSTC*ATQRLANELHKSSNNFGPILPPTKVGSETY-NH2 | SEQ ID NO: 143 | each K* independently represents an L-lysine optionally covalently bound to a lipophilic substituent, optionally via a spacer;
each k* independently represents a D-lysine optionally covalently bound to a lipophilic substituent, optionally via a spacer;
the two cysteine residues (C*) at positions 2 and 7 are optionally further bound by a disulfide bridge;
as used herein, (γGlu)$_2$ and 2(γGlu) both mean -(γGlu)-(γGlu)-; (γGlu)$_3$ and 3(γGlu) both mean -(γGlu)-(γGlu)-(γGlu)-; etc.; and
where a variable is present more than once in a given formual, each occurrence of that variable is independently determined. For example, for group -(Y)$_3$-, where Y may be γGlu, Asp, Lys, or Gly, each Y is independently selected to be one of the four amino acids. Accordingly, by non-limiting example, -(Y)$_3$- may be -(γGlu)-(γGlu)-(γGlu)-, -(γGlu)-(Asp)-(γGlu)-, -(Gly)-(Asp)-(γGlu)-, or (Gly)-(γGlu)-(γGlu)-.

In some embodiments, the present invention provides a compound set forth in the Table 3, above, or a pharmaceutically acceptable salt thereof. In some embodiments the pharmaceutically acceptable salt is an acetate salt. In some embodiments the pharmaceutically acceptable salt is a trifluoroacetic acid (TFA) salt. In some embodiments the pharmaceutically acceptable salt is a hydrochloric acid (HCl) salt. In some embodiments, the compound is A27. In some embodiments, the compound is the acetate salt of compound A27. In some embodiments, the compound is the TFA salt of compound A27. In some embodiments, the compound is the HCl salt of compound A27. In one embodiment, the compound is A57. In some embodiments, the compound is the acetate salt of compound A57. In some embodiments, the compound is the TFA salt of compound A57. In some embodiments, the compound is the HCl salt of compound A57. In one embodiment, the compound is A64. In some embodiments, the compound is the acetate salt of compound A64. In some embodiments, the compound is the TFA salt of compound A64. In some embodiments, the compound is the HCl salt of compound A64.

7. Polypeptide Intermediates

In certain embodiments, the present invention also relates to synthetic intermediates of isolated polypeptides that are amylin analogs. In some embodiments, a polypeptide intermediate of the disclosure is an isolated polypeptide comprising an amino acid sequence selected from the group consisting of amino acid sequences represented by the consensus sequence of SEQ ID NO: 210: X$_1$CX$_3$TX$_5$X$_6$CX$_8$TX$_{10}$RX$_{12}$X$_{13}$X$_{14}$X$_{15}$X$_{16}$X$_{17}$X$_{18}$X$_{19}$X$_{20}$NX$_{22}$FGPILPX$_{29}$TX$_{31}$VGSX$_{35}$TY-(OH/NH$_2$) (SEQ ID NO: 210), wherein:

X$_1$ is S, K, k, H or I;
X$_3$ is N or S;
X$_5$ is S or A;
X$_6$ is T or S;
X$_8$ is A or K;
X$_{10}$ is Q or S;
X$_{12}$ is L or K;
X$_{13}$ is A, S, E or K;
X$_{14}$ is N, n, d, Y or Q;
X$_{15}$ is E, F, f, Y, I, k, K or α-aminoisobutyric acid (Aib);
X$_{16}$ is k, K, L, Aib, N-methyl leucine (N-MeL), or l;
X$_{17}$ is H, V, Q, R, k, K or Aib;
X$_{18}$ is K, H, or R;
X$_{19}$ is S or Aib;
X$_{20}$ is S or Aib;
X$_{22}$ is N or E;
X$_{29}$ is P, R or K;
X$_{31}$ is k, K or N; and
X$_{35}$ is e, E or N;
each K independently represents an L-lysine optionally covalently bound to a protecting group or a spacer optionally bound to a protecting group;
each k independently represents a D-lysine optionally covalently bound to a protecting group or a spacer optionally bound to a protecting group;
wherein the two cysteine residues of X$_1$CX$_3$TX$_5$X$_6$C are optionally further bound by a disulfide bridge;
with the proviso that if X$_{31}$ is N, then X$_{35}$ is E, or if X$_{35}$ is N, then X$_{31}$ is K.

In some embodiments, X$_{31}$ is K. In some embodiments, X$_{31}$ is N.

In some embodiments, X$_{35}$ is E. In some embodiments, X$_{35}$ is N.

In some embodiments, X$_{31}$ is K and X$_{35}$ is E.

In some embodiments, certain amino acids represented by the consensus sequence of SEQ ID NO: 210 include the following:

In some embodiments, carboxy terminal amino acid 37 is Y—(NH$_2$). In some embodiments, carboxy terminal amino acid 37 is Y—(OH).

In some embodiments, X$_1$ is S. In some embodiments, X$_1$ is K. In some embodiments, X$_1$ is k. In some embodiments, X$_1$ is H. In some embodiments, X$_1$ is I.

In some embodiments, X$_3$ is N. In some embodiments, X$_3$ is S.

In some embodiments, X$_5$ is S. In some embodiments, X$_5$ is A.

In some embodiments, X$_6$ is T. In some embodiments, X$_6$ is S.

In some embodiments, X$_8$ is A. In some embodiments, X$_8$ is K.

In some embodiments, X$_{10}$ is Q. In some embodiments, X$_{10}$ is S.

In some embodiments, X$_{12}$ is L. In some embodiments, X$_{12}$ is K.

In some embodiments, X$_{13}$ is A. In some embodiments, X$_{13}$ is S. In some embodiments, X$_{13}$ is E. In some embodiments, X$_{13}$ is K.

In some embodiments, X$_{14}$ is N. In some embodiments, X$_{14}$ is n. In some embodiments, X$_{14}$ is d. In some embodiments, X$_{14}$ is Y. In some embodiments, X$_{14}$ is Q.

In some embodiments, X$_{15}$ is E. In some embodiments, X$_{15}$ is F. In some embodiments, X$_{15}$ is f. In some embodiments, X$_{15}$ is Y. In some embodiments, X$_{15}$ is I. In some embodiments, $X_{15}$ is K. In some embodiments, $X_{15}$ is k. In some embodiments, $X_{15}$ is Aib.

In some embodiments, $X_{16}$ is L. In some embodiments, $X_{16}$ is l. In some embodiments, $X_{16}$ is K. In some embodiments, $X_{16}$ is k. In some embodiments, $X_{16}$ is Aib. In some embodiments, $X_{16}$ is N-MeL.

In some embodiments, $X_{17}$ is H. In some embodiments, $X_{17}$ is V. In some embodiments, $X_{17}$ is Q. In some embodiments, $X_{17}$ is R. In some embodiments, $X_{17}$ is K. In some embodiments, $X_{17}$ is k. In some embodiments, $X_{17}$ is Aib.

In some embodiments, $X_{18}$ is K. In some embodiments, $X_{18}$ is H. In some embodiments, $X_{18}$ is R.

In some embodiments, $X_{19}$ is S. In some embodiments, $X_{19}$ is Aib.

In some embodiments, $X_{20}$ is S. In some embodiments, $X_{20}$ is Aib.

In some embodiments, $X_{22}$ is N. In some embodiments, $X_{22}$ is E.

In some embodiments, $X_{29}$ is P. In some embodiments, $X_{29}$ is R. In some embodiments, $X_{29}$ is K.

In some embodiments, $X_{31}$ is k. In some embodiments, $X_{31}$ is K. In some embodiments, $X_{31}$ is N.

In some embodiments, $X_{35}$ is e. In some embodiments, $X_{35}$ is E. In some embodiments, $X_{35}$ is N.

In some embodiments, certain amino acids represented by the consensus sequence of SEQ ID NO: 210 include the following:

In some embodiments, $X_1$ is S and $X_5$ is S. In some embodiments, $X_1$ is S and $X_{10}$ is Q. In some embodiments, $X_1$ is S and $X_{15}$ is E. In some embodiments, $X_1$ is S and $X_{16}$ is L. In some embodiments, $X_1$ is S and $X_{16}$ is k. In some embodiments, $X_1$ is S and $X_{17}$ is H. In some embodiments, $X_1$ is S and $X_{18}$ is K. In some embodiments, $X_1$ is S and $X_{31}$ is K. In some embodiments, $X_1$ is S and $X_{35}$ is E.

In some embodiments, $X_1$ is K and $X_5$ is S. In some embodiments, $X_1$ is K and $X_{10}$ is Q. In some embodiments, $X_1$ is K and $X_{15}$ is E. In some embodiments, $X_1$ is K and $X_{16}$ is L. In some embodiments, $X_1$ is K and $X_{16}$ is k. In some embodiments, $X_1$ is K and $X_{17}$ is H. In some embodiments, $X_1$ is K and $X_{18}$ is K. In some embodiments, $X_1$ is K and $X_{31}$ is K. In some embodiments, $X_1$ is K and $X_{35}$ is E.

In some embodiments, $X_1$ is k and $X_5$ is S. In some embodiments, $X_1$ is k and $X_{10}$ is Q. In some embodiments, $X_1$ is k and $X_{15}$ is E. In some embodiments, $X_1$ is k and $X_{16}$ is L. In some embodiments, $X_1$ is k and $X_{16}$ is k. In some embodiments, $X_1$ is k and $X_{17}$ is H. In some embodiments, $X_1$ is k and $X_{18}$ is K. In some embodiments, $X_1$ is k and $X_{31}$ is K. In some embodiments, $X_1$ is k and $X_{35}$ is E.

In some embodiments, $X_5$ is S and $X_{15}$ is E. In some embodiments, $X_5$ is S and $X_{10}$ is Q. In some embodiments, $X_5$ is S and $X_{16}$ is L. In some embodiments, $X_5$ is S and $X_{16}$ is k. In some embodiments, $X_5$ is S and $X_{17}$ is H. In some embodiments, $X_5$ is S and $X_{18}$ is K. In some embodiments, $X_5$ is S and $X_{31}$ is K. In some embodiments, $X_5$ is S and $X_{35}$ is E.

In some embodiments, $X_{10}$ is Q and $X_{15}$ is E. In some embodiments, $X_{10}$ is Q and $X_{16}$ is L. In some embodiments, $X_{10}$ is Q and $X_{16}$ is k. In some embodiments, $X_{10}$ is Q and $X_{17}$ is H. In some embodiments, $X_{10}$ is Q and $X_{18}$ is K. In some embodiments, $X_{10}$ is Q and $X_{31}$ is K. In some embodiments, $X_{10}$ is Q and $X_{35}$ is E.

In some embodiments, $X_{15}$ is E and $X_{16}$ is L. In some embodiments, $X_{15}$ is E and $X_{16}$ is k. In some embodiments, $X_{15}$ is E and $X_{17}$ is H. In some embodiments, $X_{15}$ is E and $X_{18}$ is K. In some embodiments, $X_{15}$ is E and $X_{31}$ is K. In some embodiments, $X_{15}$ is E and $X_{35}$ is E.

In some embodiments, $X_{16}$ is L and $X_{17}$ is H. In some embodiments, $X_{16}$ is L and $X_{18}$ is K. In some embodiments, $X_{16}$ is L and $X_{31}$ is K. In some embodiments, $X_{16}$ is L and $X_{35}$ is E.

In some embodiments, $X_{16}$ is k and $X_{17}$ is H. In some embodiments, $X_{16}$ is k and $X_{18}$ is K. In some embodiments, $X_{16}$ is k and $X_{31}$ is K. In some embodiments, $X_{16}$ is k and $X_{35}$ is E.

In some embodiments, $X_{17}$ is H and $X_{18}$ is K. In some embodiments, $X_{17}$ is H and $X_{31}$ is K. In some embodiments, $X_{17}$ is H and $X_{35}$ is E.

In some embodiments, $X_{18}$ is K and $X_{31}$ is K. In some embodiments, $X_{18}$ is K and $X_{35}$ is E.

In some embodiments, $X_{31}$ is K and $X_{35}$ is E.

In some embodiments, certain amino acids represented by the consensus sequence of SEQ ID NO: 210 include the following:

In some embodiments, $X_1$ is S, $X_5$ is S, and $X_{15}$ is E. In some embodiments, $X_1$ is S, $X_5$ is S, and $X_{16}$ is L. In some embodiments, $X_1$ is S, $X_5$ is S, and $X_{16}$ is k. In some embodiments, $X_1$ is S, $X_5$ is S, and $X_{17}$ is H. In some embodiments, $X_1$ is S, $X_5$ is S, and $X_{18}$ is K. In some embodiments, $X_1$ is S, $X_5$ is S, and $X_{31}$ is K. In some embodiments, $X_1$ is S and $X_{35}$ is E.

In some embodiments, $X_1$ is K, $X_5$ is S, and $X_{15}$ is E. In some embodiments, $X_1$ is K, $X_5$ is S, and $X_{16}$ is L. In some embodiments, $X_1$ is K, $X_5$ is S, and $X_{16}$ is k. In some embodiments, $X_1$ is K, $X_5$ is S, and $X_{17}$ is H. In some embodiments, $X_1$ is K, $X_5$ is S, and $X_{18}$ is K. In some embodiments, $X_1$ is K, $X_5$ is S, and $X_{31}$ is K. In some embodiments, $X_1$ is K, $X_5$ is S, and $X_{35}$ is E.

In some embodiments, $X_1$ is k, $X_5$ is S, and $X_{15}$ is E. In some embodiments, $X_1$ is k, $X_5$ is S, and $X_{16}$ is L. In some embodiments, $X_1$ is k, $X_5$ is S, and $X_{16}$ is k. In some embodiments, $X_1$ is k, $X_5$ is S, and $X_{17}$ is H. In some embodiments, $X_1$ is k, $X_5$ is S, and $X_{18}$ is K. In some embodiments, $X_1$ is k, $X_5$ is S, and $X_{31}$ is K. In some embodiments, $X_1$ is k, $X_5$ is S, and $X_{35}$ is E.

In some embodiments, $X_5$ is S, $X_{15}$ is E, and $X_{16}$ is L. In some embodiments, $X_5$ is S, $X_{15}$ is E, and $X_{16}$ is k. In some embodiments, $X_5$ is S, $X_{15}$ is E, and $X_{17}$ is H. In some embodiments, $X_5$ is S, $X_{15}$ is E, and $X_{18}$ is K. In some embodiments, $X_5$ is S, $X_{15}$ is E, and $X_{31}$ is K. In some embodiments, $X_5$ is S, $X_{15}$ is E, and $X_{35}$ is E.

In some embodiments, $X_{10}$ is Q, $X_{15}$ is E and $X_{16}$ is L. In some embodiments, $X_{10}$ is Q, and $X_{16}$ is k and $X_{17}$ is H. In some embodiments, $X_{10}$ is Q, $X_{18}$ is K, and $X_{31}$ is K. In some embodiments, $X_{10}$ is Q, $X_{31}$ is K and $X_{35}$ is E.

In some embodiments, $X_{15}$ is E, $X_{16}$ is L, and $X_{17}$ is H. In some embodiments, $X_{15}$ is E, $X_{16}$ is L, and $X_{18}$ is K. In some embodiments, $X_{15}$ is E, $X_{16}$ is L, and $X_{31}$ is K. In some embodiments, $X_{15}$ is E, $X_{16}$ is L, and $X_{35}$ is E.

In some embodiments, $X_{15}$ is E, $X_{16}$ is k, and $X_{17}$ is H. In some embodiments, $X_{15}$ is E, $X_{16}$ is k, and $X_{18}$ is K. In some embodiments, $X_{15}$ is E, $X_{16}$ is k, and $X_{31}$ is K. In some embodiments, $X_{15}$ is E, $X_{16}$ is k, and $X_{35}$ is E.

In some embodiments, $X_{16}$ is L, $X_{17}$ is H, and $X_{18}$ is K. In some embodiments, $X_{16}$ is L, $X_{17}$ is H, and $X_{31}$ is K. In some embodiments, $X_{16}$ is L, $X_{17}$ is H, and $X_{35}$ is E.

In some embodiments, $X_{16}$ is k, $X_{17}$ is H, and $X_{18}$ is K. In some embodiments, $X_{16}$ is k, $X_{17}$ is H, and $X_{31}$ is K. In some embodiments, $X_{16}$ is k, $X_{17}$ is H, and $X_{35}$ is E.

In some embodiments, $X_{17}$ is H, $X_{18}$ is K, and $X_{31}$ is K. In some embodiments, $X_{17}$ is H, $X_{18}$ is K, and $X_{35}$ is E.

In some embodiments, $X_{18}$ is K, $X_{31}$ is K, and $X_{35}$ is E.

In some embodiments, a polypeptide intermediate of the disclosure is an isolated polypeptide comprising an amino acid sequence selected from the group consisting of amino acid sequences represented by the consensus sequence of SEQ ID NO: 211: $X_1$CNTSTCAT$X_{10}$RLAN$X_{15}X_{16}X_{17}$KSSNNFGPILPPTKVGS$X_{35}$TY-(OH/NH$_2$) (SEQ ID NO: 211), wherein:

$X_1$ is S, K or k;
$X_{10}$ is Q or S;
$X_{15}$ is E or F;
$X_{16}$ is L, K or k;
$X_{17}$ is H, V or Q; and
$X_{35}$ is E or N;
each K independently represents an L-lysine optionally covalently bound to a protecting group or a spacer optionally bound to a protecting group;
each k independently represents a D-lysine optionally covalently bound to a protecting group or a spacer optionally bound to a protecting group; and
wherein the two cysteine residues of $X_1$CNTSTC (SEQ ID NO: 309) are optionally further bound by a disulfide bridge.

In some embodiments, $X_{35}$ is E. In some embodiments, $X_{35}$ is N.

In some embodiments, certain amino acids represented by the consensus sequence of SEQ ID NO: 211 include the following:

In some embodiments, carboxy terminal amino acid 37 is Y—(NH$_2$). In some embodiments, carboxy terminal amino acid 37 is Y—(OH).

In some embodiments, $X_1$ is S. In some embodiments, $X_1$ is K. In some embodiments, $X_1$ is k.

In some embodiments, $X_{10}$ is Q. In some embodiments, $X_{10}$ is S.

In some embodiments, $X_{15}$ is E. In some embodiments, $X_{15}$ is F.

In some embodiments, $X_{16}$ is L. In some embodiments, $X_{16}$ is K. In some embodiments, $X_{16}$ is k.

In some embodiments, $X_{17}$ is H. In some embodiments, $X_{17}$ is V. In some embodiments, $X_{17}$ is Q.

In some embodiments, $X_{35}$ is E. In some embodiments, $X_{35}$ is N.

In some embodiments, certain amino acids represented by the consensus sequence of SEQ ID NO: 211 include the following: In some embodiments, $X_1$ is S and $X_{10}$ is Q. In some embodiments, $X_1$ is S and $X_{10}$ is S.

In some embodiments, $X_1$ is S and $X_{15}$ is E. In some embodiments, $X_1$ is S and $X_{15}$ is F. In some embodiments, $X_1$ is S and $X_{16}$ is L. In some embodiments, $X_1$ is S and $X_{16}$ is K. In some embodiments, $X_1$ is S and $X_{16}$ is k. In some embodiments, $X_1$ is S and $X_{17}$ is H. In some embodiments, $X_1$ is S and $X_{17}$ is V. In some embodiments, $X_1$ is S and $X_{17}$ is Q. In some embodiments, $X_1$ is S and $X_{35}$ is E. In some embodiments, $X_1$ is S and $X_{35}$ is N.

In some embodiments, $X_1$ is K and $X_{10}$ is Q. In some embodiments, $X_1$ is K and $X_{10}$ is S. In some embodiments, $X_1$ is K and $X_{15}$ is E. In some embodiments, $X_1$ is K and $X_{15}$ is F. In some embodiments, $X_1$ is K and $X_{16}$ is L. In some embodiments, $X_1$ is K and $X_{16}$ is K. In some embodiments, $X_1$ is K and $X_{16}$ is k. In some embodiments, $X_1$ is K and $X_{17}$ is H. In some embodiments, $X_1$ is K and $X_{17}$ is V. In some embodiments, $X_1$ is K and $X_{17}$ is Q. In some embodiments, $X_1$ is K and $X_{35}$ is E. In some embodiments, $X_1$ is K and $X_{35}$ is N.

In some embodiments, $X_1$ is k and $X_{10}$ is Q. In some embodiments, $X_1$ is k and $X_{10}$ is S. In some embodiments, $X_1$ is k and $X_{15}$ is E. In some embodiments, $X_1$ is k and $X_{15}$ is F. In some embodiments, $X_1$ is k and $X_{16}$ is L. In some embodiments, $X_1$ is k and $X_{16}$ is K. In some embodiments, $X_1$ is k and $X_{16}$ is k. In some embodiments, $X_1$ is k and $X_{17}$ is H. In some embodiments, $X_1$ is k and $X_{17}$ is V. In some embodiments, $X_1$ is k and $X_{17}$ is Q. In some embodiments, $X_1$ is k and $X_{35}$ is E. In some embodiments, $X_1$ is k and $X_{35}$ is N.

In some embodiments, $X_{10}$ is Q and $X_{15}$ is E. In some embodiments, $X_{10}$ is Q and $X_{15}$ is F. In some embodiments, $X_{10}$ is Q and $X_{16}$ is L. In some embodiments, $X_{10}$ is Q and $X_{16}$ is K. In some embodiments, $X_{10}$ is Q and $X_{16}$ is k. In some embodiments, $X_{10}$ is Q and $X_{17}$ is H. In some embodiments, $X_{10}$ is Q and $X_{17}$ is V. In some embodiments, $X_{10}$ is Q and $X_{17}$ is Q. In some embodiments, $X_{10}$ is Q and $X_{35}$ is E. In some embodiments, $X_{10}$ is Q and $X_{35}$ is N.

In some embodiments, $X_{10}$ is S and $X_{15}$ is E. In some embodiments, $X_{10}$ is S and $X_{15}$ is F. In some embodiments, $X_{10}$ is S and $X_{16}$ is L. In some embodiments, $X_{10}$ is S and $X_{16}$ is K. In some embodiments, $X_{10}$ is S and $X_{16}$ is k. In some embodiments, $X_{10}$ is S and $X_{17}$ is H. In some embodiments, $X_{10}$ is S and $X_{17}$ is V. In some embodiments, $X_{10}$ is S and $X_{17}$ is Q. In some embodiments, $X_{10}$ is S and $X_{35}$ is E. In some embodiments, $X_{10}$ is S and $X_{35}$ is N.

In some embodiments, $X_{15}$ is E and $X_{16}$ is L. In some embodiments, $X_{15}$ is E and $X_{16}$ is K. In some embodiments, $X_{15}$ is E and $X_{16}$ is k. In some embodiments, $X_{15}$ is E and $X_{17}$ is H. In some embodiments, $X_{15}$ is E and $X_{17}$ is V. In some embodiments, $X_{15}$ is E and $X_{17}$ is Q. In some embodiments, $X_{15}$ is E and $X_{35}$ is E. In some embodiments, $X_{15}$ is E and $X_{35}$ is N.

In some embodiments, $X_{15}$ is F and $X_{16}$ is L. In some embodiments, $X_{15}$ is F and $X_{16}$ is K. In some embodiments, $X_{15}$ is F and $X_{16}$ is k. In some embodiments, $X_{15}$ is F and $X_{17}$ is H. In some embodiments, $X_{15}$ is F and $X_{17}$ is V. In some embodiments, $X_{15}$ is F and $X_{17}$ is Q. In some embodiments, $X_{15}$ is F and $X_{35}$ is E. In some embodiments, $X_{15}$ is F and $X_{35}$ is N.

In some embodiments, $X_{16}$ is L and $X_{17}$ is H. In some embodiments, $X_{16}$ is L and $X_{17}$ is V. In some embodiments, $X_{16}$ is L and $X_{17}$ is Q. In some embodiments, $X_{16}$ is L and $X_{35}$ is E. In some embodiments, $X_{16}$ is L and $X_{35}$ is N.

In some embodiments, $X_{16}$ is K and $X_{17}$ is H. In some embodiments, $X_{16}$ is K and $X_{17}$ is V. In some embodiments, $X_{16}$ is K and $X_{17}$ is Q. In some embodiments, $X_{16}$ is K and $X_{35}$ is E. In some embodiments, $X_{16}$ is K and $X_{35}$ is N.

In some embodiments, $X_{16}$ is k and $X_{17}$ is H. In some embodiments, $X_{16}$ is k and $X_{17}$ is V. In some embodiments, $X_{16}$ is k and $X_{17}$ is Q. In some embodiments, $X_{16}$ is k and $X_{35}$ is E. In some embodiments, $X_{16}$ is k and $X_{35}$ is N.

In some embodiments, $X_{17}$ is H and $X_{35}$ is E. In some embodiments, $X_{17}$ is H and $X_{35}$ is N.

In some embodiments, $X_{17}$ is V and $X_{35}$ is E. In some embodiments, $X_{17}$ is V and $X_{35}$ is N.

In some embodiments, $X_{17}$ is Q and $X_{35}$ is E. In some embodiments, $X_{17}$ is Q and $X_{35}$ is N.

In some embodiments, a polypeptide intermediate of the disclosure is an isolated polypeptide comprising an amino acid sequence selected from the group consisting of amino acid sequences represented by the consensus sequence of SEQ ID NO: 212: SCNTSTCATQRLAN$X_{15}X_{16}X_{17}$KSSNNFGPILPPTKVGS$X_{35}$TY-(OH/NH$_2$) (SEQ ID NO: 212), wherein:

$X_{15}$ is E or F;
$X_{16}$ is L, K or k;
$X_{17}$ is H, V or Q; and
$X_{35}$ is E or N;
each K independently represents an L-lysine optionally covalently bound to a protecting group or a spacer optionally bound to a protecting group;

each k independently represents a D-lysine optionally covalently bound to a protecting group or a spacer optionally bound to a protecting group; and wherein the two cysteine residues of SCNTSTC (SEQ ID NO: 310) are optionally further bound by a disulfide bridge.

In some embodiments, $X_{35}$ is E. In some embodiments, $X_{35}$ is N.

In some embodiments, certain amino acids represented by the consensus sequence of SEQ ID NO: 212 include the following:

In some embodiments, carboxy terminal amino acid 37 is Y—(NH$_2$). In some embodiments, carboxy terminal amino acid 37 is Y—(OH).

In some embodiments, $X_{15}$ is E. In some embodiments, $X_{15}$ is F.

In some embodiments, $X_{16}$ is L. In some embodiments, $X_{16}$ is K. In some embodiments, $X_{16}$ is k.

In some embodiments, $X_{17}$ is H. In some embodiments, $X_{17}$ is V. In some embodiments, $X_{17}$ is Q.

In some embodiments, $X_{15}$ is E and $X_{16}$ is L. In some embodiments, $X_{15}$ is E and $X_{16}$ is K. In some embodiments, $X_{15}$ is E and $X_{16}$ is k. In some embodiments, $X_{15}$ is E and $X_{17}$ is H. In some embodiments, $X_{15}$ is E and $X_{17}$ is V. In some embodiments, $X_{15}$ is E and $X_{17}$ is Q. In some embodiments, $X_{15}$ is E and $X_{35}$ is E. In some embodiments, $X_{15}$ is E and $X_{35}$ is N.

In some embodiments, $X_{15}$ is F and $X_{16}$ is L. In some embodiments, $X_{15}$ is F and $X_{16}$ is K. In some embodiments, $X_{15}$ is F and $X_{16}$ is k. In some embodiments, $X_{15}$ is F and $X_{17}$ is H. In some embodiments, $X_{15}$ is F and $X_{17}$ is V. In some embodiments, $X_{15}$ is F and $X_{17}$ is Q. In some embodiments, $X_{15}$ is F and $X_{35}$ is E. In some embodiments, $X_{15}$ is F and $X_{35}$ is N.

In some embodiments, $X_{16}$ is L and $X_{17}$ is H. In some embodiments, $X_{16}$ is L and $X_{17}$ is V. In some embodiments, $X_{16}$ is L and $X_{17}$ is Q. In some embodiments, $X_{16}$ is L and $X_{35}$ is E. In some embodiments, $X_{16}$ is L and $X_{35}$ is N.

In some embodiments, $X_{16}$ is K and $X_{17}$ is H. In some embodiments, $X_{16}$ is K and $X_{17}$ is V. In some embodiments, $X_{16}$ is K and $X_{17}$ is Q. In some embodiments, $X_{16}$ is K and $X_{35}$ is E. In some embodiments, $X_{16}$ is K and $X_{35}$ is N.

In some embodiments, $X_{16}$ is k and $X_{17}$ is H. In some embodiments, $X_{16}$ is k and $X_{17}$ is V. In some embodiments, $X_{16}$ is k and $X_{17}$ is Q. In some embodiments, $X_{16}$ is k and $X_{35}$ is E. In some embodiments, $X_{16}$ is k and $X_{35}$ is N.

In some embodiments, $X_{17}$ is H and $X_{35}$ is E. In some embodiments, $X_{17}$ is H and $X_{35}$ is N.

In some embodiments, $X_{17}$ is V and $X_{35}$ is E. In some embodiments, $X_{17}$ is V and $X_{35}$ is N.

In some embodiments, $X_{17}$ is Q and $X_{35}$ is E. In some embodiments, $X_{17}$ is Q and $X_{35}$ is N.

In some embodiments, the isolated peptide comprising the amino acid sequence of SEQ ID NO: 210, SEQ ID NO: 211, or SEQ ID NO: 212 further comprises a protecting group or a spacer optionally bound to a protecting group. In some embodiments, the isolated peptide further comprises a protecting group. In some embodiments, the isolated peptide further comprises a spacer. In some embodiments, the isolated peptide further comprises a spacer bound to a protecting group.

In some embodiments, the isolated polypeptide comprises a protecting group or a spacer optionally bound to a protecting group at position $X_1$, $X_{15}$, or $X_{16}$.

In some embodiments, the isolated polypeptide comprising a protecting group or a spacer optionally bound to a protecting group at position $X_1$, $X_{15}$, or $X_{16}$ is conjugated via a lysine at that position.

In some embodiments, the isolated polypeptide comprises a protecting group or a spacer optionally bound to a protecting group at position $X_1$.

In some embodiments, the isolated polypeptide comprises a protecting group or a spacer optionally bound to a protecting group at position $X_{15}$.

In some embodiments, the isolated polypeptide comprises a protecting group or a spacer optionally bound to a protecting group at position $X_{16}$.

In some embodiments, the isolated polypeptide comprising a protecting group or a spacer optionally bound to a protecting group at position $X_1$ is conjugated via a lysine at that position.

In some embodiments, the isolated polypeptide comprising a protecting group or a spacer optionally bound to a protecting group at position $X_{15}$ is conjugated via a lysine at that position.

In some embodiments, the isolated polypeptide comprising a protecting group or a spacer optionally bound to a protecting group at position $X_{16}$ is conjugated via a lysine at that position.

In some embodiments, the protecting group is selected from the group consisting of is acetyl, allyloxycarbonyl, Benzyl, Boc, Cbz, Dmb, (dimethyl-2,6-dioxocyclohex-1-ylidene)ethyl, Fmoc, tert-butyl, or trityl. In some embodiments, the protecting group is acetyl, allyloxycarbonyl, dimethyl-2,6-dioxocyclohex-1-ylidene)ethyl, Fmoc, tert-butyl, or trityl. In some embodiments, the protecting group is acetyl, allyloxycarbonyl, dimethyl-2,6-dioxocyclohex-1-ylidene)ethyl, or Fmoc, In some embodiments, the spacer is selected from the group consisting of Formula XI, Formula XII, Formula XIII, Formula XIV, Formula XV, Formula XVI, Formula XVII, and Formula XVIII. In some embodiments, the isolated polypeptide further comprises a spacer of Formula XIII. In some embodiments, the isolated polypeptide further comprises a spacer of Formula XIV. In some embodiments, the isolated polypeptide further comprises a spacer of Formula XVII. In some embodiments, the isolated polypeptide further comprises a spacer of Formula XVIII. In some embodiments, the spacer is bound to a protecting group. In some embodiments, the protecting group is selected from the group consisting of is acetyl, allyloxycarbonyl, Benzyl, Boc, Cbz, Dmb, (dimethyl-2,6-dioxocyclohex-1-ylidene)ethyl, Fmoc, tert-butyl, or trityl. In some embodiments, the protecting group is acetyl, allyloxycarbonyl, dimethyl-2,6-dioxocyclohex-1-ylidene)ethyl, Fmoc, tert-butyl, or trityl. In some embodiments, the protecting group is acetyl, trityl, or tert-butyl. In some embodiments, the spacer is not bound to a protecting group.

Exemplary Polypeptide Intermediates

In some embodiments, an isolated polypeptide of the disclosure comprises an amino acid sequence selected form the group consisting of the following peptides listed in Table 4:

TABLE 4

Exemplary polypeptide intermediates

| Compound No. | Sequence | SEQ ID NO |
|---|---|---|
| A129 | SC*NTSTC*ATQRLANEkHKSSNNFGPILPPTKVGSETY-NH2 | SEQ ID NO: 129 |
| B1 | SC*NTSTC*ATQRLANEk*(acetyl)HKSSNNFGPILPPTKVGSETY-NH2 | SEQ ID NO: 144 |
| B2 | SC*NTSTC*ATQRLANEk*(allyloxycarbonyl)HKSSNNFGPILPPTKVGSETY-NH2 | SEQ ID NO: 145 |
| B3 | SC*NTSTC*ATQRLANEk*((dimethyl-2,6-dioxocyclohex-1-ylidene)ethyl)HKSSNNFGPILPPTKVGSETY-NH2 | SEQ ID NO: 146 |
| B4 | SC*NTSTC*ATQRLANEk*(γGlu)HKSSNNFGPILPPTKVGSETY-NH2 | SEQ ID NO: 147 |
| B5 | SC*NTSTC*ATQRLANEk*(γGlu-acetyl)HKSSNNFGPILPPTKVGSETY-NH2 | SEQ ID NO: 148 |
| B6 | SC*NTSTC*ATQRLANEk*(γGlu-trityl)HKSSNNFGPILPPTKVGSETY-NH2 | SEQ ID NO: 149 |
| B7 | SC*NTSTC*ATQRLANEk*(γGlu-tert-butyl)HKSSNNFGPILPPTKVGSETY-NH2 | SEQ ID NO: 150 |
| B8 | SC*NTSTC*ATQRLANEk*(γGlu-γGlu)HKSSNNFGPILPPTKVGSETY-NH2 | SEQ ID NO: 151 |
| B9 | SC*NTSTC*ATQRLANEk*(γGlu-γGlu-acetyl)HKSSNNFGPILPPTKVGSETY-NH2 | SEQ ID NO: 152 |
| B10 | SC*NTSTC*ATQRLANEk*(γGlu-γGlu-trityl)HKSSNNFGPILPPTKVGSETY-NH2 | SEQ ID NO: 153 |
| B11 | SC*NTSTC*ATQRLANEk*(γGlu-γGlu-tert-butyl)HKSSNNFGPILPPTKVGSETY-NH2 | SEQ ID NO: 154 |
| B12 | KC*NTSTC*ATSRLANFLQKSSNNFGPILPPTKVGSETY-NH2 | SEQ ID NO: 155 |
| B13 | K*(Fmoc)C*NTSTC*ATSRLANFLQKSSNNFGPILPPTKVGSETY-NH2 | SEQ ID NO: 156 |
| B14 | K*(γGlu)C*NTSTC*ATSRLANFLQKSSNNFGPILPPTKVGSETY-NH2 | SEQ ID NO: 157 |
| B15 | K*(γGlu-acetyl)C*NTSTC*ATSRLANFLQKSSNNFGPILPPTKVGSETY-NH2 | SEQ ID NO: 158 |
| B16 | K*(γGlu-trityl)C*NTSTC*ATSRLANFLQKSSNNFGPILPPTKVGSETY-NH2 | SEQ ID NO: 159 |
| B17 | K*(γGlu-tert-butyl)C*NTSTC*ATSRLANFLQKSSNNFGPILPPTKVGSETY | SEQ ID NO: 160 |
| B18 | K*(γGlu-γGlu)C*NTSTC*ATSRLANFLQKSSNNFGPILPPTKVGSETY-NH2 | SEQ ID NO: 161 |
| B19 | K*(γGlu-γGlu-acetyl)C*NTSTC*ATSRLANFLQKSSNNFGPILPPTKVGSETY-NH2 | SEQ ID NO: 162 |
| B20 | K*(γGlu-γGlu-trityl)C*NTSTC*ATSRLANFLQKSSNNFGPILPPTKVGSETY-NH2 | SEQ ID NO: 163 |
| B21 | K*(γGlu-γGlu-tert-butyl)C*NTSTC*ATSRLANFLQKSSNNFGPILPPTKVGSETY-NH2 | SEQ ID NO: 164 |
| A130 | KC*NTSTC*ATQRLANELHKSSNNFGPILPPTKVGSETY-NH2 | SEQ ID NO: 130 |
| B22 | K*(γGlu)C*NTSTC*ATQRLANELHKSSNNFGPILPPTKVGSETY | SEQ ID NO: 165 |
| B23 | K*(γGlu-γGlu)C*NTSTC*ATQRLANELHKSSNNFGPILPPTKVGSETY | SEQ ID NO: 166 |

In some embodiments, the present invention provides a peptide intermediate set forth in the Table 4, above. In some embodiments, the peptide intermediate is a peptide having the amino acid sequence of SEQ ID NO: 129, SEQ ID NO: 144, SEQ ID NO: 145, or SEQ ID NO: 156. In some embodiments, the peptide intermediate has the amino acid sequence of SEQ ID NO: 129. In some embodiments, the peptide intermediate has the amino acid sequence of SEQ ID NO: 145. In some embodiments, the peptide intermediate is a peptide having the amino acid sequence of SEQ ID NO: 129, SEQ ID NO: 147, SEQ ID NO: 148, SEQ ID NO: 149 or SEQ ID NO: 150. In some embodiments, the peptide intermediate has the amino acid sequence of SEQ ID NO: 147. In some embodiments, the peptide intermediate is a peptide having the amino acid sequence of SEQ ID NO: 151, SEQ ID NO: 152, SEQ ID NO: 153, or SEQ ID NO: 154. In some embodiments, the peptide intermediate has the amino acid sequence of SEQ ID NO: 151.

In some embodiments, the peptide intermediate is a peptide having the amino acid sequence of SEQ ID NO: 155 or SEQ ID NO: 156. In some embodiments, the peptide intermediate is a peptide having the amino acid sequence of SEQ ID NO: 155. In some embodiments, the peptide intermediate is a peptide having the amino acid sequence of SEQ ID NO: 157, SEQ ID NO: 158, SEQ ID NO: 159, or SEQ ID NO: 160. In some embodiments, the peptide intermediate is a peptide having the amino acid sequence of SEQ ID NO: 157. In some embodiments, the peptide intermediate is a peptide having the amino acid sequence of SEQ ID NO: 161, SEQ ID NO: 162, SEQ ID NO: 163, or SEQ ID NO: 164. In some embodiments, the peptide intermediate is a peptide having the amino acid sequence of SEQ ID NO: 164.

8. Uses, Formulation and Administration

Methods of Use

According to another embodiment, the invention relates to a method of treating metabolic disease or disorder in a subject in need of treatment, comprising providing the subject with an effective amount of an amylin analog polypeptide of the disclosure or a pharmaceutical composition thereof. Metabolic diseases or disorders include type 1 diabetes, type 2 diabetes, and obesity. Additionally, the invention relates to a method of effecting weight loss in a subject, including a diabetic subject, comprising providing the subject with an effective amount of an amylin analog polypeptide of the disclosure.

Amylin analog polypeptides of the disclosure are particularly useful for the treatment of diabetes, the method comprising providing a diabetic subject with an effective amount of an amylin analog polypeptide. In some embodiments, an amylin analog polypeptide of the disclosure is used for the treatment of a subject with type 1 or type 2 diabetes to control, or reduce, concentrations of blood sugar in the subject, where blood sugar levels can be monitored or approximated based on measured blood concentrations of glycated hemoglobin (hemoglobin A1c, HbA1c).

(i) In some embodiments, an amylin analog polypeptide of the disclosure is used for the treatment of a subject with type 1 diabetes;

(ii) In some embodiments, an amylin analog polypeptide of the disclosure is used for the treatment of a subject with type 2 diabetes;

(iii) In some embodiments, an amylin analog polypeptide of the disclosure is used for the treatment of obesity; and (iv) In some embodiments, an amylin analog polypeptide of the disclosure is used to provide weight loss to a subject, such as a diabetic subject, wherein the amylin analog polypeptide of usage (i), (ii), (iii) or (iv) comprises any amino acid sequence of this disclosure including those selected from the group consisting of SEQ ID NOS: 199, 200, 204, 206, 127, 57, 128, 129, 43, 209, 130, 64, 65, 131, 109 and 27.

In some embodiments, the amylin analog polypeptide is used for the treatment of a subject with type 1 diabetes wherein the amylin analog polypeptide comprises the amino acid sequence of SEQ ID NO 27. In some embodiments, the amylin analog polypeptide is used for the treatment of a subject with type 1 diabetes wherein the amylin analog polypeptide comprises the amino acid sequence of SEQ ID NO 64. In some embodiments, the amylin analog polypeptide is used for the treatment of a subject with type 1 diabetes wherein the amylin analog polypeptide comprises the amino acid sequence of SEQ ID NO 65. In some embodiments, the amylin analog polypeptide is used for the treatment of a subject with type 1 diabetes wherein the amylin analog polypeptide comprises the amino acid sequence of SEQ ID NO 131.

In some embodiments, the amylin analog polypeptide is used for the treatment of a subject with type 2 diabetes wherein the amylin analog polypeptide comprises the amino acid sequence of SEQ ID NO 27. In some embodiments, the amylin analog polypeptide is used for the treatment of a subject with type 2 diabetes wherein the amylin analog polypeptide comprises the amino acid sequence of SEQ ID NO 64. In some embodiments, the amylin analog polypeptide is used for the treatment of a subject with type 2 diabetes wherein the amylin analog polypeptide comprises the amino acid sequence of SEQ ID NO 65. In some embodiments, the amylin analog polypeptide is used for the treatment of a subject with type 2 diabetes wherein the amylin analog polypeptide comprises the amino acid sequence of SEQ ID NO 131.

In some embodiments, the amylin analog polypeptide is used for the treatment of a subject with obesity wherein the amylin analog polypeptide comprises the amino acid sequence of SEQ ID NO 27. In some embodiments, the amylin analog polypeptide is used for the treatment of a subject with obesity wherein the amylin analog polypeptide comprises the amino acid sequence of SEQ ID NO 64. In some embodiments, the amylin analog polypeptide is used for the treatment of a subject with obesity wherein the amylin analog polypeptide comprises the amino acid sequence of SEQ ID NO 65. In some embodiments, the amylin analog polypeptide is used for the treatment of a subject with obesity wherein the amylin analog polypeptide comprises the amino acid sequence of SEQ ID NO 131.

In some embodiments, the amylin analog polypeptide is used to provide weight loss to a subject wherein the amylin analog polypeptide comprises the amino acid sequence of SEQ ID NO 27. In some embodiments, the amylin analog polypeptide is used to provide weight loss to a subject wherein the amylin analog polypeptide comprises the amino acid sequence of SEQ ID NO 64. In some embodiments, the amylin analog polypeptide is used to provide weight loss to a subject wherein the amylin analog polypeptide comprises the amino acid sequence of SEQ ID NO 65. In some embodiments, the amylin analog polypeptide is used to provide weight loss to a subject wherein the amylin analog polypeptide comprises the amino acid sequence of SEQ ID NO 131.

Amylin analog polypeptides of the disclosure, like insulin, are provided (i.e., administered) to a diabetic subject to maintain, control, or reduce blood sugar concentrations in the subject. Diabetic subjects who are treated with an amylin analog polypeptide of the disclosure as an adjunct to insulin therapy are at risk of hypoglycemia (i.e., low blood sugar), particularly severe hypoglycemia. Accordingly, reducing the dose of meal time insulin for diabetic subjects upon treatment with an amylin analog polypeptide of the disclosure is intended to decrease the risk of hypoglycemia, particularly severe hypoglycemia.

Severe hypoglycemia, as used herein, refers to an episode of hypoglycemia requiring the assistance of another individual (including help administering oral carbohydrate) or requiring the administration of glucagon, intravenous glucose, or other medical intervention.

Accordingly, administration of an amylin analog polypeptide of the disclosure, as an adjunct to insulin therapy, particularly meal-time insulin therapy, generally requires a dose reduction in the meal-time insulin necessary to properly maintain healthy blood sugar concentrations in the subject. In other words, type 1 or type 2 diabetics who already self-administer meal-time insulin at a particular dose before commencing treatment with an amylin analog polypeptide of the disclosure, will reduce (for example, up to 25%, 50%, 75%, or 100%) the dose of meal-time insulin they continue to self-administer upon commencing treatment with an amylin analog polypeptide of the disclosure.

In some embodiments, the method comprises providing an amylin analog polypeptide of the disclosure or a pharmaceutical composition thereof, to a subject in need of treatment, via injection. In some embodiments, the method comprises providing an amylin analog polypeptide of the disclosure or a pharmaceutical composition thereof, formulated for oral administration, to a subject in need of treatment.

In some embodiments, the method comprises providing an amylin analog polypeptide of the disclosure or a pharmaceutical composition thereof, to a subject in need of treatment, via implantation. In some embodiments, the method comprises providing continuous delivery of an amylin analog polypeptide, to a subject in need of treatment, from an osmotic delivery device. The delivery device, such as an osmotic delivery device, comprises sufficient amylin analog polypeptide of the disclosure for continuous administration for up to 3 months, 6 months, 9 months, 12 months, 18 months or 24 months. As such, continuous administration of an amylin analog polypeptide of the disclosure via osmotic delivery device eliminates daily, or multiple daily dosing of existing amylin analog polypeptides, such as pramlintide. Diabetics who are treated with pramlintide must coordinate dosing of pramlintide before meals with meal-time insulin administered after meals. By contrast, diabetics who are treated with an amylin analog polypeptide of the disclosure via osmotic delivery device, receive continuous delivery of the amylin analog polypeptide and need only administer meal-time insulin at reduced doses.

The substantial steady-state delivery of the amylin analog polypeptide from the osmotic delivery device is continuous over an administration period. In some embodiments, the subject or patient is a human subject or human patient.

In some embodiments of the present invention, the administration period is, for example, at least about 3 months, at least about 3 months to about a year, at least about 4 months to about a year, at least about 5 months to about a year, at least about 6 months to about a year, at least about 8 months to about a year, at least about 9 months to about a year, at least about 10 months to about a year, at least about one year to about two years, at least about two years to about three years.

In further embodiments, the treatment methods of the present invention provide significant decrease in the subject's fasting plasma glucose concentration after implantation of the osmotic delivery device in the subject (relative to the subject's fasting plasma glucose concentration before implantation of the osmotic delivery device) that is achieved within about 7 days, 6 days, 5 days, 4 days, 3 days, 2 days, 1 day or less after implantation of the osmotic delivery device in the subject. The significant decrease in fasting plasma glucose is typically statistically significant as demonstrated by application of an appropriate statistical test or is considered significant for the subject by a medical practitioner. A significant decrease in fasting plasma glucose relative to the baseline before implantation is typically maintained over the administration period.

In some embodiments, the present invention relates to a method of treating a disease or condition in a subject in need of treatment. The method comprises providing continuous delivery of a drug from an osmotic delivery device, wherein substantial steady-state delivery of the drug at therapeutic concentrations is achieved in the subject. The substantial steady-state delivery of the drug from the osmotic delivery device is continuous over an administration period of at least about 3 months. The drug has a known or determined half-life in a typical subject. Humans are preferred subjects for the practice of the present invention. The present invention includes a drug effective for treatment of the disease or condition, as well as an osmotic delivery device comprising the drug for use in the present methods of treating the disease or condition in a subject in need of treatment. Advantages of the present invention include mitigation of peak-associated drug toxicities and attenuation of sub-optimal drug therapy associated with troughs.

In some embodiments, the substantial steady-state delivery of a drug at therapeutic concentrations is achieved within a period of about 1 month, 7 days, 5 days, 3 days or 1 day after implantation of the osmotic delivery device in the subject.

The invention also provides a method for promoting weight loss in a subject in need thereof, a method for treating excess weight or obesity in a subject in need thereof, and/or a method for suppressing appetite in a subject in need thereof. The method comprises providing delivery of an isolated amylin analog polypeptide. In some embodiments, the isolated amylin analog polypeptide is continuously delivered from an implantable osmotic delivery device. In some embodiments, substantial steady-state delivery of the amylin analog polypeptide from the osmotic delivery device is achieved and is substantially continuous over an administration period. In some embodiments, the subject is human.

The present invention includes an isolated amylin analog polypeptide, as well as an osmotic delivery device comprising an isolated amylin analog polypeptide for use in the present methods in a subject in need of treatment. The subject may have type 2 diabetes. The subject in need thereof may have a baseline HbA1c % of greater than 10.0%, i.e., a high baseline (HBL) subject. The subject may not have previously received a drug for treating type 2 diabetes mellitus.

In further embodiments, the treatment methods of the present invention provide significant decrease in the subject's fasting plasma glucose concentration after implantation of the osmotic delivery device in the subject (relative to the subject's fasting plasma glucose concentration before implantation of the osmotic delivery device) that is achieved within about 7 days or less after implantation of the osmotic delivery device in the subject, within about 6 days or less after implantation of the osmotic delivery device in the subject, within about 5 days or less after implantation of the osmotic delivery device in the subject, within about 4 days or less after implantation of the osmotic delivery device in the subject, within about 3 days or less after implantation of the osmotic delivery device in the subject, within about 2 days or less after implantation of the osmotic delivery device in the subject, or within about 1 day or less after implantation of the osmotic delivery device in the subject. In preferred embodiments of the present invention, the significant decrease in the subject's fasting plasma glucose concentration after implantation of the osmotic delivery device, relative to the subject's fasting plasma glucose concentration before implantation, is achieved within about 2 days or less, preferably within about 1 day or less after implantation of the osmotic delivery device in the subject, or more preferably within about 1 day after implantation of the osmotic delivery device in the subject. The significant decrease in fasting plasma glucose is typically statistically significant as demonstrated by application of an appropriate statistical test or is considered significant for the subject by a medical practitioner. A significant decrease in fasting plasma glucose relative to the baseline before implantation is typically maintained over the administration period.

In embodiments of all aspects of the present invention relating to methods of treating a disease or condition in a subject, an exemplary osmotic delivery device comprises the following: an impermeable reservoir comprising interior and exterior surfaces and first and second open ends; a semipermeable membrane in sealing relationship with the first open end of the reservoir; an osmotic engine within the reservoir and adjacent the semi-permeable membrane; a piston adjacent the osmotic engine, wherein the piston forms a movable seal with the interior surface of the reservoir, the piston divides the reservoir into a first chamber and a second chamber, the first chamber comprising the osmotic engine; a drug formulation or suspension formulation comprising the drug, wherein the second chamber comprises the drug formulation or suspension formulation and the drug formulation or suspension formulation is flowable; and a diffusion moderator inserted in the second open end of the reservoir, the diffusion moderator adjacent the suspension formulation. In preferred embodiments, the reservoir comprises titanium or a titanium alloy.

In embodiments of all aspects of the present invention relating to methods of treating a disease or condition in a subject, the drug formulation can comprise the drug and a vehicle formulation. Alternatively, suspension formulations are used in the methods and can, for example, comprise a particle formulation comprising the drug and a vehicle formulation. Vehicle formulations for use in forming the suspension formulations of the present invention can, for example, comprise a solvent and a polymer.

The reservoir of the osmotic delivery devices may, for example, comprise titanium or a titanium alloy.

In embodiments of all aspects of the present invention the implanted osmotic delivery device can be used to provide subcutaneous delivery.

In embodiments of all aspects of the present invention the continuous delivery can, for example, be zero-order, controlled continuous delivery.

Combinations

In some embodiments, an amylin analog polypeptide of the disclosure is co-formulated in combination with a second agent. In some embodiments, an amylin analog polypeptide of the disclosure is co-formulated in combination with a second agent, wherein the second agent is an insulinotropic peptide. In some embodiments, an amylin analog polypeptide of the disclosure is co-formulated in combination with a second agent, wherein the second agent is a GLP-1 receptor agonist. In some embodiments, an amylin analog polypeptide of the disclosure is co-formulated in combination with a second agent, wherein the second agent is a (GLP-1) agonist such as exenatide, a derivative of exenatide, an analogue of exenatide, or semaglutide. In some embodiments, the GLP-1 receptor agonist is exenatide. In some embodiments, the GLP-1 receptor agonist is semaglutide.

In some embodiments, an amylin analog polypeptide of the disclosure, without being co-formulated with a second agent, is administered to a subject in combination with the second agent wherein the second agent is a (GLP-1) agonist such as exenatide, a derivative of exenatide, an analogue of exenatide, or semaglutide.

In some embodiments, an amylin analog polypeptide of the disclosure is co-formulated in combination with insulin or an insulin derivative. In some embodiments, an amylin analog polypeptide of the disclosure is co-formulated in combination with a long-acting basal insulin or long-acting basal insulin derivative.

In some embodiments, an amylin analog polypeptide of the disclosure, without being co-formulated with insulin or an insulin derivative, is administered to a subject in combination with the insulin or an insulin derivative, i.e., as an adjunct to insulin therapy. In some embodiments, an amylin analog peptide of the disclosure, without being co-formulated with insulin or an insulin derivative, is administered to a subject in combination with meal-time insulin. In some embodiments, the subject has type 1 diabetes. In some embodiments, the subject has type 2 diabetes.

In some embodiments, an amylin analog polypeptide of the disclosure is co-administered to a human patient with insulin or an insulin derivative to provide a so-called dual-hormone "artificial pancreas" therapy. In some embodiments, an amylin analog polypeptide of the disclosure, without being co-formulated with the insulin or insulin derivative, is co-administered to a subject in combination with the insulin or insulin derivative to provide dual-hormone "artificial pancreas" therapy. In some embodiments, an amylin analog polypeptide of the disclosure is co-formulated with the insulin or insulin derivative and thus singly administered to a subject in combination with the insulin or insulin derivative to provide dual-hormone "artificial pancreas" therapy. In some embodiments, the artificial pancreas therapy includes rapid acting insulin or a rapid acting insulin derivative. In some embodiments, the artificial pancreas therapy includes a long acting or basal insulin or a long acting or basal insulin derivative.

In some embodiments, any of the amylin analogs of the disclosure is formulated in combination with exenatide. In some embodiments, any of the amylin analogs of the disclosure is formulated in combination with a GLP-1 receptor agonist.

Some embodiments of the present invention comprise use of a amylin analog polypeptide in combination with a second therapeutic agent, such as a second polypeptide, such as, by way of, non-limiting example, insulinotropic peptides, peptide hormones, for example, glucagon and incretin mimetics (e.g., GLP-1 receptor agonists such as exenatide), as well as peptide analogs and peptide derivatives thereof; PYY (also known as peptide YY, peptide tyrosine tyrosine), as well as peptide analogs and peptide derivatives thereof, for example, PYY(3-36); oxyntomodulin, as well as peptide analogs and peptide derivatives thereof); and gastric inhibitory peptide (GIP), as well as peptide analogs and peptide derivatives thereof. In some embodiments, a pharmaceutical composition comprising an amylin analog polypeptide in combination with a GLP-1 receptor agonist is used to treat type 2 diabetes.

GLP-1, including three forms of the peptide, GLP-1(1-37), GLP-1(7-37) and GLP-1(7-36) amide, as well as peptide analogs of GLP-1 have been shown to stimulate insulin secretion (i.e., is insulinotropic), which induces glucose uptake by cells and results in decreases in serum glucose concentrations (see, e g., Mojsov, S., Int. J. Peptide Protein Research, 40:333-343 (1992)).

Numerous GLP-1 receptor agonists (e.g., GLP-1 peptide derivatives and peptide analogs) demonstrating insulinotropic action are known in the art (see, e.g., U.S. Pat. Nos. 5,118,666; 5,120,712; 5,512,549; 5,545,618; 5,574,008; 5,574,008; 5,614,492; 5,958,909; 6,191,102; 6,268,343; 6,329,336; 6,451,974; 6,458,924; 6,514,500; 6,593,295; 6,703,359; 6,706,689; 6,720,407; 6,821,949; 6,849,708; 6,849,714; 6,887,470; 6,887,849; 6,903,186; 7,022,674; 7,041,646; 7,084,243; 7,101,843; 7,138,486; 7,141,547; 7,144,863; and 7,199,217), as well as in clinical trials (e.g., taspoglutide and albiglutide). One example of a GLP-1 receptor agonist in the practice of the present invention is Victoza® (Novo Nordisk A/S, Bagsvaerd D K) (liraglutide; U.S. Pat. Nos. 6,268,343, 6,458,924, and 7,235,627). Once-daily injectable Victoza® (liraglutide) is commercially available in the United States, Europe, and Japan. Another example, of a GLP-1 receptor agonist is Ozempic® (Novo Nordisk A/S, Bagsvaerd D K) (semaglutide). For ease of reference herein, the family of GLP-1 receptor agonists, GLP-1 peptides, GLP-1 peptide derivatives and GLP-1 peptide analogs having insulinotropic activity is referred to collectively as "GLP-1."

The molecule exenatide has the amino acid sequence of exendin-4 (Kolterman O. G., et al., J. Clin. Endocrinol. Metab. 88(7):3082-9 (2003)) and is produced by chemical synthesis or recombinant expression. For ease of reference herein, the family of exenatide peptides (e.g., including exendin-3, exendin-4, and exendin-4-amide), exenatide peptide derivatives, and exenatide peptide analogs is referred to collectively as "exenatide."

Peptide YY (PYY) is a 36 amino acid residue peptide amide. PYY inhibits gut motility and blood flow (Laburthe, M., Trends Endocrinol Metab. 1(3):168-74 (1990), mediates intestinal secretion (Cox, H. M., et al., Br J Pharmacol 101(2):247-52 (1990); Playford, R. J., et al., Lancet 335 (8705):1555-7 (1990)), and stimulate net absorption (MacFayden, R. J., et al., Neuropeptides 7(3):219-27 (1986)). Two major in vivo variants, PYY(1-36) and PYY (3-36), have been identified (e.g., Eberlein, G. A., et al., Peptides 10(4), 797-803 (1989)). The sequence of PYY, as well as peptide analogs and peptide derivatives thereof, are known in the art (e.g., U.S. Pat. Nos. 5,574,010 and 5,552,520).

Oxyntomodulin is a naturally occurring 37 amino acid peptide hormone found in the colon that has been found to suppress appetite and facilitate weight loss (Wynne K, et al., Int J Obes (Lond) 30(12):1729-36(2006)). The sequence of oxyntomodulin, as well as peptide analogs and peptide derivatives thereof, are known in the art (e.g., Bataille D, et al., Peptides 2(Suppl 2):41-44 (1981); and U.S. Patent Publication Nos. 2005/0070469 and 2006/0094652).

Gastric Inhibitory Peptide (GIP) is an insulinotropic peptide hormone (Efendic, S., et al., Horm Metab Res. 36:742-6 (2004)) and is secreted by the mucosa of the duodenum and jejunum in response to absorbed fat and carbohydrate that stimulate the pancreas to secrete insulin. GIP circulates as a biologically active 42-amino acid peptide. GIP is also known as glucose-dependent insulinotropic protein. GIP is a 42-amino acid gastrointestinal regulatory peptide that stimulates insulin secretion from pancreatic beta cells in the presence of glucose (Tseng, C., et al., PNAS 90:1992-1996 (1993)). The sequence of GIP, as well as peptide analogs and peptide derivatives thereof, are known in the art (e.g., Meier J. J., Diabetes Metab Res Rev. 21(2):91-117 (2005) and Efendic S., Horm Metab Res. 36(11-12):742-6 (2004)).

Glucagon is a peptide hormone, produced by alpha cells of the pancreas, which raises the concentration of glucose in the bloodstream. Its effect is opposite that of insulin, which lowers the glucose concentration. The pancreas releases glucagon when the concentration of glucose in the bloodstream falls too low. Glucagon causes the liver to convert stored glycogen into glucose, which is released into the bloodstream. High blood glucose levels stimulate the release of insulin. Insulin allows glucose to be taken up and used by insulin-dependent tissues. Thus, glucagon and insulin are part of a feedback system that keeps blood glucose levels at a stable level.

Pharmaceutically Acceptable Compositions

According to another embodiment, the invention provides a composition comprising a compound, i.e., isolated polypeptide, of this invention or a pharmaceutically acceptable derivative thereof and a pharmaceutically acceptable carrier, adjuvant, or vehicle. The amount of compound in compositions of this invention is such that is effective to measurably activate one or more amylin and/or calcitonin receptors, in a biological sample or in a patient. In certain embodiments, the amount of compound in compositions of this invention is such that is effective to measurably activate human amylin 3 receptor (hAMY3) and/or human calcitonin receptor (hCTR), in the absence or presence of human serum albumin, in a biological sample or in a patient. In certain embodiments, a composition of this invention is formulated for administration to a patient in need of such composition. In some embodiments, a composition of this invention is formulated for injectable administration to a patient. In some embodiments, a composition of this invention is formulated for administration to a patient via an implantable delivery device such as an osmotic deliver device.

The terms "patient" or "subject" as used herein, refer to an animal, preferably a mammal, and most preferably a human.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

The isolated polypeptides of the disclosure (also referred to herein as "active compounds"), and derivatives, fragments, analogs and homologs thereof, can be incorporated into pharmaceutical compositions suitable for administration. Such compositions typically comprise the isolated polypeptide, or a pharmaceutically acceptable salt thereof, and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subdermal, subcutaneous, oral (e.g., inhalation), transdermal (i.e., topical), transmucosal, rectal, or combinations thereof. In some embodiments, a pharmaceutical composition or an isolated polypeptide of the disclosure is formulated for administration by topical administration. In some embodiments, a pharmaceutical composition or an isolated polypeptide of the disclosure is formulated for administration by inhalation administration. In some embodiments, the pharmaceutical composition is formulated for administration by a device or other suitable delivery mechanism that is suitable for subdermal or subcutaneous implantation and delivers the pharmaceutical composition subcutaneously. In some embodiments, the pharmaceutical composition is formulated for administration by an implant device that is suitable for subdermal or subcutaneous implantation and delivers the pharmaceutical composition subcutaneously. In some embodiments, the pharmaceutical composition is formulated for administration by an osmotic delivery device, e.g., an implantable osmotic delivery device, that is suitable for subdermal or subcutaneous placement or other implantation and delivers the pharmaceutical composition subcutaneously. Solutions or suspensions used for parenteral application, intradermal application, subdermal application, subcutaneous application, or combinations thereof can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Drug Particle Formulations

In some embodiments, provided is a pharmaceutical composition comprising any of the disclosed polypeptides formulated as a trifluoroacetate salt, acetate salt or hydrochloride salt. In some embodiments, provided is a pharmaceutical composition comprising any of the disclosed polypeptides formulated as a trifluoroacetate salt. In some embodiments, provided is a pharmaceutical composition comprising any of the disclosed polypeptides formulated as an acetate salt. In some embodiments, provided is a pharmaceutical composition comprising any of the disclosed polypeptides formulated as a hydrochloride salt.

Compounds, i.e., isolated polypeptides or pharmaceutically acceptable salts thereof, for use in the practice of the present invention are typically added to particle formulations, which are used to make polypeptide-containing particles that are uniformly suspended, dissolved or dispersed in a suspension vehicle to form a suspension formulation. In some embodiments, the amylin analog polypeptide is formulated in a particle formulation and converted (e.g., spray dried) to particles. In some embodiments, the particles comprising the amylin analog polypeptide are suspended in a vehicle formulation, resulting in a suspension formulation of vehicle and suspended particles comprising the amylin analog polypeptide.

Preferably, particle formulations are formable into particles using processes such as spray drying, lyophilization, desiccation, freeze-drying, milling, granulation, ultrasonic drop creation, crystallization, precipitation, or other techniques available in the art for forming particles from a mixture of components. In one embodiment of the invention the particles are spray dried. The particles are preferably substantially uniform in shape and size.

In some embodiments, the present invention provides drug particle formulations for pharmaceutical use. The particle formulation typically comprises a drug and includes one or more stabilizing component (also referred to herein as "excipients"). Examples of stabilizing components include, but are not limited to, carbohydrates, antioxidants, amino acids, buffers, inorganic compounds, and surfactants. The amounts of stabilizers in the particle formulation can be determined experimentally based on the activities of the stabilizers and the desired characteristics of the formulation, in view of the teachings of the present specification.

In any of the embodiments, the particle formulation may comprise about 50 wt % to about 90 wt % drug, about 50 wt % to about 85 wt % drug, about 55 wt % to about 90 wt % drug, about 60 wt % to about 90 wt % drug, about 65 wt % to about 85 wt % drug, about 65 wt % to about 90 wt % drug, about 70 wt % to about 90 wt % drug, about 70 wt % to about 85 wt % drug, about 70 wt % to about 80 wt % drug, or about 70 wt % to about 75 wt % drug.

Typically, the amount of carbohydrate in the particle formulation is determined by aggregation concerns. In general, the carbohydrate amount should not be too high so as to avoid promoting crystal growth in the presence of water due to excess carbohydrate unbound to drug.

Typically, the amount of antioxidant in the particle formulation is determined by oxidation concerns, while the amount of amino acid in the formulation is determined by oxidation concerns and/or formability of particles during spray drying.

Typically, the amount of buffer in the particle formulation is determined by pre-processing concerns, stability concerns, and formability of particles during spray drying. Buffer may be required to stabilize drug during processing, e.g., solution preparation and spray drying, when all stabilizers are solubilized.

Examples of carbohydrates that may be included in the particle formulation include, but are not limited to, monosaccharides (e.g., fructose, maltose, galactose, glucose, D-mannose, and sorbose), disaccharides (e.g., lactose, sucrose, trehalose, and cellobiose), polysaccharides (e.g., raffinose, melezitose, maltodextrins, dextrans, and starches), and alditols (acyclic polyols; e.g., mannitol, xylitol, maltitol, lactitol, xylitol sorbitol, pyranosyl sorbitol, and myoinsitol). Suitable carbohydrates include disaccharides and/or non-reducing sugars, such as sucrose, trehalose, and raffinose.

Examples of antioxidants that may be included in the particle formulation include, but are not limited to, methionine, ascorbic acid, sodium thiosulfate, catalase, platinum, ethylenediaminetetraacetic acid (EDTA), citric acid, cysteine, thioglycerol, thioglycolic acid, thiosorbitol, butylated hydroxanisol, butylated hydroxyltoluene, and propyl gallate. Further, amino acids that readily oxidize can be used as antioxidants, for example, cysteine, methionine, and tryptophan.

Examples of amino acids that may be included in the particle formulation include, but are not limited to, arginine, methionine, glycine, histidine, alanine, leucine, glutamic acid, iso-leucine, L-threonine, 2-phenylamine, valine, norvaline, proline, phenylalanine, tryptophan, serine, asparagines, cysteine, tyrosine, lysine, and norleucine. Suitable amino acids include those that readily oxidize, e.g., cysteine, methionine, and tryptophan.

Examples of buffers that may be included in the particle formulation include, but are not limited to, citrate, histidine, succinate, phosphate, maleate, tris, acetate, carbohydrate, and gly-gly. Suitable buffers include citrate, histidine, succinate, and tris.

Examples of inorganic compounds that may be included in the particle formulation include, but are not limited to, NaCl, Na2SO4, $NaHCO_3$, KCl, KH2PO4, CaCl2, and MgCl2.

In addition, the particle formulation may include other stabilizers/excipients, such as surfactants and salts. Examples of surfactants include, but are not limited to, Polysorbate 20, Polysorbate 80, PLURONIC® (BASF Corporation, Mount Olive, N.J.) F68, and sodium dodecyl sulfate (SDS). Examples of salts include, but are not limited to, sodium chloride, calcium chloride, and magnesium chloride.

The particles are typically sized such that they can be delivered via an implantable osmotic delivery device. Uniform shape and size of the particles typically helps to provide a consistent and uniform rate of release from such a delivery device; however, a particle preparation having a non-normal particle size distribution profile may also be used. For example, in a typical implantable osmotic delivery device having a delivery orifice, the size of the particles is less than about 30%, more preferably is less than about 20%, more preferably is less than about than 10%, of the diameter of the delivery orifice. In an embodiment of the particle formulation for use with an osmotic delivery system, wherein the delivery orifice diameter of the implant is about 0.5 mm, particle sizes may be, for example, less than about 150 microns to about 50 microns. In an embodiment of the particle formulation for use with an osmotic delivery system, wherein the delivery orifice diameter of the implant is about 0.1 mm, particle sizes may be, for example, less than about 30 microns to about 10 microns. In one embodiment, the orifice is about 0.25 mm (250 microns) and the particle size is about 2 microns to about 5 microns.

Those of ordinary skill in the art will appreciate that a population of particles follow principles of particle size distribution. Widely used, art-recognized methods of describing particle size distributions include, for example, average diameters and D values, such as the D50 value, which is commonly used to represent the mean diameter of the range of the particle sizes of a given sample.

Particles of a particle formulation have diameters of between about 2 microns to about 150 micron, e.g., less than 150 microns in diameter, less than 100 microns in diameter, less than 50 microns in diameter, less than 30 microns in diameter, less than 10 microns in diameter, less than 5 microns in diameter, and about 2 microns in diameter. Preferably, particles have diameters of between about 2 microns and about 50 microns.

Particles of a particle formulation comprising an isolated amylin analog polypeptide have average diameters of between about 0.3 microns to about 150 microns. Particles of a particle formulation comprising an isolated amylin analog polypeptide have average diameters of between about 2 microns to about 150 microns, e.g., less than 150 microns in average diameter, less than 100 microns in average diameter, less than 50 microns in average diameter, less than 30 microns in average diameter, less than 10 microns in average diameter, less than 5 microns in average diameter, and about 2 microns in average diameter. In some embodiments, particles have average diameters of between about 0.3 microns and 50 microns, for example, between about 2 microns and about 50 microns. In some embodiments, the particles have an average diameter between 0.3 microns and 50 microns, for example, between about 2 microns and about 50 microns, where each particle is less than about 50 microns in diameter.

Typically, the particles of the particle formulations, when incorporated in a suspension vehicle, do not settle in less than about 3 months, preferably do not settle in less than about 6 months, more preferably do not settle in less than about 12 months, more preferably do not settle in less than about 24 months at delivery temperature, and most preferably do not settle in less than about 36 months at delivery temperature. The suspension vehicles typically have a viscosity of between about 5,000 to about 30,000 poise, preferably between about 8,000 to about 25,000 poise, more preferably between about 10,000 to about 20,000 poise. In one embodiment, the suspension vehicle has a viscosity of about 15,000 poise, plus or minus about 3,000 poise. Generally speaking, smaller particles tend to have a lower settling rate in viscous suspension vehicles than larger particles. Accordingly, micron- to nano-sized particles are typically desirable. In viscous suspension formulation, particles of about 2 microns to about 7 microns of the present invention will not settle for at least 20 years at room temperature based on simulation modeling studies. In an embodiment of the particle formulation of the present invention, for use in an implantable osmotic delivery device, comprises particles of sizes less than about 50 microns, more preferably less than about 10 microns, more preferably in a range from about 2 microns to about 7 microns.

In summary, disclosed polypeptides, or pharmaceutically acceptable salts thereof, are formulated into dried powders in solid state particles, which preserve maximum chemical and biological stability of the drug. Particles offers long-term storage stability at high temperature, and therefore, allows delivery to a subject of stable and biologically effective drug for extended periods of time. Particles are suspended in suspension vehicles for administration to patients.

Particle Suspensions in Vehicles

In one aspect, the suspension vehicle provides a stable environment in which the drug particle formulation is dispersed. The drug particle formulations are chemically and physically stable (as described above) in the suspension vehicle. The suspension vehicle typically comprises one or more polymer and one or more solvent that form a solution of sufficient viscosity to uniformly suspend the particles comprising the drug. The suspension vehicle may comprise further components, including, but not limited to, surfactants, antioxidants, and/or other compounds soluble in the vehicle.

The viscosity of the suspension vehicle is typically sufficient to prevent the drug particle formulation from settling during storage and use in a method of delivery, for example, in an implantable, osmotic delivery device. The suspension vehicle is biodegradable in that the suspension vehicle disintegrates or breaks down over a period of time in response to a biological environment, while the drug particle is dissolved in the biological environment and the active pharmaceutical ingredient (i.e., the drug) in the particle is absorbed.

In embodiments, the suspension vehicle is a "single-phase" suspension vehicle, which is a solid, semisolid, or liquid homogeneous system that is physically and chemically uniform throughout.

The solvent in which the polymer is dissolved may affect characteristics of the suspension formulation, such as the behavior of drug particle formulation during storage. A solvent may be selected in combination with a polymer so that the resulting suspension vehicle exhibits phase separation upon contact with the aqueous environment. In some embodiments of the invention, the solvent may be selected in combination with the polymer so that the resulting suspension vehicle exhibits phase separation upon contact with the aqueous environment having less than approximately about 10% water.

The solvent may be an acceptable solvent that is not miscible with water. The solvent may also be selected so that the polymer is soluble in the solvent at high concentrations, such as at a polymer concentration of greater than about 30%. Examples of solvents useful in the practice of the present invention include, but are not limited to, lauryl alcohol, benzyl benzoate, benzyl alcohol, lauryl lactate, decanol (also called decyl alcohol), ethyl hexyl lactate, and long chain (C8 to C24) aliphatic alcohols, esters, or mixtures thereof. The solvent used in the suspension vehicle may be "dry," in that it has a low moisture content. Preferred solvents for use in formulation of the suspension vehicle include lauryl lactate, lauryl alcohol, benzyl benzoate, and mixtures thereof.

Examples of polymers for formulation of the suspension vehicles of the present invention include, but are not limited to, a polyester (e.g., polylactic acid and polylacticpolyglycolic acid), a polymer comprising pyrrolidones (e.g., polyvinylpyrrolidone having a molecular weight ranging from approximately 2,000 to approximately 1,000,000), ester or ether of an unsaturated alcohol (e.g., vinyl acetate), polyoxyethylenepolyoxypropylene block copolymer, or mixtures thereof. Polyvinylpyrrolidone can be characterized by its K-value (e.g., K-17), which is a viscosity index. In one embodiment, the polymer is polyvinylpyrrolidone having a molecular weight of 2,000 to 1,000,000. In a preferred embodiment, the polymer is polyvinylpyrrolidone K-17 (typically having an approximate average molecular weight range of 7,900-10,800). The polymer used in the suspension vehicle may include one or more different polymers or may include different grades of a single polymer. The polymer used in the suspension vehicle may also be dry or have a low moisture content.

Generally speaking, a suspension vehicle for use in the present invention may vary in composition based on the desired performance characteristics. In one embodiment, the suspension vehicle may comprise about 40 wt % to about 80 wt % polymer(s) and about 20 wt % to about 60 wt % solvent(s). Preferred embodiments of a suspension vehicle include vehicles formed of polymer(s) and solvent(s) combined at the following ratios: about 25 wt % solvent and about 75 wt % polymer; about 50 wt % solvent and about 50 wt % polymer; about 75 wt % solvent and about 25 wt % polymer. Accordingly, in some embodiments, the suspension vehicle may comprise selected components and in other embodiments consist essentially of selected components.

The suspension vehicle may exhibit Newtonian behavior. The suspension vehicle is typically formulated to provide a viscosity that maintains a uniform dispersion of the particle formulation for a predetermined period of time. This helps facilitate making a suspension formulation tailored to provide controlled delivery of the drug contained in the drug particle formulation. The viscosity of the suspension vehicle may vary depending on the desired application, the size and type of the particle formulation, and the loading of the particle formulation in the suspension vehicle. The viscosity of the suspension vehicle may be varied by altering the type or relative amount of the solvent or polymer used.

The suspension vehicle may have a viscosity ranging from about 100 poise to about 1,000,000 poise, preferably from about 1,000 poise to about 100,000 poise. In preferred embodiments, the suspension vehicles typically have a viscosity, at 33° C., of between about 5,000 to about 30,000 poise, preferably between about 8,000 to about 25,000 poise, more preferably between about 10,000 to about 20,000 poise. In one embodiment, the suspension vehicle has a viscosity of about 15,000 poise, plus or minus about 3,000 poise, at 33° C. The viscosity may be measured at 33° C., at a shear rate of 10-4/sec, using a parallel plate rheometer.

The suspension vehicle may exhibit phase separation when contacted with the aqueous environment; however, typically the suspension vehicle exhibits substantially no phase separation as a function of temperature. For example, at a temperature ranging from approximately 0° C. to approximately 70° C. and upon temperature cycling, such as cycling from 4° C. to 37° C. to 4° C., the suspension vehicle typically exhibits no phase separation.

The suspension vehicle may be prepared by combining the polymer and the solvent under dry conditions, such as in a dry box. The polymer and solvent may be combined at an elevated temperature, such as from approximately 40° C. to approximately 70° C., and allowed to liquefy and form the single phase. The ingredients may be blended under vacuum to remove air bubbles produced from the dry ingredients. The ingredients may be combined using a conventional mixer, such as a dual helix blade or similar mixer, set at a speed of approximately 40 rpm. However, higher speeds may also be used to mix the ingredients. Once a liquid solution of the ingredients is achieved, the suspension vehicle may be cooled to room temperature. Differential scanning calorimetry (DSC) may be used to verify that the suspension vehicle is a single phase. Further, the components of the vehicle (e.g., the solvent and/or the polymer) may be treated to substantially reduce or substantially remove peroxides (e.g., by treatment with methionine; see, e.g., U.S., Patent Application Publication No. 2007-0027105).

The drug particle formulation is added to the suspension vehicle to form a suspension formulation. In some embodiments, the suspension formulation may comprise a drug particle formulation and a suspension vehicle and in other embodiments consist essentially of a drug particle formulation and a suspension vehicle.

The suspension formulation may be prepared by dispersing the particle formulation in the suspension vehicle. The suspension vehicle may be heated and the particle formulation added to the suspension vehicle under dry conditions. The ingredients may be mixed under vacuum at an elevated temperature, such as from about 40° C. to about 70° C. The ingredients may be mixed at a sufficient speed, such as from about 40 rpm to about 120 rpm, and for a sufficient amount of time, such as about 15 minutes, to achieve a uniform dispersion of the particle formulation in the suspension vehicle. The mixer may be a dual helix blade or other suitable mixer. The resulting mixture may be removed from the mixer, sealed in a dry container to prevent water from contaminating the suspension formulation, and allowed to cool to room temperature before further use, for example, loading into an implantable, drug delivery device, unit dose container, or multiple-dose container.

The suspension formulation typically has an overall moisture content of less than about 10 wt %, preferably less than about 5 wt %, and more preferably less than about 4 wt %.

In preferred embodiments, the suspension formulations of the present invention are substantially homogeneous and flowable to provide delivery of the drug particle formulation from the osmotic delivery device to the subject.

In summary, the components of the suspension vehicle provide biocompatibility. Components of the suspension vehicle offer suitable chemico-physical properties to form stable suspensions of drug particle formulations. These properties include, but are not limited to, the following: viscosity of the suspension; purity of the vehicle; residual moisture of the vehicle; density of the vehicle; compatibility with the dry powders; compatibility with implantable devices; molecular weight of the polymer; stability of the vehicle; and hydrophobicity and hydrophilicity of the vehicle. These properties can be manipulated and controlled, for example, by variation of the vehicle composition and manipulation of the ratio of components used in the suspension vehicle.

The suspension formulations described herein may be used in an implantable, osmotic delivery device to provide zero-order, continuous, controlled, and sustained delivery of a compound over an extended period of time, such as over weeks, months, or up to about one year or more. Such an implantable osmotic delivery device is typically capable of delivering the suspension formulation, comprising the drug, at a desired flow rate over a desired period of time. The suspension formulation may be loaded into the implantable, osmotic delivery device by conventional techniques.

Implantable Delivery

A dose and delivery rate can be selected to achieve a desired blood concentration of a drug generally within less than about 6 half-lives of the drug within the subject after implantation of the device. The blood concentration of the drug is selected to give the optimal therapeutic effects of the drug while avoiding undesirable side effects that may be induced by excess concentration of the drug, while at the same time avoiding peaks and troughs that may induce side effects associated with peak or trough plasma concentrations of the drug.

The implantable, osmotic delivery device typically includes a reservoir having at least one orifice through which the suspension formulation is delivered. The suspension formulation may be stored within the reservoir. In a preferred embodiment, the implantable, drug delivery device is an osmotic delivery device, wherein delivery of the drug is osmotically driven. Some osmotic delivery devices and their component parts have been described, for example, the DUROS® delivery device or similar devices (see, e.g., U.S. Pat. Nos. 5,609,885; 5,728,396; 5,985,305; 5,997,527; 6,113,938; 6,132,420; 6,156,331; 6,217,906; 6,261,584;

6,270,787; 6,287,295; 6,375,978; 6,395,292; 6,508,808; 6,544,252; 6,635,268; 6,682,522; 6,923,800; 6,939,556; 6,976,981; 6,997,922; 7,014,636; 7,207,982; and 7,112,335; 7,163,688; U.S. Patent Publication Nos. 2005/0175701, 2007/0281024, 2008/0091176, and 2009/0202608).

The osmotic delivery device typically consists of a cylindrical reservoir which contains the osmotic engine, piston, and drug formulation. The reservoir is capped at one end by a controlled-rate, semi-permeable membrane and capped at the other end by a diffusion moderator through which suspension formulation, comprising the drug, is released from the drug reservoir. The piston separates the drug formulation from the osmotic engine and utilizes a seal to prevent the water in the osmotic engine compartment from entering the drug reservoir. The diffusion moderator is designed, in conjunction with the drug formulation, to prevent body fluid from entering the drug reservoir through the orifice.

The osmotic device releases a drug at a predetermined rate based on the principle of osmosis. Extracellular fluid enters the osmotic delivery device through a semi-permeable membrane directly into a salt engine that expands to drive the piston at a slow and even delivery rate. Movement of the piston forces the drug formulation to be released through the orifice or exit port at a predetermined shear rate. In one embodiment of the present invention, the reservoir of the osmotic device is loaded with a suspension formulation wherein the device is capable of delivering the suspension formulation to a subject over an extended period of time (e.g., about 1, about 3, about 6, about 9, about 10, and about 12 months) at a pre-determined, therapeutically effective delivery rate.

The release rate of the drug from the osmotic delivery device typically provides a subject with a predetermined target dose of a drug, for example, a therapeutically effective daily dose delivered over the course of a day; that is, the release rate of the drug from the device, provides substantial steady-state delivery of the drug at a therapeutic concentration to the subject.

Typically, for an osmotic delivery device, the volume of a beneficial agent chamber comprising the beneficial agent formulation is between about 100 µl to about 1000 µl, more preferably between about 120 µl and about 500 µl, more preferably between about 150 µl and about 200 µl.

Typically, the osmotic delivery device is implanted within the subject, for example, subdermally or subcutaneously to provide subcutaneous drug delivery. The device(s) can be implanted subdermally or subcutaneously into either or both arms (e.g., in the inside, outside, or back of the upper arm) or the abdomen. Preferred locations in the abdominal area are under the abdominal skin in the area extending below the ribs and above the belt line. To provide a number of locations for implantation of one or more osmotic delivery device within the abdomen, the abdominal wall can be divided into 4 quadrants as follows: the upper right quadrant extending at least 2-3 centimeters below the right ribs, e.g., at least about 5-8 centimeters below the right ribs, and at least 2-3 centimeters to the right of the midline, e.g., at least about 5-8 centimeters to the right of the midline; the lower right quadrant extending at least 2-3 centimeters above the belt line, e.g., at least about 5-8 centimeters above the belt line, and at least 2-3 centimeters to the right of the midline, e.g., at least about 5-8 centimeters to the right of the midline; the upper left quadrant extending at least 2-3 centimeters below the left ribs, e.g., at least about 5-8 centimeters below the left ribs, and at least 2-3 centimeters to the left of the midline, e.g., at least about 5-8 centimeters to the left of the midline; and the lower left quadrant extending at least 2-3 centimeters above the belt line, e.g., at least about 5-8 centimeters above the belt line, and at least 2-3 centimeters to the left of the midline, e.g., at least about 5-8 centimeters to the left of the midline. This provides multiple available locations for implantation of one or more devices on one or more occasions. Implantation and removal of osmotic delivery devices are generally carried out by medical professionals using local anesthesia (e.g., lidocaine).

Termination of treatment by removal of an osmotic delivery device from a subject is straightforward, and provides the important advantage of immediate cessation of delivery of the drug to the subject.

Preferably, the osmotic delivery device has a fail-safe mechanism to prevent an inadvertent excess or bolus delivery of drug in a theoretical situation like the plugging or clogging of the outlet (diffusion moderator) through which the drug formulation is delivered. To prevent an inadvertent excess or bolus delivery of drug the osmotic delivery device is designed and constructed such that the pressure needed to partially or wholly dislodge or expel the diffusion moderator from the reservoir exceeds the pressure needed to partially or wholly dislodge or expel the semi-permeable membrane to the extent necessary to de-pressurize the reservoir. In such a scenario, pressure would build within the device until it would push the semi-permeable membrane at the other end outward, thereby releasing the osmotic pressure. The osmotic delivery device would then become static and no longer deliver the drug formulation provided that the piston is in a sealing relationship with the reservoir.

The suspension formulations may also be used in infusion pumps, for example, the ALZET® (DURECT Corporation, Cupertino, Calif.) osmotic pumps which are miniature, infusion pumps for the continuous dosing of laboratory animals (e.g., mice and rats).

EXAMPLES

The following examples are put forth so as to provide those of ordinary skill in the art with a complete disclosure and description of how to practice the present invention, and are not intended to limit the scope of what the inventors regard as the invention. Efforts have been made to ensure accuracy with respect to numbers used (e.g., amounts, concentrations, and percent changes) but some experimental errors and deviations should be accounted for. Unless indicated otherwise, temperature is in degrees Centigrade and pressure is at or near atmospheric.

Example 1: Generation of Amylin Analog Polypeptides

Amylin analog polypeptides of the invention, as provided in Table 3, were synthesized on a Prelude peptide synthesizer (Protein Technologies Inc., Tucson, AZ)) by solid-phase methods using Fmoc strategy with N-[(dimethylamino)-1H-1,2,3-triazolo-[4,5-b]pyridin-1-ylmethylene]-N-methylmethanaminium hexafluorophosphate N-oxide (HATU) or 2-(6-chloro-1-H-benzotriazole-1-yl)-1,1,3,3-tetramethylaminium hexafluorophosphate (HCTU) activation (5-fold molar excess to amino acid) in N,N-dimethylformamide (DMF), and N'N-diisopropylethylamine (DIEA) was used as base. A 20% piperidine/DMF solution was used for Fmoc deprotection. The resin used was Rink Amide MBHA LL (Novabiochem) with loading of (0.30-0.40) mmol/g on a (20-400) µmol scale.

Final deprotection and cleavage of the peptide from the solid support were performed by treatment of the resin with (92.5% TFA, 2.5% phenol, 2.5% water and 2.5% triisopropylsilane) for 2-3 hours. The cleaved peptide was precipitated using cold diethyl ether. The diethyl ether was decanted, and the solids triturated again with cold diethyl ether and pelleted by centrifugation. The crude solids were next dissolved in a 1:1 solution of ACN/water, 0.01% TFA. Disulfide bridge formation was afforded via the addition of a solution of iodine/acetic acid (35 mg/ml) to a solution of the crude product until the solution turned consistently amber in color. The reaction solution was allowed to stir until analysis via LC/MS indicated completion of the reaction. A 2% solution of ascorbic acid in $H_2O$ was added until the solution turned clear. The final crude product solution was lyophilized in preparation for final purification.

The lyophilized solid was re-dissolved in a 1:1 solution of acetonitrile/water, with 0.1% TFA (10-15 mL), purified via reverse phase HPLC on a Waters XBridge™ BEH 130, CIS, 10 μm, 130 Å, 30×250 mm ID column, using a 30 gradient within the ranges of 5-75% acetonitrile/water with 0.1% TFA over 30-45 minutes at a flow rate of 30 mL/min, λ—215 nm.

Example 2: Purification and Characterization of Amylin Analog Polypeptides, i.e., Linear Polypeptide, without any Lipophilic Substituent and Optional Spacer The purified product was lyophilized and analyzed by ESI-LC/MS and analytical HPLC, and was demonstrated to be pure (>98%). Mass results all agreed with calculated values.

Characterizations of peptide analogs were performed via $C_{18}$ HPLC and LC/MS analysis (Acquity SQD Waters Corp, Milford, MA) and UV detection provided by dual absorbance signals at 215 nm and 280 nm, using one of Method A, Method B, Method C or Method D.

Method A, LC/MS conditions: performed using a Phenomenex UPLC Aeris™ Peptide XB C18 35 column, 1.7 μm, 2.1×100 mm or ACQUiTY BEH300 or BEH130 CT8 column, 1.77 μm. 2.1×100 mm using 5-65% acetonitrile/water with 0.05% TFA over 30 minutes with a flow rate 0.5 mL/min, λ—215 nm, 280 nm.

Method B, C18 HPLC conditions: UPLC analysis was conducted on an Acquity BEH130, C18 column, 1.7 μm, 100×2.10 mm column at 25° C., 5-65% acetonitrile/water with 0.05% TFA over 30 minutes, flow rate 0.5 mL/min, 1 215 nm, 1 280 nm.

Method C, UPLC conditions: UPLC analysis was conducted on an Acquity BEH130, C18 column, 1.7 μm, 100×2.10 mm column at 25° C., 5-65% acetonitrile/water with 0.05% TFA over 20 minutes, flow rate 0.5 mL/min, 1 215 nm, 1 280 nm.

Method D, UPLC conditions: UPLC analysis was conducted on an Acquity BEH130, C18 column, 1.7 μm, 100×2.10 mm column at 25° C., 5-65% acetonitrile/water with 0.05% TFA over 10 minutes, flow rate 0.5 mL/min, 1215 nm, 1 280 nm. 5.0 μL of sample was injected using a PLNO (partial loop w/needle over-fill) injection mode.

Table 3 provides exemplary amylin analog polypeptides of the disclosure.

Polypeptide analogs without a lipophilic substituent and optional spacer are sometimes referred to herein as "linear polypeptides." Polypeptide analogs having at least one covalently bound lipophilic substituent and optional spacer are sometimes referred to herein as "conjugated polypeptides."

Example 3: Synthesis of Amylin Analog Polypeptides Intermediates

Synthesis of Polypeptides with Modifications at D-Lys16 or L-Lys16 Positions e.g. (Compounds B2, A129, B4, and B8)

Upon completion of synthesis of the linear polypeptide, as described in Example 1, the resin was washed with dichloromethane (DCM) and dried under vacuum for 30 minutes. For analogs containing the Alloc-protecting group, its removal was facilitated via a solution of $Pd(PPh_3)_3$ in (chloroform/acetic acid/n-methyl-morpholine, 37:2:1). The resulting de-protected resin was washed with 2% sodium diethyldithiodicarbamate trihydrate/DMF (6×30 secs), 2% DIEA/DMF (6×30 secs), and finally DMF (6×30 secs). Elongation of the spacer region was carried out in stepwise manner with the manual addition of each building block under pre-activation conditions. Into a 1 ml of 200 mmol solution of Fmoc-γGlu-(OH)-OtBu in DMF was added 0.5 ml of DIEA (800 mmol), followed by 0.5 ml of HCTU (400 mmol) and the resulting reaction solution was allowed to stir for 5 minutes wherein it was added to the deprotected residue on the linear sequence. The reaction mixture was allowed to stir under nitrogen for 30 minutes. The resin was drained and washed with DMF (6×30 secs). Subsequent removal of the Fmoc protecting group was facilitated using 20% piperidine/DMF followed by a final wash with DMF (6×30 secs). Final deprotection and cleavage of the peptide from the solid support were performed by treatment of the resin with (95% TFA, 2% water, 2% thioanisole, and 1% triisopropylsilane) for 2-3 hours. As each building block was incorporated using the method described above each intermediate was isolated and characterized via HPLC/MS.

Synthesis of Polypeptides with Modifications at N-Terminus e.g. (A130, B22, and B23)

Synthesis of the linear sequence was carried out as described in Example 1. Addition of the albumin-binding moiety was facilitated by removal of the N-terminus Fmoc-protecting group via a 20% solution of piperidine/DMF. The resin was washed with DMF and incorporation of the side-chain building blocks was carried out in a step-wise manner under pre-activation conditions. Into 1 ml of 200 mmol solution of Fmoc-γGlu-(OH)-OtBu in DMF was added 0.5 ml of DIEA (800 mmol), followed by 0.5 ml of HCTU (400 mmol). The resulting reaction solution was allowed to stir for 5 minutes wherein it was added to the deprotected linear sequence. The reaction mixture was allowed to stir under nitrogen for 30 minutes. The resin was drained and washed with DMF (6×30 secs). Final deprotection and cleavage of the peptide from the solid support were performed by treatment of the resin with (95% TFA, 2% water, 2% thioanisole, and 1% triisopropylsilane) for 2-3 hours. Each intermediate was isolated and characterized via HPLC/MS. The chemical data for both the internally modified polypeptides and N-terminal modified polypeptide intermediates is recorded in Table 5 below.

TABLE 5

Exemplary intermediate compounds

| Compound No. | Parent MW | Calculated Mass (M + 3/3) | Observed Mass (M + 3/3) |
|---|---|---|---|
| B2 | 4065.51 | 1356.14 | 1356.7 |
| A129 | 3981.44 | 1328.15 | 1329.2 |

TABLE 5-continued

Exemplary intermediate compounds

| Compound No. | Parent MW | Calculated Mass (M + 3/3) | Observed Mass (M + 3/3) |
|---|---|---|---|
| B4 | 4110.55 | 1371.18 | 1372.6 |
| B8 | 4239.67 | 1414.22 | 1415.2 |
| A130 | 4007.52 | 1336.84 | 1338.2 |
| B22 | 4136.63 | 1379.88 | 1381.5 |
| B23 | 4265.75 | 1422.92 | 1424.4 |

Example 4: Covalent Attachment of Lipophilic Substituent and Optional Spacer to Amylin Analog Polypeptides, i.e., Conversion of Linear Polypeptides to Conjugated Polypeptides Synthesis of amylin analog polypeptides conjugated with one or more albumin-binding lipophilic substituents and optional spacer was carried out with modifications to the synthetic method described in Example 1.

Upon completion of synthesis of the linear polypeptide, as described in Example 1, the resin was washed with dichloromethane (DCM) and dried under vacuum for 30 minutes. For analogs containing the alloc-protecting group, it's removal was afforded via a solution of Pd(PPh$_3$)$_3$ in (chloroform/acetic acid/n-methyl-morpholine, 37:2:1). For analogs containing the BOC-Lys(Fmoc)-OH, the Fmoc protecting group was removed using 20% piperidine/DMF. The resulting de-protected resin was washed with DMF (6×30 secs). Next, elongation of the spacer region was carried out in step-wise manner with the manual addition of each building block under pre-activation conditions. Addition of the lipophilic substituent (also referred to as "acyl chain") was carried out under normal SPPS conditions with no pre-activation step. Final deprotection and cleavage of the peptide from the solid support were performed by treatment of the resin with (95% TFA, 2% water, 2% thioanisole, and 1% triisopropylsilane) for 2-3 hours. The cleaved peptide was precipitated using cold diethyl ether. The diethyl ether was decanted, and the solids triturated again with cold diethyl ether and pelleted via centrifugation.

The crude product was next dissolved in a solution of ACN/H$_2$O, 0.1% TFA. A solution of iodine/acetic acid (35 mg/mL) was added to each solution of crude peptide product until the solution turned consistently amber in color. The reaction solution was allowed to stir until analysis via LC/MS indicated the desired disulfide bridge had formed. To the reaction solution was added a 2% solution of ascorbic acid in H$_2$O was added until the solution turned clear. The solution was frozen and lyophilized. Purification was afforded via the methods described in Example 1.

An exemplar synthesis of a conjugated peptide is described. Synthesis of A09: Synthesis of the linear sequence was carried out as described in Example 1. Addition of the albumin-binding moiety was facilitated by removal of the N-terminus Fmoc-protecting group via a 20% solution of piperidine/DMF. The resin was next washed with DMF and incorporation of the side-chain building blocks was carried out in a step-wise manner under pre-activation conditions. To a 1 ml, 200 mmol solution of Fmoc-γGlu-(OH)-OtBu in DMF, was added 0.5 ml of DIEA (800 mmol), followed by 0.5 ml of HCTU (400 mmol). The resulting reaction solution was allowed to stir for 5 minutes wherein it was added to the deprotected linear sequence. The reaction mixture was allowed to stir under nitrogen for 30 minutes. Next, the resin was drained and washed with DMF (6×30 secs). The Fmoc-protecting group of γGlu was removed by a 20% piperidine/DMF. Followed by coupling with octadecanedioic acid (C18) (200 mmol) in DMF using HATU (400 mmol) and DIEA (800 mmol) under normal solid-phase conditions.

Cleavage was afforded using a solution of 95% TFA/2% water/2% thioanisole/1% TIPS. The crude product was next dissolved in a solution of ACN/H$_2$O, 0.1% TFA. A solution of iodine/acetic acid (35 mg/ml) was added to the solution of crude peptide product until the solution turned consistently amber in color. The reaction solution was allowed to stir until analysis via LC/MS indicated the desired disulfide bridge had formed. To the reaction solution was added a 2% solution of ascorbic acid in H$_2$O was added until the solution turned clear.

Lyophilization of the crude product afforded an off-white solid which was purified via the methods described in Example 2.

Example 5: Stability of Amylin Analog Polypeptides

Several amylin analog polypeptides described herein were tested, as the trifluoro acetate salt, for stability in DMSO (i.e., organosulfur solvent) or in aqueous (i.e., in DI water) at 1 mg/ml solution. These analog polypeptides were incubated at 37° C., and samples were withdrawn at various time intervals and analyzed by LC/MS and HPLC for determination of purity and mass of the parent peptide and extent of any degradation products. The purity results of these analyses are shown in Tables 6A & 6B and are considered indicative of stability.

TABLE 6A

Stability of Amylin Analog Polypeptides

| Cmpd | Assay Buffer | Day 0 room temp | Day 5 37° C. | Day 8 37° C. | Day 12 37° C. | Day 19 37° C. | Day 25 37° C. | Day 32 37° C. |
|---|---|---|---|---|---|---|---|---|
| A27 | DI Water | 95.6 | 95.2 | 94.9 | 94.8 | 94 | 92.6 | 89.8 |
| A27 | 20% DMSO in DI Water | 96.8 | 96.4 | 96.1 | 96.1 | 95 | 94.4 | 90.5 |
| A109 | DI Water | 95.7 | 92.7 | 88.1 | 86.4 | 84.9 | 83.9 | 81.7 |
| A109 | 20% DMSO in DI Water | 96.5 | 93.6 | 92.3 | 91.8 | 91.4 | 89 | 87.2 |
| A64 | DI Water | 100 | 99.1 | 98.1 | 98.1 | 97.4 | 97.3 | 88.5 |
| A64 | 20% DMSO in DI Water | 98.8 | 98.1 | 98.6 | 97.9 | 97.2 | 97.3 | 97.2 |

TABLE 6A-continued

Stability of Amylin Analog Polypeptides

| Cmpd | Assay Buffer | Day 0 room temp | Day 5 37° C. | Day 8 37° C. | Day 12 37° C. | Day 19 37° C. | Day 25 37° C. | Day 32 37° C. |
|---|---|---|---|---|---|---|---|---|
| A53 | DI Water | 93.6 | 93.6 | 93.1 | 93.3 | 92.8 | 91.8 | 90.7 |
| A53 | 20% DMSO in DI Water | 93.6 | 93 | 92.4 | 92.4 | 92.4 | 91.6 | 91.2 |
| A102 | DI Water | 96.1 | 96 | 95.8 | 94.9 | 94.1 | 92.9 | 92.4 |
| A102 | 20% DMSO in DI Water | 98.1 | 96.7 | 96.5 | 95.7 | 94.9 | 93.2 | 92.5 |
| A103 | DI Water | 90.9 | 90.7 | 91 | 90.5 | 89.1 | 88.5 | 88 |
| A103 | 20% DMSO in DI Water | 88.5 | 87.4 | 88.4 | 89 | 88.2 | 88 | 87.2 |
| A81 | DI Water | 91.8 | 89.8 | 89.7 | 89.3 | 89.1 | 87.1 | 83.8 |
| A81 | 20% DMSO in DI Water | 88.9 | 88.2 | 87.7 | 86.4 | 85.1 | 84.4 | 84 |
| A82 | DI Water | 89.2 | 87.5 | 87 | 85.7 | 85.7 | 85.4 | 83.3 |
| A82 | 20% DMSO in DI Water | 90.3 | 89.9 | 89.2 | 88.2 | 87.8 | 86.4 | 86.1 |
| A79 | DI Water | 92.9 | 92.8 | 92.5 | 92.2 | 92.1 | 90.8 | 90.5 |
| A79 | 20% DMSO in DI Water | 96.1 | 94.8 | 94.1 | 93.8 | 92.9 | 92.2 | 91.4 |
| A76 | DI Water | 94.8 | 93.1 | 93.2 | 93.4 | 92 | 91.4 | 90.4 |
| A76 | 20% DMSO in DI Water | 91.9 | 91.3 | 90.3 | 90.1 | 89.5 | 89.3 | 88.5 |

TABLE 6B

Stability of amylin analog polypeptides

| Compound | Assay Buffer | Day 0 room temp | Day 5 37° C. | Day 8 37° C. | Day 12 37° C. |
|---|---|---|---|---|---|
| A53 | DI Water | 93.6 | 93.6 | 93.1 | 93.3 |
| A53 | 20% DMSO in DI Water | 93.6 | 93 | 92.4 | 92.4 |
| A102 | DI Water | 96.1 | 96 | 95.8 | 94.9 |
| A102 | 20% DMSO in DI Water | 98.1 | 96.7 | 96.5 | 95.7 |
| A103 | DI Water | 90.9 | 90.7 | 91 | 90.5 |
| A103 | 20% DMSO in DI Water | 88.5 | 87.4 | 88.4 | 89 |
| A81 | DI Water | 91.8 | 89.8 | 89.7 | 89.3 |
| A81 | 20% DMSO in DI Water | 88.9 | 88.2 | 87.7 | 86.4 |
| A82 | DI Water | 89.2 | 87.5 | 87 | 85.7 |
| A82 | 20% DMSO in DI Water | 90.3 | 89.9 | 89.2 | 88.2 |
| A79 | DI Water | 92.9 | 92.8 | 92.5 | 92.2 |
| A79 | 20% DMSO in DI Water | 96.1 | 94.8 | 94.1 | 93.8 |
| A76 | DI Water | 94.8 | 93.1 | 93.2 | 93.4 |
| A76 | 20% DMSO in DI Water | 91.9 | 91.3 | 90.3 | 90.1 |

Example 6: Solubility of Amylin Analog Polypeptides

The analog polypeptides described herein were tested for solubility in saline 20% DMSO in water (i.e., bioassay buffer) or in aqueous (DI water) at room temperature. Samples were visually inspected for clarity of the sample, any appearance of turbidity or haziness. The results of this analysis are shown in Table 7.

TABLE 7

Solubility of amylin analog polypeptides

| Compound No. | Salt | Solution | Solubility (mg/mL) |
|---|---|---|---|
| A27 | Acetate | 20% DMSO in DI H$_2$O | 66.6 |
| A27 | TFA | 20% DMSO in DI H$_2$O | 57.6 |
| A27 | Acetate | DI H$_2$O | 94.4 |
| A27 | TFA | DI H$_2$O | 105.2 |
| A27 | Acetate | Saline | 80.6 |
| A64 | Acetate | 20% DMSO in DI H$_2$O | 122.7 |
| A64 | TFA | 20% DMSO in DI H$_2$O | 56.0 |
| A64 | Acetate | DI H$_2$O | 104.2 |
| A64 | TFA | DI H$_2$O | 103.0 |
| A64 | Acetate | Saline | 88.3 |
| A109 | TFA | 20% DMSO/DI H$_2$O | 59.0 |
| A109 | TFA | DI H$_2$O | 14.1 |
| A66 | TFA | DI H$_2$O | 78.3 |
| A67 | TFA | DI H$_2$O | 70.6 |
| A13 | TFA | DI H$_2$O | 63 |
| A65 | TFA | DI H$_2$O | 138 |

Example 7: Functional Assays: Human Calcitonin Receptor and Amylin 3 Receptor Activation of the human calcitonin receptor (hCTR), or human amylin 3 receptor (hAMY3R), leads to an increase in cellular cyclic adenosine monophosphate (cAMP). In the presence of the non-specific cAMP/cGMP phosphodiesterase inhibitor 3-isobutyl-1-methylxanthine (IBMX), accumulating cAMP can be measured in vitro using common detection methods. Thus, it is possible to estimate an in vitro potency (pEC50) for peptides activating each of these receptors using fit dose-response curves for cAMP accumulation.

Cells, Culturing, and cAMP Assay

HEK293-CNG cells stably expressing the human calcitonin receptor (hCTR) or the co-expressing human calcitonin receptor and the human receptor activity modifying protein 3 (hAMY3R) (Codex Biosolutions #CB-80200-258 and #CB-80-200-271, respectively) were grown in 90% DMEM, 10% FBS, 250 µg/ml G418 and 1 µg/ml puromycin (hCTR cells), or 90% DMEM, 10% FBS, 250 µg/ml G418, 1 µg/ml puromycin, 150 µg/ml hygromycin B (hAMY3R cells). Cells were carried in growth media for no more than 10 passages prior to testing.

On the day of the assay, cells expressing hCTR or hAMY3R were counted and dispensed at 500 cells per well in white 384-well OptiPlates (PerkinElmer #6007299) in 5 mcL of stimulation buffer consisting of 1×HBSS, 5 mM HEPES, 0.5 mM IBMX, and 0.1% bovine serum albumin (BSA) or 1×HBSS, 5 mM HEPES, 0.5 mM IBMX, and 0.1% casein with 0%, 0.1%, or 4% human serum albumin (HSA).

Peptides were serially diluted in the same buffer as above for each given assay condition. Two assay control solutions consisting of 50 mcM forskolin (cAMP system maximum) or assay buffer only (cAMP system minimum) were also prepared in the appropriate stimulation buffers. Five microliters of each peptide-concentration, or assay control was added to triplicate wells and incubated for thirty minutes at room temperature. During this incubation step a 4× europium labelled cAMP tracer solution and a 4× Ulight®-anti-cAMP solution (consisting of an anti-cAMP monoclonal antibody labelled with Ulight™ dye) was prepared according to the manufacturer's protocol (PerkinElmer LANCE Ultra cAMP kit). Following this incubation, 5 mcL europium labelled cAMP and 5 mcL Ulight anti-cAMP antibody was added to wells. The plate was covered with an adhesive cover to prevent evaporation and incubated for 60 minutes at room temperature in the dark. Plates were read on an Envision fluorescent plate reader (PerkinElmer).

Data Analysis

Test values were first normalized to the forskolin induced cAMP system maximum and system minimum averaged values in Excel using the formula: (test value−system minavg)/(system maxavg−system minavg)*100. Normalized test values represent a baseline corrected percentage of the system maximum cAMP response induced by forskolin. Normalized data was analyzed from triplicate tests and used to estimate the EC50 for each peptide on each receptor. Data was fit in GraphPad Prism software (v7.04) using a 4-parameter logistic curve model: Y=Bottom+(Top−Bottom)/(1+10^((Log EC50−X))). The Hill slope was constrained to 1.0. EC50 values were converted to pEC50 values using the formula: pEC50=−Log (EC50).

Data Interpretation

For a given receptor, in vitro potency estimates (pEC50) in the absence of HSA are comparable across all peptides, as they reflect an albumin independent binding (free peptide) value (0% HSA, Table 8). However, in the presence of albumin (BSA or HSA), potency measures across acylated peptides are not readily comparable (Table 8). This is due to variability in albumin-acylpeptide binding efficiency, which is dependent collectively on the amino acid sequence, acyl binding motif, attachment site, and linker length engineered into each peptide. For a given conjugated polypeptide however, a reduction in potency (decreased pEC50 value) in the presence versus absence of HSA is qualitatively indicative of an albumin-peptide interaction (Table 8, FIGS. 2A and 2B). In contrast, linear polypeptides (pramlintide, hCalcitonin) are unaffected by the presence of HSA, (Table 8, FIGS. 2C and 2D) reflecting their poor albumin binding efficiency.

TABLE 8

Conjugated polypeptide and linear polypeptide potency estimates (pEC$_{50}$ values) measured at human hAMY3 and hCTR in the absence and presence of human serum albumin

| Cmpd No. | hAMY3R 0% HSA | hAMY3R 0.1% HSA | hAMY3R 4% HSA | hCTR 0% HSA | hCTR 0.1% HSA | hCTR 4% HSA |
|---|---|---|---|---|---|---|
| *Pramlintide | 12.5 | 12.6 | 12.5 | 11.4 | 11.2 | 11.1 |
| *hCalcitonin | 10.2 | 10.2 | 10.0 | 12.3 | 12.2 | 12.2 |
| A107 | 12.5 | 11.6 | 10.3 | 11.5 | 10.5 | 9.0 |
| A27 | 12.8 | 11.8 | 10.4 | 11.9 | 10.6 | 9.0 |
| A99 | 10.9 | 9.5 | 8.6 | 10.4 | 8.5 | 7.6 |
| A13 | 12.4 | 11.4 | 10.1 | 11.6 | 10.3 | 8.5 |
| A96 | 11.7 | 9.7 | 8.5 | 10.8 | 8.5 | 8.0 |
| A100 | 11.1 | 8.8 | 7.6 | 10.5 | 8.1 | 7.1 |
| A64 | 12.0 | 10.4 | 9.1 | 11.2 | 9.0 | 8.1 |
| A112 | 11.6 | 9.3 | 8.0 | 10.9 | 8.5 | 7.5 |
| A5 | 12.3 | 10.8 | 9.2 | 10.8 | 9.5 | 7.8 |
| A65 | 11.5 | 10.1 | 8.7 | 10.5 | 9.0 | 7.9 |
| A79 | 11.5 | 10.4 | 9.4 | 10.3 | 9.9 | 9.5 |
| A75 | 11.9 | 10.5 | 8.9 | 10.8 | 10.0 | 7.7 |
| A88 | 10.8 | 10.1 | 8.7 | 9.8 | 9.0 | 7.8 |
| A80 | 11.3 | 10.4 | 8.7 | 10.2 | 9.2 | 7.7 |
| A76 | 11.7 | 10.5 | 8.7 | 10.5 | 9.4 | 8.1 |
| A73 | 12.1 | 10.6 | 8.8 | 11.3 | 9.6 | 7.9 |
| A114 | 12.2 | 10.7 | 9.5 | 11.7 | 10.4 | 8.8 |
| A55 | 12.2 | 11.2 | 9.6 | 11.3 | 10.2 | 8.8 |
| A116 | 12.0 | 10.8 | 9.5 | 11.7 | 10.5 | 9.3 |
| A109 | 12.2 | 11.1 | 9.6 | 11.7 | 10.5 | 9.0 |
| A120 | 11.4 | 9.7 | 8.4 | 10.3 | 8.9 | 7.4 |
| A115 | 12.3 | 10.7 | 9.4 | 11.5 | 9.9 | 8.5 |

TABLE 8-continued

Conjugated polypeptide and linear polypeptide potency estimates (pEC$_{50}$ values) measured at human hAMY3 and hCTR in the absence and presence of human serum albumin

| Cmpd No. | hAMY3R 0% HSA | hAMY3R 0.1% HSA | hAMY3R 4% HSA | hCTR 0% HSA | hCTR 0.1% HSA | hCTR 4% HSA |
|---|---|---|---|---|---|---|
| A119 | 11.9 | 10.2 | 8.5 | 11.2 | 9.5 | 7.9 |
| A113 | 12.3 | 10.6 | 9.0 | 11.3 | 9.7 | 8.1 |

*non-acylated

Figure 3B:
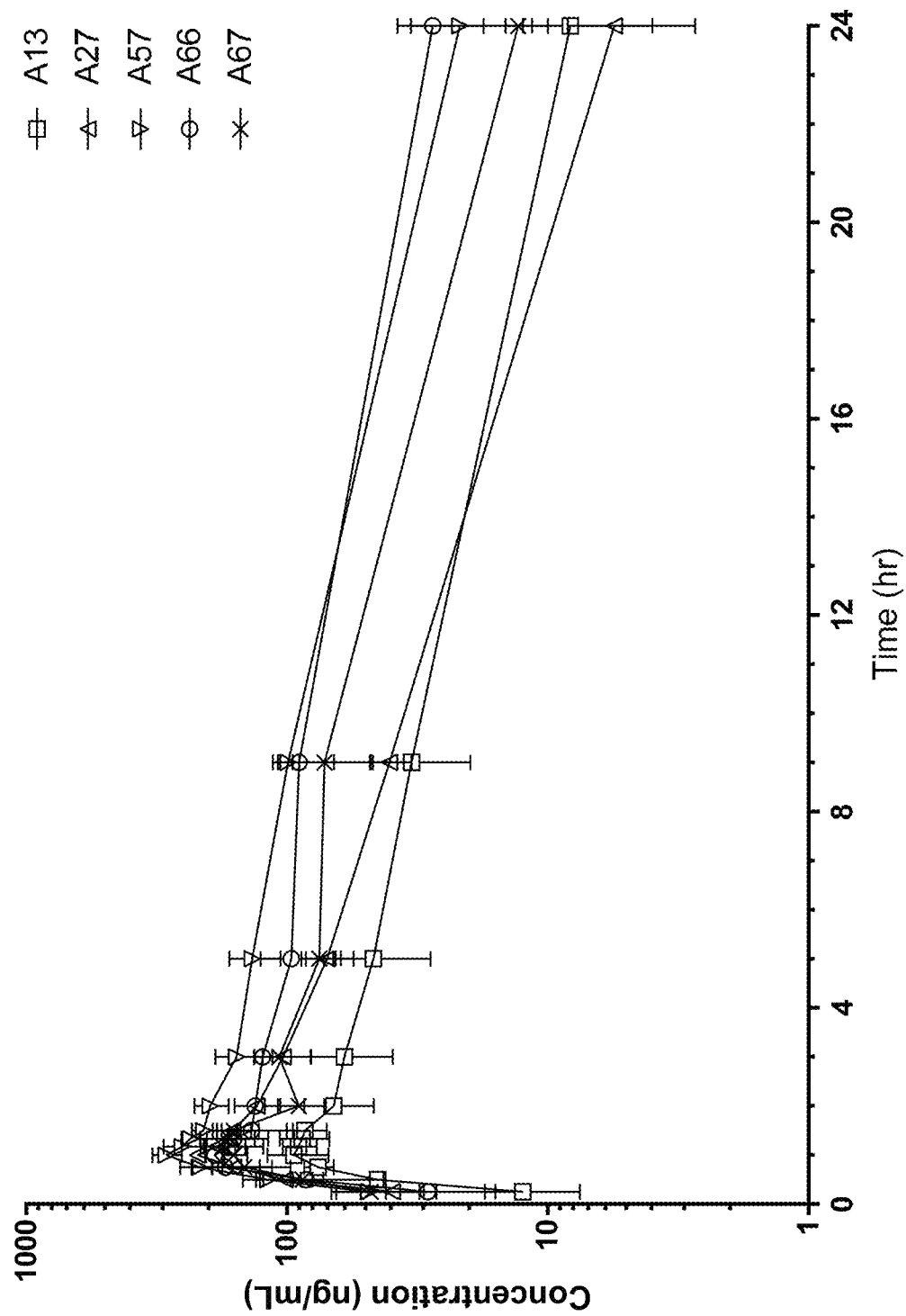

Example 8: Intravenous Infusion of "Linear" (i.e., Non-Acylated) Amylin Analog Polypeptides: Pharmacokinetic Studies to Assess Clearance from Kidney (CL) of Linear Amylin Analog Polypeptides Peptides were dissolved in sterile saline and administered as a 3-hour intravenous infusion to non-fasted male Sprague-Dawley rats (n=3 per group) via femoral vein cannula at a final dose of 0.100 mg/kg. Formulations were administered at a rate of 1.67 mL/kg/h. Blood samples (approximately 250 μL) were collected for pharmacokinetic analysis via a jugular vein cannula at 0.25, 0.5, 1, 2, 3, 3.17, 3.33, 3.5, 4, 4.5, 5, and 6 hr post-start of infusion (long method) or at 1, 1.5, 2, 2.5, and 3 hr post-start of infusion (steady-state screening method). All samples were collected into microtainer tubes containing K2EDTA as anticoagulant and 25 μL of a protease inhibitor cocktail. Plasma was prepared by centrifugation and stored at −80° C. until analysis. The results of this analysis are shown in Table 9 and few exemplars in FIGS. 3a-3b.

Example 9: Intravenous Infusion of Conjugated (i.e., Acylated) Amylin Analog Polypeptides: Pharmacokinetic Studies to Assess Clearance from Kidney (CL) of Conjugated Amylin Analog Polypeptides Peptides were dissolved in sterile saline and administered as a 1-hour intravenous infusion to non-fasted male Sprague-Dawley rats (n=3 per group) via femoral vein cannula at a final dose of 0.033 mg/kg. Formulations were administered at a rate of 1.67 mL/kg/h. Blood samples (approximately 250 μL) were collected for pharmacokinetic analysis via a jugular vein cannula at 0.25, 0.5, 0.75, 1, 1.17, 1.33, 1.5, 2, 4, 6, 8, 24, 30 and 48 hr post-start of infusion into microtainer tubes containing K2EDTA as anticoagulant and 25 μL of a protease inhibitor cocktail. Plasma was prepared by centrifugation and stored at −80° C. until analysis. The results of this analysis are shown in Table 9 and few exemplars in FIGS. 3a-3b.

TABLE 9

Pharmacokinetic analyses

| Compound No. | CL (mL/min/kg) | Vss (mL/kg) | Half-Life (hr) |
|---|---|---|---|
| A4 | 13.6 | ND | ND |
| A5 | 0.135 | 137 | 15 |
| A6 | 26.4 | ND | ND |
| A10 | 3.72 | 245 | 0.965 |
| A12 | 1.55 | 252 | 2.47 |
| A13 | 0.705 | 398 | 7.53 |
| A14 | 0.183 | 163 | 11.3 |
| A15 | 14.4 | ND | ND |
| A17 | 20 | ND | ND |
| A18 | 19.4 | 805 | 0.508 |
| A19 | 0.150 | 136 | 11.5 |
| A21 | 0.178 | 131 | 10.4 |
| A25 | 0.788 | 249 | 4.97 |
| A27 | 0.478 | 174 | 5.16 |
| A28 | 0.485 | 170 | 5.41 |
| A31 | 18.9 | 570 | 0.404 |
| A32 | 19.5 | ND | ND |
| A33 | 17.7 | ND | ND |
| A34 | 15.5 | ND | ND |
| A36 | 3.93 | 244 | 1.32 |
| A39 | 1.35 | 502 | 4.85 |
| A41 | 17.5 | ND | ND |
| A42 | 23.7 | 552 | 0.391 |
| A43 | 23.2 | ND | ND |
| A44 | 14.2 | ND | ND |
| A45 | 21.1 | ND | ND |
| A53 | 0.478 | 174 | 5.16 |
| A56 | 1.34 | 469 | 4.29 |
| A57 | 10.7 | ND | ND |
| A57 | 10.7 | ND | ND |
| A61 | 22.8 | ND | ND |
| A62 | 18.8 | ND | ND |
| A63 | 2.66 | 540 | 2.81 |
| A64 | 0.0641 | 182 | 37.2 |
| A65 | 0.101 | 175 | 22.6 |
| A66 | 0.259 | 194 | 9.59 |
| A67 | 0.357 | 198 | 7.14 |
| A70 | 3.08 | 187 | 0.752 |
| A72 | 1.54 | 172 | 3.44 |
| A73 | 0.0449 | 92.4 | 26.6 |
| A74 | 12.2 | 331 | 0.331 |
| A75 | 0.0781 | 121 | 24.1 |
| A76 | 0.105 | 176 | 21.3 |
| A79 | 0.162 | 115 | 7.80 |
| A82 | 0.667 | 152 | 3.17 |
| A83 | 0.499 | 123 | 4.06 |
| A85 | 0.0496 | 146 | 36.7 |
| A86 | 0.297 | 93.6 | 4.65 |
| A87 | 0.108 | 143 | 17.7 |
| A91 | 0.194 | 194 | 13.2 |
| A93 | 0.109 | 129 | 16.7 |
| A94 | 0.0365 | 84 | 29.3 |
| A96 | 0.0996 | 153 | 20.1 |
| A97 | 0.0604 | 99.5 | 21 |
| A98 | 0.119 | 159 | 17.4 |
| A99 | 0.0948 | 128 | 19.5 |
| A100 | 0.0791 | 140 | 21.4 |
| A101 | 0.0675 | 149 | 28.4 |
| A104 | 0.108 | 137 | 16.6 |
| A108 | 6.45 | 396 | 1.01 |
| A109 | 0.150 | 154 | 16.0 |
| A111 | 20.0 | ND | ND |
| A112 | 0.0409 | 99.8 | 32.6 |
| A121 | 2.11 | 239 | 1.80 |

TABLE 9-continued

Pharmacokinetic analyses

| Compound No. | CL (mL/min/kg) | Vss (mL/kg) | Half-Life (hr) |
|---|---|---|---|
| A122 | 1.95 | 763 | 5.13 |
| A123 | 0.580 | 146 | 3.20 |
| A124 | 1.72 | 273 | 2.14 |
| A125 | 3.56 | 211 | 0.963 |

Example 10: Subcutaneous Infusion: Pharmacokinetic Studies to Assess Clearance from Kidney (CL) of Amylin Analog Polypeptides Peptides were dissolved in sterile saline and administered as a 1-hour subcutaneous infusion to non-fasted male Sprague-Dawley rats (n=3 per group) at a final dose of 0.033 mg/kg via a cannula placed into the subcutaneous space between the scapulae. Formulations were administered at a rate of 0.145 mL/h/kg. Blood samples (approximately 250 µL) were collected for pharmacokinetic analysis via a jugular vein cannula at 0.25, 0.5, 1, 1.5, 2, 4, 6, 8, 24, 30 and 48 hr post-start of infusion into microtainer tubes containing K2EDTA as anticoagulant and 25 L of a protease inhibitor cocktail. Plasma was prepared by centrifugation and stored at −80° C. until analysis. The results of this analysis are shown in Table 9.

Example 11: Subcutaneous Bolus Injection: Pharmacokinetic Studies to Assess Clearance from Kidney (CL) of Amylin Analog Polypeptides Peptides were dissolved in sterile saline and administered to non-fasted male Sprague-Dawley rats (n=3 per group) at a dose of 0.3 mg/kg via a single bolus injection into the subcutaneous space between the scapulae. Blood samples (approximately 250 µL) were collected for pharmacokinetic analysis via a jugular vein cannula at 0.083, 0.167, 0.25, 0.5, 1, 2, 4, 8, 24, 30 and 48 hr post-dose into microtainer tubes containing K2EDTA as anticoagulant and L of a protease inhibitor cocktail. Plasma was prepared by centrifugation and stored at −80° C. until analysis. The results of this analysis are shown in Table 9.

Example 12: Method of Plasma Sample Preparation for Pharmacokinetic Studies

Protein Precipitation

A 60 µL aliquot of each plasma sample was placed into to a 96-well plate. To each well was added 6 µL of 0.5% Tween-20. Plates were then vortexed mixed for 10 minutes at 1200 rpm before 180 µL of 0.1% TFA in 2:1 ethanol: acetonitrile containing an appropriate internal standard was added to each well. Plates were vortex mixed for 5 min at 1300 rpm, and then centrifuged for 10 min at 2844×g. Supernatants (180 µL) were placed into a clean 96-well plate and evaporated under a nitrogen stream at 45° C. Residues were reconstituted in 80 µL of 20% acetonitrile (aq) containing 0.1% formic acid.

Solid-Phase Extraction

A 60 µL aliquot of each plasma sample was diluted with 180 mL of 10 mM ammonium acetate (pH 6.8) containing an appropriate internal standard and loaded onto an Oasis WCX microElution plate (Waters Corporation, Milford, MA) that had been pre-conditioned with 200 mL of methanol and 200 mL of deionized water. Samples were washed with 200 mL of 5% ammonium hydroxide (aq) followed by 200 mL of 20% acetonitrile in water. The analyte was eluted with 200 mL of 5% formic acid in 75:25 acetonitrile:water. The eluent was dried under a nitrogen stream. Residues were reconstituted in 80 µL of 20% acetonitrile (aq) containing 0.1% formic acid.

Example 13: LC/MS Quantification of Amylin Analog Polypeptides in Plasma

All calibration standards were prepared in control rat plasma containing K2EDTA and protease inhibitor cocktail.

Samples and standards were analyzed by Turbolon-Spray™ UPLC-MS/MS using a system consisting of a CTC HTS PAL auto-injector (Leap, Carrboro, NC), an Agilent Infinity 1290 system with column oven (Palo Alto, CA), a Valco switching valve (Houston, TX), and either an AB Sciex API 5600 TripleTOF™ or Sciex API 4000QTrap mass spectrometer (Framingham, MA). Samples were injected onto a 2.1×50 mm reverse phase $C_{18}$ analytical column, typically a Waters CORTECS UPLC C18+, 1.6 µm (Waters Corporation, Milford, MA) or similar. Chromatographic separation was achieved with a gradient method using water containing 0.1% formic acid (A) and acetonitrile containing 0.1% formic acid (B) as mobile phase. Initial conditions consisted of 90% A and 10% B. The organic component was increased to 95% B over a period of 3-4 minutes, depending on the peptide. Typical flow rates were 600 µL/min. The column temperature was held constant at 40 or 50° C. Peptides were quantified by monitoring one or more product ions produced from a multiply charged parent ion.

Example 14: In Vivo Efficacy of Amylin Analog Polypeptides with Food Intake Inhibition in Rats Acute food intake was measured continuously for a 72 hr period using a BioDAQ food monitoring system (Research Diets, New Brunswick, NJ) to determine the amount of food intake inhibition exhibited by these amylin analog polypeptides. Long Evans rats were obtained at approximately 8 weeks of age. The rats were singly housed and acclimated to 45% high fat diet for at least 2 weeks prior to dosing. After 1 week of acclimation all rats were singly housed in Bio-DAQ cages (Research Diets, New Brunswick, NJ) and maintained at constant temperature (approximately 22° C.) and 30-70% relative humidity with 12 hr light/dark cycle (lights on from 7:00 AM to 7:00 PM). The rats were given ad libitum access to water and pellet chow (Research Diets D12451i, 45 kcal % fat, Research Diets, New Brunswick, NJ). All procedures were performed in compliance with the Animal Welfare Act, USDA regulations and approved by the Mispro Institutional Animal Care and Use Committee. Animals were randomized into treatment groups according to body weight (n=8 rats/group). Animals were dosed (SC bolus injection) with either an amylin analog polypeptide at the specified concentration or vehicle control (saline) and were dosed between 6:00 and 6:30 prior to lights out with hoppers gated while animals were being dosed. Hopper gates were opened and continuous data collection started immediately following completion of dosing. Data was analyzed using the BioDAQ Viewer software (version 2.3.07) and bout filters were set if needed to reduce noise in data associated with non-feeding behavior. All the data are expressed as % inhibition from vehicle control and summarized as mean. The data were analyzed for statistical significance with Microsoft Excel (Redmond, WA) by 2-sample t-test. P-values <0.05 were considered to indicate a significant difference between treatment groups. Acute % food intake inhibition from vehicle control results for the amylin analog polypeptides are shown in Table 10.

TABLE 10

Acute % food intake inhibition in rats after acute SC dosing of amylin analog polypeptides.

| Compound | Acute Food Intake % Inhibition vs vehicle | | |
|---|---|---|---|
| | 0-24 hr | 25-48 hr | 49-72 hr |
| A5 | 37% | (+) 2% | (+) 8% |
| A13 | 67% | 37% | 6% |
| A27 | 86% | 57% | 13% |
| A53 | 44% | 33% | 8% |
| A57 | 17% | 5% | nd |
| A64 | 51% | 44% | 21% |
| A65 | 50% | 25% | 14% |
| A66 | 40% | 19% | 5% |
| A67 | 20% | 24% | (+) 5% |
| A109 | 88% | 77% | 36% |
| A98 | 23% | 24% | nd |
| A101 | (+) 3% | nd | nd |
| A72 | 82% | 16% | nd |
| A18 | 18% | (+) 17% | nd | nd = not determined;
Bold = P < 0.05 vs. vehicle

Example 15: In Vivo Efficacy with Body Weight Changes in LE DIO Rats after 13 Days Chronic (13 days) in vivo dose-response efficacy studies were conducted in a rodent model for obesity (Long Evans (LE) diet-induced obese (DIO) rat) to investigate the efficacy and durability of the amylin analog polypeptides on weight loss. Male LE DIO rats were used (Envigo Laboratories, Inc., Indianapolis, IN) and beginning at weaning, the rats were fed a high fat chow (Teklad TD 95217, 40% kcal from fat, Harlan Laboratories, Madison, WI). Rats were 15-17 weeks old at the start of the study. The rats were housed 1 per cage and given ad libitum access to high fat diet (Harlan TD.95217, 4.3 kcal/g) and water, maintained on a 12 hr light/dark cycle from 5:00 AM to 5:00 PM at 21° C. and 50% relative humidity and allowed to acclimate for at least 10 days prior to the surgeries. All procedures were performed in compliance with the Animal Welfare Act, USDA regulations and approved by the Mispro Institutional Animal Care and Use Committee. Body weight measurements were taken 2 times/week starting three days before the surgery. Baseline fat mass and non-fat mass measurements were taken 3 days before the start of peptide infusion using a QMR instrument (Echo Medical Systems, Houston, TX). Rats were randomized according to their percent body fat mass and/or body weight into the various treatment groups (n=4-6 rats/group). Alzet mini-osmotic pumps (2 week; Model 2002, Durect Corporation, Cupertino, CA) were filled under sterile condition with either vehicle or peptide one day prior to the surgery. On the day of surgery, rats were anesthetized under isoflurane and the dorsal skin surface was shaved and cleansed. Rats were injected SC with Flunexin (2.5 mg/kg). A 1-2 cm surgical incision was made between the scapulae. Using blunt dissection, a 2-3 cm subcutaneous tunnel was created into which the sterile, filled, mini-osmotic pump was introduced. The skin opening was closed with a skin staple. Each rat was implanted one or two osmotic pumps containing vehicle or peptide according to their treatment group. The data were analyzed in Excel and/or Prism (GraphPad Software, Inc., La Jolla, CA) using one-way ANOVA to compare each group to the appropriate control group. P-values <0.05 were considered to indicate a significant difference between treatment groups. The mean weight loss (%) from baseline and vehicle control (ΔΔ) from the 13-day studies are shown in Table 9.

Example 16: Weight-Loss Efficacy of Amylin Analog Polypeptides in Combination with Exenatide in LE DIO Rats Chronic studies were conducted to determine the effects and durability of continuous administration of amylin analog polypeptides in combination with exenatide (GLP-1 receptor agonist) on body weight after 27 days of treatment in the LE DIO rat. Male LE DIO rats at 18 weeks of age (14 weeks on high fat diet) were either subcutaneously (SC) implanted with two (2) Alzet osmotic mini-pumps containing specified doses of either amylin analog polypeptide and/or exenatide (10 mcg/kg/d=ED50 for weight loss) or vehicle (20% DMSO in water) (n=8 animals/treatment group). Amylin analog polypeptides whose PK supported every other day dosing (eod) were dosed by SC injection eod instead of mini-pump administration. All other procedures were the same as described for previous example. The mean weight loss (%) from baseline and vehicle control (ΔΔ) results from the chronic combination studies with exenatide are shown in Table 11.

Example 17: Anti-Diabetic Efficacy of Amylin Analog Polypeptides in Combination with Exenatide in ZDF Rats Chronic studies were conducted to determine the antidiabetic effects of continuous administration of amylin analog polypeptide in combination with exenatide on HbA1c (a primary anti-diabetic parameter) after 27 days of treatment in Zucker Diabetic Fatty (ZDF) rats. Male ZDF rats were obtained at six (6) weeks of age (Charles River, Raleigh, NC) and used on study at eight (8) weeks old. Upon receipt, the rats were housed one animal per cage with free access to Purina 5008 chow (Lab Diet, St. Louis, MO) and water, maintained on a 12-hour light/dark cycle from 5:00 AM to 5:00 PM at 21° C. and 50% relative humidity and allowed to acclimate for nine (9) days before the start of the study. Blood samples were taken as pre-bleeds (Day −3) via tail vein to measure glucose levels and HbA1c. The ZDF rats were randomized into treatment groups (n=10/group) with similar mean HbA1c and glucose. They were subcutaneously (SC) implanted with Alzet osmotic mini-pumps (two (2) pumps/animal) containing either specified doses of amylin analog polypeptide and/or exenatide (10 mcg/kg/day) or vehicle (20% DMSO in water) (n=10 animals/treatment group). Amylin analog polypeptides whose PK supported every other day dosing (eod) were dosed by SC injection eod instead of mini-pump administration. All other procedures were the same as described for previous example. Blood samples were taken again on Days 14 and 27 (end of study) to measure glucose levels and HbA1c. Final whole blood samples were collected by cardiac puncture under isoflurane anesthesia (Day 27). HbA1c analysis was performed by using a Carolina Chemistries CLC720i Clinical Chemistry analyzer (Mindray Inc., Mahwah, NY) with the protocol and method parameters as described by the manufacturer. HbA1c results expressed as the mean % change from baseline and vehicle control (ΔΔ) from the chronic combination studies with exenatide are shown in Table 11.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 11

Summary of weight loss and HbA1c changes in rats treated with amylin analog polypeptides

| Compound | DIO Dose Response 13 d weight loss | | DIO Combination + Exenatide 27 d weight loss | | ZDF Combination + Exenatide 27 d HbA1c (%) | |
|---|---|---|---|---|---|---|
| | ΔΔ % weight loss | $ED_{50}$ mcg/kg | ΔΔ % weight loss | Dose mcg/kg + Exenatide 10 mcg/kg | ΔΔ % HbA1c | Dose mcg/kg + Exenatide 10 mcg/kg |
| A13 | 5% | 55 | 9, 12, 12% | 3, 10, 30 | nd | nd |
| A27 | 5% | 36 | 9, 12, 17% | 3, 10, 30 | 3.3% | 30 |
| A53 | 5% | 63 | nd | nd | nd | nd |
| A57 | 4% | 67 | 5, 7, 12% | 1, 10, 100 | nd | nd |
| A64 | 5% | 43 | 7, 11, 15% | 10, 60, 200 | 3.3% | 200 |
| A65 | 3% | 70 | 8, 9, 12% | 100, 300, 600 | nd | nd |
| A66 | 6% | 270 | nd | nd | nd | nd |
| A67 | 5% | 95 | nd | nd | nd | nd |
| A36 | 7% | 214 | nd | nd | nd | nd |
| A109 | 3% | 20 | 6, 8, 8, 10% | 3, 10, 30, 100 | 3.4% | 100 | nd = not determined;
Bold = P < 0.05 vs. vehicle

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated polypeptide, comprising the amino acid sequence of SEQ ID NO: 203:

$X_1CNTX_5TCATX_{10}RLANX_{15}X_{16}X_{17}X_{18}$SSNNFGPIL-PPTKVGSETY-(OH/NH$_2$) (SEQ ID NO: 203), wherein:

$X_1$ is k or K;
$X_5$ is S;
$X_{10}$ is Q or S;
$X_{15}$ is E or F;
$X_{16}$ is L;
$X_{17}$ is H, V, and Q; and
$X_{18}$ is K, H, or R;
wherein:
each K independently represents an L-lysine optionally covalently bound to a lipophilic substituent, optionally via a spacer;
each k independently represents a D-lysine optionally covalently bound to a lipophilic substituent, optionally via a spacer; and
the two cysteine residues of $X_1CNTX_5TC$ (SEQ ID NO: 308) are optionally further bound by a disulfide bridge.

2. The isolated polypeptide of claim 1, comprising the amino acid sequence of SEQ ID NO:209:

$X_1$CNTSTCAT$X_{10}$RLAN$X_{15}X_{16}X_{17}$KSSNNFGPILPP-TKVGSETY-(OH/NH$_2$) (SEQ ID NO:209), or a pharmaceutically acceptable salt thereof, wherein:

$X_1$ is K or k;
$X_{10}$ is Q or S;
$X_{16}$ is E or F;
$X_{16}$ is L; and
$X_{17}$ is H, V or Q;
each K independently represents an L-lysine optionally covalently bound to a lipophilic substituent, optionally via a spacer;

each k independently represents a D-lysine optionally covalently bound to a lipophilic substituent, optionally via a spacer; and wherein the two cysteine residues of X₁CNTSTC (SEQ ID NO: 318) are optionally further bound by a disulfide bridge.

3. The isolated polypeptide of claim 1, comprising the amino acid sequence of:

(SEQ ID NO: 130)
KC*NTSTC*ATQRLANELHKSSNNFGPILPPTKVGSETY-(NH₂), or a pharmaceutically acceptable salt thereof,
wherein the two cysteine residues denoted C* at positions 2 and 7 are further bound by a disulfide bridge.

4. The isolated polypeptide of claim 1, comprising the amino acid sequence of:

(SEQ ID NO: 64)
K*((γGlu)₂(CO(CH₂)₁₈CO₂H))C*NTSTC*ATQRLANELHKSSNNF

GPILPPTKVGSETY-(NH₂), or a pharmaceutically acceptable salt thereof,
wherein:
K* represents an L-lysine covalently bound to (γGlu)₂(CO(CH₂)₁₈CO₂H); and
the two cysteine residues denoted C* at positions 2 and 7 are further bound by a disulfide bridge.

5. The isolated polypeptide of claim 1, comprising the amino acid sequence of:

(SEQ ID NO: 65)
K*((γGlu)₂(CO(CH₂)₁₆CO₂H))C*NTSTC*ATQRLANELHKSSN

NFGPILPPTKVGSETY-(NH₂), or a pharmaceutically acceptable salt thereof,
wherein:
K* represents an L-lysine covalently bound to (γGlu)₂(CO(CH₂)₁₆CO₂H); and
the two cysteine residues denoted C* at positions 2 and 7 are further bound by a disulfide bridge.

6. The isolated polypeptide of claim 1, selected from the group consisting of:

(SEQ ID NO: 131)
KC*NTSTC*ATQRLANFLQKSSNNFGPILPPTKVGSETY-(NH₂), or a pharmaceutically acceptable salt thereof,
wherein the two cysteine residues denoted C* at positions 2 and 7 are further bound by a disulfide bridge.

7. The isolated polypeptide of claim 1, selected from the group consisting of:

(SEQ ID NO: 109)
K*(γGlu-CO(CH₂)₁₆CO₂H)C*NTSTC*ATSRLANFLQKSSNNF G

PILPPTKVGSETY-NH₂, or a pharmaceutically acceptable salt thereof,
wherein:
K* represents an L-lysine covalently bound to γGlu-CO(CH₂)₁₆CO₂H; and
the two cysteine residues denoted C* at positions 2 and 7 are further bound by a disulfide bridge.

8. The isolated polypeptide of claim 1, comprising an amino acid sequence selected from the group consisting of any of SEQ ID NOS: 55, 64, 65, 109, 112-120, 126, 130, 131, and 143, or a pharmaceutically acceptable salt thereof.

9. The isolated polypeptide of claim 1, or a pharmaceutically acceptable salt thereof, further comprising a lipophilic substituent, and optionally comprising a spacer.

10. The isolated polypeptide of claim 9, or a pharmaceutically acceptable salt thereof, further comprising a lipophilic substituent and a spacer of Formula VI:

$$-(Y1)_{n1}-(V)_r-(Y2)_{n2}-CO-(CH_2)_m-Z \quad \text{Formula VI}$$

wherein
Z is —CH₃ or —CO₂H;
m is from 4 to 24;
Y1 is selected from the group consisting of γGlu, Asp, and Gly;
Y2 is selected from the group consisting of γGlu, Asp, and Gly;
V is —[COCH₂(O(CH₂)₂)ₜOCH₂NH]—, and t is from 1 to 8;
r is from 1 to 8;
n1 is from 0 to 10; and
n2 is from 0 to 10.

11. The isolated polypeptide of claim 9, or a pharmaceutically acceptable salt thereof, further comprising a lipophilic substituent and a spacer of Formula III:

$$-(\gamma Glu)_n-CO-(CH_2)_m-Z \text{ (``}(\gamma Glu)_n\text{'' disclosed as SEQ ID NO: 311)} \quad \text{Formula III}$$

wherein
Z is —CH₃ or —CO₂H;
m is from 4 to 24; and
n is from 1 to 10.

12. The isolated polypeptide of claim 10, or a pharmaceutically acceptable salt thereof, wherein the lipophilic substituent, —CO—(CH₂)ₘ—Z, is linked to the ε-amino group of a lysine of the isolated polypeptide via the spacer, —(Y1)_{n1}—(V)_r—(Y2)_{n2}—, which spacer forms a bridge between the amino group of the disclosed polypeptide and the CO— group of the lipophilic substituent.

13. The isolated polypeptide of claim 11, or a pharmaceutically acceptable salt thereof, wherein the lipophilic substituent, —CO—(CH₂)ₘ—Z, is linked to the ε-amino group of a lysine of the isolated polypeptide via the spacer, -(γGlu)ₙ- ("(γGlu)ₙ" disclosed as SEQ ID NO: 311), which spacer forms a bridge between the amino group of the disclosed polypeptide and the CO— group of the lipophilic substituent.

14. The isolated polypeptide of claim 9, or a pharmaceutically acceptable salt thereof, wherein:
the lipophilic substituent is —CO—(CH₂)ₘ—CO₂H; and
m is from 14 to 20.

15. The isolated polypeptide of claim 14, or a pharmaceutically acceptable salt thereof, wherein the spacer is γGlu or 2(γGlu).

16. A pharmaceutical composition comprising the isolated polypeptide of claim 1 or a pharmaceutically acceptable salt thereof.

17. The pharmaceutical composition of claim 16, wherein the composition further comprises an insulinotropic polypeptide.

18. The isolated peptide of claim 1, or a pharmaceutically acceptable salt thereof, wherein X₁₇ is H or Q.

19. The isolated peptide of claim 2, or a pharmaceutically acceptable salt thereof, wherein X₁₇ is H or Q.

20. The isolated polypeptide of claim 1, consisting of the amino acid sequence of:

(SEQ ID NO: 130)
KC*NTSTC*ATQRLANELHKSSNNFGPILPPTKVGSETY-(NH$_2$), or a pharmaceutically acceptable salt thereof,
wherein the two cysteine residues denoted C* at positions 2 and 7 are further bound by a disulfide bridge.

21. The isolated polypeptide of claim 1, consisting of the amino acid sequence of:

(SEQ ID NO: 64)
K*((γGlu)$_2$(CO(CH$_2$)$_{18}$CO$_2$H))C*NTSTC*ATQRLANELHKSSNN FGPILPPTKVGSETY-(NH$_2$), or a pharmaceutically acceptable salt thereof,
wherein:
K* represents an L-lysine covalently bound to (γGlu)$_2$(CO(CH$_2$)$_{18}$CO$_2$H); and
the two cysteine residues denoted C* at positions 2 and 7 are further bound by a disulfide bridge.

22. The isolated polypeptide of claim 1, comprising the amino acid sequence of:

(SEQ ID NO: 65)
K*((γGlu)$_2$(CO(CH$_2$)$_{16}$CO$_2$H))C*NTSTC*ATQRLANELHKSSNN FGPILPPTKVGSETY-(NH$_2$), or a pharmaceutically acceptable salt thereof,
wherein:
K* represents an L-lysine covalently bound to (γGlu)$_2$(CO(CH$_2$)$_{16}$CO$_2$H); and
the two cysteine residues denoted C* at positions 2 and 7 are further bound by a disulfide bridge.

23. The isolated polypeptide of claim 1, selected from the group consisting of:

(SEQ ID NO: 131)
KC*NTSTC*ATQRLANFLQKSSNNFGPILPPTKVGSETY-(NH$_2$), or a pharmaceutically acceptable salt thereof,
wherein the two cysteine residues denoted C* at positions 2 and 7 are further bound by a disulfide bridge.

24. The isolated polypeptide of claim 1, selected from the group consisting of:

(SEQ ID NO: 109)
K*(γGlu-CO(CH$_2$)$_{16}$CO$_2$H)C*NTSTC*ATSRLANFLQKSSNNF GPILPPTKVGSETY-NH$_2$, or a pharmaceutically acceptable salt thereof,
wherein:
K* represents an L-lysine covalently bound to γGlu-CO(CH$_2$)$_{16}$CO$_2$H; and
the two cysteine residues denoted C* at positions 2 and 7 are further bound by a disulfide bridge.

25. The pharmaceutical composition of claim 16, wherein said pharmaceutical composition is formulated for injection.

26. The pharmaceutical composition of claim 16, wherein said pharmaceutical composition is formulated for oral administration.

27. A pharmaceutical composition comprising the isolated polypeptide of claim 20 or a pharmaceutically acceptable salt thereof.

28. A pharmaceutical composition comprising the isolated polypeptide of claim 21 or a pharmaceutically acceptable salt thereof.

29. A pharmaceutical composition comprising the isolated polypeptide of claim 22 or a pharmaceutically acceptable salt thereof.

30. A pharmaceutical composition comprising the isolated polypeptide of claim 23 or a pharmaceutically acceptable salt thereof.

31. A pharmaceutical composition comprising the isolated polypeptide of claim 24 or a pharmaceutically acceptable salt thereof.

32. An isolated polypeptide, comprising the amino acid sequence of SEQ ID NO: 211:

(SEQ ID NO: 211)
X$_1$CNTSTCATX$_{10}$RLANX$_{15}$X$_{16}$X$_{17}$KSSNNFGPILPPTKVGSX$_{35}$TY-(OH/NH$_2$), wherein:
X$_1$ is K or k;
X$_{10}$ is Q or S;
X$_{15}$ is E or F;
X$_{16}$ is L;
X$_{17}$ is H, V or Q; and
X$_{35}$ is E;
wherein:
each K independently represents an L-lysine optionally covalently bound to a protecting group or a spacer optionally bound to a protecting group;
each k independently represents a D-lysine optionally covalently bound to a protecting group or a spacer optionally bound to a protecting group; and
the two cysteine residues of X$_1$CNTSTC (SEQ ID NO: 309) are optionally further bound by a disulfide bridge.

33. The isolated peptide of claim 32, selected from the group consisting of:

(SEQ ID NO. 155)
KC*NTSTC*ATSRLANFLQKSSNNFGPILPPTKVGSETY-NH2;
and (SEQ ID NO. 156)
K*(Fmoc)C*NTSTC*ATSRLANFLQKSSNNFGPILPPTKVGSETY-NH$_2$, or a pharmaceutically acceptable salt thereof,
wherein:
each K* represents an L-lysine covalently bound to a protecting group; and
the two cysteine residues denoted C* at positions 2 and 7 are further bound by a disulfide bridge.

34. The isolated peptide of claim 32, selected from the group consisting of:

(SEQ ID NO. 157)
K*(γGlu)C*NTSTC*ATSRLANFLQKSSNNFGPILPPTKVGSETY-NH$_2$;

(SEQ ID NO. 158)
K*(γGlu-acetyl)C*NTSTC*ATSRLANFLQKSSNNFGPILPPTK VGSETY-NH$_2$;

(SEQ ID NO. 159)
K*(γGlu-trityl)C*NTSTC*ATSRLANFLQKSSNNFGPILPPTK

VGSETY-NH$_2$;
and (SEQ ID NO. 160)
K*(γGlu-tert-butyl)C*NTSTC*ATSRLANFLQKSSNNFGPIL

PPTKVGSETY-NH$_2$, or a pharmaceutically acceptable salt thereof,
wherein:
each K* independently represents an L-lysine covalently bound to a spacer or a spacer bound to a protecting group; and
the two cysteine residues denoted C* at positions 2 and 7 are further bound by a disulfide bridge.

35. The isolated peptide of claim 32, selected from the group consisting of:

(SEQ ID NO. 161)
K*(γGlu-γGlu)C*NTSTC*ATSRLANFLQKSSNNFGPILPPTKVG

SETY-NH$_2$;

(SEQ ID NO. 162)
K*(γGlu-γGlu-acetyl)C*NTSTC*ATSRLANFLQKSSNNFGPI

LPPTKVGSETY-NH$_2$;

(SEQ ID NO. 163)
K*(γGlu-γGlu-trityl)C*NTSTC*ATSRLANFLQKSSNNFGPI

LPPTKVGSETY-NH$_2$;
and (SEQ ID NO. 164)
K*(γGlu-γGlu-tert-butyl)C*NTSTC*ATSRLANFLQKSSNN

FGPILPPTKVGSETY-NH$_2$, or a pharmaceutically acceptable salt thereof, wherein:

each K* independently represents an L-lysine covalently bound to a spacer or a spacer bound to a protecting group; and the two cysteine residues denoted C* at positions 2 and 7 are further bound by a disulfide bridge.

* * * * *